(12) United States Patent
Harvey et al.

(10) Patent No.: US 7,507,873 B2
(45) Date of Patent: *Mar. 24, 2009

(54) TRANSGENIC AVIANS CONTAINING RECOMBINANT OVOMUCOID PROMOTERS

(75) Inventors: Alex J. Harvey, Athens, GA (US); Markley C. Leavitt, Watkinsville, GA (US); Youliang Wang, Monroe, GA (US)

(73) Assignee: AviGenics, Inc., Athens, GA (US)

( * ) Notice: Subject to any disclaimer, the term of this patent is extended or adjusted under 35 U.S.C. 154(b) by 3 days.

This patent is subject to a terminal disclaimer.

(21) Appl. No.: 11/649,543

(22) Filed: Jan. 4, 2007

(65) Prior Publication Data

US 2007/0113299 A1 May 17, 2007

Related U.S. Application Data

(63) Continuation of application No. 11/047,184, filed on Jan. 31, 2005, now Pat. No. 7,335,761, which is a continuation-in-part of application No. 10/856,218, filed on May 28, 2004, now Pat. No. 7,294,507, which is a continuation-in-part of application No. 10/496,731, filed as application No. PCT/US02/38413 on Dec. 2, 2002, now Pat. No. 7,375,258, which is a continuation-in-part of application No. 09/998,716, filed on Nov. 30, 2001, now Pat. No. 6,875,588, said application No. 11/047,184 is a continuation-in-part of application No. 10/790,455, filed on Mar. 1, 2004, now abandoned.

(60) Provisional application No. 60/509,122, filed on Oct. 6, 2003, provisional application No. 60/505,562, filed on Sep. 24, 2003, provisional application No. 60/476,596, filed on Jun. 6, 2003.

(51) Int. Cl.
*A01K 67/027* (2006.01)
*A01K 67/00* (2006.01)
*A01K 67/033* (2006.01)

(52) U.S. Cl. .......................... 800/19; 800/8
(58) Field of Classification Search .................. 800/19, 800/21, 8

See application file for complete search history.

(56) References Cited

U.S. PATENT DOCUMENTS

| 4,237,224 | A | 12/1980 | Cohen et al. |
|---|---|---|---|
| 4,603,112 | A | 7/1986 | Paoletti et al. |
| 4,722,848 | A | 2/1988 | Paoletti et al. |
| 4,769,330 | A | 9/1988 | Paoletti et al. |
| 5,174,993 | A | 12/1992 | Paoletti et al. |
| 5,175,384 | A | 12/1992 | Krimpenfort et al. |
| 5,338,683 | A | 8/1994 | Paoletti et al. |
| 5,494,807 | A | 2/1996 | Paoletti et al. |
| 5,505,941 | A | 4/1996 | Paoletti et al. |
| 5,580,859 | A | 12/1996 | Felgner et al. |
| 5,589,466 | A | 12/1996 | Felgner et al. |
| 5,591,639 | A | 1/1997 | Bebbington |
| 6,808,925 | B2 * | 10/2004 | Calos .................... 435/462 |
| 6,825,396 | B2 * | 11/2004 | MacArthur ............... 800/19 |
| 6,875,588 | B2 * | 4/2005 | Harvey et al. .......... 435/69.51 |
| 7,294,507 | B2 * | 11/2007 | Harvey et al. .......... 435/320.1 |
| 2003/0126629 | A1 * | 7/2003 | Rapp et al. ............... 800/19 |

FOREIGN PATENT DOCUMENTS

| WO | WO 92/06180 | 4/1992 |
|---|---|---|
| WO | WO 92/19749 | 11/1992 |
| WO | WO 92/20316 | 11/1992 |
| WO | WO 92/22635 | 12/1992 |
| WO | WO 93/04701 | 3/1993 |
| WO | WO 93/25234 | 12/1993 |
| WO | WO 94/06920 | 3/1994 |
| WO | WO 94/11524 | 5/1994 |
| WO | WO 97/47739 | 12/1997 |
| WO | WO9747739 A2 * | 12/1997 |
| WO | WO 99/19472 | 4/1999 |
| WO | WO 03/048364 | 6/2003 |

OTHER PUBLICATIONS

Molecular Structure and Flanking Nucleotide Sequences of the Natural Chicken Ovomucoid Gene, Lai et al; Cell 18:829-842 (Nov. 1979).

DNA methylation: organ specific variations in the methylation pattern within and around ovalbumin and other chicken genes, Mandel et al; Nucleic Acids Research 7:2081-2103(1979).

Ovoinhibitor Introns Specify Functional Domains as in the Related and Linked Ovomucoid Gene, Scott et al; Journal of Biol. Chemistry, 262:5899-5907(1987).

Deoxyribonuclease I Sensitivity of the Ovomucoid-Ovoinhibitor Gene Complex in Oviduct Nuclei and Relative Location of CR1 Repetitive Sequences, Scott et al; Biochemistry 26:6831-6840 (1987).

Isolation and characterization of the chicken ovomucoid gene, Lindenmaier et al; Nucleic Acids Research, 7:1221-1232 (1979).

The chick ovomucoid gene contains at least six intervening sequences, Catterall et al; Nature 278:323-327 (Mar. 1979).

Effect of Estrogen on Gene Expression In the Chick Oviduct. Regulation of the Ovomucoid Gene, Tsai et al; Biochemistry 17:5773-5780 (1978).

(Continued)

*Primary Examiner*—Michael C. Wilson
(74) *Attorney, Agent, or Firm*—Kyle D. Yesland

(57) ABSTRACT

Transgenic avians having a recombinant ovomucoid gene expression controlling region operably linked to one or more useful amino acid coding sequences.

20 Claims, 42 Drawing Sheets

OTHER PUBLICATIONS

Identification of potential ovomucoid mRNA precursors in chick oviduct nuclei, Nordstrom et al; Nature 278:328-331 (Mar. 1979).

mRNA Complexity and Egg White Protein mRNA Content in Mature and Hormone-Withdrawn Oviduct, Hynes et al; Cell 11:923-932 (Aug. 1977).

Multiple Initiation and Polyadenylation Sites for the Chicken Ovomucoid Transcription Unit, Gerlinger et al; J. Mol. Biol. vol. 162, p. 345-364 (1982).

Identification and fine mapping of IgG and IgE Epitopes in Ovomucoid, Mine et al; Biochem Biophys Res Comm, vol. 292 p. 1070-1074 (2002).

Heterogenous Initiation Sites for Transcription of the Chicken Ovomucoid Gene, Lai EC et al, J. of Supramolecular Structure and Cellular Biochemistry, No. 1157 p. 429 (abstract).

Chicken Ovomucoid Gene, 5' End Region, Gerlinger p. et al; Lai et al; Database Accession No. J00894 (1986).

Gallus Gallus Isolate No. 26 Ovomucoid Gene, Promoter Region and Partial cds, Wang et al, Database Accession No. AF453747.

Expression of Exogenous Protein in the Egg White of Transgenic Chicken, Harvey et al. Nature Biotechnology vol. 19 p. 396-399 (2002).

* cited by examiner

| | | |
|---|---|---|
| OVINs1: | GGGAAACAATCTGCCTTGCA | SEQ ID NO: 3 |
| OVINs2: | TAGGCAGAGCAATAGGACTCTCAACCTCGT | SEQ ID NO: 1 |
| OVINs4: | AGATGAGGTGGATGGTTTAC | SEQ ID NO: 7 |
| OVINs5: | CAGCTTCTGCTAGCGTAGGT | SEQ ID NO: 8 |
| OVINs6: | ACGTGAACTCAAAGAGGCAC | SEQ ID NO: 9 |
| OVINs7: | ATCTCCTGAGCTCGGTGCTT | SEQ ID NO: 10 |
| OVINs8: | ACGAGGTTCCATGTCTTTCA | SEQ ID NO: 11 |
| OVMUa1: | AAGCCACAAAGCACGAAAGAG | SEQ ID NO: 4 |
| OVMUa2: | AAGCTTCTGCAGCACTCTGGGAGTTACTCA | SEQ ID NO: 2 |
| OVMUa3: | TAAATAGCACAGAACGCTGAGGGGAGTAAGG | SEQ ID NO: 12 |
| OVMUa4: | GAAGAGCTTGGTAGAAGACT | SEQ ID NO: 13 |
| OVMUa5: | ATGGAAATATGGGTTTCCTTC | SEQ ID NO: 14 |
| OVMUa6: | GCAGCTTATGGCTAATCGCT | SEQ ID NO: 15 |
| OVMUa7: | AGTGACCACTATCTGACCTG | SEQ ID NO: 16 |
| OVMUa8: | TAATCAGGAAGGCACACAGC | SEQ ID NO: 17 |
| OVMUP4.7.1: | AGATCTGGAGCAGCACTTGT | SEQ ID NO: 18 |
| OVMUP4.7.2: | AGCATGAAGTTCCTCACCCA | SEQ ID NO: 19 |
| OVMUP4.7.3: | ATGGAGAGGAATATTCCCTT | SEQ ID NO: 20 |
| OVMUP4.7.4: | ATTTCTCCAGGCGTGTGG | SEQ ID NO: 21 |
| OVMUP5.5.1: | ATTTCTCCAGGCGTGTGG | SEQ ID NO: 22 |
| OVMUP5.5.2: | ATGCGAGTGAAGGAGAGTTC | SEQ ID NO: 23 |
| OVMUP5.5.3: | GCAGCACGTGTAAGCTTGTA | SEQ ID NO: 24 |
| OVMUP5.5.4: | CAAGGCAAATTATCAGCAGA | SEQ ID NO: 25 |
| OVMUa9: | AAATGAAGCCGGCTGTTTTC | SEQ ID NO: 27 |
| OVINs9 | CTCTCAGCCACTCTGAACAA | SEQ ID NO: 28 |

*Fig. 3*

```
TAGGCAGAGCAATAGGACTCTCAACCTCGTGAGTATGGCAGCATGTTAACTCTGCACTGG    60
                OVOINHIBITOR 3' UNTRANSLATED REGION
AGTCCAGCGTGGGAAACAATCTGCCTTGCACATGAGTCTTCGTGGGCCAATATTCCCCAA
                OVOINHIBITOR 3' UNTRANSLATED REGION
CGGTTTTCCTTCAGCTTGTCTTGTCTCCTAAGCTCTCAAAACACCTTTTTGGTGAATAAA
                OVOINHIBITOR 3' UNTRANSLATED REGION
CTCACTTGGCAACGTTTATCTGTCTTACCTTAGTGTCACGTTTCATCCCTATTCCCCTTT

CTCCTCCTCCGTGTGGTACACAGTGGTGCACACTGGTTCTTCTGTTGATGTTCTGCTCTG   300
ACAGCCAATGTGGGTAAAGTTCTTCCTGCCACGTGTCTGTGTTGTTTTCACTTCAAAAAG
GGCCCTGGGCTCCCCTTGGAGCTCTCAGGCATTTCCTTAATCATCACAGTCACGCTGGCA
GGATTAGTCCCTCCTAAACCTTAGAATGACCTGAACGTGTGCTCCCTCTTTGTAGTCAGT
GCAGGGAGACGTTTGCCTCAAGATCAGGGTCCATCTCACCCACAGGGCCATTCCCAAGAT
GAGGTGGATGGTTTACTCTCACAAAAAGTTTTCTTATGTTTGGCTAGAAAGGAGAACTCA   600
CTGCCTACCTGTGAATTCCCCTAGTCCTGGTTCTGCTGCCACTGCTGCCTGTGCAGCCTG
TCCCATGGAGGGGGCAGCAACTGCTGTCACAAAGGTGATCCCACCCTGTCTCCACTGAAA
TGACCTCAGTGCCACGTGTTGTATAGGGTATAAAGTACGGGAGGGGGATGCCCGGCTCCC
TTCAGGGTTGCAGAGCAGAAGTGTCTGTGTATAGAGTGTGTCTTAATCTATTAATGTAAC
AGAACAACTTCAGTCCTAGTGTTTTGTGGGCTGGAATTGCCCATGTGGTAGGGACAGGCC   900
TGCTAAATCACTGCAATCGCCTATGTTCTGAAGGTATTTGGGAAAGAAAGGGATTTGGGG
GATTGCCTGTGATTGGCTTTAATTGAATGGCAAATCACAGGAAAGCAGTTCTGCTCAACA
GTTGGTTGTTTCAGCCAATTCTTGCAGCCAAAGAGCCGGGTGCCCAGCGATATAATAGTT
GTCACTTGTGTCTGTATGGATGACAGGGAGGTAGGGTGACCTGAGGACCACCCTCCAGCT
TCTGCTAGCGTAGGTACAGTCACCACCTCCAGCTCCACACGAGTCCCATCGTGGTTTACC  1200
AAAGAAACACAATTATTTGGACCAGTTTGGAAAGTCACCCGCTGAATTGTGAGGCTAGAT
TAATAGAGCTGAAGAGCAAATGTTCCCAACTTGGAGATACTAGTTGGTATTAGTATCAGA
GGAACAGGGCCATAGCACCTCCATGCTATTAGATTCCGGCTGGCATGTACTTTTCAAGAT
GATTGTAACTAACAATGGCTTATTGTGCTTGTCTTAAGTCTGTGTCCTAATGTAAATGT
TCCTTTGGTTTATATAACCTTCTTGCCATTTGCTCTTCAGGTGTTCTTGCAGAACACTGG  1500
CTGCTTTAATCTAGTTTAACTGTTGCTTGATTATTCTTAGGGATAAGATCTGAATAAACT
TTTTGTGGCTTTGGCAGACTTTAGCTTGGGCTTAGCTCCCACATTAGCTTTTGCTGCCTT
TTCTGTGAAGCTATCAAGATCCTACTCAATGACATTAGCTGGGTGCAGGTGTACCAAATC
CTGCTCTGTGGAACACATTGTCTGATGATACCGAAGGCAAACGTGAACTCAAAGAGGCAC
AGAGTTAAGAAGAAGTCTGTGCAATTCAGAGGAAAAGCCAAAGTGGCCATTAGACACACT  1800
TTCCATGCAGCATTTGCCAGTAGGTTTCATATAAAACTACAAAATGGAATAAACCACTAC
AAATGGGAAAAGCCTGATACTAGAATTTAAATATTCACCCAGGCTCAAGGGGTGTTTCAT
GGAGTAATATCACTCTATAAAAGTAGGGCAGCCAATTATTCACAGACAAAGCTTTTTTTT
TTCTGTGCTGCAGTGCTGTTTTTCGGCTGATCCAGGGTTACTTATTGTGGGTCTGAGAGC
TGAATGATTTCTCCTTGTGTCATGTTGGTGAAGGAGATATGGCCAGGGGAGATGAGCAT   2100
GTTCAAGAGGAAACGTTGCATTTTGGTGGCTTGGGAGAAAGGTAGAACGATATCAGGTCC
ATAGTGTCACTAAGAGATCTGAAGGATGGTTTTACAGAACAGTTGACTTGGCTGGGTGCA
GGCTTGGCTGTAAATGGATGGAAGGATGGACAGATGGGTGGACAGAGATTTCTGTGCAGG
AGATCATCTCCTGAGCTCGGTGCTTGACAGACTGCAGATCCATCCCATAACCTTCTCCAG
CATGAGAGCGCGGGGAGCTTTGGTACTGTTCAGTCTGCTGCTTGTTGCTTCCTGGGTGCA  2400
CAGTGGTGATTTCTTACTCACACAGGGCAAAAACCTGAGCAGCTTCAAAGTGAACAGGT
TGCTCTCATAGGCCATTCAGTTGTCAAGATGAGGTTTTTGGTTTCTTGTTTTGTAAGGTG
GGAAGAAGCACTGAAGGATCAGTTGCGAGGGCAGGGGTTTAGCACTGTTCAGAGAAGTCT
TATTTTAACTCCTCTCATGAACAAAAAGAGATGCAGGTGCAGATTCTGGCAAGCATGCAG
TGAAGGAGAAAGCCCTGAATTTCTGATATATGTGCAATGTTGGGCACCTAACATTCCCCG  2700
CTGAAGCACAGCAGCTCCAGCTCCATGCAGTACTCACAGCTGGTGCAGCCCTCGGCTCCA
GGGTCTGAGCAGTGCTGGGACTCACGAGGTTCCATGTCTTTCACACTGATAATGGTCCAA
                                    CR1
TTTCTGGAATGGGTGCCCATCCTTGGAGGTCCCCAAGGCCAGGCTGGCTGCGTCTCCGAG
                                    CR1
CAGCCCGATCTGGTGGTGAGTAGCCAGCCCATGGCAGGAGTTAGAGCCTGATGGTCTTTA
                                    CR1
```

FIG. 4A

```
AGGTCCCTTCCAACCTAAGCCATCCTACGATTCTAGGAATCATGACTTGTGAGTGTGTAT 3000
                              CR1
TGCAGAGGCAATATTTTAAAGTTATAAATGTTTTCTCCCCTTCCTTGTTTGTCAAAGTTA
       CR1
TCTTGATCGCCTTATCAATGCTTTTGGAGTCTCCAGTCATTTTTCTTACAMCAAAAAGAG
GAGGAAGAATGAAGAGAATCATTTAATTTCTTGATTGAATAGTAGGATTCAGAAAGCTGT
ACGTAATGCCGTCTCTTTGTATCGAGCTGTAAGGTTTCTCATCATTTATCAGCGTGGTAC
ATATCAGCACTTTTCCATCTGATGTGGAAAAAAAATCCTTATCATCTACAGTCTCTGTA 3300
CCTAAACATCGCTCAGACTCTTTACCAAAAAGCTATAGGTTTTAAAACTACATCTGCTG
ATAATTTGCCTTGTTTTAGCTCTTCTTCCATATGCTGCGTTTGTGAGAGGTGCGTGGATG
GGCCTAAACTCTCAGCTGCTGAGCTTGATGGGTGCTTAAGAATGAAGCACTCACTGCTGA
AACTGTTTTCATTTCACAGGAATGTTTTAGTGGCATTGTTTTTATAACTACATATTCCTC
AGATAAATGAAATCCAGAAATAATTATGCAAACTCACTGCATCCGTTGCACAGGTCTTTA 3600
TCTGCTAGCAAAGGAAATAATTTGGGGATGGCAAAAACATTCCTTCAGACATCTATATTT
AAAGGAATATAATCCTGGTACCCACCCACTTCATCCCTCATTATGTTCACACTCAGAGAT
ACTCATTCTCTTGTTGTTATCATTTGATAGCGTTTTCTTTGGTTCTTTGCCACGCTCTGG
GCTATGGCTGCACGCTCTGCACTGATCAGCAAGTAGATGCGAGGGAAGCAGCAGTGAGAG
GGGCTGCCCTCAGCTGGCACCCAGCCGCTCAGCCTAGGAGGGGACCTTGCCTTTCCACCA 3900
GCTGAGGTGCAGCCCTACAAGCTTACACGTGCTGCGAGCAGGTGAGCAAAGGGAGTCTTC
ATGGTGTGTTTCTTGCTGCCCGGAAGCAAAACTTTACTTTCATTCATTCCCCTTGAAGAA
TGAGGAATGTTTGGAAACGGACTGCTTTACGTTCAATTTCTCTCTTCCCTTTAAGGCTCA
GCCAGGGGCCATTGCTGAGGACGGCATCGGGGCCCCTGGACCAAATCTGTGGCACAGAT
GGTTTCACTTACATCAGTGGATGTGGGATCTGCGCCTGTAATGTGTCCTTCTGAAGGAAG 4200
GAACGTGCCTTCCAAGTGCCAGCCCCACAGCCCCCAGCCCCTCCCTGTGCTGCTCCAATT
CATCTCCTCTTCCTCCTTCTCCCTTTGCTGTTTGTGCTCGGGTAGAAATCATGAAGATTT
AGAAGAGAAAACAAAATAACTGGAGTGGAAACCCAGGTGATGCAGTTCATTCAGCTGTCA
TAGGTTTGTCGTTGCTATAGGTCTGTATCAGAGATGCTARCACCACTTTGCTGTCGGTGC
TTAACTCGGGTGAACTCTCCTTCACTCGCATCATTTGCGGGCCTTATTTACATCCCCAGC 4500
ATCCATCACCCTCTGGGAAAATGGGCGCACTGGATCTCTAATGGAAGACTTTCCCTCTTT
CAGAGCCTGTGGGATGTGCAGTGACAAGAAACGTGGAGGGGCTGAGCAGCAGCACTGCCC
CCAGGGAGCAGGAGCGGATGCCATCGGTGGCAGCATCCCAAATGATGTCAGCGGATGCTG
AGCAGGCAGCGGACGAACGGACAGAAGCGATGCGTACACCTTCTGTTGACATGGTATTTG
GCAGCGATTTAACACTCGCTTCCTAGTCCTGCTATTCTCCACAGGCTGCATTCAAATGAA 4800
CGAAGGGAAGGGAGGCAAAAAGATGCAAAATCCGAGACAAGCAGCAGAAATATTTCTTCG
CTACGGAAGCGTGCGCAAACAACCTTCTCCAACAGCACCAGAAGAGCACAGCGTAACCTT
TTTCAAGACCAGAAAAGGAAATTCACAAAGCCTCTGTGGATACCAGCGCGTTCAGCTCTC
CTGATAGCAGATTTCTTGTCAGGTTGCGAATGGGGTATGGTGCCAGGAGGTGCAGGGACC
ATATGATCATATACAGCACAGCAGTCATTGTGCATGTATTAATATATATTGAGTAGCAGT 5100
GTTACTTTGCCAAAGCAATAGTTCAGAGATGAGTCCTGCTGCATACCTCTATCTTAAAAC
TAACTTATAAATAGTAAAACCTTCTCAGTTCAGCCACGTGCTCCTCTCTGTCAGCACCAA
TGGTGCTTCGCCTGCACCCAGCTGCAAGGAATCAGCCCGTGATCTCATTAACACTCAGCT
CTGCAGGATAAATTAGATTGTTCCACTCTCTTTTGTTGTTAATTACGACGGAACAATTGT
TCAGTGCTGATGGTCCTAATTGTCAGCTACAGAAAACGTCTCCATGCAGTTCCTTCTGCG 5400
CCAGCAAACTGTCCAGGCTATAGCACCGTGATGCATGCTACCTCTCACTCCATCCTTCTT
CTCTTTCCCACCAGGGAGAGCTGTGTGTTTCACTCTCAGCCACTCTGAACAATACCAAA
CTGCTACGCACTGCCTCCCTCGGAAAGAGAATCCCCTTGTTGCTTTTTTATTTACAGGAT
CCTTCTTAAAAAGCAGACCATCATTCACTGCAAACCCAGAGCTTCATGCCTCTCCTTCCA
CAACCGAAAACAGCCGGCTTCATTTGTCTTTTTAAATGCTGTTTTCCAGGTGAATTTTG 5700
GCCAGCGTGTTGGCTGAGATCCAGGAGCACGTGTCAGCTTTCTGCTCTCATTGCTCCTGT
TCTGCATTGCCTCTTTCTGGGGTTTCCAAGAGGGGGGAGACTTTGCGCGGGGATGAGAT
AATGCCCCTTTTCTTAGGGTGGCTGCTGGGCAGCAGAGTGGCTCTGGGTCACTGTGGCAC
CAATGGGAGGCACCAGTGGGGGTGTGTTTTGTGCAGGGGGGAAGCATTCACAGAATGGGG
CTGATCCTGAAGCTTGCAGTCCAAGGCTTTGTCTGTGTACCCAGTGAAATCCTTCCTCTG 6000
TTACATAAAGCCCAGATAGGACTCAGAAATGTAGTCATTCCAGCCCCCCTCTTCCTCAGA
TCTGGAGCAGCACTTGTTTGCAGCCAGTCCTCCCCAAAATGCACAGACCTCGCCGAGTGG
AGGGAGATGTAAACAGCGAAGGTTAATTACCTCCTTGTCAAAAACACTTTGTGGTCCATA
```

FIG. 4B

```
GATGTTTCTGTCAATCTTACAAAACAGAACCGAGAGGCAGCGAGCACTGAAGAGCGTGTT
CCCATGCTGAGTTAATGAGACTTGGCAGCTCGCTGTGCAGAGATGATCCCTGTGCTTCAT  6300
GGGAGGCTGTAACCTGTCTCCCCATCGCCTTCACACCGCAGTGCTGTCCTGGACACCTCA
CCCTCCATAAGCTGTAGGATGCAGCTGCCCAGGGATCAAGAGACTTTTCCTAAGGCTCTT
AGGACTCATCTTTGCCGCTCAGTAGCGTGCAGCAATTACTCATCCCAACTATACTGAATG
GGTTTCTGCCAGCTCTGCTTGTTTGTCAATAAGCATTTCTTCATTTTGCCTCTAAGTTTC
TCTCAGCAGCACCGCTCTGGGTGACCTGAGTGGCCACCTGGAACCCGAGGGGCACAGCCA  6600
CCACCTCCCTGTTGCTGCTGCTCCAGGGACTCATGTGCTGCTGGATGGGGGGAAGCATGA
AGTTCCTCACCCAGACACCTGGGTTGCAATGGCTGCAGCGTGCTCTTCTTGGTATGCAGA
TTGTTTCCAGCCATTACTTGTAGAAATGTGCTGTGGAAGCCCTTTGTATCTCTTTCTGTG
GCCCTTCAGCAAAAGCTGTGGGAAAGCTCTGAGGCTGCTTTCTTGGGTCGTGGAGGAATT
GTATGTTCCTTCTTTAACAAAAATTATCCTTAGGAGAGAGCACTGTGCAAGCATTGTGCA  6900
CATAAAACAATTCAGGTTGAAAGGGCTCTCTGGAGGTTTCCAGCCTGACTACTGCTCGAA
GCAAGGCCAGGTTCAAAGATGGCTCAGGATGCTGTGTGCCTTCCTGATTATCTGTGCCAC
CAATGGAGGAGATTCACAGCCACTCTGCTTCCCGTGCCACTCATGGAGAGGAATATTCCC
TTATATTCAGATAGAATGTTATCCTTTAGCTCAGCCTTCCCTATAACCCCATGAGGGAGC
TGCAGATCCCCATACTCTCCCCTTCTCTGGGGTGAAGGCCGTGTCCCCCAGCCCCCCTTC  7200
CCACCCTGTGCCCTAAGCAGCCCGCTGGCCTCTGCTGGATGTGTGCCTATATGTCAATGC
CTGTCCTTGCAGTCCAGCCTGGACATTTAATTCATCACCAGGGTAATGTGGAACTGTGT
CATCTTCCCCTGCAGGGTACAAAGTTCTGCACGGGGTCCTTTCGGTTCAGGAAAACCTTC
ACTGGTGCTACCTGAATCAAGCTCTATTTAATAAGTTCATAAGCACATGGATGTGTTTTC
CTAGAGATACGTTTTAATGGTATCAGTGATTTTTATTTGCTTTGTTGCTTACTTCAAACA  7500
GTGCCTTTGGGCAGGAGGTGAGGGACGGGTCTGCCGTTGGCTCTGCAGTGATTTCTCCAG
GCGTGTGGCTCAGGTCAGATAGTGGTCACTCTGTGGCCAGAAGAAGGACAAAGATGGAAA
TTGCAGATTGAGTCACGTTAAGCAGGCATCTTGGAGTGATTTGAGGCAGTTTCATGAAAG
AGCTACGACCACTTATTGTTGTTTTCCCCTTTTACAACAGAAGTTTTCATCAAAATAACG
TGGCAAAGCCCAGGAATGTTTGGGAAAGTGTAGTTAAATGTTTTGTAATTCATTTGTCG  7800
GAGTGCTACCAGCTAAGAAAAAGTCCTACCTTTGGTATGGTAGTCCTGCAGAGAATACA
ACATCAATATTAGTTTGGAAAAAAACACCACCACCACCAGAAACTGTAATGGAAAATGTA
AACCAAGAAATTCCTTGGGTAAGAGAGAAAGGATGTCGTATACTGGCCAAGTCCTGCCCA
GCTGTCAGCCTGCTGACCCTCTGCAGTTCAGGACCATGAAACGTGGCACTGTAAGACGTG
TCCCCTGCCTTTGCTTGCCCACAGATCTCTGCCCTTGTGCTGACTCCTGCACACAAGAGC  8100
ATTTCCCTGTAGCCAAACAGCGATTAGCCATAAGCTGCACCTGACTTTGAGGATTAAGAG
TTTGCAATTAAGTGGATTGCAGCAGGAGATCAGTGGCAGGGTTGCAGATGAAATCCTTTT
CTAGGGGTAGCTAAGGGCTGAGCAACCTGTCCTACAGCACAAGCCAAACCAGCCAAGGGT
TTTCCTGTGCTGTTCACAGAGGCAGGGCCAGCTGGAGCTGGAGGAGGTTGTGCTGGGACC
CTTCTCCCTGTGCTGAGAATGGAGTGATTTCTGGGTGCTGTTCCTGTGGCTTGCACTGAG  8400
CAGCTCAAGGGAGATCGGTGCTCCTCATGCAGTGCCAAAACTCGTGTTTGATGCAGAAAG
ATGGATGTGCACCTCCCTCCTGCTAATGCAGCCGTGAGCTTATGAAGGCAATGAGCCCTC
AGTGCAGCAGGAGCTGTAGTGCACTCCTGTAGGTGCTAGGGAAAATCTCTGGTTCCCAGG
GATGCATTCATAAGGGCAATATATCTTGAGGCTGCGCCAAATCTTTCTGAAATATTCATG
CGTGTTCCCTTAATTTATAGAAACAAACACAGCAGAATAATTATTCCAATGCCTCCCCTC  8700
GAAGGAAACCCATATTTCCATGTAGAAATGTAACCTATATACACAGCCATGCTGCATC
CTTCAGAACGTGCCAGTGCTCATCTCCCATGGCAAAATACTACAGGTATTCTCACTATGT
TGGACCTGTGAAAGGAACCATGGTAAGAAACTTCGGTTAAAGGTATGGCTGCAAAACTAC
TCATACCAAAACAGCAGAGCTCCAGACCTCCTCTTAGGAAAGAGCCACTTGGAGAGGGAT
GGTGTGAAGGCTGGAGGTGAGAGACAGAGCCTGTCCCAGTTTTCCTGTCTCTATTTTCTG  9000
AAACGTTTGCAGGAGGAAAGGACAACTGTACTTTCAGGCATAGCTGGTGCCCTCACGTAA
ATAAGTTCCCCGAACTTCTGTGTCATTTGTTCTTAAGATGCTTTGGCAGAACACTTTGAG
TCAATTCGCTTAACTGTGACTAGGTCTGTAAATAAGTGCTCCCTGCTGATAAGGTTCAAG
TGACATTTTTAGTGGTATTTGACAGCATTTACCTTGCTTTCAAGTCTTCTACCAAGCTCT
TCTATACTTAAGCAGTGAAACCGCCAAGAAACCCTTCCTTTTATCAAGCTAGTGCTAAAT  9300
ACCATTAACTTCATAGGTTAGATACGGTGCTGCCAGCTTCACCTGGCAGTGGTTGGTCAG
TTCTGCTGGTGACAAAGCCTCCCTGGCCTGTGCTTTTACCTAGAGGTGAATATCCAAGAA
TGCAGAACTGCATGGAAAGCAGAGCTGCAGGCACGATGGTGCTGAGCCTTAGCTGCTTCC
TGCTGGGAGATGTGGATGCAGAGACGAATGAAGGACCTGTCCCTTACTCCCCTCAGCATT
```

FIG. 4C

```
CTGTGCTATTTAGGGTTCTACCAGAGTCCTTAAGAGGTTTTTTTTTTTTGGTCCAAAA   9600
GTCTGTTTGTTTGGTTTTGACCACTGAGAGCATGTGACACTTGTCTCAAGCTATTAACCA
AGTGTCCAGCCAAAATCAATTGCCTGGGAGACGCAGACCATTACCTGGAGGTCAGGACCT
CAATAAATATTACCAGCCTCATTGTGCCGCTGACAGATTCAGCTGGCTGCTCCGTGTTCC
AGTCCAACAGTTCGGACGCCACGTTTGTATATATTTGCAGGCAGCCTCGGGGGGACCATC
TCAGGAGCAGAGCACCGGCAGCCGCCTGCAGAGCCGGGCAGTACCTCACCATGGCCATGG  9900
```
OVOMUCOID 5' UNTRANSLATED REGION

```
CAGGTGTCTTCGTGCTGTTCTCTTTCGTGCTTTGTGGCTTCCTCCCAGGTGAGTAACTCC
```
OVOMUCOID CODING REGION

```
CAGAGTGCTGCAGAAGCTT                                          9979
```

FIG. 4D

```
AAGCTTTGTGCTTTCTGCCTGAATAAAAGAAACCTGAACTCTGTTCACCCAGTCCCTGTC  60
AGGCAATTACTGACAGAGCACCTATGGTCTGTGTTTGGCCAGAACATAGGCTAAGGAAGA
TACCTCCTGTTTATAAAGCACGCCTTTGGCATCTGGCAAGTAATTAGTGATGGCGCATGA
GAGCTCTGACTAGGGCAGGGTGTGGGACAGGCTGGCTCTAATTGTGCCCTGTTTATCTTG
TTGATGCACACGGCTGGTTTCTTTCACCCACAGCTGTCTCTCTAGACAACATACCTTTAT  300
GGAGAGGAACGTGTCTTTTCCAATCTTGGGTTTTCATTCAGAATTGGAGTGAACTGGTCT
CCATCAGATAGCATTGGCTGCGGTGATTTATTCTTTTACACTTCCTAGTTAAGCAGGATA
ACTCTCTGGCTCTGCTGTGTCTAGGCAATTTAAATGATTTATAAAGCATAGCTGTTTTAA
GGAAATCTTTTTTAAACATTTGACTTGCCAATGTGTGGTCCTAAAGGCAGAAGGACTGT
TCCAGAGTGTCAGGCAGAGACCTACCCTGGATTTCGTTGTTCAGCTACCCATTCAGTGTG  600
GCTTTTGGCAAGGAATTCTCTGGACCTGACTTCCCTACCTGCAGAGCTGGGATAAGCTAT
CAAACCATCTCCTCCACACACTGTGAGGGTGGGAAAAAACCCAAACCCTTAAAAGTGCT
GTATAAAGGCGCCTTAAGGCTCAGTATAGCATGTGTGCTGCTGATGCCCCAGACCTGTTT
GCGGGTCCTGAAGGTCATAGGAGAACTGCTCAGAAGAGACAGAAATGCTTAAGAAGGTTT
TACTACAAAAGTCTTGTGATGTTAACACATAATATCACATTGTGCAGAAGGTACAAATGC  900
CCCCTCCTATCCCTGCACACCTGGAAGCTCAAGGTATGGAAGGGTTTGTTGTCTGCAGCC
TCTTCGCTGCCCTCTGCTTTTTAAGATCCTGGGTAGTGTGCTCAGTGTGTGCCCTCAGCA
GTTTGGGAAACGGACATCTTCATGCAAAATTAAGCAAGGAAGTGTTGCTTTTATACTCAG
AGTAGAATCTAAGTTCTTCAGGCAGGCTCTTGTGTGCCGCCTCTATTAGAAATAAAACTC
CCCCGGATCAGAAGATGAATGTGCTCAGCTAAGAACACAGATTTATTTGCTTTACAATGC  1200
GTGCTATGGTTTAAGAAAAACACATCAGGCAAACAATTTATGGTTTGCCACTGAGTTGTG
CCTGAAGGAAACACAACTGTTAGAGATGTAATTGATTGGGCGGTGACGCTGTGTGGATTC
ATGGGAGATGCATCTTGGTCAGCATGTCTGTGTGAAACCACATTTCTGGTGCTGCTGCAG
GACGAGTGCCGGGAGTTCCGGGATCTGTTCAAGAATGGGAAGCTTTCCTGCACGAGGGAG
AATGATCCCGTCCGGGATTCCTCGGGGAAGCAGCACAGCAATAAGTGCATCATGTGTGCG  1500
GAGAAGTTGTGAGTAGAGGAAGCCAATGTTTGTTATCGAGAGTGGCAATGGGGCCGGGT
GGGCTCCTACAGCAATGTTCTCCTCACTTTCTCATCCTTCTCTTTCAGCAAAAGGGAGAA
TGAGCAGAAGGCGACCTCAACCAGAGGGAAACAAAAGGTGAGGTTAAAGTATTGGGTTCA
TATACAAGTCTATAGGATTCTTACCCAATATTACCACACTTGATTTCTTTGTCACTCTGG
GGATCCATGTGGCTTTTCCTGCTTGTATCTCGTTGATGCTCTTTCATGCCCTGAGAGAAT  1800
AGTTTGTCTGAACGCTGCAGTCTATCCCACTGACCGCAGTGACATGGGAGCAAACCCCAT
CGCAATAAGAAGCTGAGCAGAACTGCCCTGACATCTGGCACAAGGGCAAGAAGGCACTGC
TGCTGAGAGCGCTAATGAGGTTGAAAAGAAAATCTGGGTGAGAAGCTTTAAATGTGAGCT
CTGAGATGCTCAAAAGTTCATTATGTCGTGGGAGGAGAGTTCAGCCCTGTGCTGTCCCTG
GGGTGGCTCGGTTTCAGCTTTCCCTGATTGGAAACCTCACTCTCATGATGCAGCTGCTGT  2100
GCCCTTGTGCACCGATACTTCTCTGGTGAGAGCAATTCAGCAAGGGGAAGGAAAAGAAG
CACTAAGTAAATCTTGCCATTTCTGTCTTGCGAGGAACTGGTACGGTCCCCTTAAGCCTC
ATTCTTGGGGATAATCCTGTTTCAGTGCTTTTCCTAATGACAGTGGCACAAAAAAAATGG
AAGCGTTAATGAAACTTGCTGATGGCAAAGCTGGGAGGGAGGATCAGCAGATCACTCAGG
ACTAATTGGATAGCACTGAGGCCTGGAGTAATAGAAACAAGATAAAATGTAATAACAGAG  2400
AGTGCAAGATCACACAGGCAGTGATTAACGAGAATTCCTGCTCATCAATTAGAAATGACA
AAGGATAAGAAAGCTCTGCATTTATTAGTGGGTCACGGATGCGGCAGGCCTGAGAAGGAG
GCAAATGCACATCTCAGCAAGGTCTGTGCAGCAGAGGTCGGGCTGGCAGCAAATCTCCAG
AAATACTGCTTTGAAGAGAGGGTTTGAGAGACGCTGTTAGGGAGAAGCAGCTCTGCCA
CAGCAGGTCTGGGGTTCACCTGGGGTTTGGCTCATTGCCTCCCTGTGTCCCTCCTCCACG  2700
CTGCCAGTGCTGCACTGGGAAGGTGTGGGTAAGAAGCAATGGCTAAGGGATCTGGTTATA
CACCTCCTGTATCTGCTATTTGGGATTGGCTACTGCAGGGCCTCAGGTCCCTGACTTAAA
AGTGGGGACTTCGAAGCATGTTTGCATTGTGCTGTCGTGCCTTAGATGTTGCTGCTGGGT
CCTCAAAGTCCTGTTGGTTGTGGGTGGGGGGACTTCTTGCTTCCTATGTGAAGTTTTC
TGAGCTGCAACTTCAGCAACAGCTGTAAGAGTGCATTAAGGGCAGTGGGAGAAGTGGGAG  3000
GGACCCCATTACCTCATCGGGTATCGCTGGCATGCTTTGGATAGCCCCACGTGGAGCGTG
ACAATTAGAGCACGGCAGAGAGCTCCCAACACGTGCCATGCAGGCAGAGGCACCCGCCGC
TCTTCTGACTCACTCTGTTTGTAGCCATGAGGCTGTGCCACGTGCCCTCTTCTCTCTCTC
ACACCTGGGCTCTCCTGGGGCGCGTTTGGGAAGCCTCTGGAGGATCGGAGGGATGTGGCA
```

FIG. 14A

```
GGGTGCCCTGACTGCTGCTCCTTCCGCAGGATGACTGCAGTGAGTACCGCTCCCAGTTTG 3300
AGGCTGGCGGACGCCTGTCCTGCACGCGGGAGAACGACCCCGTCAGGGATTCCTCTGGCA
AGCAGCACACCAACAAGTGCCTCATGTGTGCCGAGAAGCTGTGAGTACAGTTCCTGGCAA
CAGCAAAGAGGGAAACCTCACATTGCGAAACTGCAGCTTCTGCCTGTGTGGCTGCGCCTG
GGGGAGTCCCGAGTCCCAGCGGCCCCCCAGGAGCTGCTCCTGCTGTAGGGCTGTGGCTAC
TGCCCCTCTTCCCACCTCCCCCCTAACCCCTCAGGGAGCAGAGGAGAAGCAGGGTTGATA 3600
GAGAGCAGCCCTTTCCTTGGGGCAGCTCCCAAGGAAAGTTTCCCACGCGTGTACTTTGCC
TTCCAGATGCTCTCTACTCCCATAGAGCATATGCAGAAGCAGCCCTGATATGAAAGCA
GCCACCTGGAGCCGGGATGTAGCATACAGTGGGAATGGTGAGGAGAAGGGAGAAGGCTTA
GGGGTGGGAATTAGGTGCAGGGCCACCAGGGATGGGGAGGCTGGTGCCTAATGACATGAT
GCTGGCTTGCAGGGCAGCCCCAGGTCCTGGCAGCGTTCGCACTGCCATAGTGCTCCTTTC 3900
TTTCTCCTCTCCCTTTTTTCCAGCAAAAAGAAGCTCAAAGAGGAGGTCAGTCTGGTGGA
ACTGCCCAGCGCAACAAGCAGTCCACTGCAGAGTGTGCAAACCAGGTGAGACTGAGCTCA
GAGCCTCACCAGGCTTGGGAAAAGGGGTTGGTGGATCTGGGGACCCCGATGGTCAAGGGC
TGCCTGTGGTCCTGGTGTTTGGGGTGCAGGAGCCTGCTGGTGATGGCAGAGAGGCAGGTT
GCATTGCAAGCCCTGCTAGTTCATGGGATGGGTTTGTGTATGAGCGTGCATAGTGGGCAG 4200
TTCTGGACTCCTCTATGGGGCACGCATCAGAGCTATTTCTTCAGAAAGAGCCCCATGGTT
CCTAGGGTCCAGGGGGATGAGAGGGAAGGACAGGAGCTGCTTTAATCTCACTGCTTTACT
GCTTGGTTGTCAAACACGATCCTGCCCCTTTTCCAGAAGAGCTGCAGTGGCTCAGGGTTA
CAGCGGGGTGTAAATGAGAGACGGCCGTTCTCCACAAACAGAGGGTGAGTACAGCAGCAC
TGGGATCCCAGCCTGGCCCCACAAGTCCTGGGGTCTTGACACTGAGAAGAAACACATAAA 4500
ATAGGGCATATACAACCCTTTCTCCTTTCCAAAGACATTCTTGCTTCCCCTGCACACGAA
GCACTGGTGACTGCTACACTCAAAATCCCTCCCCAGCCTTGCCCCTGAATCCTGCCTCC
TGGCAGGCACACACTTGTCCTGCTGCCTGGTCCAGCGCATCCTCATCTGCTGACCTGAGG
CAGTGCTGTGTGTGCACCATGTGCTGTCTGGGCACTGAGCGACTCCTCTGGGTTTTTAGG
GCTGCCAGGCTCTGGCAGGGTGCAGATGCTGTGTTATCTAAGCCTTGAGGAACTCTCTTA 4800
GTCTTCCTGTTTTTGTTGGTGAGGCCCATTCATCTGCCCCCAGTCAGCACTGCCAGCAGA
CAAACAGTGCACAGCTCTCCATGGCAGCAATGGCTGTAGCATATGTAGGGCCAGGTTTC
TGGGATCATCTCTGTGACGGACATCTCTTGCTGACCGCCCATAAGGACTCAAAAGTCCCG
TTGCAGGGAGTGCCTCCATCCCATGGCAAGCCAAGTGCCCTGTTGAAAAAACAAGGTGCA
GAATAATGGCAATGGACCTTAGTGCAGTTTAATTCCACCCTGGGGTGATGATGTGGCTGA 5100
GTGGGTCTGCATACCCTTGGCTGTGCCATGAGCTCTGTGCTTTCTCTCCCTGCCAGCCCA
CAAGGAGACTTGGCTCAGGACTGCAGCCCGGCACCTGGCCGCCAGGGACAGAGCGGAGGC
ACCAACACCTACCAGCCGGTATGCCCAGCTCATGTGGGTCAGGCACAGCCTTTCCCAGCA
GCTGCCCCAGTTTCCATTGTCAACCTAAAGCCTCACAATGGGACCTGTATCCTTGGAGGG
GTTTAAATGGGTGGTAGAGTCCGTACCCTGATGCTGTCCCCTGGCCTCAAAGAGGAGTGA 5400
GGCTGCACACGTCCAAACGGGAGTCACTGAAGCCAGTGCTGCTGCTGGTGTTGGCTCACT
GTAGAAGTATGTCAGGTATGAGAGAGCATCCTCCAGGAGGTGATGGTGGTGTCCCTTCCT
GCATGCTGAGATGTTGGGTTGAAGACTGTGGCCAGAGCAGGGTGCTGGGGCTGAGCGGGG
GATAAGGACAAGGCTGATAAGAGGAGGGAGAGGGAGTAGTGGGGAGGACACGGTGAGC
AATAGATAACGACTGTTTGTGGAATCATGTGGGAGGGAGAAGAGGGTGTATGCTCTCTCC 5700
ATCTCCACAAAAAGAAAATTTGTTATTTTCAACCAAGCTAAAGCAGAAATTATGAAACTA
ATAGGAGAAATAAGTTACTATAAAAAGGATGACTAACCTGTGGATCTTGCTGTCACGGG
GTGTTGCCAAGAGCTACAGTGATTAAAAAAAATGACTTGCCACTTATAGTCCATACAGCA
ATTAGGTAACATTTTGGAAGGGATAGGAAATGCCTTTCTGTGGGCTGGAGGGACCTGA
GTGCAGACTGCCTTAACTCTCTCTGAAGTCTCTGTCACTGACTGCCCTTAGAAAATGAT 6000
ATTAGAATAGAAAACCAGGGAGGCGGTTCAGGTATGGCAGTTTTAATGCATTCCAGAGG
AAGCATTAGGCATAATAATGCCAGTCTGCTTCAGGGCTTAGTGGTATTTCCTGGTAGCTC
CGGTGAAGGAGTGGATGCTGATCAGCCTGACTGACGAGGGTGATTCAGAGAGCAGATCT
GTGTCTCTCCTCGCTGCAGGGCCACCCGTGGGCTCTGTCCCAGGGAGATGCTGTCCTGAA
GGAGAGGTGGCAGTCACTGTGAGGACTGTGGGGACTGTTGGTGTGGCGGCGGTTGCACA 6300
CGCGTGGGTCACACCGTGGGCAGTGGTGTCTGGTGTGTGGGAAGGCATCTGGCAGGGAAC
TGCAAAGGTCAGCGCTGTCTGTCTTTGTGTCATCGTTAATTACCCAGGTGAGGGAGGAAG
CAGCACATTAATGAAATTAGCAAGTGATGTTTAAACAGAGGGTGTTACTGCAGCAACCTG
```

FIG. 14B

```
TGCCACTGAACCCCCTGCATTGCCCAGCTGGGAAACCTTTCTTCTCCATGGTGCTTTCAA
CCCCATAGTGCTGCTGACCCCAGCAAAGCAATGAGCCATTGCTTAGTGCTGAATGGGGTT      6600
TTTTTTCTCCAAGTGGGACAGGAGGTGAGATGTCCTTCCTGCAGCTCTTCTCCAATTGCA
CCATTTGCAGTCATTGCAACATTTTTTATAGGACCTGGAGAAGGGGATGGGAACAGAGAA
TTCACTCCTTTTGTCTCTGCATCTTTTTTTTTTGGCCTTTGGTGCAGAGGTGGGCAGTG
AGGCTGAGGAAGAGAGGGGGCTGTAGGATCTCTGACCTCTGCTGTCTGAAACTTGCCATG
ATTCTGCAGGCACCTGTGCCAGAATGCTCATGGGCTGATAATCTAATCATGAGGAGTCTT      6900
GTTCCTCCTGCTCCGAGCTCTTTCTAGCTGTGCCACGTCTGCTTTGTAGGAAATTCGATG
CCTAGATGCTCCTGCTGTTATGCTGGAGAATAAAACGAGAGGGCACGCTTAATTAGTCAG
AGCTTTTCATACATGTTTGCATCTCTTCATTCCGTGGGTGTCAAGTTGTGCTGTGTGTCG
GGCTGCCCTTGGGCAGCTGGACTCAATTGTCAAGGTTTTCCCTTTGTTTCTGCCAAGTGG
CTTGCAGAAGCAACAGGTGTGAAAGCTCTGATAAAGGACAAAGGACAGGTAGCAGAAGTT      7200
TATTGTATTCTCGTGGATTTGCAGGGAGAAGTAAAAGTGCCCTGGACTGAGATGTCAGGG
TGGATCAGATGAGTGTATCCATGCCTGGCAATGGGGTCAGGGCAGCTTTGTCCCCACATC
GTGGCTGGTTGGCCCAATAGGAGGCGTTACCTCTTTGCTGAAGGTGTGATGGAGCTCAGG
GCAACGCCTGGTTTGTGAGTGCTTTGAGCGGTGCGCAGGAGGGTCTTGCAAGAGAACCAG
CACCAAATGTGATTTCTTTCTCTCTTCAGCTGGACTGTGATCGAATTCTGCACGGGGTAA      7500
AGGGTGGAAGGATTTTCTGCAGCGAATCCTCACAACCCGTCTGTGGCACTGATGGGAAAA
CATACAGAAATGAATGTGACTTGTGTTCAGCTGCCATGTGAGTAGGCGGAGAGATTTCAG
TAATACAGGGCCATCCACCATTCCCGAGTGTCTTTTGCAGCACAGTGTTTGTTTTGATAT
ACCATGACTCACTATCAAGTGTGTCCTTGGTGCCTCGCTGTTAAGCAAACATAGATCAAA
TGTCTGAGATTAATATGATGACAGCTAATTAAGATACACAACTTTCCAGAGTCCCTTATT      7800
CCCTTTCTGCTCAATCATAGGATTGTTTGGGGAGTAATAAATGCCATCAAATTGGAAGTA
GCATCAAAGGTTTAAGGAGCCCACAGAGGACCACCGTGACGATGTCAGGGAGCTGTGGCA
CTGGAAGTGAATAAGCAATGTCTTGTTCTCCCTTTGCAGGAGAGCATCAGTTTACATCAC
GGTAAACTACCGAGGTGAATGCCGAAGACTGTCCCTGAAATGGTAAGTGCCTCCCTGCT
GTGGCATCCCATTTCTTGTTCTGGGTGTGTGCTGGAGACCCAGCCTGGATCCCGTATCTG      8100
TGGTGGGATCATCAGAGCCCTGTTAGCAGGGTGCTTGTGGTTCACATGCGTAAATACACT
TCAGGCTTGGATTTAAGGCATTTTGAGGCATAATCTCCACGTTTTTTCCAGGCTGTGTGG
TAGGGGAGTGACATGTCTGGGAAAACATGTGGCTTTCCTCCTGGGATTTTGGTGAGGCCA
AGAAAAGATTGCAATCGCACAAACCATAAGGGCCTAATTTCCCAAATGATATCCAGGCAG
TTGGTTGGGAAGGAAATATATTCCCTAAGTGGTATCCTTTTGGGAAAGGTCTTGAATCTT      8400
GTGTGATTGCCTTGTAGTAGATGAGTCAAAGATTTGTTAGTGGTGCTTTGTCTTCCCGCT
CGTGGCAGCTCAGCGGCATTCAGAGCTTTGGTTTGGAGCCAGGGTGTCCCAGTTTGTGTG
TCTTGAGTGTATGGGACTGACCTTAGTGTTGGCATGGACTGTTGGAAAGCTGAGTATTCA
TTTCCCCAGGGAAACACCGACATCTATCCCCATTCCAAACTTGGAATGAATCAAAATATC
AAATCAGCCAAATGGAGAAGTTGTGCAAGTTTTTTTGCAATGAGAGAGATGGCTTCTGA      8700
ATATGAATTTGCTGACAGTTTGTAGGTAAACAGTATTGCCCGTTGAAAGCTTTAGAGC
AAAATTACCATCATAGGGCTTTTACTCTCCTCTGCTTATTGACAGGATGCCCACCCATCC
CCACAACATTAGAAATGAGGCATCCCCATTCCTCTTCCTCTCTTCTGTGAAGTACCAGAG
TGCTCTCAACGCTGTTTAAAGCTGAAGAAAAATGCAGAGAAAGAGTTTTGCTTGTGATC
GTGCTGGAGGTCTTTGTGTCTCGCCCTTTGGTGCGATGGAGCCATTGCTGGTTTGTGTAT      9000
GCTGGGAGTGGAGGCACTATGCATACCTGCTGGTGGCTGTGCTAATGATGCTGGAGACAG
ACAAGGTTGGGTGTACCACGGCAACTGAAAACCAGAGAGGACTCCCTCAGAGTTGTGCCT
GGCTGGGATTCCTCACCATTTTGTGTTTTACCAAGACGTTTTACCAGCTCTCCAGTCTTT
GCAGTTAGAGGAATATGCCATACACTAAAAGTCAGACAATTTGTAGCTATTCCAAGGAGA
GCTGGAAGCAATTAAAGGGAAAGTGATAAGGTTTTTCCACTGGGGAAAATCCCCCACAAA      9300
AAACACCCCTCCAAACAAAGACTTATTATTTCGTTCTTTATGTATATTGTGTCACCTGAA
GAATCAGATTGGAAATTTATGGAAGCCCATTTCCTTAGCAAACCCCTTGTGTCCATCAAA
GACTTCCCTTTTTTTTCTCAGTTGGAAGCTTATGAACAATGTACTGACCAGTGTTATTTT
ATGCCTCTGAAATTCATGCTAACATTCAGCTTAATGCATCCTTCTGAAGGCCCAGGCACT
CGCTGTGTGAAGGAGATCACAGTGCCTTTGGCGTCAGAAATGATTTCAGGCTGTTGCAAT      9600
ACGCAGCACGAAGATGCAAAGGCCCAAAGACTTGAGCCTTGGAAAAAGATAGGAGATTGC
```

FIG. 14C

```
TGCCCGAAAATGTAGTTTGTCCTTGAGTTGTGTTTTGAAATTAGCCACGGTAATGCTGTG
TTGCCTGCCAAAATGTGTGTCCAAGCTCAGAGCCTGCAGCCATTCCTGCTAGCAAAGCCC
CTCCTGGATTTCCAGCAGTTTGTGGCAGTCCTTCCCTAGCAGTGGCTGGATTGCCATCAG
GGAGGGATGGCTGTAGGAAGGGACAGGAGAAATGTGGTTGGAGAGAGATCTGACATTAAA  9900
GGGTGCATCCGGACAGCCTGCACTGATGTGGTGGAAAACCTTCCTGCAGAGAGAGCCCTG
GGGCTGGCTGGCAGCTGGGCCCTGCTGCCTGTGTGAGCTCTGTGCCACAACCAGCCTCC
TCTGATCCTGTTCTGCTTTACTGCAGATGAATGTAGCTGAGTCTAGGGTTTAGATTTCTA
TGTTTATTTTTAACAAGGCAGCTGGCCTCTGCGTCCTCCATGCTGTGACATACAGCTGTA
TTAATGGTGGGTCTTTCCAGAATGTTTCACTTTCAATGCTGTATTTTTTTTATTTTGCA  10200
GTTTCTCTTTTTGTTCAGATGCTTTTCACACATCTCCCATGTGACAGATACCAGTCTGT
CCATGTTAGTTGACAGGTCAGGCAAAAAAAAAAAGGGATATCCAGTTTCTCCTTTTTAA
TCTGTTTTCTAAAGAACAAAGAACTCCCAGCTTTCTAATGGGCAAGGCCATTTTCTTACA
GTGCTCTTTTTGTCATACCTTTCTTAAGAATGTAGTAGAAGGGAAAAGAAACAAACAAAA
AACCCAGGACCTTTTCCAGCTTGATATTGGTTTTGGAAAGCACACAGATCCAGGCTGAAA  10500
TCTGTTTGTTTTCTGAGTCTGGCAGTGACCCATCCACTGCCCCATCCCACCTGGTTCCTG
TGGCCACTGAGCTGCCCAAAGGGGCTGTCATGTAGCCCCTAATGCTCTGCCAGCGTAACA
GCAGTGGATGTACTTGTGGATCCACTTATATTTTGCTCTTTCTTTCCAGAAATAATGGAG
TTCAGACTGCCAGCAAATACCAGGGATCAGCTGTGACCAAAGGTACAGTGGTGCGGTGAT
TTGCTCCCTCTTGGACAACTTGTCCGCATTTCACAAGGGTTTGGGTGTCAGACCTTGCCT  10800
GGGCAGGCTGCTGGGTATGTCTGGGGCAAAGGGCTCTGCAACACACCCTTCCCTATTGCC
ACAGCACAAGAATGAGGCGTGTGTCTTTTGCAGAAGTAGCAAGGTGATGGGAAGCCCCTG
CCAAGGGGGCTGAGCCCTTTGGGGTGTGCAAACTTCATGAGGACCTCCTCATCTCTCAGG
GGTGGGCCTTGCCCGTTCCTTTTCCCTCAGATATCCCTGCAGAGGGGGAAGGATGCTGGC
AGAGCAGAGTACTGCAGTCCCTCCTCACAAGGAGGTGGAGGTGGCCCAAAGCAACCTGGC  11100
TTTGAGCTTTCCTTGTGGTTCTTCTGTGTCCCTTGCCTTTTGGAGCCATAGTAATAAACC
CGTCTGCCCCCTGTTTCTCTAGGACAAGTAAAGGAAGATCTGATGTCAGGCACCAGGGAA
GCTGCTGAGTTCCCCAGTGCTGTTGGATCCACCTTCATCTCCTTCTGCAGCCAACGGGCC
TGTCCTTGCTCAGGTGGAGGGTGAAGGGCTGTGGGGACCCAGTGGTGGCTTCCCACGTTG
GCCCCACGCATGTTGTTGTAGTCGCTGCTCGGCTCGGGCTCTGCCGCCTCGCTGTGTCTT  11400
AGCATGTTCTACAATAAAGATAACTCCACAGCGTCCTGTCGCTTTTCTTCACTGAGCCT
CACGGGAGGGACGTGTGAGTCCCCGCTCCGGCTGCTCGCCACGCGTCCCTTGAGCTCTAA
AGCACCAAACCCAAGCGGAGATGTCAGACGCAGAGAAGAAGAACGTGGTCTGGGTTCTGT
TAGCAGGGACCAGCAGTTGGGTTCTCTGACTCGCTGTGTAGGGCTTTGGGTGTATCTCTT
TGTCTCCCTTCAGCCCTTTTCTCTTGCCTGTAAAACGGACATTAAAGGATGCTTACCTA  11700
CCTCAGAGGGTTGTTTGGAGATTTTAATTGGTTTACGTTAGAGAGCCCACGGGTGGAATT
CTGTTCCTATGTGCCAATGCTGGTGTGCAGGAGGTTTAACTGTTGCAGTCATGGCCTCTT
CCAGCCAACACCCGATGGGCCGTATGTATTTCCTGTTCTTTCGTTTATGGCTGTTACTTA
AAGCAAATATGTTCTTATTTGTATAAACTTTATTGCAGGACATTTCCAGAAGACCTTGAG
TGAACGTACAGTGTTTGAGTCCACTTTAGCTGTGACCTGATCTGCAAATACACTCTGCTG  12000
TAGATAAGGCTGGAGTAACTTTCAGATTTGGCAGGGTTTCGCTCAATGCCAATTAATTT
GGCTCCCTCCACAGATATTGATTTTTTTTTCTTTTCAATTAAGTTATCGAGATCTTTT
TTTCTTAATGCAGCTAATGAAAATCGATTTTACTCTCATAAAGTACTTCCGCATGTGTC
ACATTGATCTGTCTATGGCTTGATTATCGGCAGGCTTTGACATGAGGTTAATATTTTGTG
TGCTGGTTTTTTTCACCGTGTGCAAACACTGTGGTTTAGAAATATGTTACCGCTGCTTA  12300
TTTCTACGTGGAAAATCCCACGGCGTGGTTATGCATGGCAGAAGTCACCAGTTTGATCCA
ATTTAGCTGTTTCTAGGGATGCAAGATTCCTCTGCCTTTGAGCGGTGAATCCTCGGGTG
TTATTTATACATTCTGAGAAGGATGAACAGAAGACGGTAAAACGTTTGCTAATGATGTC
TGCTGGCTGATTCCGGCTAAAATCGTGTGCAGGGACCTCGACGTGATTTTTATAAAGGCA
GCTCACAATTTGAGGCTTAAAGTAAGTTCTTGCAAATGAAAATGGGCGCACTTGAGCGCG  12600
CTATTATAACTTGTAGTGATTTCAAGCACTTAGATTTTGAAATAATCGCCCATAAAAACC
TGCATTAATTGTGCTCCAAAACCAATGAGCTGATGAGGAGGGTGCCCTGGTAGCCTCTTT
TGCTGGATTTGAGCACCTTCTGAATTTCCTGCCACCAGCAGAAATTAGCCACAGAAAT
```

FIG. 14D

```
CATAGCTGCTATAAGGGTTTATTAATCAGATTACGAAACTGCTAAGAAGGCACACAACAG
TGACTTGCTGAAGCTGCCTGTGCTGCTGTTAGCGAGCCTCCCGTAGGTAGCAATGCTAAC  12900
TCCTTCCTTTTAGCAGTTTACCCACTGCTTCCTTCCATCACTCCTTCCTTTTGTAGGGCC
TACTTTTGCAGTTTGATCCAGTGGCTTGCAGGCAATATCTGTCCCCAGCGGTGCTCTATG
CAGCTGACCTCCAGGTAGGGCTCCATGTGAGCGATGCAATGTGTTATTTCCATGGGGTTC
CTAAGAAGGAGGAAGCAAAAAGCTCAGGAGGTGCTCCAAATATATTATCCTGTCCTCTGT
TTTGCTCTTTGTGGTGCCCTTTAACACTGTAAAGAGACCATAGGAGTCCTCTATGAACCT  13200
GGAAAGGTACCAGCACTATGGGAGGTCTTCAGTTTGCTGTAAATTATGCTTTATTAGAGG
TATTTCTTCTGCCAAGACCCACTGACCCCATGCGGCTCACAGTGTTTTCTAAGGCTTTGC
AGGACTGGTGTTACGAATTGGCACCCTCCAGGCCTCTCACAAATCTCCTGCTTCTCACAG
CGTTTCTTCAAGTTCTCCCAAGCACAGCTGAGTTTTGAGCTCAACTGCTCCCTGCAGGGG
CCTTGAGCCTCCTGCCTTTTGCATAAAAGGTGTCAGGTACTTATGCAATCCTTAGAGGC  13500
ATGCAAATGCTGCTCTGGTTATATACTGAGGACTGTTGATTCTGGCAGAACCCTTTGCAG
ACCTTGTACTCCCTTGCTATTTCCCAATCCCTGCAGCCTAGCAGCTCTGCCTAACAACTG
CCATAGCCAACACAGCAGCAGGCTGTGCATGGTGCAAGGTGATGTGGAAAGGGATGATTG
TATGAAAGCGTGATGCTGTGGTACTGCCTCTGCAGGAGACTCGCACTATTTGTGTAAGAG
GACCTTATTTGTCTGCTGCAGAGCTGTTTCAAGGCTGTCCATACACCCTGTGATGCTGA  13800
GCCCCTCCAAGCAATGCACTGGGAAAAGGAGGCTGGGGGAGACCTTATTGCTCTCCTCC
AATATTTGAAAGGTGCTTACAGCGAGAGCAGGGTTGGTCTCTTCTCACTGGTGACAGGAT
GAGGGGAAATGGCCTCAAGTTGCACCAGGGTATGTTTAGATTGGATATCAGGAAACACTT
ATTTACTAAAAGGTTGTTAAGCACTGGAATCAGCTCCCCAGGGAGGTGGTTGAGTCACCA
TCCCTGGATGTGTTTAAAAACTGTTTGGATATGGTGCTCAGGGACATGATTTAGCGGAGG  14100
GTTGTTAGTTAGGGTAGTGTGGTTAGGTTGTGGTTCACTCGATGGTCTTTAAGGTCTTTT
CCAACCTGAGCAATTCTATGATATGGATCCCTGGGGCTTTCAGTCTTATCTCCCTGGATT
ATCACAGGTTCAGCTCTATGGCCCATTTGATTTATACCGGGGTCTGATGAACAGGTTTTT
CTCTTGGCTCTTCAGGGATCCTATTTAGCACTTTTTGGTACATTCCCCTGCCCTACAAGT
CTCCCTGATACACAGAGCTCTTATCCAAGACTTGGGACCTTCCCTACTCCAGCCCTCTGC  14400
AGGAGGTTTCTTGCTAACCAGTCCTCCAACCAGGACTGCAGTACACGACAAAGAGCTGGA
AGAGGTCTGCAATACTTCCCCAGCATGAAGGTATGAGCACTCCTTTTGAGTAGGTTACTG
AAAGTAGTAAGATGTCAATACAACCAACTGCAAGATACAAAACCGCATGAAAATTCAGTT
TACTTGATGCTGAAGGGCTGAAAAGAAATGCTGTGGTGTTAGCACAGATGCACTGCTGG
CAAAGTGAAAATGAGCAAAGAGGATGAGATGGATGGACAGCTGATGGAAAAACTCTTCCT  14700
AATTGCTCCACAGAGCAGCTTGCTCGCCTGCAGGGCTGCAGCATGGAGCTGCTTGTGCAT
AATGCAGACACCCCAAGACCAGTGCTGTTTGTCTTAGCCAAGACACAGTTGCAGCTGCAG
CAATTTTTTCTAGATGTCAGTTCCTTCCCTATGTTGCTGACAGGTGTTTGCTGTTCTGTC
CCTTTAATCTGTATCCTACAGCAAACATTCCTTGAATTTAATAACTTAGCTGGAAGACAA
TTGCTGTGATCTTGATAGAACATGCTGAGCCAATCTATTTTAACTGCAGATTTAGTTTGC  15000
AAATACTGTCTCCTTGCCGATAAGATTCAGGTGTCATCTTTGTGGACATTGGCAGGAATT
TTCTTGACCGTGACAGGTTTTACAGAGTCTGGCAATTAAGCTGTCAAGACACATTTTCCT
CTGCCAGGAAGCATTAATTGATGATAGTCTTGGCTGCAATAGGCACAGAGAGATGGATAT
TGTAATCAGAATGAATAGAGGTCCTTGTAGTTGAGAGCTACGTTGGTCCAAAGTTTTGTA
GTCGTTGACGTTTGGTGATACTGAGATAAGGAACAAGGCACGAGATATTAGAGCTAAATA  15300
TCAGGCACAGCATGAGAATAAAGACCTCTCTAGCTGGAACTGTTGGTATCTGGGGAGATT
TTAACTTTCTGGATGCATACTGCAAAGTACTAATATTAGTAGAGCTACTGGATGCGAGAG
CAAATAGTTTTCCATTAAGTAATCCCAAAAATCATGTTGTTGTTGGTTTGCTTTTCAAGT
GCGAGGGGTGTTGGAGATGTATTTCCCTCAGAAAATAAACCTGATATGATTCAACCTGAG
CTCTCTCTGTTTAAATCACACTGAAAATAGATCTGCAAATGGGGATTTTGATTACCGAGT  15600
ACAGAATATGAAAGATTAAAACTTGGGAAAGTTAGGGTTCTGATTGAGAAACTTTTGTT
TTTGTGGCCGACCCTTGCAGCTTACAAAAATCTGCCTAAATAAAGGAGAAAACCACATTT
AGAACCCATCCAAGCTATGCTACTTCAGTACTGGGCAAAACTTCAGGAGACGTTTGAAGA
AAACTGAAGACGTGAAGTATAAAGGAATGATTGATGTGCACAGTAAACTTTCTTGGAAGG
TAATCACGCATGGGCTAATATCAATCTTTACAAAGTTGGCTGACTTCCTAGATAAAGGAA  15900
```

FIG. 14E

```
GTACAGTAGATCTAGTCTACCCAGGCAGCAAAAATGTTTGACCTGTTGCCCTGTGGGGTG
GTGTCACCTGGGCTTGGGGAGGGGGGTCAGGATGAGGTTACAGGGGATGTGGAAGCATAC
TGTGGAGGAGCAGGTGGGGCACCCACAGGAGTTAGCAGTGAGCAGACAGAAAGGTGGATC
TGAGGACCGAACTTCGTATTTTGTTCCTTGCATTAATACACAAAAAGCAGACACACACA
CAGAGCAGATTGCTGCTGGTTTTTGTTTCTTTTTAAACAGCAGAAGAGCAGGATTTTT    16200
CCCACAGAGAATGGGGTGACCTTCTAGGCTGTGATTGCCTGGGCTCAAGCTGAGATGAAA
CGCAGTGATGAGGAGCACAAAACCGTGCTCTGAGGTTAAATAATGAGGGCTTCGGCTATC
AGTTCAGAGCTCAGTAAAAACTGCAGAGGAGGAGGAAGACCTAATTGCATGTAGCCAGCC
ACAGGGCAAATGAGAGCTGCAGCGTGCTGGGGCAGATCCGGGAGCAGAGGGGCCGTGGCA
CGCTCCCTGTTCACTGGCTCCCCTGGAGCCACACAAAAGGCCCCTTCCTGGCAATTGTGC    16500
CCACATCAATCATTAGCTAGAAACCCAGAGCTGGGTAAATACGTTTTGGCTTCCCGTCTT
GATGACAGATTGGGTGTTACATCACAAGGTGGGACCACTTGATATGACAACACGCTATAT
ATTCCCGCTGCTACCTCTGCCCTTCCTCCCCACTCTGAGAGCAAGCGGGCTGTGTGTGC
ACCGAGGTGCTCTGCCATGAGGACTGCCAGGCAGTTTGTACAGGTGGCTCTGGCCCTCTG
CTGCTTTGCAGGTGAGTGTTTCCTGCTATACCCGTAGGTGACTATAGCTAGACCAGAGA    16800
CTAGGCTATCTGTGAGAGTATCTGGGTATTGTAATGTGTTAGAGAGCCTTGTTCCATGAA
GGAATGCTCTTTCTGACAGTGTAGCAAAACACCAGACTGCAAGATCCAGGTTTCAGCAAA
CCTCATACAGACGACTGTTTTCGTCGTGGTTTATAGGAGCAAATTGCTGAGGGAGCAGTG
CTAGTGCAGGGCAGGAGCTTGCACGTGCAAGCACTGAGTATAACGGCAAAGCAAAGCTAT
GTGAAATGGCTCCTGTGTCCATGTAAGCAATACAAACACTGCATCTTGTATCATCTATAA    17100
ATTTTCTGTGCTGTTCCTGGCAGCTGAGAAGTTTGTTGTGGGAAGAACAGTGCTAGTGGT
CAACAGCCACCTGAAACGTGCATGTCTGAGCTCCTGCAAGTCAAATACAGAGTCTTGCAG
AAGAGTTTAAACTCAGTGCAGGCTTGAAAATACCTACATTTCTTCCCTGGGGCATCTTAG
GAACTGGCTAACACATGTGGCCTCCTACTGAAAGTGCAGTGAAACTTCATTTAATAACCT
CTGATTCATTTTATGGACGTACATCACTGGCATAATGTAAAATTGCATTTTCCTAAACCC    17400
AATAAGCCAATCAACAACGGTATCTAAATGTAACTGTTTCATCGAAAGATTTGCATATGT
CATCTCTGCATATTAATAATATGTATTTATTTTCTGTCTCTACTTTTCTTTTAGATATTG
CCTTTGGAATTGAGGTGAGTTACAGATTTTTTTTCCCATTTATTCTTTTCTATTCCAGGC
TTCTGGTCAAATAAGAGCAGTATATAATTACCTGATGAGCAAGTGGATTAATCTAATGAA
AGCCTGGTTGCTCAAATAATACTTGCCAGTGCATGATTGAATGATATTGCCAAGTCACGA    17700
AAAAGTAAAACACACCCCGTTTATACTATTTTCCATTCATGCAATAAAATGAAGAAAGGA
AGAATTGTACGATCCTATTATGTTAACTTTTGGATATAACTGCGTTAGTCCAAGTCAAGG
GGTGGTAGTTACCTCCTCGAGAGGAAAGCTGTCTTAAGATGATAAGCTCCAAAGCATCAA
AGACAGTGATTCTGGTATCTTTTTCTATACAGTAAGACACACACTACAGTGTTCCTGCCT
ATACCCATATCAAAGCGAGGAAAGCAGCAGGGTCTGTGCAGTGCATTTGTCTGCAGGTTC    18000
TTCCCACGCAGTTATGAGATTCCTGCAAATCACCAGAGACTGCAGCGTGATTGGAAACGA
TCAGATTTTGAGTTGAGCGGCTGTGGAGCATGGCCAGGCTCCCAATTACCAGCTGCCTTC
GTTAGGCGCTGTCTCACCCACAGCTCTCCTTCCTCCATGTCATGCTTCCCCCAGTCCCCC
GCAGGAAAGCGTGATCAGAAGAAGATTCCCACCTCCTGACTGCCTGAGCAGATTCCAAAT
GATACCTCAGGTGTTTGTCCCGGCTGGAGCTGTGGGTGGCAGGAGGTTTCCATACTGTCT    18300
TTTGTTGTGGAAACTGACCCCAGGGCTGATGTTGTGCTGCTTCCATAGGTTAATTGCAGC
CTGTATGCCAGCGGCATCGGCAAGGATGGGACGAGTTGGGTAGCCTGCCCGAGGAACTTG
AAGCCTGTCTGTGGCACAGATGGCTCCACATACAGCAATGAGTGCGGGATCTGCCTCTAC
AACAGGTGAGCTTATGTGGAAGCCCAGGGGAGCTGCAGGGCAGGAGACTCGAGGTGAGGG
CGGCAGCTCTGTCCCCAAAATATGGTCTGTGTGGAGGAGTATGTGAGTTAGTACCAGGAT    18600
GCTGACCTCCAGCCTGGGGGTGGTGGCTGCTCTGCCATCTCTGACACAGATCTGCGTT
CTTCCAGGGAGCACGGGGCAAACGTGGAGAAGGAATATGATGGAGAGTGCAGGCCAAAGC
ACGTTACGGTAAGTCCAACAGTAAGATGAAGTCTTGCTCTGTTGGTGCCCATAAAGACTT
ATTTTTATTTCATAGAATCATTGAACAGCTTAGGTTGGAAGGGACCTTAAAGATCATTGG
GCTCTAACCCCCCTGGCCTGGCCGGGCTGCCTTCAACCAAATCAGTTTGCCCAGTCAAAT    18900
GGGCCTTGGGCACCTCCAGGGATGGGGCACCTGCTCTGCTCAGCCTGTTACTTATTTACT
TGTTTTTTTCCCATTCCTGCTATCCTTACAGATTGATTGCTCTCCGTACCTCCAAGTTGT
AAGAGATGGTAACACCATGGTAGCCTGCCCAAGGATTCTGAAACCAGTCTGTGGCTCAGA
TAGCTTCACTTATGACAACGAATGTGGGATTTGCGCCTACAACGCGTAAGTCTTTTCTGT
```

FIG. 14F

```
GGAGCATCCTTCTGGGTAATTAGAGATGGCTAAGTCCCTTGGAAACGCTTACATAAAACA     19200
CTTTCTAAGCCTTTCTTAGGGTAGATGTTTCTGTGGGACTCTTTGAAGCTGGCTACTTGT
GATTCTCCAGCCAGCTGCAGATTTCTTCCCCATCCTCTGTCTGTGCTCATGAAGGGAATC
ACAAAAAAGACAGAGGACAACCCACAGCAGAGGCATGAATAGATCAAAGTGTTGCTCAGT
GCTGTGTGATATGGAAATACCATGCATTTTCTGCTCACAAGTGGTTGCTACCACCTGTGG
GCTGCATCCAGACCACTCAGCAGTTCCTTACGTGAAGGGTGGGACCTTGCTTTCTTGCCC     19500
CAGTATCTAAGGCTTTTCACGAGGCTCTCTAACTAAAACAGCTCTTTCTTTCAGAGAACA
TCACACCAACATTTCCAAACTGCACGATGGAGAATGCAAGCTGGAGATCGGCTCGGTAAG
TGTAACAGAAATAAAAATCCATCTCCTAGGGCTGTTAACGGAGAGAATCCCATTGATTTT
CCTAAGAAAATGTATGACCGGGCTGATCGGGGGTCCCGGTCCACGCTCTGCTTCCTGCCT
GGTGAGGGTGGCTTCTGAAACAAAGCGGTAAAGGAAGAGGCCCCAGATTTTCCTTGCATT     19800
GTGCTGTGCAGATTGGCAGGTTTCTCTCTGGAGGCGACAAGCATTTCCACCCTTTGTAAC
AAGCATTCAAAATTCTAGTGCTGGTAGCTTGGTTAGATATAGTGAGATTCATAAGAGCAC
CAAGCATACATATTTATAGGGTATAGCTTATTGTATATTTATACTGGGGTAAGAGTCCAG
TGCCTCAGGAAGAAAGCTTATATATTTCAGCACAAAAATTCTGGGATGCAGGGAGTCCG
TTCTCCAACAGACGGATTCCTCCTTTATCACTTCAACTCCCGTGCTTAACTGCAGGGAAT     20100
CTGAATTATTAAGCAATCACAGCACTGGGGAAGGAAGGAGAAAAACCAACACAAACCAAA
ACAATGTTAATCAGATTTCCAGCTGTTGGAAAATATTTCCCACTTAATTCAAGGCTGTTG
TGTCGATGAGAAGAGGGCTGAAAAGGCTGTTTTCAGTTCCTCTGCCTGAAGGTTTCATTC
TCTAAGAGAGGTCCCTTTTCTTGTCTCCTAGAGAATGAGGGTAGTGTTCTGAAAGCCTAT
TTCTGATAGACAGTTTAGTTAAGTGTAGCAGGGCTTTGTCCTGTCACAAAAACTAGGAAG     20400
CCGGGAATACAGGATGAAAAGGTGTTACATTGACTTCTCCCGTGTAGCACAGGCTCCGGG
AGGGCTTATTCTCCTTATTTTGGCAGGTTGACTGCAGTAAGTACCCATCCACAGTCTCTA
AGGATGGCAGGACTTTGGTAGCCTGCCCAAGGATCCTGAGCCCGGTTTGCGGCACCGATG
GTTTCACCTATGACAACGAATGCGGGATCTGCGCCCACAATGCGTAAGTGCTGCTCATCT
CCCACTCCTCCAAAGTAGCCAGCAATGCTTTGCCGTGCTGGGAGCCTTCCTTCTACGTTG     20700
CTGCTTATGCCTGTTTCTTCAAGCCTCTTAGAAACTGCATTTTTTTGTTGTTGTTCTTA
CTGAGTTTTCTTCTGATGCCTTCTTTGTGATCACGAGGGGAAATCTGCAAGACTCAGAAC
ACAGCTCCTTGGATTAGTCTGTGGGCTGGGCAGTGACTGAGCAGAGAAAGGAATAGTTCA
GAATCTTGCTTTAAATAACACGAGAAGACGTGATGAGCTTGTTAACGAGCAGAGTAATGT
AGCTATATCAATACAATCGTGCAGAGAGGCTGAAGCCCTACTTTGTTAGGTACCTGCTTT     21000
AGGCTACGTCTGGTTCATTCTGCATGCAAGTGTTTAAACCAAGAGTTAAAGCATCTCCTT
ACTCACTTTGTCTCCCTCTTTCAGAGAGCAGAGGACCCATGTCAGCAAGAAGCATGATGG
AAAATGCAGGCAGGAGATTCCTGAAGTGAGTATACAACGTAAGGTGTATTTCTCCCCTTG
CCTCTGCCCACTGAGCTATTTGCTGAGGCCACGTCTACTCTGAAAGTGAGCTGGCTTGAA
GCCTGGCTCTCTGCACGTGTCCTTTGGGATGTGCCAACGTGTATCCAACACACAAACAGT     21300
GTGGAAGTTGGGCAGGGGGAACTTAGGTCTTTTAAGGATGATCACTAAATGCATTGCCAG
CAAAGTCCTTTTGTGCCAGTGAAGTCCTATTATGTTTGCCTTCTTTTGTTTCATTCTATA
GTGCAGAGAGAAAAGGAGATGATATATCTTTGTTGGTTTTTTTTTGTTTGTTTGTTTTG
CTTTTCTGCCATATCTAGCAAACTGTTTCAGTAGGTTGTGACCCCTTTGGATCACAAGTG
AAGCTCAGTGGCATTTGGGATTGACTGAGCTGTCTGCCCTGGTGATTTGGCATCTCACAG     21600
ATTACACAGCGCCATGTAGCTCCTCCTGGGCATGAGAGTTTCTGCAGAGCTGACTCAG
GCTGGCTTTGAGAGAACTGAAGTGTAGCACCAGCGTTGTTTCAGCATCCCAGCGTAAAAG
ACATGGATTGCAGCAGGAGGCAATGCTAGGGTTTGTCTTTGAGAGCAAGGGCTTTTTCAG
GGCTGACGCTCCTACTTTTTGCAGATTGACTGTGATCAATACCCAACAAGAAAAACCACT
GGTGGCAAACTCCTGGTGCGCTGCCCAAGGATTCTGCTCCCAGTCTGTGGCACAGACGGA     21900
TTTACTTATGACAACGAGTGTGGCATTTGTGCCCATAATGCGTAAGTACTGCAAACAGGA
CTTCCTTTTGTAGCGACTAGCCACGTTAGTACTGCAGATGGCTTCCCCTCCACCCTTCAT
CTTCTTCTTTCTTTCTTTTTTTTGATAGCAGTATGTCTATATGTCTCCTGTTCTTCCTT
CAACCTCCTGAAGCTCTGTCGCCTCGGTTTCCTTTCCTGATGTGCTCCTCAGGGAGCTGT
GGGAGAGCCAGCTAACAGCTGAGTGTCCTATGAGGGCTGTGGCATTTGTGCAGAGGAAAA     22200
AGAGAATGGGTCTGCTACAAGTAGACCTGAGAAGCCTGTAACTTCTTAGGATCATGATCC
```

FIG. 14G

```
CTAATGGCAGCCTTTCCCTTTCAGACAACATGGGACTGAGGTTAAGAAGAGCCACGATGG
AAGATGCAAGGAGCGGAGCACCCCGGTAAGTGGGGATGGATGTCAGATGAGCGCCAGCTC
CTGTACGTGCCTTGTGGCTGCAGAGGTTGCTAACCAGGGTCTGTCCATTCAGGCAGCAGA
GAAGGGGAATGGGCCAGGATTTAGGTAACAAAATGTCCCAATACTGCAGGTCTCTGGAGG   22500
GAAACATCAGAGGCAGCCCAGAACAGCACAGCCTGTTTTAGCACAGTAGGAGAGGAAGAG
CAGAAGCTGTGTTAGATGCCTGTGTAGTCATTCAGTGCTAGGATTTCCATTGCAGCAGAC
AGGTTAAAAAATCTCTGTACCGTGGTCAGCCAAGAAAGGCTGCTTGCAGGAATGCACGC
AGAAATAGCTCTATAAACATGCACGGTAACAATATGTGCTGATAATATCTCAGCACATTT
ATTCTGCTTATGCAGAGCAGCTCTAAAACACTGAAAATAACTTTGTGCATCTCAAGGGAT   22800
TGCTGTATCTTTTCTGTAGTAAAGACACACTGTTATGGTGCTGTCTTTGCTATAATTTGC
TCTTGGACTGTGTGGGAAATATGGGTAATAAGAGCTACTACACAGGGGAAGGTATGCAA
AACGATTGTGAAGTGTCAGAAGCTTAGCCAGTGTAGACTGACTTCCAGTGCCATCAGTAG
ATACTTGCTTATTTATCCTCAAATATTGGAACTGTTTTAAGTACTGTGAGGATTTCTGC
AGCAGCAGCTGATGAGCTGATGGAACAGTTTCTTCTTGCCGTTTTGAAAACGTGGAAACA   23100
AAATCTAAGGCTTAGCTAAGTCAGGCATGACCTAATGTCAAACTGGACATAACATCAAAC
TCCTTATATCAAATTCCTTTGAATAATGCTTGTTTTGAAACTTGGACATACGCTGCATAA
GGAAGATGATCTTTCTGGTCTGCTATTCCTTTGCGTTCCCTTTGTTAGTGAGCAATATCA
AACCCAACCACAATTAGTTCATTTATAATGGGAGACTAAACTGAAATCAACCCTGATTTT
TCCTATGGCTCGAGGCAGTCTGTCCCCAGCTCCCAGCACCTGACTCAGCATCCTTACTG   23400
TTTTCTCCCAGCTTGACTGCACCCAATACCTGAGCAATACCCAAAACGGTGAAGCCATT
ACCGCCTGCCCCTTCATCCTGCAGGAGGTCTGTGGCACTGACGGCGTCACCTACAGCAAC
GACTGTTCTCTGTGTGCCCACAACATGTAAGCCCTGCAGGTCACCCACTCGTGTGTCACC
GCAGCTGCTTGTTGAGCTTTGTCAACTCTGTTTTCTCTCTTCCAGTGAATTGGGAACC
AGCGTTGCCAAAAAGCACGATGGGAGGTGCAGAGAGGAGGTTCCTGAGGTAAGCGATAAA   23700
GAAAACAAGAGCTTGAGGTGGTGCTTATTGCCTAACAAGTACAACGCTGGCTGGTTTTGG
TGATGCTGGGTCATGCCCTCCTGCTGCCATCCTTCCTGCAGGTAAACATCAACCCTGGCA
GCAGGGATGCTGTGCATTTTCTGCATGTAGTCAGGGAAAGAAAGAGAAGAGGACGGGTGA
GGAATGAGTTATGATGCAGGTAGCATAAATGATTTAAGGCGTTACGAAGAAATCTCTTTC
CCACAGCAGTCTATCATACCTGCCGTGGGAGTGTAGCTGTCTGTTCTGGCAATATGGGAA   24000
AGGGACACAGAGCACCCGCAGGTACCTGGTGCCTTCTGGATACCTGTGCTGTGCAAAAGG
ATGTTGTGCAAAGATCAGAAAACTACCTGCATTTTGAATGCTTTTACCTAATGTACCAGA
GGATTCAAACACCTCTCTCTTCCTATTGTAAATGCGATATAATGTAATGTATACCAACAA
TGAATCTTGTAAAAATACCAGATAAACTATATTTGGCCAGCTCTAAACTATTTACGCTCA
CTGGGGAATAGAAAAACAAAGCCATCTCATTATCTTGTGTTTGAAAGAGTCAACGTCGTG   24300
AGTCAGATATTTCATTTCTATGCAAACAGACTATGAATGTCATTGCTTTGTTTCCTGCG
TATGCTCTGTGCTCAGACCAAGTCAGATGCATAAATCAGTGAGGAAGAGCTCACACTGGA
GAAACTGGGATAGCTGAAACTCAAGGCCAGTTCTTCAAATGGCATAAATCATTTTGAACT
GCTGTTGGTCCTTCTGTCCGATTGCAACACACAGAACCAGCCCCTCGCAACAAAGGCAT
GTCAGCACATCTCCTCAGTTCTTGTGGGCCGTGACACACTCCTTGGCCACACTGAGCTTC   24600
TCTTGCAGGAATTGCATAAATCACGCCAGTTTGATTTGCAGATTATTTATGAGCTGCGTT
TTGCAGCGTCCCAGCAAGTGGTTCAGCAAGCTCTAAGGGCATCGTGATAAATGCAGGGCT
GAATGAGTGATACGCGCCTTCAAGCTTTGATTCAGTCTTCTCCAGTATAAGGCTGTGACA
GAAAATTGATAGTTTTCAATGAAGAATGAGTCAATGCATAACCATAATCCATCCTGTGGC
AGATCTTGAAAGGCAGAGGCGTAAGGAAGGGGTTGTGTCTGAGCACCCTTACACAGAGC   24900
ATTTGCTGCCTTTGTTTCCTAGCTTGACTGCAGCAAGTACAAAACCTCCACGCTGAAGGA
TGGCAGACAGGTGGTGGCCTGCACCATGATCTACGATCCCGTCTGTGCTACCAATGGTGT
CACCTATGCCAGCGAATGCACGCTGTGCGCTCACAACCTGTAAGTACTCATTCATCTCCA
GGGGGACCCACCGTGGCTGTGACTGGACACATCTTTGAGTGCTGAATAACATGCAAGGGC
TCTGTCTAAAATCTCGTGCTGCATGGGTCCTGTCTGCCTATCCCCGTTTCCCTGGTTGCC   25200
ATGGTTGGTGTTTGAGATGGGCATTTAGCAAGGCCCACTGCCCCAGTGACCCAGAAAAA
GGGTTCACTGCCTGGGAAAGCATTATTCCAAAAGACACATCCCTAGTCCTTAAGGGCATG
TTCTTGCTAATGCTTCTCAGGCAATGCTTAGCTAATTTATCTGAAATTGTCCTGTGTACC
```

FIG. 14H

```
ACATGGGAACGAGGTTGTGCTCTTGTACTACGGTTGTAAATGGGAAGGGTTTCTGCTAAT
ATCCATCTCTCCTTCCTCCAGGGAGCAGCGGACCAATCTTGGCAAGAGAAAGAATGGAAG  25500
ATGTGAAGAGGATATAACAAAGGTGAGTGTGAAAGGATGGGCACAAAGAGTTACAGTCGT
AGGGGACCGTCCTCTGCTCCACATCAAAAACTGGGGGAGCGGTGTGCAGCCCTGGCGAGG
TCGCTTGGGAATGTCATACTGGTTATAGAATAGCTGCCATCCATCCCATGGGAATGGACA
TGGCAGTGAACAGGAACAGTGTGAGGTCACATCCCTCACCAGGAGGAACTGAGCTGATTA
CTGCCGTAATTTTCCAGTTTCACTCTTTGTGCTGGGGAATACTGTTTGCTCCCAGGCAG  25800
AGACTCACATCTTCCTTGTGTGTGCAGGAACATTGCCGTGAGTTCCAGAAAGTCTCTCCC
ATCTGCACCATGGAATACGTACCCCACTGTGGCTCTGATGGCGTAACATACAGCAACAGA
TGTTTCTTCTGCAACGCATATGTGTAAGTATAGGAGTGAAACCCTTCCTGTAACTGCTAC
AAACGCAGAGTTGATTTATAAGGAGTTCTTTACTAACACTTTATGGGTGTGTGCTAGAC
ATTTCGGATGCACCGTGACGTGCAAGGAGGTGCTTTTTTGCTTTTTAAGAAAAAATGCAA  26100
AGCACCCACATCTGCCCATGTGTATGTGGCTTCCTGTTTTATTTAGTTTCAAAGACATTT
TGCTAATTTTCACCAGCATAGTTTGTCCCACAAGCTCATCAGGGTATGGGAAAGTACTT
CACCAAACTACCTGGAGCGTTTCAAGTGTGTGAAACCTGTCATCTTTCCTTTAATTTCA
TAATGAAAGGAAGTGGTTGGCCTTCTGAGACTGTTCTTTATCTTCTGCCAACATTATCAA
CATTGGGCTGGTAAGGAGAGGAACAAGGCTGCAGCACAAATTCTATTGTGTTTAATCCT  26400
TTCTTCTCTTTTCATTAGGCAGAGCAATAGGACTCTCAACCTCGTGAGTATGGCAGCGTG
TTAACTCTGCACTGGAGTCCATCGTGGGAAACAATCTGCCTTGCACATGAGTCTTCGTGG
GCCAATATTCCCCAACGGTTTTCCTTCAGCTTGTCTTGTCTCCCAAGCTCTCAAAACACC
TTTTGGTGAATAAACTCACTTGGCAACGTTTATCTGTCTTACCTTAGTGTCACGTTTCA
TCCCTATTCCCCTTTCTCCTCCTCCGTGTGGTACACAGTGGTGCACACTGGTTCTTCTGT  26700
TGATGTTCTGCTCTGACAGCCAATGTGGGTAAAGTTCTTCCTGCCATGTGTCTGTGTTGT
TTTCACTTCAAAAAGGGCCCTGGGCTCCCCTTGGAGCTCTCAGGCATTTCCTTAATCATC
ACAGTCACGCTGGCAGGATTAGTCTCTCCTAAACCTTAGAATGACCTGAACGTGTGCTCC
CTCTTTGTAGTCAGTGCAGGGAGACGTTTGCCTCAAGATCAGGGTCCATCTCACCCACAG
GGCAATTCCCAAGATGAGGTGGATGGTTTACTCTCACAAAAAGTTTTCTTACGTTTTGCT  27000
AGAAAGGAGAGCTCACTGCCTACCTGTGAATTCCCCTAGTCCTGGTTCTGCTGCCACCGC
TGCCTGTGCAGCCTGTCCCATGGAGGGGGCAGCAACTGCTGTCACAAAGGTGATCCCACC
CTGTCTCCACTGAAATGACCTCAGTGCCACGTGTTGTATAGGATATAAAGTACGGGAGGG
GAATGCCCGGCTCCCTTCAGGGTTGCAGGGCAGAAGTGTCTGTGTATAGAGTGTGTGTCT
TAATCTATTAATGCAACAGAACAACTTCAGTCCTGGTGTTTTGTGGGCTGGAATTGCCCA  27300
TGTGGTAGGGACAGGCCTGCTAAATCACTGCAATCGCCTATGTTCTGAAGGTATTTGGGA
AAGAAAGGGATTTGGGGGATTGCCTGTGATTGGCTTTAATTGAATGGCAAATCACAGGAA
AGCAGTTCTGCTCAACAGTTGGTTGTTTCAGCCAATTCTTGCAGCCAAAGAGCCGGGTGC
CCAGCGATATAATAGTTGTCACTTGTGTCTGTATGGATGACAGGGAGGTAGGGTGACCTG
AGGACCACCCTCCAGCTTCTGCCAGCGTAGGTACAGTCACCACCTCCAGCTCCACACGAG  27600
TCCCATCGTGGTTTACCAAAGAAACACAATTATTTGGACCAGTTTGGAAAGTCACCCGGT
GTATTGTGAGGCTAGATTAATAGGCTGAAGGCAAATGTTCCCAACTTGGAGATACTGTTG
GTATTGTATCAGGGAACAGGGCCATAGCACCTCCATGCTATTAGATTCCGGCTGGCATGT
ACTTTTCAAGATGATTTGTAACTAACAATGGCTTATTGTCTTGTCTTAAGTCTGTGTCC
TAATGTAAATGTTCCTTTGGTTTATATAACCTTCTTGCCGTTTGCTCTTCAGGTGTTCTT  27900
GCAGAACACTGGCTGCTTTAATCTAGTTTAACTGTTGCTTGATTATTCTTAGGGATAAGA
TCTGAATAAACTTTTTGTGGCTTTGGCAGACTTTAGCTTGGGCTTAGCTCCCACATTAGC
TTTTGCAGCCTTTTCTGTGAAGCTATCAAGATCCTACTCAGTGACATTAGCTGGGTGCAG
GTGTACCAAATCCTGCTCTGTGGAACACATTGTCTGATGATACCGAAGGCAAACGTGAAC
TCAAAGAGGCACAGAGTTAAGAAGAAGTCTGTGCAATTCAGAGGAAAAGCCAAAGTGGCC  28200
ATTAGACACACTTTCCATGCAGTATTTGCCAGTAGGTTTCATATAAAACTACAAAATGGA
ATAAACCACTACAAATGGGAAAAACCTGATACTGGAATTTAAATATTCACCCAGGCTCAA
GGGGTGTTTCATGGAGTAACATCACTCTATAAAAGTAGGGCAGCCAATTATTCACAGACA
AAGCTTTTTTTTTTTTCTGTGCTGCAGTGCTGTTTTTCGGCTGATCCAGGGTTACTTATT
GTGGGTCTGAGAGCTGAATGATTTCTCCTTGTGTCATGTTGGTGAAGGAGATATGGCAG  28500
```

FIG. 14I

```
GGGGAGATGAGCATGTTCGAGAGGAAACGTTGCATTTTGGTGGCTTGGGAGAAAGGTAGA
ACGATATCAGGTCTACAGTGTCACTAAGGGATCTGAAGGATGGTTTTACAGAACAGTTGA
CTTGGCTGGGTGCAGGCTTGGCTGTAAATGGATGGAAGGATGGACAGATGGGTGGACAGA
GATTTCTGTGCAGGAGATCATCTCCTGAGCTCGGTGCTTGACAGACTGCAGATCCATCCC
ATAACCTTCTCCAGCATGAGAGCGCGGGGAGCTTTGGTACTGTTCAGTCTGCTGCTTGTT   28800
GCTTCCTGGGTGCACAGTGGTGATTTTCTTACTCACACAGGGCAAAAACCTGAGCAGCTT
CAAAGTGAACAGGTTGCTCTCATAGGCCATTCAGTTGTCAAGATGAGGTTTTTGGTTTCT
TGTTTTGTAAGGTGGGAAGAAGCACTGAAGGATCGGTTGCGAGGGCAGGGGTTTAGCACT
GTTCAGAGAAGTCTTATTTTAACTCCTCTCATGAACAAAAAGAGATGCAGGTGCAGATTC
TGGCAAGGATGCAGTGAAGGAGAAAGCCCTGAATTTCTGATATATGTGCAATGTTGGGCA   29100
CCTAACATTCCCTGCTGAAGCACAGCAGCTCCAGCTCCATGCAGTACTCACAGCTGGTGC
AGCCCTCGGCTCCAGGGTCTGAGCAGTGCTGGGACTCATGAGGTTCCATGTCTTTCACAC
TGATAATGGTCCAATTTCTGGAATGGGTGCCCATCCTTGGAGGTCCCCAAGGCCAGGCTG
GCTGCGTCTCCGAGCAGCCCGATCTGGTGGTGAGTAGCCAGCCCATGGCAGGAGTTAGAG
CCTGATGGTCTTTAAGGTCCCTTCCAACCTAAGCCATCCTACGATTCTAGGAATCATGAC   29400
TTGTGAGTGTGTATTGCAGAGGCAATATTTTAAAGTTATAAATGTTTTCTCCCCTTCCTT
GTTTGTCAAAGTTATCTTGATCGCCTTATCAATGCTTTGGAGTCTCCAGTCATTTTTCT
TACAACAAAAAGAGGAGGAAGAATGAAGAGAATCATTTAATTTCTTGATTGAATAGTAGG
ATTCAGAAAGCTGTACGTAATGCCGTCTCTTTGTATCGAGCTGTAAGGTTTCTCATCATT
TATCAGCGTGGTACATATCAGCACTTTTCCATCTGATGTGGAAAAAAAAATCCTTATCAT   29700
CTACAGTCTCTGTACCTAAACATCGCTCAGACTCTTTACCAAAAAAGCTATAGGTTTTAA
AACTACATCTGCTGATAATTTGCCTTGTTTTAGCTCTTCTTCCATATGCTGCGTTTGTGA
GAGGTGCGTGGATGGGCCTAAACTCTCAGTTGCTGAGCTTGATGGGTGCTTAAGAATGAA
GCACTCACTGCTGAAACTGTTTTCATTTCACAGGAATGTTTTAGTGGCATTGTTTTTATA
ACTACATATTCCTCAGATAAATGAAATCCAGAAATAATTATGCAAACTCACTGCATCCGT   30000
TGCACAGGTCTTTATCTGCTAGCAAAGGAAATAATTTGGGGATGGCAAAAACATTCCTTC
AGACATCTATATTTAAAGGAATATAATCCTGGTACCCACCCACTTCATCCCTCATTATGT
TCACACTCAGAGATACTCATTCTCTTGTTGTTATCATTTGATAGCGTTTTCTTTGGTTCT
TTGCCACGCTCTGGGCTATGGCTGCACGCTCTGCACTGATCAGCAAGTAGATGCGAGGGA
AGCAGCAGTGAGAGGGGCTGCCCTCAGCTGGCACCCAGCCGCTCAGCCTAGGAGGGACC   30300
TTGCCTTTCCACCAGCTGAGGTGCAGCCCTACAAGCTTACACGTGCTGCGAGCAGGTGAG
CAAAGGGAGTCCTCATGGTGTGTTTCTTGCTGCCCGGAAGCAAAACTTTACTTTCATTCA
TTCCCCTTGAAGAATGAGGAATGTTTGGAAACGGACTGCTTTACGTTCAATTTCTCTCTT
CCCTTTAAGGCTCAGCCAGGGGCCATTGCTGAGGACGGCATCGGGGCCCCCTGGACCAAA
TCTGTGGCACAGATGGTTTCACTTACATCAGTGGATGTGGGATCTGCGCCTGTAATGTGT   30600
CCTTCTGAAGGAAGGAACGTGCCTTCCAAGTGCCAGCCCCACAGCCCCCAGCCCCTCCCT
GTGCTGCTCCAATTCATCTCCTCTTCCTCCTTCTCCCTTTGCTGTTTGTGCTCGGGTAGA
AATCATGAAGATTTAGAAGAGAAAACAAAATAACTGGAGTGGAAACCCAGGTGATGCAGT
TCATTCAGCTGTCATAGGTTTGTCATTGCTATAGGTCTGTATCAGAGATGCTAACACCAC
TTTGCTGTCGGTGCTTAACTCGGGTGAACTCTCCTTCACTCGCATCATTTGCGGGCCTTA   30900
TTTACATCCCCAGCATCCATCACCCTCTGGGAAAATGGGCACACTGGATCTCTAATGGAA
GACTTTCCCTCTTTCAGAGCCTGTGGGATGTGCAGTGACAAGAAACGTGGAGGGGCTGAG
CAGCAGCACTGCCCCCAGGGAGCAGGAGCGGATGCCATCGGTGGCAGCATCCCAAATGAT
GTCAGCGGATGCTGAGCAGGCAGCGGACGAACAGACAGAAGCGATGCGTACACCTTCTGT
TGACATGGCATTTGGCAGCGATTTAACACTCGCTTCCTAGTCCTGCTATTCTCCACAGGC   31200
TGCATTCAAATGAACGAAGGGAAGGGAGGCAAAAGATGCAAAATCCGAGACAAGCAGCA
GAAATATTTCTTCGCTACGGAAGCGTGCGCAAACAACCTTCTCCAACAGCACCAGAAGAG
CACAGCGTAACCTTTTTCAAGACCAGAAAAGGAAATTCACAAAGCCTCTGTGGATACCAG
CGCGTTCAGCTCTCCTGATAGCAGATTTCTTGTCAGGTTGCAAATGGGGTATGGTGCCAG
GAGGTGCAGGGACCATATGATCATATACAGCACAGCAGTCATTGTGCATGTATTAATATA   31500
TATTGAGTAGCAGTGTTACTTTGCCAAAGCAATAGTTCAGAGATGAGTCCTGCTGCATAC
CTCTATCTTAAAACTAACTTATAAATAGTAAAACCTTCTCAGTTCAGCCACGTGCTCCTC
```

FIG. 14J

```
TCTGTCAGCACCAATGGTGCTTCGCCTGCACCCAGCTGCAAGGAATCAGCCCGTGATCTC
ATTAACACTCAGCTCTGCAGGATAAATTAGATTGTTCCACTCTCTTTTGTTGTTAATTAC
GACGGAACAATTGTTCAGTGCTGATGGTCCTAATTGTCAGCTACAGAAAACGTCTCCATG   31800
CAGTTCCTTCTGCTCCAGCAAACTGTCCAGGCTATAGCACCGTGATGCATGCTACCTCT
ACTCCATCCTTCTTCTCTTTCCCACCAGGGAGAGCTGTGTGTTTTCACTCTCAGCCGCTC
TGAACAATACCAAACTGCTACGCACTGCCTCCCTCGGAAAGAGAATCCCCTTGTTGCTTT
TTTATTTACAGGATCCTTCTTAAAAAGCAGACCATCATTCACTGCAAACCCAGAGCTTCC
TGCCTCTCCTTCCACAACCGAAAACAGCCGGCTTCATTTGTCTTTTTTAAATGCTGTTTT   32100
CCAGGTGAATTTTGGCCAGCGTGTTGGCTGAGATCCAGGAGCACGTGTCAGCTTTCTGCT
CTCATTGCTCCTGTTCTGCATTGCCTCTTTCTGGGCTTCCAAGAGGGGGGGAGACTTTG
CACGGGGATGAGATAATGCCCCTTTTCTTAGGGTGGCTGCTGGGCAGCAGAGTGGCTCTG
GGTCACTGTGGCACCAATGGGAGGCACCAGTGGGGTGTGTTTTGTGCAGGGAGGAAGCA
TTCACAGAATGGGGCTGATCCTGAAGCTTGCAGTCCAAGGCTTTGTCTGTGTACCCAGTG   32400
AAATCCTTCCTCTGTTACATAAAGCCCAGATAGGACTCAGAAATGTAGTCATTCCAGCCC
CCCTCTTCCTCAGATCTGGAGCAGCACTTGTTTGCAGCCAGTCCTCCCCAAAATGCACAG
ACCTCGCCGAGTGGAGGGAGATGTAAACAGCGAAGGTTAATTACCTCCTTGTCAAAAACA
CTTTGTGGTCCATAGATGTTTCTGTCAATCTTACAAAACAGAACCGAGGGCAGCGAGCAC
TGAAGGCGTGTTCCCATGCTGAGTTAATGAGACTTGGCAGCTCGCTGTGCAGAGATGATC   32700
CCTGTGCTTCATGGGAGGCTGTAACCTGTCTCCCATCGCCTTCACACCGCAGTGCTGTC
CTGGACACCTCACCCTCCATAAGCTGTAGGATGCAGCTGCCCAGGGATCAAGAGACTTTT
CCTAAGGCTCTTAGGACTCATCTTTGCCGCTCAGTAGCGTGCAGCAATTACTCATCCCAA
CTATACTGAATGGGTTTCTGCCAGCTCTGCTTGTTTGTCAATAAGCATTTTTTCATTTTG
CCTCTAAGTTTCTCTCAGCAGCACCGCTTTGGGTGACTTCAGTGGCCGCCTGGAACCCGA   33000
GGGGCACAGCCACCACCTCCCTGTTGCTGCTGCTCCGGGGACTCACGTGCTGCTGGATGG
GGGGAAGCATGAAGTTCCTCACCCAGACACCTGGGTTGCAATGGTTGCAGTGTGCTCTTC
TTGGTATGCAGATTGTTTCTAGCCATTACTTGTAGAAATGTGCTGTGGAAGCCCTTTGTA
TCTCTTTCTGTGGCCCTTCAGCAAAAGCTGTGGGAAAGCTCTGAGGCTGCTTTCTTGGGT
CGTGGAGGAATTGTATGTTCCTTCTTTAACAAAAATTATCCTTAGGAGAGAGCACTGTGC   33300
AAGCATTGTGCACATAAAACAATTCAGGTTGAAAGGGCTCTCTGGAGGTTTCCAGCCTGA
CTACTGCTCGAAGCAAGGCCAGGTTCAAAGATGGCTCAGGATGCTGTGTGCCTTCCTGAT
TATCTGTGCCACCAATGGAGGAGATTCACAGCCACTCTGCTTCCCGTGCCACTCATGGAG
AGGAATATTCCCTTATATTCAGATAGAATGTCATCCTTTAGCTCAGCCTTCCCTATAACC
CCATGAGGGAGCTGCAGATCCCCATACTCTCCTCTTCTCTGGGGTGAAGGCCGTGTCCTC   33600
CAGCCCCCCTTCCCACCCTGTGCCCTGAGCAGCCCGCTGGCCTCTGCTGGATGTGTGCCC
ATATGTCAATGCCTGTCCTTGCAGTCCAGCCTGGAACATTTAATTCATCACCAGGGTAAT
GTGGAACTGTGTCATCTTCCCTGCAGGGTACAAAGTTCTGCACGGGGTCCTTTCGGTTC
AGGAAAACCTTCGCTGGTGCTACCTGAATCAAGCTCTATTTAATAAGTTCATAAGCACAT
GGATGTGTTTTCCTAGAGATACGTTTTAATGGTATCAGTGATTTTTATTTGCTTTGTTGC   33900
TTACTTCAAACAGTGCCTTTGGGCAGGAGGTGAGGGACGGGTCTGCCGTTGGCTCTGCAG
TGATTTCTCCAGGCGTGTGGCTCAGGTCAGATAGTGGTCACTCTGTGGCCAGAAGAAGGA
CAAAGATGGAAATTGCAGATTGAGTCATGTTAAGCAGGCATCTTGGAGTGATTTGAGGCA
GTTCATGAAAGAGCTACGACCACTTATTGTTGTTTCCCCTTTTACAACAGAAGTTTTC
ATCAAAATAACGTGGCAAAGCCCAGGAATGTTTGGGAAAAGTGTAGTTAAATGTTTTGTA   34200
ATTCATTTGTCGGAGTGTTACCAGCTAAGAAAAAGTCCTACCTTTGGTATGGTAGTCCT
GCAGAGAATACGACATCAATATTAGTTTGGAAAAAAACACCACCACCACCAGAAACTGTA
ATGGAAAATGTAAACCAAGAAATTCCTTGGGTAAGAGAGAAAGGATGTCGTATACTGGCC
AAGTCCTGCCCAGCTGTCAGCCTGCTGACCCTCTGCAGCTCAGGACCATGAAACGTGGCA
CTGTAAGACGTGTCCCTGCCTTTGCTTGCTCACagatctctgccctcgtgctgactcctg   34500
cacacaagagcatttccctgtagccaaacagcgattagccataagctgcacctgactttg
aggattaagagtttgcaattaagtggattgcagcaggagatcagtggcagggttgcagat
gaaatcctttctaggggtagctaagggctgagcaacctgtcctacagcacaagccaaacc
agccaagggttttcctgtgctgttcacagaggcagggccagctggagctggaggaggttg
```

FIG. 14K

```
tgctgggactcttctccctgtgctgagaatggagtgatttctgggtgctgttcctgtggc  34800
ttgcactgagcagctcaagggagatcggtgctcctcatgcagtgccaaaactcgtgtttg
atgcagaaagatggatgtgcacctccctcctgctaatgcagccgtgagcttatgaaggca
atgagccctcagtgcagcaggagctgtagtgcactcctgtaggtgctagggaaaatctct
ggttcccagggatgcattcataaggacaatatatcttgaggctgtgccaaatctttctga
aatattcatgcatgttcccttaatttatagaaacaaacacagcagaataattattccaat  35100
gcctcccctcgaaggaaacccatatttccatgtagaaatgtaacctatatacacacagcc
atgctgcatccttcagaacatgccagtgctcatctcccatggcaaaatactacaggtatt
ctcactatgttggacctgtgaaaggaaccatggtaagaaactcaggttaaaggtatggct
gcaaaactactcataccaaaacagcagagctccagacctcctcttaggaaagagccactt
ggagagggatggtgtgaaggctggaggtgagagacagagcctgtcccagttttcctgtct  35400
ctattttctgaaatgtctgcaggaggaaaggacaactgtactttcaggcatagctggtgc
cctcacgtaaataagttccccgaacttctgtgtcatttgttcttaagatgctttggcaga
acactttgagtcaattcgcttaactgtgactaggtctgtaaataagtgctccctgctgat
aaggttcaagtgacattttagtggtatttgacagcatttaccttgctttcaagtcttct
accaagctcttctatacttaagcagtgaaaccgccaagaaaccttcctttatcaagct  35700
agtgctaaataccattaacttcataggttagatacggtgctgccagcttcacctggcagt
ggttggtcagttctgctggtgacaaagcctcctggcctgtgcttttacctagaggtgaa
tatccaagaatgcagaactgcatggaaagcagagctgcaggcacgatggtgctgagcctt
agctgcttcctgctgggagatgtggatgcagagacgaatgaaggacctgtcccttactcc
cctcagcgttctgtgctatttagggttctaccagagtccttaagaggttttttttttttt  36000
ttggtccaaaagtctgtttgtttggttttgaccactgagagcatgtgacacttgtctcaa
gctattaaccaagtgtccagccaaaatcaattgcctgggagacgcagaccattcctgga
ggtcaggacctcaataaatattaccagcctcattgtgccgctgacagattcagctggctg
ctctgtgttccagtccaacagttcggacgccacgtttgtatatatttgcaggcagcctcg
gggggaccATCTCAGGAGCAGAGCACCGGCAGCCGCCTGCAGAGCCGGGCAGTACCTCAC  36300
CATGGCCATGGCAGGCGTCTTCGTGCTGTTCTCTTTCGTGCTTTGTGGCTTCCTCCCAGG
TGAGTAACTCCCAGAGTGCTGCAGAAGCTTTGTGCCTGCCAGTCCTGGCTCTCCTTAGCA
GAACATGGTGGTGACCATCAGAGAGAGACTCCCCTACAAAGTGCCTGCAAAGGCTGCCTC
AGTACATCAGTATTAAACGGATTACTGTTGTGCTGGGTGTCTGTTGGGTTCTGTGCTCCC
AACACATTTCTTACGCTCTCAGCTCTGTTACACTGCTTGCATTTGCTGCACAGTTGCATA  36600
GAATGGATAAATGCTTGAAACAAGGCCATAACGAGGTGGTCAGACCTCCAGGAACTAGTT
AGGGAAATATTGTCATGGCCCAAGCAAGCTCTGTGCAGGAACCTGGCAGCTTTCCTGCAA
TGCTTTTGCTGCTAATGGAGAAACAAGAGATGCAAACAAGCCAGGATCTGATGTTCTCCT
TCTGTATTTACATCTCATGAAATTACAAAGTCAAAGACAAGCGTGGTTTATTTCTTACAC
TCAGCTTCTTTAAAATGTATATCCCTGACAACAGATGCTGTGTATGTTTGCTTATCCTGT  36900
ATGTGACTATTTGCATTTGCATTTATCTCTATTGACTCAGGTTTCTTTTCAGATATGTGA
TAGATGTTTTCTAGGGACAAAACGGATGTGTAATAGATAAGGAAGGAAAGATATTCAT
TTTTCAATTAATAAATCTACCTATCTCTTAACTTTTTTTTTTTTAAGAACAGAGCTAT
TCAAGAACTCGTTTCATCAGCCAGCAATAAGAAGCTAAATTATGTTTATCAGCATTAAAC
AAAAATCATATATAGTTTGCTTAGTTCAAGAATCGAATCGGTGGAAATCACTCAGTTTGG  37200
TTCTCTGTGCTGGAGTTTTGCACACACATTTCAGCTAGCTGTGGTCTCACTGATCAGACT
GCCTTTGTTTCCCATTTTTGTCCCCTTTTTTCCCCAGATGCTGCCTTTGGGGCTGAGGT
GAGTAAGAGAGTTCTTCTTGTCCACTTTTCTCTTTTCTCTTTTCTCTCTCTCTCTTTTTT
TCCCCCGTCTTAATTAGTATCACTATAATCAGATCCCAGAGTGTAAATGTTAAATTAT
GCAGTTCTGAGCTCTACATCTATGCTGCATGTAAGTAATGTAGCAGTGATATAAAACTGT  37500
TAGATGAATTAATTTCTGACCAACTCTGAACTGGTCTAAGCTTTAAGTTGATCATATGTT
CTACTAAATAATACAGTGGTTTGGGTTGGAAGGGTCCTTTAAGATCATCTACTTCCAACC
CCTCTGCTATAGGCAGGGACAACTCCCACTAGACAAGATTGCTCAAAGCTCCATCCATAT
GATCAGCTGTAGACTGATGGCTGTAGACTATAGCATTAAAAACTACCCCAAAGCAGCCTA
CTGAAAGAAGAAAGTACTGTGAGGTGCTACAGCTTCCAAATCCCATGTTGTTAGACCTGT  37800
TCTTTTGAATAAACGTGTTTGTACGTTGAGAATGAATGAGTAACAATGGCAGAACACTGG
```

FIG. 14L

```
AGGGGCCAACTCTCAGGCTTTGCAAAATGGTGCCTGGGGGGCATGATAGATCCCTGCTGG
TTTATCACATGGGGAGCTGCATGGCTATAACCCCATTGCCCAGTTCTCTCCCACTGCATG
GAGAGAAGGCTGGATCTGGTCGCTGCCCTGCTGAAAATGGCAGATGTAACTACAAAATGT
CACTTTGTCCTGTTACTGTGTGTTTCTTTGTCAGGTGGACTGCAGTAGGTTTCCCAACGC  38100
TACAGACAAGGAAGGCAAAGATGTATTGGTTTGCAACAAGGACCTCCGCCCCATCTGTGG
TACCGATGGAGTCACTTACACCAACGATTGCTTGCTGTGTGCCTACAGCATGTGTGTACT
GCAGAGAGAGCTCATACTGCAAGCAAGCAGCTGTGCTTAGGGCTCCTGACAGCACCCCTT
TCCAACAAACAGTGATCTGTCACATGTCACTTATGTCAACTCTTTCAGGGAAAGCTTGAG
TATCACTGCGTGACACTCGGTTGCCTAGACATCACTTTGGTTACTGTGTCTTTTTTGTTG  38400
ATGTAATTTATTCAGGTTTTTCTCCTCCATCTCGGGGATGAGGCAGATGACAGCCCCTAG
GGCATATTTCATCCCAGCAAAAAGGAGCAAAAGGATGGAGAGGTGCTCCAGTCTGAATG
GTCCAAAACAGTCCTAAAGATTTCAGAGTCTTTAGATCCCTGCCAGCCACTCAGTATGGC
ACTACCCTCTCCAATACAAATATATATATACAAAGATGACTTAGCCAGACTCAGCCTC
ATTGCATTAGGTACATATTCCCAATAACGAGAAGCTGAGCTTCCTAATACCTGTTTTCCC  38700
TCTTCAGAGAATTTGGAACCAATATCAGCAAAGAGCACGATGGAGAATGCAAGGAAACTG
TTCCTGTAAGTGAAACCAAGTTCATCCTTTGTGCAGCCAAAACTGCTTATTGACTTGCCC
AATAAATAATGTAAATGCTGACTAAGAGGCCATGTGAGATGTCAGAATCTTGTATTGATC
ATCTTCAGGTGAAGTTTCATCACAATAACACAAAAAAGACTTTATTTCCTGCTGAGGTG
GCATTTTAGGAGACCCAACGCACGCGCTCCGCTGGTCTACGTGGTCCCTGTAAGCCCTCA  39000
CCAGCGCTTTGCTGTGTGCTCCTTCCACAGATGAACTGCAGTAGTTATGCCAACACGACA
AGCGAGGACGGAAAAGTGATGGTCCTCTGCAACAGGGCCTTCAACCCCGTCTGTGGTACT
GATGGAGTCACCTACGACAATGAGTGTCTGCTGTGTGCCCACAAAGTGTAAGTACCGAGC
TGTGCTCCCTTGGCAGGAATGGGTCCTGCGCTCCTGGCAGCCACTCTTTGAGCACTGGGA
TTTCCAATGAGGCTTTTTCTGTATGGCTCTTGGACTCCGTCCCTCCTCTCCCTGATAACC  39300
TCATGCTGTTTTCCTTTGTGATTAGAAAGAGAACTGTGGCTTTGATCTTGAGAGAGAAGC
AGAGAGCTGGGTGGGGACTTAAGAGAAGCACTCTGTTCTGTGTTAACTAAGTTAAAAGGG
TCTGTGTGGCACACACTGCCTTGCAGAGGACAGCAGTGAACCTCTGCTGCACCTATATTG
TAAAACAACCTAGCTCCTAGGCCATGACAGCCTGTCACCTCTCCTCCTTTGCATCATGCA
ATACTGCAACACTGTGGCACATAGTACCACCTCCCATAAGGACTGATATGTTGAACCAGT  39600
GTGTCAGAGACCAGTAGCATCTCTGTCTTCAGGATCATCAGGTAGCATTCTATATACAGG
GTGTTGCCCAGGACTCCGAGTCCCATGAAGTATGGCAGGGGTTTTGGAACTGGATGACCT
TCGAGGTCACTTCCAACCCAAGCCATTCTATTATTCTGTGAAAGCCAGGGAGGTGGGGGT
GCTTGCAGGGCTGGTATCTTGAGCAGTGTGGGCACAAACTAGGCTGGGCATCTGCAGCCC
ATCAGCACTGCGGGGATGTGGAGTTCAGCACAGCAGGATGCAGGCACAGCTCCCTAACAT  39900
GGATTTTTTTCCTTTCAGAGAGCAGGGGGCCAGCGTTGACAAGAGGCATGATGGTGGATG
TAGGAAGGAACTTGCTGCTGTGAGTGTGAGTAGCACAATGAAGGAGCAGGTTCTGGTCCC
ACTGATGTCAAGGGAAACATGGCCAGCATCTTTAGTAGCCTCAGGAGCATCAGTTGTGCT
TCAGCACAGAGAAGATTTTACTTTCTACACACGTAATACACATTATCCACAGTAATGTCA
GGAAGGGAAGAGGATGACTGCACAGGCAGGGATCAGTAAAAGACCATAAGCAGAAATAAC  40200
CCATGAGGGCAGAACTGAGAATAAGAACTGAGACTAGATCCAGGGGGTCAGACCAATGGG
CCATCAAACCCATGATGGTTTGATGCAGAGTCCACTCTTTCAGCATTCATAAGAATTGAG
TAGGGGGGAGTAAGGGTGGGGTGAGTACGTACGGATCTTCCCAAACACCCTTCCAACCTA
CAGCTATGCACCTCAGCCAGGTGTGATTTCTGTGTAGTTCACAAGCCTCAGTGGATTTCT
CTCCCATGGGATTCTCCAGCCTCTTTCTGGACCTGTATACACGGTAGTTGGGTTGGTTTT  40500
TTTTTTCTGTCTCTCTTTTTTTCCCCCACTACAATGTCCCTCAGCAAACATAGTCCTCA
TCTCTCAAACAAACAAATCTCATTCTCTAAGTACCCAGATAAGAGCTGATTTTGCTTTA
AGCCTGTGGGGAGATGCTGGACTATTATAAAGGTATCAGTGCTGCCTCTTCTCCAGACA
CCAATGTTTTTCCATTTAATTTCCTGAACAGGTCAGGAACACGGTGCAACATGATTGTA
AGCACAGCACGTTCATGGAGCGAGCTGCTGCTGCAGCTCAGAAATGCAGCAGTCAGATTG  40800
TGATATGCATCTCTTACACAGGAAATTATGCTCTATTTTATATTATTAAATCTAGCATA
CGAGAAAGGACATCCAGTTTATATCAGATCGTGCAAGGAAGTTAATTATTTTTAGTTTGA
TCATTATCATCGGCACTGCAGCTGTAGCTAGGGAGGGGTTGAAGCTCTTCAGCTATCGAC
```

FIG. 14M

```
TCCTTCATATCCTCCACGTTACAATTGTGTTTTGCAGGTTGACTGCAGCGAGTACCCTA
AGCCTGACTGCACGGCAGAAGACAGACCTCTCTGTGGCTCCGACAACAAAACATATGGCA  41100
ACAAGTGCAACTTCTGCAATGCAGTCGTGTACGTACAGCCCTGATTGCATTCACGTTGTC
GGCTGCCTCCTACAGGCACCAGCTTGCACAGTTCCTGCTTTCGTTGCTGATTGCTGACCA
GGATCTGGGGCAGAAAAGAACACCGGGCATCACGCCAGCCATTCATTTGATTTTTCACC
AGAGCTTGTCTGGTTTGTTAGGATGGATGTTTTGAACGCCATTAACCTTAAGGGAAGTTT
TCCTTGCTGCGAAGAAAATCAGATTTGGTGTTTCATTATAGTTTTCAGAAGGGGTTAAAC  41400
GATTTCACTCATCTCCTAATAATCAGGTAGCTGAGGAGATGCTGAGTCTGCCAGTTCTTG
GGCTCTGGGCAGGATCCCATCTCCTGCCTTCTCTAGGACAGAGCTCAGCAGGCAGGGCTC
TGTGGCTCTGTGTCTAACCCACTTCTTCCTCTCCTCGCTTTCAGGGAAAGCAACGGGACT
CTCACTTTAAGCCATTTTGGAAAATGCTGAATATCAGAGCTGAGAGAATTCACCACAGGA
TCCCCACTGGCGAATCCCAGCGAGAGGTCTCACCTCGGTTCATCTCGCACTCTGGGGAGC  41700
TCAGCTCACTCCCGATTTTCTTTCTCAATAAACTAAATCAGCAACACTCCTTTGTCTTGT
TTAATGCTCTGCCTCATGCAATGTTTTCTTCTGATTTGTTGGACGGTGATACCAGACTCA
ATATGTTCCATGCTCGTGGCTCTGGGGTATAACAAGAACAACATCTTGCTCCCATCCCTG
TCATAAAAGGCAGAAAATTAAATACAGATGCATAAACCTCGGCTGTGTGACTTTGCGCAT
AAATGACAGTCAGCCTCCATTAGTGTTCAGACCCTTTTAGACAGCTGAAATACTGCTACG  42000
AACTGCTGATGCTGGCTGAGCTCCCCATGGTACGTGTGGTGCACTTTCCTGCGCAGCAT
TAGCAGTGAAAGCAGCTCAGGGTGCGGTGGTGGCCAAACCCAGGGCCGATCCCACGGCCT
CCTGTACCTGGTCATACCCACGGGCACAGCTGCTAGTGAGGTGCGTGCTTTTCAGACACG
TCATATAAGTGTGCCCTGCCTACATGTCTGGGTCCTCCAAATGACGTTGCAAGGTTTATC
TCATCTTGGAATTGTCCCTTACTGACCACCAAGTGTTTTGAGATGAATGCCCTCCTAGGT  42300
CTGGTTCTGCTCTTGCCTGCTGGTCTTTTCTCATAGTAGTCCTTGCCAGCCCAAGTATCT
GAGCAGTGTTTTGCAATCCAAGGACAAAGTACCCCTCTGCCTTTGAGAGTGTGACCTCTG
TCATTGGCACATTGTCCGTGAAATATATTTTGCTTTTGTCCTTTGTTGGTGTATTGAACT
GATGTTTTCTTGATCCACATGAGAGAAACTTTAATAAAAATTATAAAAAATAATGCCTCC
CTTAAGCATTTCTTTTCCCTGATGGAATGAGGCCATTCAAAAGAAGGATGCTTTGGCGGT  42600
AAAACAGAGGATTTATGTTGAGATGGGCAGATGAATCAAGCAGTGATTTCCAGTTTGGAT
TGAACTTTTCTGGGATCCAGGCTGTGGGCCTCATGTCATTCTGTCATCATCAGGCTATCA
GTCTGCTGCTGCAAATCCTCCCCACAACGCTAATGGCTTTTAGGGAAAATCGCAATTGTT
AGTTCTTTGCTAATGCCCATAAAACTTCTTCCATCACTTGTCCAGCTCCAGGACTCCCTT
CAGCCCCAGGTTTCCCTCTTGCTCTCTCTCCCAGTTCAGTTTTTCTGGATTTGCTATGAT  42900
TTGATGATGCATTATTGACAGGACAAGGGGAAATGGTTTCAAACCAGAGGAGAGGAGATT
TAGACTGGACATAAGCAAGACATTTTTACAATGGTGGTGAGGCACTGACAGAGGTTGCC
CAGAGAGGTGGTGGTGCCCCATCCATGGAGACAGCCAAGGTCAGGAGGGGCTCTGAGCAC
TGATGGAGCTGTGGGTGCCCCTGTTCATTGCAGGGGGTTGGACCAGATGGCCTTTAAAGA
TCCCTTCCAACTCAAATGCTTCAATGATTCTGTGATTCTATTGGGTTGAAGCATGCCAAC  43200
TAAGACTTTCCACTCTGGAAAACATTCAATTCAGTTCAACAACATTTTCCAGCAACAGTG
AGAAAGCACTGCATATAGGTAAGCACTGATAACATGCACATGGAGGAAATCCTGCAGCAT
TCTCTCTTCAGGTTTGTACAGTTGCCCTTTTGCCCACAGGAATTTTCCATGGTCCTTCAG
CAGGCACCTGTCACACACTTCACTGGAAATAATGAAGCCGAGGGCGTACTTCACATATTT
AAACCTGCAATTGCTGTTGATAAAGAAGCATTCTTTGTGGCTCACTTGTGTAAGTGCCAT  43500
CAAGATTTACAACCCTGACACCAGAGCTGGAACGCTGGTTATTTCAAAGTAGGGGTGGC
TAAACCAAACGTGAATGCACACAGCCACGCACACACAGATCAGGTGGCCATCCAAGGGCA
GAAGGGCCGCATTCCATGAGCACGATGCACTTCTGCCCTTTGCTGCTGCCCAGGTGAGTG
GCTGTGCTCCTGCTCCGTGCTTCGTCGAGTGCTGGCTGTAAAAACACAACAAACATCCTC
AGACTGGAAAGAGCTGTGTTCTACAAGGACTTATTTACTCCTAGAGGGATGGTGTTGAAA  43800
AGACTTGACATCAAAGACTATCACTTATGGGGTAATATTTTAGCAACAGAACTGAGTGGG
TAAGAACAACTGTGGGAACAGCTCCGCGCTCGGTGCTAGTTTATGCATAATGAAAGCAGT
GACACGTACGTGGTACCACGACATCCACCATTGAACCTCCGAAACGCTGCAGAATACAA
ATTCTTTTACTGAATGGAAGCGAGCGTTTCCCGCAGTCATCCTGAACTGAGATGCAATTG
GAGGGGCTGAGCGGCTGCAGCAGCGTTAGGGGAGTTTCACCTCGCTGAGCCCTCCCGTTA  44100
```

FIG. 14N

```
TTTCAGTGCTGTTGTGGAGCTGCACGCAGGAGCTGCCGCCAGTCCGTGCCAGCTCTGCGG
CCCTGCTTCCCCGGCACCTTGCTTATCTCTGAGCACCTGTCCTTGCTCATCCTGTGAATC
ACGGAGAATTGCTTTCTCTTCCTCCCTTTCATTTCGCGCGTCCTTCTCCACCCGGGCTGT
AACCCTCCTGAGAAAAAACGTAGTACGGAATCGATGTTGTAAACACTCAGCGTGGCACAA
CGTTTTGCCTGAAATCCCTTTTGTCTGAGAGTCACACACTGAATTGCAAGTTGTTTATTC  44400
AGGACATGCACTCACGGATTTTAACACTAACGAAGGAGATGAATTGCATTTGTGTCACAC
TTCCTATTCCCTTCTTTACTCCAGACCCCACTGCACTGAAGGTAAGGGACAGATCTTTCA
GGTTTTTTTTTTTTTCTCCATCATTTCTTTCCTCAAAGCAGTTTCCGTATAAATCATT
ACTAATCGCATTGTGATCGAGCGTTTGAAAGCCCTGAGTCATCCCACAGCCTGAGCAATA
TTTGCTACAGATATTACCGAGTGAAATGGCCATTTTCATCTGATGGTTTCAAAAAAAAA   44700
AAAAGATAATAATAATAATAATAATAATAAATAAATAGCGCAGCATTCAGTTGGTGTCCA
AGTTATTGTCACGGTTACTGCAGCAGCACTGAGGATGTTTACATGGATTTACATCACTG
GAGGCTGAAAGGGCACTGCAGGCGTGTACCGCGCTATTCGCTGCCCCATCCTTAAGCTCT
TCTTTGACATCTGCTGATGGTCGGTGCTGGGGAAGCCCGGGGCTGTGGGGGTCTCCTGG
CATCTGCCCTGCTGATAGCTGTGCTGCTGAGGGTATTTCTGTGAGCACAAGGCTGCATCG  45000
ATCCACAGGGCGACTGCAGTGCCTGCGCCGTACCCGCAATTTCTGCTCTCGGGAGCGCA
TCCCACACTGCGGGTCTGATGGCGTAACATATGCCAGCGAGTGTTTATTCCGCAATGCAT
TTCTGGGTGTATGAAAATAAATCTCTTCGCTCACTGAGTGGTGAACTTCAACTGTCTTAT
CAACCTCAGGGACTGCCTGGAGATGGAAGGTGGTTGTGTTTGGCGCTCTCCTCTTCTCTT
GCTAGCAAGGGCAGCACTTTTTTTTTTAAACTGGGAGGATTTACCAGGGACTCCTTTCTT  45300
TCAGGTAAAAAGAAGTCACATTTAGCAGAGATCTTCATCTCCACGTTGGGTAATTTGCTG
AAGAGCTCGCTTCCAGCAAATACAGTCTATTTCCTACAGCCTATTTGTTCTTCTTTTAAA
TTAAGTCTTTATCGTGCCTTTGAATGTTAGTAATAAGAGGAAGTAGCTGGAATAGCTTTC
CGAATGTTCTGTTTTGGTTAAGTTCCTCTGTGATGTATCCTTAAGCAGAGGGAGGGATGC
ACAGCAGAAGCGCAGAGGTTCAATCTCTGAGGCCCTGAGCTCTTTCTCTCCAGAACTCAT  45600
TGAGTTCTCACCTTGCTGTGCCCTGCGCAGCGCTCACATCACAGCCCACCGGGCTCCAGC
TCAGACAGGAGGACCCTCTCTGGCTGTGTTCCTTACAGGGGATGCTGCCCAAAGCCTCGT
CCTGAACTTTGAGTGCTCCTGATAAAGCCTGAAGCTATGCTCAATAAAAAAAAAAACCT
TCAGCATTTTGGTCTTGCTTTCATACTACGTATCATGCTGTTGTTTTTTTTCTTAAGAT
GCTGTGTGATTGCATCACTGCAACAGTCCTGGGGTGTGGGTCTTAATGGGAAAATTACAG  45900
GGAGAAAGAACGGGTTGTCTGATTTATGAAGAAATCAACCCCTCCAAAAGGCCATGAGCT
TCTGCTTTCTTCCAGATTTCCAAAAGAAAGCCACTGCTGGGGATGAGATCCAGTGCAGTG
TTCAGGGCATCCTGTGCAGACATTGACTCCTTAGGAGCTGAAAATAAAGTAGTGGTGGGT
ACCCGTAGGTGTGGGAAGCCTTTCTGCAGCCACCTGGTCTGCCTCCCAAAGCAGAGGATG
GGATGTTTTCCCCTCCGGGCAGCACCAACAGAGGGTGGCAGCAGGGTGAGGAAGATGAT  46200
TGGCCCCTCTGCTCTGCTCTTGTGGGGACCACATGCAGTATTGCATCCAGGCCTGGGGCC
CCAGCATGAGAAAGACGTGGAACTGTTGGAGTGGGTCCATAGGAGGCCATGAAGACAATC
ACAGGGCTGGAGCACCTCTCTTATGAAGAAAGGCTGAGGGAGCTGGGCTTGTTCAGCATC
AAGAAGGGAAAGCTGAGAGGACACCTCATTGGAGTCTTCCAGTACTTGAAGGGAGCTTGC
AAGCAGGAAGGGGAACAAACTTCTACATGGTCTGACAGAGATAGAACAAGGGGGAGTGGC  46500
TTTAAGCTAAAAGAGGGAAGATTTGGGTGAGATGTTGGGAAGAAATACTTTACTCAGAGG
TTGGTGTGACACTGGCACTGCTGCCCAGAGCTGTGGGTGCCCCATCCCTGTACATGAGCT
GAAGGCCAGATTGGATGGGGCTCTGTGCAGCCTGATCTGGTGGGGGCAGCCAGCCCATG
GCAGGGGTTGGGGTAGATGGGTTGTATGGCCCTTTTCAACCCAAACCATTCAATGATTCT
ATGATTCTCAGATAAGCCTGCCTGCCCACATCTGAGCTCACGGTGCTCGCTGGGGGTGGG  46800
GTATGGTACACTAAATGATGCTCAGAGGACTGCACGCAGGACCTGCCGCAGACGTTTATC
ACCTCACCCACCACTTAGCTGCTGCTTGTAGTTAATTACGTCAGCTGTCACTTGTAGAGA
ATCCTTTGAGATCCTTGGGCCTCCGGAAATCTTGGCTGATGAAAGGAAGGGCTCAGAGTC
ATAGCGTTAATTTATTATTCATTAACACCAAAGTGTCGGCTGTACGGGCAGTGGGCTCAC
AGTCAAATAGTTAATGATCTTAAGTGACAATGTGTCACTTTGCAGACAGCAGAGAGAACA  47100
GCTCTCCTAAGGGAGACAGCATCTTTCCAATTCTGCAGCCATTCAGTGCCAAGCTCCTCT
TTGGGACGAAAGTGAAGATGAGGAAGGCAATGAGGATGAGGAGGGGCCTCAAGGAACCTG
```

FIG. 140

```
GCTGGCTTGGAGACAAGTGATGATCCCAGCTGCTCTCAGGGTCCCAGCGGTCTTCAAAGG
GCATCTTGCAGGGGCTGTGTCCTCTGAACAGCAAACCCAGGTCATAGAGGGGAAAGTGT
GAGCAGAGATGGGACAAATCTCCCATCCTGCCACGGAGCTGCACTGCTAAGGGGGTGATG   47400
GGGAGCAGCATGGGACCCCAGCGTTCCCCCCATCCCTGCACCAGGCCCAGCTCTGCGGGA
TGGCGAGGAGGACAAGGCTCTGTCACAAGCATCGCTGGCAATTATTATTTTGTTGTTGCT
GCTCAATAAATCCTGACACAGTACAACACAATATCCTCTCATCATTACTAATCTAACTC
TCCCTCCAGGAAATTTCAGGCAGGAAACGTTGTCTGCCTGCCGAGGTGCTTTATGGCACT
GTTCTTTAGTGGTACCTCAGCACTTCGTGTCATTATCTGGTGTCAGTGAATTTAGGAAAT   47700
GCCATTCAATTACCCCGCAAACTGATTAACGCATTGCGTGCAGTTATTTTGTTCTGCTCT
ATTTTATATCAGTTCCTCTGTTTTATGTATTTCTCTACTTGTTGCTGGCCAGAACACACC
TCGGGCCAGTCTAGACCTTGCTGTTGATGCAGCTTTTCCCCAGGGCTTCATCAGCACAAA
TGGTTTGTCAACGTGGGGAAAAATAAAATTATGCTTAAAATAAAACCACCTGGAGATGC
TGTTCTGGGGTCTGGCTGTGTCACAGCTATTGCAGCGATGGAGCTGAGGGATTGGGATGT   48000
GCTGGGCCGGATCCTCAGCGCTTTGCTATAAGCCAAATAATTCCAGACACCCTTCTTCCC
TCAGATATCATCTGTGCTTAAGCAGCAGGAGATATGCAGGCAGCGATCAGATAGCTGAGC
TGCAAGGAGAAATATCACAAGAGCGCGGCTTAGAGCAGGGGCTTTGCTCGCTCTAAATTG
AATTCCCATCCTCATAGGAGATCCAGTCCTGCCCCGTGTGCATCGCTCCGGTAACAGCA
ATGTGTTTTGCTCCATCTTGCAGAGGGTCCAGAAGCTGGGGAAAGGAAATGTGTCGTGCG   48300
TTCGTCCCTGCAGCAGCTCGGCCCATAAAATTAATGAAAATCTTTTTTAGGTCATGGTAG
ATTACAGATTTCTTTGAGATAGAGAATCTCAAGAGCAGAGGAGAAGATTCTCAGAAAATA
GCAGTGATATGAGATGGCATAACGCTGAGTTGGAAACTGGGGAGGATTTCCAGGGTTACT
GGAAATTTACTTAAGCACGAGAGAATGCATCGTGTGACTGCCAGTGCTTCCCCACTCACA
TGGCTATAACCTTCTTGCATACAATTACCATCTTGGAACTTGAAATAGCTGAAGAGTTT    48600
TATTTGATCTTTTCAATGGATCTTACATCTGCAGAAAAAAAAAAAAAAGGCTAGAAATAA
TCCTGCACTCAAACTCACTTTACTGAACCACCATCATGAAACTCCAGCAACACACAGGGA
TTTGGGCAGGCGTGTTCATCTTCCTCTTCCCATTTGCAACATGTGTATGGCATTTCCTGA
AGCTCACTCCTCCAAATGCATTGAGACAGTTGTTTTTCATTCTTCCTAATGCCTGCATCC
ACCCATCTGCTGATCGGCAATTATTTCTATCCCATTCCCTTCTGTTTCTTATTAATCAAG   48900
CTCTTTATGCAATCCCACGTAACACTTTGCCCAGCTGCCCTGCCCTAACCACTACCAATT
ATCTCATCCTGTTTTATAGACCCTGTAGCAAGACTCTGGCCTTGCTCCTCTTCCTCTCCC
TGATAGAGCTTTTGGTGCAGGGCTGGCTGGCTCCTCAGGTGTTCAGAGGATCAGAGGTCT
CCCAGAAGGATCTTGTTAATCAAGGACAGGTGCTGGCTATATGGGAGGATGGCACCGTAT
CCTAAAGCTCTACAAGAAGGAGACGGAGCTCAGCCTGGGAGGACAGAGAGAAGCAGCAGC   49200
ACAGGTTTCAGGATCCAGGGATGGCAGACCTGGGTGTGGGCTCATAGGATTGAAGAAGGG
ATAGGCTGTGCTCCTGTAGCCTCACTGCAGAAGCAGCACTGCTATCTCCCCAGCGAAGCT
GTGTGTGCCCCATCCCTGGAGGTGCTCAGGACCAGGTGGGATGGGGCCCTGGGCAGTCTG
AGCCGGAGGGAGCAGCCGGCCCACAGCAGGGGTTGGAATGGGGTGGGTTTTAAGTTCCCC
TCCAACCAAAGCCATTTCTTGATCTCTGTTGGTGGCTGGTGCAAGTTCTGAGGAAACCTC   49500
ATTTTCAGCTCAGGCGTTCTTGTCCCTGGGGAAAATCAATATTAATGCTTCAGTGATTA
CTGCTCGCCTTCCAAATGTGCTTCTGATCAGTTCAAGAAATCTGACAGTCACGTCGCTCA
GGATGCTAAGAATACAACAGAAACAGCTTTGAAAGGAACCCTTCAACTCTTGATATTTGT
GAATGAGCTCCAAAGAACATTACTCATTTATTTTCAGGAAATGATTTCATTGACATGA
ACAGGCCAAAGCCTACAAGCTCTGTTTTGTGACTGCAGCTCCTTACACTTTCAGCTGCAT   49800
TTTCATGATTTATGTGCCCATGATGAGACTTGAACACCTCCCAGGATAATGGGAAAAGCA
GTTCTGATTTCCCATTTAAAACGTAGGCTGCCTTTAAGCCATGTGTGTGGCTCAGGCTCC
TTCTGAAGCACAAAGGTGTTCCACCCCTCGCTCCTTTTTCATTACAACTTTCAATCAAAA
ATGTGTTTTATGAGATATTTGTTTTGCCATGTATCTGTGACGGAGTTGAACCCCTTAGTG
AAACCTCTGTTCTTCACTTAGCTGAGAGGTATTTCTTAGGGAATGTGATGCCCTAAATTT   50100
ATTGTGGTGTAATAGAAGGGGGGATGTGTGGACTCACCTTCTGTTTGTTGTGGCTGCAGT
GGTTTTATGCACTACCTGAGTATTAAGCAAGCCCTTTTCATCTGCACGGAACACCTCCTG
CTTGCCAGTGGGATGAAACAACAACAACAAAGATTTAAGGTTTGCTATTCTCAATGTTTC
TTAATCGGGTTCACATTGATTGCCAACAGATGAATAATTCCTCCTTCTCCATGGATGTAC
```

FIG. 14P

```
CTCTTAAACTTGTGAAGTCTTAGGTAACGCTTTTCTGCTGTGATGACTGTTTCAGTCCCC  50400
TCAGTGAGAAATCAGGCGCACCAGTAAGACACAAAGGAGACCGTGGAGATGTTCATTGTG
CCCTCAGCATCTCCAAAAGGCACTGCTGCCTGCCGAGCCCCAGACTTCGCTCCTGTAAAA
GCAAAGCATGTCCAATTCTGCTGTGCCATAAGAGTCCTGTGGAGCCCAGACACGGCGTAG
CGTGTGTAACATAGCGTGCACGAGCTCAAACGCTTTCAACAAATCAGCTTTTTTGCTTTG
CCAACTTCCATATGTAATTTCACAACATCTAGTATTGAGACAGTGCTGTTGTTTGGGCAG  50700
CATAAATCACTCATTGTACAGCAGGGCGCCTCTCTTAACAAGTTGGGTGTAGTTCATGTT
TTTGTCTAATTCCTCTGCGCATCTCTCTAACAAACAACTATTCTTTAGGGCTCGACTCAA
TAATCAATACATTTTTTTCAGTTTACAGAGCAAATAATTACTTGACCTGATGACTTCACA
AGGTTAGGGAGATGGGTGTATAAAGTCTGCAGTGTGAAGGCAGAGCAACATCTCTGCAGA
CCTTGAGAGCAACAGGTCTGCAAGTAACAGGCTGCACAGCCACCTCTGCCATGGAGGCAA  51000
TGAGAGCTGCTGCCCTCCTTGGATTGGTGCTTCTCAGCTCCTTTCCTGGTAAGTTGTTTT
TGTTACATTCTCTGCTTATATCTCTACTCCTACTGAACTAAATGTGGTTCAGGATGCCTT
TAGAATCCTAAAAGAGAGCTCAGCCTGCCGGAGAAGTGATGGTTTGGTAAAACATGAGCT
CTCTTCTAATGATCTTATCCTTGTGCAAATATTTACGTAACTCTAGCAGGATGCCTCTG
TCTGACATAAACTCATTATCCTCAGTAAGTCTCATAGCACTCGAGAGAGAAAATGTATAC  51300
CCTATTTCTTCCTTAGTGAGTCAAAGTTTATATTTTCACCCAAAATGGCTATTTTTTTA
ATCATAGGATATAGCTTGCTTATAGGAACTGGATAAAATATTTAGGAAACAAGTAATTCT
CAGTGATAAAAAGAAGTATGTGATGACTCTGTAGGGAAATTGATAATTCCAGAGGAATT
GTAACCAAGGACGCCGTAACATTCTGTATTTTATAACCTCTGTTTTTTCCAGATATTGTT
TCTGGTCATCAACGGGTGAGTAGCAGATCTGCATCATTTAGTTGTGGTTTCTATGAATAG  51600
ATGAATAATTCATACTCACACCATATCCTACGGGAGCCTAGAGGGAGAAAAAAAAAAAG
AAAAGAAATAACAAGGGAAGGAGAAAAGGGCCCCCAGGAATTATGTGACATTTTTCCC
CCAGCAAATAAGAAAACATCTTTGTCAGAGAAAGATAACGTACCACGTTGGTGATAAGAG
TTGGCAATTAATAATGCAGAGTGGGAGCCGGCGTGGCACAGCGTGCCAGCAGAAAATCTG
CACAGCTTTTCCCTAACTGCCTCCATATCTCCCTGCCTGATTCCTGAGGACCCATCAG  51900
TCAGTCGTGTGTCTGCCATGCCAAAAGCCTCAGTAGTGACACTGTGCTCAGGCATACTGT
AAGGAACGCTGTAATTTGCTCCCACTTCTTCACCGTGGAGGAGTGACAGAGAATAAAATG
ACCGCCTGCAGCACGGCTATGCGTGGAAAACACAAGCAGACCCTTCCGTGCCCTGCAGAG
CTGTCCCACTTGTGCTCTTCCCAGGCCTCCTGCGGTGAGTACCGGCTGTTAGGCAGCAGG
AACCTCGCCTGTTCCAGGATCTTCCAGCCCGTCTGTGGCACCAATAACATCACCTACCCC  52200
AATGAGTGCTCGCTCTGCAGAGAAATCCTGTGAGTAGCGATCGCCCGATTACCCATCGTG
ATGGCTCAGGTGGCAGACAGAAGCCTTTTGAATTGTGACTAATCACGGGTGGATTCGATT
TTTTTTCCCCCTGTTTCTGTCTTCCCAGAGTGCAGGCTGTGTTTCTTCCTTGTCAAAACT
CCTGAGTCTAATTAATTAGTGGGGCTGGGCGTGGAGAGGCTTGATGAGTGAGGTGACTGC
ATGGCACCACCAGGTTAACCCTTCCCCTCCTTCTCTCCTAGCCGGAGTGGGACGGTTGAC  52500
AAGAAGCACGATGGGAGGTGTGTGAAGGTATGGTTCCAGCTCAGCCACTGTGTGGAGCGA
TGGCAGAATCCCTTCCCAGCACTGATTGTACATTTAGAATGGACAGCTCCAAACCCATTG
GAAATGTAACAGAAAGGAAGAATTTCAGGTCTTTTATATATATATATATATATATATATA
TGTATGTATTAATTTCATTTGAACAGTGCAAATCTGTTTAACGGTGAGTTTTGAGATG
TTATCTTGTGTAGCACAGCTGACTTAAAACAGAATCCTCTCATTTCAATAATCCTTTGG  52800
TGTTGTTGAAATAGTTCCCTTTAGACTTAGACAGAAGTCTGTTGAAATTAAGAAGTTCCC
CAAGGAAGTCTGGATTTTGACTAAATCATAATTTTGTAACAGGGAAAAGAAAAAAAAAA
AGGATTCCATCAGAACATCTACCCTGAGGTTTGTTTATCAATACACGGAGCTGCCACGAA
GTGGAGAAGTGTCTCTATTTTAGATTAGAGAGATAATGTAAAGAAACACTCCGGCTGTG
CAATTGAACATAATGCTACAATTTTCACTTCAGTACACTCAGAGTAATGGCAGGAACACC  53100
GAGGTGAGCATCAGCTCCATTTTCAAGTGGAGCAGACATTTCACAGCAGCAGTTGCTGCC
ATGTAGGGCATGTTAGGCACAGATCCTATGTGGTGGCATTTGGGGTGGAAAGCCCTAAGA
TGACACCAACAAAACCCATTCTGTGAACCCATTTCCTCCAGGATTCTGCTGGGCTCATGT
CCTCAAAGGCAGGACTTCACCTGCCTGTGCTCCCTTGCCCGCACTGTGCTGGGTTGGAAG
CTCACATCTCCATACAGCCCCACTCACCGTGAGTCTGGGGGTGGGAGACACCTCTCACAC  53400
CATGCACCATTACACAGGGCTGACGGAAGTGTTGTTCTGTGGCTGTTTCAGGTTGATTGC
```

FIG. 14Q

```
ACTGGCTACATGAGAACAACTGATGGGCTTGGAACAGCCTGCATCCAGCAGTACAGCCCG
CTCTATGCCACCAACGGGCTCGTCTACAGCAACAAGTGCACCTTCTGCTCGGCAGTGGCG
TGAGTGGTGGGTCACACCCTGGGTGCTGGGGTCTGGGTGGTGGTGTTTGCAGCATATTGA
GGCTTCTGGAGTGGCTGTGCTGTGCTCATTCATTCTCAACTTGCTTTCTTCCCCAAGGAA  53700
TGGAGAGGACATAGATCTGCTCGCTGTTGGAAAAGAGCCCGAGGTAAAGCTCGAAAGTCT
GCGCTATGAACTGTTGTTATAATATATTATACAGCACAAATTCAGTGAGTCAGAACTACG
CAATAGCAATGTCTTCACTGTGCTGGTGTATTTGTCCTGGAAAAAGGGTTTGAGGAAAAT
GACTCAAGTATGCCAGGGTCAGAGGACGATGAACAAAACTCCTGGCTCCTGTGTCAGTAT
CACCTGCACAGCCCTGACAGGGGTTGATGCTCAGAGCATTGTTCAGATGGTGGCTGTGC  54000
CAGAGGTGCTCACCGCTCCTGGTGAGCGTGGGCTCATGCAGCACCAGCTGTCATTACTT
GGGTGGGTGGACTTCATAGTGTGCTGTTGGAGACACACTGCTTCCTGGCAGCCCTCTCT
GCTGGCTGCTGAACCAGAGCAGAGCAGGTAGCGGGCCGCCAGCCGGGGAGCACTGCTTTG
GCTGTGTCGCTGCTTCTGAGGGTATTTAGTAGATTTTTCCCTCTGACTTCTCCTTTTGTG
CTCTGCTGGGCAAGAGCATTAGAATTTGCAGAGTTGCTAGAACAACAGGAGCCTGCATCT  54300
GAAAAAATGTTTTTTTTGCTTTGCCATGACATAAATGTAAAGCGCCCATGTAGGAAAATA
CACCAAACAAAGGCTTCTCAATACGTTCTTGCTCCATTACCTACAGATTGACTGCAGTGA
ATTCAAGAGCACTGATGCCTACTGCACTGAAGAGTACATGCCCCTTTGCGGCTCTGACGG
CGTAACGTATGGGAACAAATGCCACTTCTGCATTGCAGTTTTGTAAGTACAGTGCTCCCC
ATGCAGCCATGAAACCACTGCTGTGCCGGAGTATGAAGGCAGAAGCTGCCAGGAAGCCTT  54600
TGTGCTCCCGTTATCCCCTTGGTAAATCCGTCCCCATCCCCAACCTGATCCCAGCTCTAC
CTCTGCTGTGCCTTCCCCAAGCACTGCAGATCTTGAACACAGGTGAGTCTTCTCCCTCCC
TCACCATTAAATTCAGATTCTCATTTGCGGGCTCATAGCGCTCCTGATCCATCCCTGCGA
GAGTAATTTGAGTGGTAACTGTAGAAGGAGTATCCAAAATTACAGGGTTTGTCCCAGATC
TCTCTAACATGACAAAACGTGTAACCTGGGGAATCAGGAGACGGGTGAAGGTGCAACTGG  54900
GACAGCATGGAGCATTGGCTTGCCCATGCAAAGTCAGCAGTGGCACCATCAGGGCTATAA
AACCACCTTCCATGTCAGTGATTTTGGCCTCCTCCTTTCTCTGCAGGAAGAGTCATGGAT
CTCTGTCTCTGCAGCACCGTGGAGAATGCTGAATGCTGGATCGTAACCTTTACCCTCATC
CATCTTTCACTTCCAAAGCCTGCAATTCCAACACGCTCTTCCCCGCTCCCTGCTGTACAT
TGCTTTCTGCCTTGACCCGCCAGTAAATCACAGACAGCAACTCTCTTCGCCATGGGCTGG  55200
TGTGTTATTTATTTATTTATTTATTGTTGTTATTATTTTTCCAGGGCAGAGGTAA
AAGTCTTCAGGCTTTCAGGCACTTATCTGTCAGGCAGGAGAAGTTTTGAAATAAACCACA
ATAAAGGCCAAAGTGCAACACCCATCACACAAAAGCCATAAGCCCTCACGAAAGTGCGTC
ACCCCATTCCAAACCATCAGAAGAGGAAATGTTGCTATAAAACACATGCTGCTCTCCCA
GTTCTGTGTCTTACAGCACATAAATGGATTTGCTTTAAGAGTCAGGATGTGGCTTTGTAG  55500
AAGCACGGAGCCCTGGAGGAAGCAGTCCTTTTGGGAGCCTTGGTATGGAGGAAAGATGGC
TTTGATACACCTGAGCAAGGGGCAAGTCTGGCGGCACGTTACAAGGAGGCTTATGGCAAA
GGGAGGAGACTATCTCACAGGGAAGAAAATTAGGAACTGTTGCTTCCTTGAAGGGTGTGT
CCCTTGAGAGTGTGGTGATCAGCAGAAAATTGCAGCCAGCTGGGCAAGGCTGTAATGAGC
CTAATGAGGACCAGAGGAGAAACCAGATTGGGCTCAGGCTTCTTGGAAAAGAGATCTGAA  55800
AAGCTGCACTGGGAGCGTTTGAGGCAGAGGAAAGAGAAAGGACTCTTCAGGAAAAGGTTT
GGGAGTCTTCATGCCTAGAAAAGAAAGGACAGAAGGAGTGCTTGGTAGCTCCAAGGTCGT
TTCTGTCTGCAGTGAAAGGTGATGTGTGGATGATGCGTGTGAGCGTTCACAGTGATGTGC
CATCTCTTTGGGCGAGTCAAGGAATGAGTATGCAAACAACAGGTGAAAAGTCCCAAGTGC
CTCCACTCATGCCACCTTCCCCTTCCTTTCTCCACCTCCCATCCTCTCATTACGTAGGAA  56100
GACATTCAGCTGTTCAGGCTGATATTGAGGACAAAATCTGTGACTTCCAAGCTTTTCTCT
GGCTTTATTTCCTGAAATAGGCTGTATCTTGACCTAGAAATCTTATGGGTGCTTCCTGCC
AGAAGATGGGAAGCTGTCCTTTAATAGCGTGTCAGGGCAGTGCTCCGTCCTAGGAAGACA
GATGGAACTTTGAAATGTTTATTCTATTAGCACAGGCAGTATAAAGCACAGTGTGCCTCT
GTGCCTGCTGGTGAGAAAAGGCAAGCTGCAGAGCCGTGAGGGTGCTCCCTGCTAATCTGC  56400
CTAGAAGGGAAAAGAGTAGACAAGAAATAGCATATGCTACTACTGAATGTGAGCAGAAGA
CCTTTAGTGAAGGACACAGCTCAGCTGTAATGTCCTGTTGGCCAGGAGGTTTGTTGAGTT
ATCGCAGAGCGGTAGAGTTCTGGTCAGAGCAGGAAGGTGCCTTCAACAGCAAGATCCCAT
```

FIG. 14R

```
GGTAGGCCTCTTCTGCAGTGTGCTGGCACAAGCCTGGTACCTGCTCAGGAGCAAAAAAG
GCTTTGGAAAAGCTCAAAGAAGGGCTGATGTCTTACAGGGAAAGGGAGGGCAAAAGGCAA    56700
GTGCAGAGCATATGGCTGTACAGACAAAAACCCTTCAGAAAATGGAAAAGGTTTTTATCA
AGTAAGCCCAGAAGTTGGCCCAGTGCAGGTAAACACTTGGCTAGGTAACAGTGAGGCTCT
GCCCAGCCATACCCATTCCTCTGTAAGGCAAATCCCAGGTGCCTTTGTCTTGTCTGGTCC
TGTTCTGTTCCTATTTTTCTGAGAAATCAGACAGAACTTCCCCACCTACAGCATCAAGCA
GCTACTTTATAGGTGAAGAAGTGCAAAGAGAAGCAATAAGGATAATCACCACTTGGCTAA    57000
TTTAGTCTCTTCCTCTCAGCCCACAAAGGACTGGTCCCTGTGGTACATTTTCTAAGGCTT
TTCCCAGTCAGCTGTGCTGTAGCAAATGAAATGTTTGGCTAGATAAAGAGCTGAGGTATT
AGTGCTGGGGCGGCGAGCAGTGTCTGGAGCAAGAAAAGGCAAACGAGGGATTCTGCGAGT
GGCAGAACTAAGCCTGATTTTGAATGGCGTTGTGGCTGGCGGACTTGTAAATTATATGAG
AGGCTGTGCTGTGAGCTCACCCTAATAGACATCTGAGAACTCACCTGTCAATCGCGGTTC    57300
CTCTGCTGTGTGGGTTTTATGGTGTCTAGTGAGCTGCAAGCTCTAATGCTTTCCCAGGTG
CAGGGCAGTTGTGGCATTGCTCTCCTACAGAAACTCTCACTTGCTGGCTGAGGATGTTTA
GGAAGTCCTTGGTTGCTAGAAAAATATATTGAAGTGCTTTTTTGTTTGTTTGTTTTCC
ATTCTTGTGTGAAATTTTGTTGGAATCACAGAATCATAGAGGTTGAAAGAGAAACTCTGG
AAATTATCAAGTTCAACCCCTTGCTAAAGCAGGCTTCATACAGTAGGTTGCAGTTACAAC    57600
ATTTGCTGGGGAAATGAATATGAAGATCTGTCTATAAAGAGTGTTCCCATAGCACTTGTT
TCTTTAGGAAAGCATGCTGAAATTCTAAAGGCTGTGCCTATCTGAAGAGATACTTTGCAA
GTGGTGCAACTAAATGCTGCTCTTGGTGGAGAGATGGCTGGAGATGGATCGATGGTTGGG
TGATCTTCGTGGTCTTTTCCAACTTTAATGATTCTATGATTCTATACTCTTTACACAGAA
TCAGCTGGGAATAGAGTGAGAGTCTCCTGATTCCCCACCAAATTCCTTTGATTGATGCTT    57900
GGTGTGGAAGCAGAGCTCTGGGACACGTTGGTGAGTGTGAAAACTGGAAAACATTGACAG
CTATAGTTTAAATAGTTCAGGGAGGAGAGGCAGCCATCCTATGTGGGACTCTGCACACGG
CTATGAGAGCATCAGTGCGCTTCTCCACCCCAACCCAACAAATTTAGAGCCATCCTCCAA
AATAGCCAGGGAACAACGCATAATTGGTTTCACAGACAACACATTCTCATGCTGTGATTT
ATTTCGTAATGTCTGGTGAGTGTCATCACGCCGTGCTCAAAGCCTGGAGCTGGCATTCAG    58200
CGAGGACCCAGAGAATGAAAATTACCAGCTTCCCGATGAATCACCACTTTGAAAATTCA
CCCTTGTGAGAATCCTGTGACTATTCAGAAAAAAAAAAAAAAAGAAGAAGAAGAAGAAG
AAGATATTACAGGCCCAAGTCTATCAGTCATGTAATTAGCCCTTTCTAGGTTTGATGTGG
ACAGGGCGGCATTCCTAAAGCACCATAAACACGGCCGGGACCAATAATGGCTCTAGAATC
GAAGCGGAGAAGTTCTCACAATTAAGGTGAGGAATGAGGCCAGCAGCGGATAGGTACATA    58500
AATACACGGAGGCAGGGCCGTGAGCACGCTGTGGGCTTGTGGCTGAGACAACACCTCCCA
AACCGGTCGCTTGCCGGGGACTAAAAGAGCAGCATGAAGGCAACAGGCACCTCGGTGCTC
CTCAGCCTGCTGCTGCTGCTGTCGTTCTTCTCGGGTAAGTTATATTTCTGTAGCCTAGAA
AGAAACTTTATGACGAGAGCAACTTCAGAGAGCCTTGATCAACGGATGACAGGCTTGAAG
AGAAAGCTGAGCAAGTAGAAAATATCTGCGGGACTCGCTTGCTTGTGTCACATCTTTCCA    58800
TTCCTCGTGTGCCTCCGCAGTGAATAACACTGTGGAGGTGTCACTGGGAGACAGAATGAG
CAAATTGTAAGCAGCTCGTTCAGCAGAGGCACCAAAGCAGAGCGTAATTATGAGTTTTGG
TGGAAATGTTTGCTGGAGAGCTTTGCTGAACCAGTTAGAGAAGAAACTCATACCTCAGGG
TCATCAGCTCCTGTTCTGATGCTAAGCACTTGGGGGTTGGTGTTCTCCTCAGAGATGTGG
CAGCGTAATTAGATGAAAGTTTCAGCTTCCAAATACGTTGCAGAGGAGGGCTCGAAAATT    59100
AAATTCAGATGTCCTCGAGGAACCCGAACAAAGAGGGCAAATTGAAAGGGTCCAGCGTTT
ATTTATCTTGAGGTTTACACGTCTCTCTGTTGGTCTGGGGAGGCTGGCTGATGGTTTGGG
GGTGTGTAGGGCACACCGGGGTGCTCAAATGCTCGCGTGCGGCCGATGCGAATGTGGAAG
CGTTGCGGTGGCCATTACTGAAGACTGCAGACCAAGGATTATTTATACTTGTTTTCTGT
GAATAATTTGAATAAAGAATTCGCTTGAGAAAATCGCAGGCTGTGCATGGAGAGAAGAGG    59400
TGAATTACTTTGTACACATCATTAATTATGAAATATTCATCTGTCTTTAATTGAGTCTTA
ATTGGGGCTGGGTTCCGTCAGAGTGCTAAAGCTTCTTTCCAAGGCCAGGCAGAATAGCAG
CAAACTCTGTGATCTCAAATAAGATAAACAGATGCCAAGAGACGTTCTCACAAAGTCTTG
TGTAGCTGCATGTAATATTTATAAAAATTATCTAATGAGCTGTTTTGTAAATAATATGCA
GATAGCCCTAACGGCGGCTTCCCTGTCCAGCCTAGCTGAGGATGTGACAGATACAGCAGT    59700
```

FIG. 14S

```
GGCAAGGATCAAACACTGAAAGGCATCGCAGCAGGCAGAAGCTGGGTGGGGTGATGGATG
GTCCGCTGAGCGTGATGCTGCAATGCTCCCAGCCTGCACCCTAACCAAAGGGATGCCCC
ATTGCAATGCGCCCCAGCCCCTGCAGCGCTGTGTGCAGCCCACTCCCTGTCCCGACACC
ACAGGATCCATCCCGTGGCTGTGACCTGGCCCCATGCAAAGTTTGCAGGCAGGAAATAGC
AAAGAGGATGGACTGATTGTCTCCAGGCCCAGAGCCTGTGCCTGCAGCAGGTATTTTTGC    60000
TCTGCTGCTGTCTGGCACTGCCTGTTCTGCCCCAGATCACGCCAGGCTATCCCTTTGTAT
CTCATCCGGATGAGGCTGTTCTGGGAGCCTCGGCTGTGCTGTACTGCAGACGGCTCTGAT
GCTGACTGCGGGGTCTCCTCCATCTCCCCTGTGTGCTTTTGTTACCGTACTGGCCAGTTT
TGTAATTCAGAGGTGCAAGAGCCTAAAAGCCATAAGACTCAATGAAGCTTTAAAATCTCT
GCTGAGAGAGGCTCAGCTCTTACATAGCTCCCCGCTTCCCCGGCGGTGGCTGCCTGCCAG    60300
GGAGATGGGTTTATGTGTCTGTGGTGCAGTTAGCAGCTGAATGACTGATTACATGGTATT
TTAGTAACATTTTTCAAATAGCAAATACTGAAAGCAATTCCGATAATGTATTTCCTAC
CCCTCCTCCACCACACAGAACGGCAGAGGAGGGAAAACCTGGTGTGTGCTGTGCTGCAGT
TTGCAAAGGGATTTGTGACTTCGGTTCAGTCCTCTCAGAAAATAATGCTAATGTGGATAA
AATCTTTTTTTTGTTGCAATTCTAGGTGTAGCAGCTCAAGACATTGAAGAGGTTAGTGC    60600
AGCTCTTTCTGCTTTCTGAATCTGCATTTTCTCCTGGCTCTGGAAGAATGCTTTTCTAAC
AGATCTTGGTGCATTGGTGCATGCTGAACTGCTTTGGGTTTTGCTGGGATCAGGTGGGTC
CTGCCAAGGTGCCCCAATGCTTCGGAGTGCTCACACAGTACAGGGGTGTTAGCTATGGCC
ACAGTAGCAAACAAGTTGGGGATGATTTAGCTGGTTTAGCACATGCTCCCCATGGTCTGA
TCCAGCACAGGGCTGTCTGCAGTATCGCTTCTGTCTGCTTTGCTCCTCCACGAAACAAAT    60900
GTGATATCAGGAGTGATATACTCCTTTAAACCATATCCATAACTGGGGCTTGTCCAAAAG
CCTGTTCACTTCATAGAATCATTAAGGTTGGAAAGACCACTATGGTCATCGAGTGCAACC
ACTCCATGCCCAGATCCCTGTGTATGGCAGCCCCAGGCCACGTGGTGGTGTGAGCTGCAT
GGTACCGGGCACTGATATGGGGCTGCATCAGTGCTGATGCTCTCCTGTTGAACCCACTCA
TGTTCTTGGAACACCAGAGCTGCTCCCTGGTGGTGACAGCTTCCCTCCTCTGCCACAGGG    61200
CAGAAATTCCCCCATTTCAGCCAGTTCTGACAGGCCTTTGTTTTCAAGTAAGCAGGCCG
TGCCTCGTTGCTGCTTTTGGCCTCTGGGTGGGAAGAAGATCACATTAGAGATCTTCTTTC
CTGTTTGGAAAGCGAAACCCGACGGTTTATTGCTGTTATTATTTTTGATTTCTTTTGCAG
ATCTGCAAAGAGTTCTTAAACAGGAGCGTGTTCTGCACCAGGGAGTCCAACCCTCACTGC
GGCACGGATGGCGTGACGTACGGCAACAAGTGTGCCTTCTGCAAGGCCGTGCTGTAAGTG    61500
GGGGCGGTGGGATACGGACCCACACAGGGATGGTCCACTTCCAACCCCGCGCTGCTGCTC
CCCTCACACAGAGCAATCCCTGGCCATAGAATCATAGAACTAGAGAATGGTTAAGGTTGG
AAAAGACCAATAAGTGCATCTAGTTCAAATGGCAGCTCCTCACCGCCACGCTTGGGAATA
TTTCAGCTTAATGTTGATTCATTTCTAGGCTTAGTGTGATGCTCATAGCCGTACAGAGAT
GGCACAGAGCCTGGGAGGCCATTGTACCTGCCTGTACCTTCTGCGTGGGCTAAATTGATG    61800
CACATTTTCCTCTGTGTGCCACAGGCTGAAGCTCTCCCTGTCCACACCTCTGGATGCTGA
AGTGTGTGGAGGAACGCAGGCTTATGCATGCCAAATTATTAGAGGAAAGTCATAGACTCG
TAGAATCATAGATTCGTTTGAGTCGAATGGGACCTTTGAAGGTCATCTGGTCCAGCATCC
CTGCAACGAGCAGGGAAAGTGCTGAAATGAAAGTCTGAATGGACTTAGTGGAAAAGTACA
CAAAATCTCAGAGGAAGGGCTGCAGTTTCTCCTCTCCTGTCTCCTCTAAAGGAGCTGTAA    62100
TAGGAGCCAACACCTCTGGACTGAAGGCCTGCAAAAATTGATTTATCCTTATCAATCCTG
CACTCTGGAGGCTGCCTTATCCTAAGGGAAATTAGAGAAGAGGGAAAGATGGCTTGATGC
TCCCTGTGAGGCACCAGAGTGAGGCAAATGATCGTGCTCGGAGGGACAAGCTCCCTGTCC
CAGCCGCTGTGTCTGTGCTGGATGCCATACACTGCTTTGTTTCCATACCGCTCCTTTTAC
AGGAGGAGTGGAGGGAAGATACGATTGAAGCACATGGGGAAGTGCTGAGCCTGAGCACCA    62400
AGCACTGATCTTCGTCGGTCACAGGTGCAGGAGCCTGGGCACGGCAGCAGCTGTCCTCAT
CTCTGCCATATCTGCTCAATAAAGTAAAGCTCAGCACACCTCCTTGACTGGATTCCTTTT
TCCATAACACCCGGATAAGCCTTCCATGCAGCCGTGCTAGCAGCTAAAATGTTTGCCGCA
CTGTGCTGTTACATCTTAGAATCACAGAATCAGGCACCATGCTGCCTGAGCAGGAGCAAT
GATTCCCACAGCTCTTCCATGCCATGCCATGCCATGCCATGCCATGCCATGCCATGCCAT    62700
GCCATGCCATGCCATGCCATGCCATGCCATGCCATGCCATCCCATCCCATCCCATCCCAT
CCCATCCCACTGACAAATGGACACATGGCCACCCAGCTTGACTGTCCCATGGGTGGGTGA
```

FIG. 14T

```
CAGCATGCAACGTTGCCTCTCAGCAGCCTCCCCATATGTGTCCCTCTCGCTGAGGTGTGA
GCATGAAGGTGGCAGAGAGCTATGAGTGGTGTGGCTGTGGATGCCTCATCTGCTTGGGAA
GCCAGAAGCAAACAGGCTGAGGCTGAGGAGTGTTGCTGCATGTAAGCCTGCACCGGGAAG   63000
GTGGCAGGGGAAGCTGGCTTTAGGCAGAAACACAAAGGCTTTGCTTTCCTTGTGTGTCCT
AAGAGAGGACTTTGCCTCAAAGACTGTCAACTCGCCAGCATCAGGTTGCAGTTGCACACA
AACTTGATTTCTTTCTTTAGTTTTCACACTGCTGCTCTCTCTCCTTGATGCTGGCTGG
AAAATCCTTCTTTGCGCCAGCGAGGGAAAATAAAGCCTATAGTCTCTCCCCATTCGCTGT
ACAAAATATACACAGGGAAATGCTTGTGGCATCCCCTCGTTAAAACGTTGGCAGCACATC  63300
AATGGGACTCTACTCACTTAATGTTGAACACTTAAGTTTCAAAGGGAGCTTTAGATTTTA
TCGTGAGGTCAGCCAACTCATTTTGCAAACACCTCTATGCTGAGCATCTCAGCTCCTGGA
TGGTGTTTGGACAGAGCTGAGTGTTTGCCTGTGGTGCCACGCTGCAGGCTTTGAAGTGAA
TTGGGACATTATATTTTGTAGCCAAGGAGAGTTGCAGTTTGCTTTGTTCCAATTCAGATG
TTTCTTTAGTAAACACAACAGCTAGACCTCCAGAACATGGATAAGCTTGAGGGGAGGAAA  63600
AAGCACCTCCTGCACGAGGACAGCTGATCACAAAGGACCCCAGTGGGCAGTGGGAGAACC
TTCATCATCCTCTCTACCGCCTGGATCAGGATGAGCCCTGCATACCCTTTCCAACTGGAG
TTACCCTGTGAGCCAACTTGTGGCTCTGGAGTAGTGCTGTATCTCAATACAGTTTCTCAG
ATGGGAAGAGGCATTTCAATGAGAGGGGGGATATGGGACATTTCTATGCCTGAGATGGCT
CTCGGAGACTCCAAAAGCCTCACGGCGTATCCCCATGCCTAATCCTTTTAATCTGGAGG  63900
CTGAAATAACAAGGACAGATCACAAGAGAACAGAAGCGGCGAGACTTCTCTGCTTTATAA
TCAGCCTGCATTTTGCTCTTTCAGTGCAAACAGCAAATAGAACCGCCTCTGTACCCCTCC
AGACCCAACCACCATCCCCAGCAACACTGTGGCAGGCTGGAGAAGGGTGGCTCTGCCCCT
CCTTGCCTCAACTGGTTGTGTCAGCACGACCATAACCAGAGCTCTCCTTGGCCCCAGCTG
GGCTTATCCATGTAAACCTCTCAGTGCCCCAGGAGCTGGCTGGTGGTCCTGTCCATTTCA  64200
CTTTCCTCCAGCAGGTGTTCCCTTTAACAAGCATCCAAGTGCCTGGAGCAGGAGCAGGCA
CTGCAGAAGATGAGCTCAGGCAAGGACATGGCATGTGGGATCCATGCTGTTGTGCAATG
CAGATGACGTTAGATACGTGCAAAGCAGATCTCAGCAATCACCCAACGACTCATAACTGC
AATCATGGAACGCAATTGCATCTGGAAGTATAAAAGCACAGTGATACCAGGAAGCTCTTG
TTAATGGCACAGCCATTTTGGAGCAATTTGCCCAGGTGGGGAGAGCCCTCACAGCGCCTT  64500
CAGTCACAGGGAGTGGTGTGAGTGCCCCCATGGCTGCTCCCAGCCCCCAGCCCTGGGTGA
TGGGGGTCACTTGGCTGTAACCCTCTGAACACAGGGACAGTGAGACAGCCCTCTGGCCTG
GCTGAGCTCTTGGCTACGTCCAGCTGCAGTCCTGGGCACATACTGAACCAGAAAGCAAGC
ATTCAGCTGGTATTTTCCTTTAATTTCCTTCCTCCACATTTTAAGTTGTGGGATTTTTT
TTTTTTTTTTTGACAGCTTTGAGAGATGAGTGAGTCACGAAGCACTCGAGATCTCTATT  64800
AGATAACAGAGCATCTCTGCAGCTCTTCCTGGGGAGGGAGTTCCTTGGACCAAGGGCCAA
GGCTGGGTGAGAATTGTCCCAGCATCACAGTGGCTGCTCCATCACCTGACACAGCCCCTC
TGCAGTGAAACAAGGGAAGCATTACATCTTTGCACGGCTGCTTTCACTGAACAAAAAGCG
CTGCTTCACAGCTGAGCACCATGATGAAGGGGAAGGAGCATCTCCATGATGAAGGGGAAG
GAGCATCTCCACATCTCCATCACGAGCTCTGCTCTGCTGGTGATGCGGCTGACACCATGG  65100
TGTGCCCTGACTCCTGGCCCATTTAACTGCTGTGCACCAGTGCCTCCTCCCCAGCATAGC
CCTGTGTCCCTGCCACAACTCATTGCAATCCTTTGTCCTACTTCTTCCCTTGACATTCAC
AGCTCTTGATAAGGCTTTTTGAGCCACTCCTGGCTGATGTGGCTGGTGGTTCCTGCTGC
AGGGTTCCACCACCCAGCTGGGCAGCATTCGGTTGTTGTTCCAGTTCCCAGGGGATTGG
GACAGATTGGAAGGGTCTTTGGGACTGTGGAAGAGTATCTCCTGAAGTCAGGGCAGACTG  65400
CTCAGCGCTTTGTCCCATCCAGACTTGAAAACATCCAAGGGTGGAGAACACACAGACTCC
CTGGGCTGCCAGTCCCAGAGTTTGACTGTCATCACGTTGAAGACTTTTTGCCTTGTCTCC
ATTTGCAACCTCTTTCCTTTCAGCTGCCCCATCTCTCAGCCATGCACCACTGGGGAGCCC
AGCTCTGTCTGGTCAGGAACAGAGCCCTTACAGAGCCACAGCATCCTCCTGAAGTGTCCA
TCTCACCACTCAGCCTCAGCAAGTGCTCCAGCCCTCAACTCCCATTTTCCATTATCTTTC  65700
TATCACTGGATATGGGAGGGAAGGCAGAGCTGTGGGGCCAAGAGAAACGATTGCTCAGGA
GGCAGTTGGGAGAACTTTATTGCAAAGCACTGAAGAGATATAAAGTGACATTTGCAGGAA
AAAGTAGAAGGGTATCTGTGTGTGTTGGTTCCTTTAAGGATTAGAGAGCAGCTGAGCTTT
GGGATGAGAGGGCTCCCAGATGCTGTGAATCAGCTAACAGATCCCTCCACCCCGTCATTG
```

FIG. 14U

```
GTGGTGAAGTTAAATAGGGGCCCAGGGGAAACATCAGGGTTGTTTTTCTTTTTACGGACT  66000
CCAGAGCAAGGAGAAGGTGAGGGGGTTGTGCTTTGGAATGGGAGTGAAAGAGTTTGTTGG
TGTTTTCCTCTCCCCAGAATAAGTAGTGTGGTGTAGGAGCGTCTCATAGGAGTAGCTGCG
TTAATTGTGGCTGGTGTTAGCATCCTATAATGTTGCTCCAGAAATGCTGGAGCAGGCTTA
TAATGATGTGTATGTATTACCATAATACATGAAGGGAGAATGGGGGGGGGGGGGTAGAT
TTAAGATGTATGCCCTTAGAAAGGCGGGTGTCACTTAAAGAAGTACTTGCTTTATAGCTC  66300
CAGTGATAGAATTCATTGAGATACTCTGAACCTATGGGCATGAAGTGACCAGATCTTCA
GTTTGGTCAGCTCTGGGGGTTTCTGGGGGGAGCGGGGATAGAGCCTCAATCCAGGTCTGA
AAGACAAGGCTGAGATGTGCTGGGCCTGGGGTGCTGCCCTGAGCAACGTGGGGCTGGCCC
TAGAGAGCAGCATTAGTGCCTGCAGCAGGGCTGGCCCTTGTGCCCAGTGTGTGGGGTAAG
GTGGGGAACGTAGGTGCTGCATAATGTGGTGCTTCTGATCTAAAACTGCTCTGTTAATTG  66600
GGAGTGACCAGAGATGGCCCTATGGCTTTCTTCCCAAAGAGCTCTGTGTCCTTCTCTGCA
GGGTAATCTGTGATAAAAACATCGCCTATGCTCTGCCCTGCAGATGCAGGGGTTTTTGTC
ATCCTCCTTCTCGAGACATACTCTAATCCTTACGCAAGCAGGGAGCTCCAAGCTTTTGGT
GATAACCTCTCAAGGAGGAGCTGGAAGGGCAGCTCTGCCGAGCAGTGACTGCGCTGCACG
GGGCGCATCCTGCAGGAGGCGGTGGTGTAAGCGGGACTCCGCTCGTTCCCGGCTATGGGG  66900
CTCCCCCTGCTGACCGCCGGGCGGTGGCCAGGAGACCTCGGGGCCGCTGCTGCCCCTCGG
TGGTGCTTTTCGGGACAGCTTTCAGGATGGGGCAGCCCAGCTGCTCTCGCGGGGAATTAA
GCGGCTCGGTGCAGGGCGGCACGGCGCTGAGCTGCCCCAGCAAAGCGCCGCTCGTCCCGC
GGCACCTTCGGTAGATGCTCTCTGCTTGGCAGCTCCTTGGTCGTTCTCTTGGCCGGTGGC
CACCCCAGCATCGCTCGGGGCTCGGTGCCATCCCCCCAGGGCCTGCGGAGGTGCCGGTG  67200
CCCGTCCCGGGGTGGCGGACGGGCGGTGCAGTACCGATGCTGGGCGCTGGGTGCTGCCG
CAGACCGAGCGGCGCTGCGCGGCTCCGGGGCGCTCCTGGAGTGCGAGCTGAGCAACCTGG
TAGAAAAATAAGTGTTGTCCCGTGATAAACGTCATCGTGCTGAGCTCTCAGACTCTGCCA
GAGGCCTGAATGAAGCTGCGTCAGGGGAGAATCAGGTTGGGGCTAAGGAAAGGTCCTGCC
CCAGAGGGCGGTGGGTATAGAAGGGGTGCCCAGGGCAGTGGGTGCAGTGCTGGGCTCCCA  67500
GAGCTGGAGGAGCGTCTGGACAGTGCTCAGGTTTGGATGTTGGGTGGTTTTCTGAAGGGA
CGGATTCTGGGCTCGTTTATCCTGAGGGTCCCTTCCAACTTGGGTTGTTCTATTCAATGA
ATATTGTTTATGTTCATTCTATTCTATGATCTTGTTCAGGCTCTCACTGCTGCCTCCAAG
GGTTCAGCTCCCCCAGAGCTGGCAGGGCTTCAGCCACTTGCTTACAGTGCTCATTTCATG
CCTGGCCCATGGCTTCTGCCTGAGCCTTGTGGGAGATCAGCTGCTGCCAGAAACCCAGCC  67800
CTCAGCACTCCACTTGCCCAGCTTGCTGCCTTAGTAGTCTAACTTGGCAGTGGTCTGACA
TGACTTGAGGTTGTTTTTTATTTCCAAGGTGCCACTGACTTTTTTCCTTCCATAGTTTCT
GGAAGCATTTCCTTCCTACTTGACTGAGTCGTGCTCTGTGGATCTGTAATTATCCACCTT
GGCTATGTGTCCTTTACGGGATTTTATATGTTAACCTCCCAAGATCATTTTGCTGCTCTC
ATCTTAGTGGCTGCTGTGAGCTCCACCAGCACCACACTGGATGAGCTGCAGGCTGAGGCC  68100
GGGCACCTCCTGACTCTGCTCTTCTCTGACCCCAGAGCTGTGCAGTTGGGATCCTAAC
ACCATGCAGATGCTCCAGGACCTGCACCGAGCCCCAGCACTGGCACTCATCTCTTCTTTC
CACCCCTCTGAGAGCAACAAGTGGCTCTGCAATGGCAATGTAAGTGAAACCGGGCGGGTA
TCTTAGAGCACCTGG
```

FIG. 14V

TRANSGENIC AVIANS CONTAINING RECOMBINANT OVOMUCOID PROMOTERS

RELATED APPLICATION INFORMATION

This application is a continuation of U.S. patent application Ser. No. 11/047,184, filed Jan. 31, 2005, now U.S. Pat. No. 7,335,761, issued Feb. 26, 2008, which is a continuation-in-part of U.S. patent application Ser. No. 10/856,218, filed May 28, 2004, now U.S. Pat. No. 7,294,507, issued Nov. 13, 2007, which is a continuation-in-part of U.S. patent application Ser. No. 10/496,731, filed May 21, 2004 now U.S. Pat. No. 7,375,258, which is a 371 of PCT/US02/38413, filed Dec. 2, 2002, which is a continuation-in-part of U.S. patent application Ser. No. 09/998,716 filed Nov. 30, 2001, now U.S. Pat. No. 6,875,588, issued Apr. 5, 2005. The disclosure of each of these three continuation-in-part applications and the PCT application is incorporated in its entirety herein by reference. U.S. patent application Ser. No. 11/047,184, now U.S. Pat. No. 7,335,761, issued Feb. 26, 2008, is also a continuation-in-part of U.S. patent application Ser. No. 10/790,455, now abandoned, filed Mar. 1, 2004, which claims the benefit of U.S. Provisional Patent Application No. 60/476,596, filed Jun. 6, 2003, U.S. Provisional Patent Application No. 60/505,562, filed Sep. 24, 2003 and U.S. Provisional Patent Application No. 60/509,122, filed Oct. 6, 2003. The disclosure of the continuation-in-part application is incorporated by reference herein in its entirety.

GOVERNMENT RIGHTS STATEMENT

This invention was made with government support under a grant from the National Institute of Standards and Technology. Therefore, the U.S. Government may have certain rights in this invention.

FIELD OF THE INVENTION

The present invention relates generally to avian gene expression controlling regions, for example, from the chicken. The invention includes recombinant nucleic acid molecules and expression vectors, transfected cells and transgenic animals that include an avian gene expression controlling region operably linked to a nucleic acid of interest.

BACKGROUND

The field of transgenics was initially developed to understand the action of a single gene in the context of the whole animal and the phenomena of gene activation, expression, and interaction. This technology has also been used to produce models for various diseases in humans and other animals and is amongst the most powerful tools available for the study of genetics, and the understanding of genetic mechanisms and function. From an economic perspective, the use of transgenic technology for the production of specific proteins such as substances of pharmaceutical interest (Gordon et al., (1987) Biotechnology 5: 1183-1187; Wilmut et al., (1990) Theriogenology 33: 113-123) offers significant advantages over more conventional methods of protein production by gene expression.

Heterologous nucleic acids have been engineered so that an expressed protein may be joined to a protein or peptide that will allow secretion of the transgenic expression product into milk or urine, from which the protein may then be recovered. These procedures have had limited success and may require maintenance of herds of large species, such as cows, sheep, or goats. Such animals typically have exceedingly long developmental periods and are costly to maintain.

One useful alternative that has shown great promise for heterologous gene expression is the avian reproductive system. The production of an avian egg begins with formation of a large yolk in the ovary of the hen. The unfertilized oocyte or ovum is positioned on top of the yolk sac. After ovulation, the ovum passes into the infundibulum of the oviduct where it is fertilized, if sperm are present, and then moves into the magnum of the oviduct which is lined with tubular gland cells. These cells secrete the egg-white proteins, including ovalbumin, ovomucoid, ovoinhibitor, conalbumin, ovomucin and lysozyme, into the lumen of the magnum where they are deposited onto the avian embryo and yolk.

The hen oviduct offers outstanding potential as a protein bioreactor because of the high levels of protein production, the promise of proper folding and post-translation modification of the target protein, the ease of product recovery, and the shorter developmental period of chickens compared to other animal species used for heterologous gene expression. As a result, efforts have been made to create transgenic chickens expressing heterologous proteins in the oviduct.

Chicken oviduct cells, when stimulated by steroid hormones during egg-laying, secrete three principal amino acid sequences, ovalbumin, ovomucoid and lysozyme (Tsai et al., (1978) Biochemistry 17: 5773-5779). The mRNA transcript encoding ovalbumin constitutes about 50% of the total mRNA of these cells. Ovomucoid and lysozyme mRNAs contribute about 6.6% and 3.4% respectively of the total mRNA of the steroid stimulated cells (Hynes et al. (1977) Cell 11:923-932).

Detailed restriction enzyme analysis of fragments of chicken genomic DNA have shown that the ovomucoid-encoding sequence includes seven intronic sequences (Lindenmaier et al. (1979) Nuc. Acid Res. 7:1221-1232; Catterall et al. (1979) Nature 278:323-327; Lai et al. (1979) Cell 18:829-842). Short stretches of the 5' flanking region of the ovomucoid gene have been sequenced (Lai et al. (1979) Cell 18:829-842; Genbank Accession No. J00897), but extending only 579 bases upstream of the recognized transcription start site. The 5' flanking region of the ovomucoid gene has been isolated (Catterall et al. (1979) Nature 278:323-327; Lai et al. (1979) Cell 18: 829-842), but not generally characterized beyond low-resolution restriction site mapping. Scott et al. (1987) Biochemistry 26:6831-6840, identified a CR1-like region within the approximately 10 kb chicken genomic DNA located between the ovoinhibitor-encoding region and the downstream ovomucoid gene. The ovoinhibitor-encoding cDNA and the attached 3'-untranslated region, which extends into the approximately 10 kb ovoinhibitor-ovomucoid region, were also sequenced (Scott et al. (1987) J. Biol. Chem. 262: 5899-5907). There is no evidence that any of the previously identified portions of the ovomucoid gene are capable of regulating gene expression. In particular, there is no indication that any of these known portions are functional to assist in the initiation of transcription of the ovomucoid coding sequence. The chicken ovomucoid gene is highly expressed in the tubular glands of the mature hen oviduct and represents a suitable candidate for an efficient promoter for heterologous protein production in transgenic animals, especially avians, such as chickens.

What is needed are functional ovomucoid gene expression controlling nucleic acid sequences, such as ovomucoid promoters.

SUMMARY OF THE INVENTION

The present invention relates in part to nucleic acids which include an avian ovomucoid gene expression controlling region useful for expression of nucleotide sequences encoding one or more amino acid sequences of interest, such as peptides, polypeptides or proteins.

In one useful embodiment, the ovomucoid gene expression controlling region is effective to facilitate expression of certain nucleotide coding sequences in avian cells, for example, oviduct cells. In one embodiment, the amino acid sequence is heterologous, for example, the amino acid sequence is not the native ovomucoid protein product, and may be a mammalian, for example, a human amino acid sequence.

One aspect of the invention provides for a gene expression controlling region which includes nucleotide sequence found upstream of an ovomucoid coding sequence and/or nucleotide sequence found downstream of an ovomucoid coding sequence. In one aspect of the invention, fragments of an ovomucoid promoter gene which are effective to control gene expression of a nucleic acid sequence of interest are provided. For example, the invention provides for a nucleic acid fragment isolated from a region upstream of a transcription start site of an ovomucoid gene effective to control or regulate gene expression. In another example, the nucleic acid fragment is isolated from a region downstream of a transcription start site of an ovomucoid gene effective to control or regulate gene expression. In another embodiment, the fragment is isolated from a region upstream and downstream of a transcription start site of an ovomucoid gene effective to control gene expression.

In one embodiment of the present invention, the ovomucoid gene expression controlling region is isolated from a chicken. In a specific embodiment, the ovomucoid gene expression controlling region has a nucleotide sequence of OMC 70, which is included in the sequence of SEQ ID NO: 36. In one useful aspect, all or substantially all or a functional fragment of OMC 70 is employed to control the expression of a nucleic acid sequence of interest. The sequence of OMC 70 is included in the sequence of SEQ ID NO: 36 which is a BAC clone. A BAC clone which is believed to contain the nucleotide sequence represented by SEQ ID NO: 36 designated OMC24 has been deposited with the ATCC Patent Depository and has been assigned the deposit number of PTA-6234. The avian nucleotide sequence of PTA-6234 is included in the present application as are all functional fragments of the ovomucoid gene expression controlling sequence or region of PTA-6234. In one particularly useful aspect of the invention, the ovomucoid gene expression controlling region is a fragment or portion of OMC 70 which is effective to control gene expression in a cell, for example, an avian cell (e.g., a chicken cell). In a very useful aspect, fragments of the ovomucoid gene expression controlling region are operably linked or attached to a heterologous coding sequence such as a nucleotide sequence encoding a therapeutic protein.

In certain embodiments, the gene expression controlling region of the invention is at least 60% or at least 75% or at least 85% or at least 90% or at least 95% or at least 99% identical or homologous to an ovomucoid gene expression controlling region disclosed herein (e.g., the ovomucoid gene expression controlling region included in SEQ ID NO: 36) or fragments thereof and can regulate or control expression of a nucleotide sequence in a cell, such as an avian cell (e.g., a chicken cell).

In one embodiment, the avian ovomucoid gene expression controlling region of the present invention is useful for directing tissue-specific expression of an amino acid sequence-encoding nucleic acid. The gene expression controlling regions of the invention may be operably linked to a nucleic acid of interest (i.e., a nucleic acid insert) wherein the nucleic acid insert encodes an amino acid sequence desired to be expressed in a transfected cell. In one embodiment, the nucleic acid insert may be cloned in frame with a nucleotide sequence encoding a signal peptide. Translation may start with the signal peptide and continue through the nucleic acid insert, thereby producing an expressed amino acid sequence having the desired amino acid sequence including a signal sequence.

The nucleic acid of the present invention may include an untranslated 3' region which may include a polyadenylation coding sequence allowing the transcript directed by the ovomucoid gene expression controlling region of the invention to include, in addition to a certain heterologous amino acid sequence (i.e., not the ovomucoid protein that is expressed from the endogenous gene containing the ovomucoid gene expression controlling region), a 3' untranslated region that may include a polyadenylated tail. Any functional polyadenylation signal sequence may be linked to the 3' end of the nucleic acid insert including the SV40 polyadenylation signal sequence, bovine growth hormone adenylation sequence or the like. There are many know useful signal sequences including those disclosed in U.S. Pat. No. 5,856,187, the disclosure of which is incorporated in its entirety herein by reference.

The nucleic acid of the invention may include certain gene expression controlling elements, such as promoters, enhancers, IRES's from a source other than an ovomucoid gene, for example, from a non-avian gene.

The sequence of the expressed nucleic acid insert may be optimized for codon usage by the host cell or host organism. Codon usage can be determined by methods well known in the art. For example, codon usage may be determined for an avian by methods known in the art, for example, by examining nucleotide sequences which encode proteins such as ovalbumin, ovomucoid, ovomucin and ovotransferrin produced by a chicken and comparing the encoded amino acids to the corresponding codons.

Yet another aspect of the invention relates to expression vectors suitable for expressing the nucleic acid coding sequences as disclosed herein. Expression vectors of the present invention may include an avian ovomucoid gene expression controlling region operably linked to a nucleic acid insert encoding a non-ovomucoid amino acid sequence, and optionally, a non-coding sequence such as a polyadenylation signal sequence. The expression vector may also include a bacterial plasmid sequence, a viral nucleic acid sequence, or fragments or variants thereof or other sequences that will allow for maintaining the vector in a suitable host. As contemplated in the present invention, the vector may be a YAC, BAC, HAC, MAC, bacteriophage-derived artificial chromosome (BBPAC), cosmid or P1 derived artificial chromosome (PAC).

The present invention further relates to nucleic acid vectors and transgenes inserted therein that incorporate multiple amino acid sequence-encoding regions, wherein a first amino acid sequence-encoding region is operatively linked to a transcription promoter and a second amino acid sequence-encoding region is operatively linked to an Internal Ribosome Entry Sequence (IRES). For example, the vector may contain coding sequences for two different heterologous proteins (e.g., the heavy and light chains of an immunoglobulin), both sequences under the control of the same promoter. In one useful embodiment, the promoter is an ovomucoid gene expression controlling region as disclosed herein.

Nucleic acid constructs of the invention, when inserted into the genome of a bird and expressed therein, will produce amino acid sequences that may be post-translationally modified, for example, glycosylated or, in certain embodiments, be present as complexes, such as dimmers, (e.g., heterodimers).

Another aspect of the present invention is a method of expressing an amino acid sequence in a eukaryotic cell by transfecting the cell with a recombinant DNA comprising a gene expression controlling region of the invention operably linked to a nucleic acid insert encoding the amino acid sequence and, optionally, a non-coding sequence such as a polyadenylation signal sequence, and culturing the transfected cell in a medium suitable for expression of the amino acid sequence under the control of the gene expression controlling region. In certain embodiments, the amino acid sequence is a therapeutic protein such as a cytokine, growth factor, enzyme, structural protein, an immunoglobulin, or other therapeutic protein including, but not limited to, those disclosed elsewhere herein, or subunit or fragment thereof. In other embodiments, the amino acid sequence is a mammalian, such as a human, amino acid sequence or is substantially similar to a human or mammalian amino acid sequence.

Also within the scope of the present invention are recombinant cells, tissues and animals, for example, avians such as chickens, containing recombinant nucleic acid molecules of the present invention. In certain embodiments, the level of expression of a heterologous protein is greater than 1 μg, 5 μg, 10 μg, 50 μg, 100 μg, 250 μg, 500 μg, 750 μg, 1 mg, 2 mg, 5 mg, 10 mg, 20 mg, 50 mg, 100 mg, 200 mg, 500 mg, 700 mg, 1 gram, 2 grams, 3 grams, 4 grams or 5 grams in an egg produced by the transgenic avian of the invention. In one embodiment, the heterologous protein is present mostly or exclusively in the egg white.

In one embodiment of the invention, the cell is a chicken oviduct cell and the nucleic acid comprises a chicken ovomucoid gene expression controlling region, a nucleic acid insert encoding a heterologous amino acid sequence of interest, which optionally is codon optimized for expression in an avian cell, and a non-coding sequence such as a polyadenylation sequence, for example, an SV40 polyadenylation sequence. In one particularly useful embodiment, the oviduct cell is present in a live avian, such as a chicken.

The present invention includes nucleic acid molecules, for example, DNA, which comprise an artificial chromosome comprising an ovomucoid gene expression controlling region and methods of using the nucleic acid molecules, such as for the production of transgenic avians comprising an artificial chromosome.

In one embodiment, the gene expression controlling region of the present invention is a nucleotide sequence that hybridizes to the nucleotide sequence of SEQ ID NO: 36 or portions thereof such as Fragment A, Fragment B or Fragment C as disclosed in FIG. 14. In another embodiment, the gene expression controlling region of the present invention is a nucleotide sequence that hybridizes to the complement of the nucleotide sequence of SEQ ID NO: 36 or portions thereof such as Fragment A, Fragment B or Fragment C as disclosed in FIG. 14. In one embodiment, the hybridizations are under stringent conditions. High stringency conditions, when used in reference to nucleic acid hybridization, may comprise conditions equivalent to binding or hybridization at 65° C. in a solution consisting of 6×SSPE, 1% SDS, 5× Denhardt's reagent and 100 μg/ml denatured salmon sperm DNA followed by washing in a solution comprising 0.1×SSPE, and 0.1% SDS at 65° C. for about 15 to about 20 minutes. In certain embodiments, the wash conditions may include 50% formamide at 42° C. instead of 65° C. High stringency washes may include 0.1×SSC to 0.2×SSC and 1% SDS at 65° C. for about 15 to about 20 min. (see, Sambrook et al., Molecular Cloning—A Laboratory Manual (2nd ed.) Vol. 1-3, Cold Spring Harbor Laboratory, Cold Spring Harbor Press, N.Y., 1989, the disclosure of which is incorporated herein in its entirety by reference). Exemplary medium stringency conditions are as described above for high stringency except that the washes are carried out at 55° C. or at 37° C. when in the presence of 50% formamide. In a most useful aspect of the invention, a nucleotide sequence that hybridizes to an ovomucoid gene expression controlling region and its complement, such as a nucleotide sequence that hybridizes to the nucleotide sequence of SEQ ID NO: 36 or portions thereof such as Fragment A, Fragment B or Fragment C as disclosed in FIG. 14 and their complement, which serves as a functional gene expression controlling region, is operably linked or attached to a heterologous coding sequence such as a nucleotide sequence encoding a therapeutic protein. In one embodiment of the invention, fragments or portions of the ovomucoid gene expression controlling region as disclosed herein are useful as hybridization probes as is understood in the field of molecular biology.

In one embodiment, the ovomucoid gene expression controlling region is that of SEQ ID NO: 36 or portions thereof such as Fragment A, Fragment B or Fragment C as disclosed in FIG. 14. In another embodiment, the ovomucoid gene expression controlling region comprises a functional portion of SEQ ID NO: 36 or portions thereof such as Fragment A, Fragment B or Fragment C as disclosed in FIG. 14. The ovomucoid gene expression controlling region may also include the complement of SEQ ID NO: 36 or the complement of portions thereof such as the complement of Fragment A, the complement of Fragment B or the complement of Fragment C as disclosed in FIG. 14. In a particularly useful embodiment of the invention, a functional portion of SEQ ID NO: 26 or a functional portion of the avian nucleic acid contained in SEQ ID NO: 36 is operably linked or attached to a heterologous coding sequence such as a nucleotide sequence encoding a therapeutic protein.

In one embodiment, functional portions of the nucleotide sequence of the avian ovomucoid gene expression controlling region contained in SEQ ID NO: 36 are shown in FIG. 14. For example, Fragment A is an approximately 10 kb fragment which spans from about nucleotide 26,416 to about nucleotide 36,390 of FIG. 14 and of SEQ ID NO 36. Fragment B is an approximately 3.9 kb fragment which spans from about nucleotide 32,364 to about nucleotide 36,299 of FIG. 14 and of SEQ ID NO 36. Fragment C is an approximately 1.8 kb fragment which spans from about nucleotide 34,473 to about nucleotide 36,248 of FIG. 14 and of SEQ ID NO 36.

In another example, a potentially useful functional portion of the ovomucoid gene expression controlling region is the portion of SEQ ID NO: 36 which extends from the SbfI site at about nucleotide 14,727 to the EcoRI site at about nucleotide 48,185. Another example of a potentially useful functional portion of the ovomucoid gene expression controlling region is the portion of SEQ ID NO: 36 which extends from the HindIII site at about nucleotide 24,742 to the EcoRI site at about nucleotide 48,185. Another example of a potentially useful functional portion of the ovomucoid gene expression controlling region is the portion of SEQ ID NO: 36 which extends from the EcoRI site at about nucleotide 27,028 to the EcoRI site at about nucleotide 48,185. Another example of a potentially useful functional portion of the ovomucoid gene expression controlling region is the portion of SEQ ID NO: 36 which extends from the HindIII site at about nucleotide 28,381 to the EcoRI site at about nucleotide 48,185. Another example of a potentially useful functional portion of the ovomucoid gene expression controlling region is the portion of SEQ ID NO: 36 which extends from the EcoRI site at about nucleotide 27,028 to the EcoRI site at about nucleotide 54,424. In addition, a useful ovomucoid gene expression controlling region may extend from about nucleotide 35,861 to about nucleotide 36,252.

Methodologies are well known in the field that are useful to identify gene expression controlling regions within specified nucleic acid sequences (see, for example, Reese, M. G. and Eeckman, F. H. (1995) "Novel Neural Network Algorithms for improved Eukaryotic Promoter Site Recognition" The seventh international Genome sequencing and analysis conference, Hyatt Regency, Hilton Head Island, S.C. Sep. 16-20, 1995 and Reese, M. G., Ph.D. Thesis (2000) UC Berkeley/University Hohenheim). Numerous computer programs are known in the art which can be used to identify gene expression controlling sequences such as promoter sequences within a certain nucleotide sequence. Using such sequence analysis programs, potential gene expression controlling regions can be identified and thereafter tested for gene expression controlling activity by methods known in the field of molecular biology such as those disclosed herein. For example, a 50 nucleotide sequence spanning from nucleotide 36,209 to nucleotide 36,258 was shown to be a potential promoter site with a relatively high degree (match score of 1.0) of certainty using the computer program available at http://www.fruitfly.org/seg_tools/nnppAbst.html.

In one embodiment, the gene expression controlling region comprises a nucleotide sequence that is at least 50% homologous or identical to the ovomucoid gene expression controlling region of the nucleotide sequence of SEQ ID NO: 36 or portions thereof such as Fragment A, Fragment B or Fragment C as disclosed in FIG. 14 or is at least 50% homologous to the complement of the ovomucoid gene expression controlling region of the nucleotide sequence of SEQ ID NO: 36 or portions thereof such as Fragment A, Fragment B or Fragment C as disclosed in FIG. 14. For example, the gene expression controlling region may comprise a nucleotide sequence that is at least 60% homologous or identical to the ovomucoid gene expression controlling region of the nucleotide sequence of SEQ ID NO: 36 or portions thereof such as Fragment A, Fragment B or Fragment C as disclosed in FIG. 14 or is at least 60% homologous to a complement thereof. In another example, the gene expression controlling region comprises a nucleotide sequence that is at least 70% homologous or identical to the ovomucoid gene expression controlling region of the nucleotide sequence of SEQ ID NO: 36 or portions thereof such as Fragment A, Fragment B or Fragment C as disclosed in FIG. 14 or is at least 70% homologous to a complement thereof. In another example, the gene expression controlling region comprises a nucleotide sequence that is at least 75% homologous or identical to the ovomucoid gene expression controlling region of the nucleotide sequence of SEQ ID NO: 36 or portions thereof such as Fragment A, Fragment B or Fragment C as disclosed in FIG. 14 or is at least 75% homologous or identical to a complement thereof. In another example, the gene expression controlling region comprises a nucleotide sequence that is at least 80% homologous or identical to the ovomucoid gene expression controlling region of the nucleotide sequence of SEQ ID NO: 36 or portions thereof such as Fragment A, Fragment B or Fragment C as disclosed in FIG. 14 or is at least 80% homologous or identical to a complement thereof. In another example, the gene expression controlling region comprises a nucleotide sequence that is at least 85% homologous or identical to the ovomucoid gene expression controlling region of the nucleotide sequence of SEQ ID NO: 36 or is at least 85% homologous or identical to a complement thereof. In another example, the gene expression controlling region comprises a nucleotide sequence that is at least 90% homologous or identical to the ovomucoid gene expression controlling region of the nucleotide sequence of SEQ ID NO: 36 or portions thereof such as Fragment A, Fragment B or Fragment C as disclosed in FIG. 14 or is at least 90% homologous or identical to a complement thereof. In another example, the gene expression controlling region comprises a nucleotide sequence that is at least 95% homologous or identical to the ovomucoid gene expression controlling region of the nucleotide sequence of SEQ ID NO: 36 or portions thereof such as Fragment A, Fragment B or Fragment C as disclosed in FIG. 14 or is at least 95% homologous or identical to a complement thereof. In another example, the gene expression controlling region comprises a nucleotide sequence that is at least 99% homologous or identical to the ovomucoid gene expression controlling region of the nucleotide sequence of SEQ ID NO: 36 or portions thereof such as Fragment A, Fragment B or Fragment C as disclosed in FIG. 14 or is at least 99% homologous or identical to a complement thereof.

In one embodiment, nucleic acid molecules of the invention include an attB site. The use of attB is disclosed in, for example, U.S. patent application Ser. No. 10/790,455, filed Mar. 1, 2004, the disclosure of which is incorporated in its entirety herein by reference.

The nucleic acid molecules of the present invention may also include a signal sequence coding region which may be useful for secretion of an amino acid sequence product from a cell. In one embodiment, the signal sequence is cleaved from the amino acid sequence product during the secretion process. For the purposes of the present invention, "signal sequence peptide" refers to amino acid sequences of about 15 to about 25 amino acids in length which are known in the art to be generally located at the amino terminus of proteins and which are capable of facilitating secretion of a peptide or amino acid sequence from a cell.

In one particularly useful embodiment, the nucleic acid molecules of the present invention include an artificial chromosome. Any useful artificial chromosomes are contemplated for use in the present invention. In one embodiment, an artificial chromosome is a DNA molecule which includes a telomere and is capable of self replication in a cell, for example, in an avian cell. In another embodiment, an artificial chromosome includes a telomere and a centromere. Artificial chromosomes include, without limitation, BACs (bacterial artificial chromosomes), YACs (yeast artificial chromosomes), HACs (human artificial chromosomes) MACs (mammalian artificial chromosomes), BBPACs (bacteriophage derived artificial chromosomes) or PACs (P1 derived artificial chromosomes) or combinations thereof. Artificial chromosomes may include a gene expression controlling region as disclosed herein and may be present in cells of a transgenic avian such as a chicken or may be present in cells in culture.

The present invention also relates to compositions and methods for expressing certain peptides and amino acid sequences (e.g., peptides or proteins). The compositions can include a nucleic acid molecule comprising an artificial chromosome and an ovomucoid gene expression controlling region, as disclosed herein, which may be operably linked to a nucleotide sequence encoding an amino acid sequence. The nucleic acid may be inserted into a cell, for example, into a cell of an avian, where the amino acid sequence is expressed. In one embodiment, the nucleic acid molecule is present in cells of a transgenic avian including oviduct cells, for example, tubular gland cells of a transgenic avian. The coding region may encode any useful polynucleotide including pharmaceutical or therapeutic proteins which comprise an amino acid sequence.

The nucleic acid molecules of the present invention may be introduced into a cell, for example, into the cell of an avian, by any useful method. Such methods include, without limitation, microinjecting, transfection, electroporation and lipofection. The nucleic acid molecules may be introduced into a germinal disc or an avian embryo cell such as an early stage avian embryo. In one embodiment, the nucleic acid molecules of the present invention are introduced into an avian embryo cell such as a stage I avian embryo, stage II avian embryo, stage III avian embryo, stage IV avian embryo, stage V avian embryo, stage VI avian embryo, stage VII avian embryo, stage VIII avian embryo, stage IX avian embryo, stage X avian embryo, stage XI avian embryo or stage XII avian embryo.

Certain specific examples of pharmaceutical or therapeutic proteins which are contemplated for production as disclosed herein include, with out limitation, Factor VIII (e.g., Recombinate®, Bioclate®, Kogenate®, Helixate® (Centeon), B-domain deleted Factor VIII (e.g., ReFacto®), Factor VIIa (e.g., NovoSeven®), Factor IX (e.g., Benefix®), anticoagulant; recombinant hirudin (e.g., Revaso®, Refludan®) Alteplase, tPA (e.g., Activase®), Reteplase, tPA, tPA—3 of 5 domains deleted, Ecokinase®, Retavase®, Rapilysin®, insulin (e.g., Humulin®, Novolin®, Insuman®) insulin lispro (e.g., Humalog®, Bio Lysprol, Liprolog®), insulin Aspart, iNovoRapid®, insulin glargine, long-acting insulin analog (e.g., Lantus®), rhGH (e.g., Protropin®, Humatrope®, Nutropin®, BioTropin®, Genotropin®, Norditropin®, Saizen®, Serostim®), glucagons (e.g., Glucagen®), TSH (e.g., Thyrogen®, (Gonal F®, Puregon®), follitropin-beta, FSH (e.g., Follistim®), EPO (e.g., Epogen®, Procrit®, Neorecormon®), GM-CSF (e.g., Leukine®, Neupogen®), PDGH (e.g., Regranex®), hormones such as cytokines, IFN alpa2a (e.g., Roferon A®), INF-apha (e.g., Infergen®), IFN alpa2b (e.g., Intron A®, Alfatronol®, Virtron®), ribavirin & INF-alpha 2b (e.g., Robetron®) INF-beta 1b (e.g., Betaferon®), IFN-beta 1a (e.g., Avonex®, Rebif®), IFN-gamma1b (e.g., Actimmune®), IL-2 (e.g., Proleukin®) rIL-11 (e.g., Neumega®), rHBsAg (e.g., Recombivax®), Combination vaccine containing HBsAgn as one component (e.g., Comvax®, Tritarix®, Twinrix®, Primavax®, Procomax®), OspA, a lipoprotein found on the surface of B burgoeri (e.g., Lymerix®), murine MAb directed against t-lymphocyte antigen CD3 (e.g., Orthoelone OKT3®), murine MAb directed against TAG-72, tumor-associated glycoprotein (e.g., OncoScint CR/OV®), FAb fragments derived from chimeric MAb, directed against platelet surface receptor GPII(b)/III(a) (e.g., ReoPro®), murine MAb, fragment directed against tumor-associated antigen CA125 (e.g., Iadimacis®), murine MAb fragment directed against human carcinoembryonic antigen, CEA (e.g., CEA-scan®), murine MAb fragment directed against human cardiac myosin (e.g., MyoScint®), murine MAb fragment directed against tumor surface antigen PSMA (e.g., ProstaScint®), murine MAb fragments (FAb/FAb2 mix) directed against HMW-MAA (e.g., Tacnemab®), murine MAb fragment (FAb) directed against carcinoma-associated antigen (e.g., Verluma®), MAb fragments (FAb) directed against NCA 90, a surface granulocyte nonspecific cross reacting antigen (e.g., LeukoScan®), chimeric MAb, directed against CD20 antigen found on surface of B lymphocytes (e.g., Rituxan®), humanized MAb directed against the alpha chain of the IL2 receptor (e.g., Zenapax®), chimeric MAb, directed against the alpha chain of the IL2 receptor (e.g., Simulect®), chimeric MAb, directed against TNF-alpha (e.g., Remicade®), humanized MAb, directed against an epitope on the surface of respiratory synctial virus (e.g., Synagis®), humanized MAb directed against HER 2, i.e., human epidermal growth factor receptor 2 (e.g., Herceptin®), human MAb, directed against cytokeratin tumor-associated antigen (e.g., Humaspect®), anti-CTLA4, chimeric MAb directed against CD 20 surface antigen of B lymphocytes (e.g., Mabthera®), dornase-alpha DNAse (e.g., Pulmozyme®), beta glucocerebrosidase (e.g., Cerezyme®), TNF-alpha (e.g., Beromun®), IL-2-diphtheria toxin fusion protein that targets cells displaying a surface IL-2 receptor (e.g., Ontak®), TNFR-IgG fragment fusion protein (e.g., Enbrel®), Laronidase, Recombinant DNA enzyme, (e.g., Aldurazyme®), Alefacept, Amevive®, Darbepoetin alfa (Colony stimulating factor) (e.g., Aranesp®), Tositumomab and iodine 1 131 tositumomab, murine MAb, Bexxar®, Alemtuzumab, Campath®, Rasburicase, Elitek®), Agalsidase beta, Fabrazyme®, FluMist®, Teriparatide, Parathyroid hormone derivative (e.g., Forteo®), Enfuvirtide Fuzeon®, Adalimumab (lgG1) (e.g., Humira®), Anakinra, Biological modifier (e.g., Kineret®), nesiritide, Human B-type natriuretic peptide (hBNP) (e.g., Natrecor®), Pegfilgrastim, Colony stimulating factor (e.g., Neulasta®), ribavarin and peg Intron A (e.g., Rebetron®), Pegvisomant, PEGylated human growth hormone receptor antagonist, (e.g., Somavert®), recombinant activated protein C (e.g., Xigris®), Omalizumab, Immunoglobulin E (lgE) blocker (e.g., Xolair®) and lbritumomab tiuxetan (murine MAb) (e.g., Zevalin®).

In one particularly useful embodiment, the amino acid sequence such as a pharmaceutical or therapeutic protein encoded by the nucleotide sequence operably linked to the ovomucoid gene expression controlling region is present in egg white produced by a transgenic avian of the present invention (i.e., an avian comprising a cell which includes a nucleic acid molecule of the present invention) In one aspect of the invention, the nucleic acid molecule includes a nucleotide sequence encoding a light chain and/or a heavy chain of an antibody or a portion of a light chain and/or a heavy chain of an antibody which is operably linked to the ovomucoid gene expression controlling region. The antibody may be IgG (e.g., IgG1, IgG2, IgG3 or IgG4), IgA (e.g., IgA1 or IgA2), IgD, IgM or IgE. In addition, the light chain of the antibody may be a kappa light chain or a lambda light chain.

The present invention also contemplates the production of useful fusion proteins. For example, an antibody or a portion of an antibody may be produced as a fusion protein with another useful amino acid sequence.

The techniques used to isolate and characterize the nucleic acids and proteins of the present invention are well known to those of skill in the art and standard molecular biology and biochemical manuals may be consulted to select suitable protocols without undue experimentation. See, for example, Sambrook et al. (2001) Molecular Cloning: A Laboratory Manual, 3rd ed., Cold Spring Harbor Press, the content of which is herein incorporated by reference in its entirety.

Any combination of features described herein is included within the scope of the present invention provided that the features included in any such combination are not mutually inconsistent. Such combinations will be apparent based on this specification and on the knowledge of one of ordinary skill in the art.

Definitions

Definitions of certain terms used in the present application are set forth below.

As used herein the terms "amino acid sequence" and "protein" refer to a polymer of amino acids of three or more amino acids in a serial array, linked through peptide bonds. The term "amino acid sequence" includes proteins, protein fragments, protein analogues, oligopeptides and the like. The term amino acid sequence as used herein can also refer to a peptide. The term "amino acid sequences" contemplates amino acid sequences as defined above that are encoded by nucleic acids, produced through recombinant technology (isolated from an appropriate source such as a bird), or synthesized. The term "amino acid sequences" further contemplates amino acid sequences as defined above that include chemically modified amino acids or amino acids covalently or noncovalently linked to labeling ligands.

The term "animal" is used herein to include all vertebrate animals, including humans. It also includes an individual animal in all stages of development, including embryonic and fetal stages.

The term "antisense DNA" as used herein refers to a gene sequence DNA that has a nucleotide sequence complementary to the "sense strand" of a gene when read in reverse orientation, i.e., DNA read into RNA in a 3' to 5' direction rather than in the 5' to 3' direction. The term "antisense RNA" is used to mean an RNA nucleotide sequence (for example that encoded by an antisense DNA or synthesized complementary with the antisense DNA). Antisense RNA is capable of hybridizing under stringent conditions with an antisense DNA. The antisense RNA of the invention is useful for regulating expression of a "target gene" either at the transcriptional or translational level. For example, transcription of the subject nucleic acids may produce antisense transcripts that are capable of inhibiting transcription by inhibiting initiation of transcription or by competing for limiting transcription factors; the antisense transcripts may inhibit transport of the "target RNA", or, the antisense transcripts may inhibit translation of "target RNA".

The term "avian" as used herein refers to any species, subspecies or race of organism of the taxonomic class ava, such as, but not limited to, such organisms as chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, New Hampshire, Rhode Island, Ausstralorp, Minorca, Amrox, California Gray, Italian Partidge-colored), as well as strains of turkeys, pheasants, quails, duck, ostriches and other poultry commonly bred in commercial quantities.

The term "antibody" as used herein refers to polyclonal and monoclonal antibodies and fragments thereof, and immunologic binding equivalents thereof. The term "antibody" refers to a homogeneous molecular entity, or a mixture such as a polyclonal serum product made up of a plurality of different molecular entities, and may further comprise any modified or derivatised variant thereof that retains the ability to specifically bind an epitope. A monoclonal antibody is capable of selectively binding to a target antigen or epitope. Antibodies may include, but are not limited to polyclonal antibodies, monoclonal antibodies (mAbs), humanized or chimeric antibodies, camelized antibodies, single chain antibodies (scFvs), Fab fragments, F(ab')$_2$ fragments, disulfide-linked Fvs (sdFv) fragments, e.g., as produced by a Fab expression library, anti-idiotypic (anti-Id) antibodies, intrabodies, synthetic antibodies, and epitope-binding fragments of any of the above.

The term "cytokine" as used herein refers to any secreted amino acid sequence that affects the functions of cells and is a molecule that modulates interactions between cells in the immune, inflammatory or hematopoietic responses. A cytokine includes, but is not limited to, monokines and lymphokines regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-alpha) and Tumor Necrosis Factor beta (TNF-beta).

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of an ovomucoid gene expression controlling region or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° C. in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

1 to 1.0 M Na ion concentration (or other salts) from about pH 7.0 to about pH 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1× to 2×SSC at 50 to 55° Celsius. Exemplary moderate stringency conditions include hybridization in 40 to 45% formamide, 1 M NaCl, 1% SDS at 37° Celsius, and a wash in 0.5× to 1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

The term "coding region" as used herein refers to a continuous linear arrangement of nucleotides which may be translated into a protein. A full length coding region is translated into a full length protein; that is, a complete protein as would be translated in its natural state absent any post-translational modifications. A full length coding region may also include any leader protein sequence or any other region of the protein that may be excised naturally from the translated protein.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, may further comprise modified bases wherein a modified adenine may form hydrogen bonds with a thymine or modified thymine, and a modified cytosine may form hydrogen bonds with a guanine or a modified guanine.

By the use of the term "enriched" in reference to nucleic acid it is meant that the specific DNA or RNA sequence constitutes a significantly higher fraction of the total DNA or RNA present in the cells or solution of interest than in normal or diseased cells or in the cells from which the sequence was taken. Enriched does not imply that there are no other DNA or RNA sequences present, just that the relative amount of the sequence of interest has been significantly increased, for example, by 1 fold, 2 fold, 5 fold, 10 fold, 50 fold, 100 fold, 500 fold, 1000 fold, 10,000 fold, 100,000 fold, or 1,000,000 fold. The other DNA may, for example, be derived from a yeast or bacterial genome, or a cloning vector, such as a plasmid or a viral vector.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, an amino acid sequence or a portion thereof.

The term "expression vector" as used herein refers to a nucleic acid vector that comprises the ovomucoid gene expression controlling region operably linked to a nucleotide sequence coding at least one amino acid sequence. As used herein, the term "regulatory sequences" includes promoters, enhancers, and other elements that may control gene expression. Standard molecular biology textbooks such as Sambrook et al. eds "Molecular Cloning: A Laboratory Manual" 3rd ed., Cold Spring Harbor Press (2001) may be consulted to design suitable expression vectors that may further include an origin of replication and selectable gene markers. It should be recognized, however, that the choice of a suitable expression vector and the combination of functional elements therein depends upon multiple factors including the choice of the host cell to be transformed and/or the type of protein to be expressed.

The term "fragment" as used herein can refer to, for example, an at least about 10, 20, 50, 75, 100, 150, 200, 250, 300, 500, 1000, 2000, 5000, 6,000, 8,000, 10,000, 20,000, 30,000, 40,000, 50,000 or 60,000 nucleotide long portion of a nucleic acid (e.g., cDNA) that has been constructed artificially (e.g., by chemical synthesis) or by cleaving a natural product into multiple pieces, using restriction endonucleases or mechanical shearing, or enzymatically, for example, by PCR or any other polymerizing technique known in the art, or expressed in a host cell by recombinant nucleic acid technology known to one of skill in the art. The term "fragment" as used herein may also refer to, for example, an at least about 5, 10, 20, 30, 40, 50, 75, 100, 150, 200, 250, 300, 400, 500, 1000, 2000, 5000, 6,000, 8,000 or 10,000 amino acid portion of an amino acid sequence, which portion is cleaved from a naturally occurring amino acid sequence by proteolytic cleavage by at least one protease, or is a portion of the naturally occurring amino acid sequence synthesized by chemical methods or using recombinant DNA technology (e.g., expressed from a portion of the nucleotide sequence encoding the naturally occurring amino acid sequence) known to one of skill in the art. "Fragment" may also refer to a portion, for example, of about 5%, about 10%, about 20%, about 30%, about 40%, about 50%, about 60%, about 70%, about 80% about 90% about 95% or about 99% of a particular nucleotide or amino acid sequence.

"Functional portion" or "functional fragment" as used herein means a portion or fragment of a whole capable of performing, in whole or in part, a function of the whole. For example, a biologically functional portion of a molecule means a portion of the molecule that performs a biological function of the whole or intact molecule. For example, a functional portion of a gene expression controlling region is a fragment or portion of the specified gene expression controlling region that, in whole or in part, regulates or controls gene expression (e.g., facilitates either in whole or in part) in a biological system (e.g., a promoter). Functional portions may be of any useful size. For example, a functional fragment may range in size from about 20 bases in length to a length equal to the entire length of the specified sequence minus one nucleotide. In another example, a functional fragment may range in size from about 50 bases in length to a length equal to the entire length of the specified sequence minus one nucleotide. In another example, a functional fragment may range in size from about 50 bases in length to about 70 kb in length. In another example, a functional fragment may range in size from about 500 bases in length to about 70 kb in length. In another example, a functional fragment may range in size from about 1 kb in length to about 70 kb in length. In another example, a functional fragment may range in size from about 1 kb in length to about 20 kb in length. In another example, a functional fragment may range in size from about 1 kb in length to about 10 kb in length. Functional portions may include, for example, and without limitation, one or more of a matrix attachment region, a transcription enhancer, a hormone responsive element or a CRI repeat element.

The term "gene" or "genes" as used herein refers to nucleic acid sequences (including both RNA or DNA) that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by foreign, heterologous or foreign exogenous genes and are, therefore, not naturally expressed in the cell.

The term "gene expression controlling regions" as used herein refers to nucleotide sequences which regulate, in whole or in part, the expression of the nucleotide sequence, for example, regulate, in whole or in part, the transcription of a nucleotide sequence. Exemplary transcription regulatory sequences include enhancer elements, hormone response elements, steroid response elements, negative regulatory elements, and the like. The "transcription regulatory sequences" may be isolated and incorporated into a nucleic acid vector to enable regulated transcription in appropriate cells of portions of the vector DNA. The "transcription regulatory sequence" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in other regions of nucleic acid sequence. In addition, to "control gene expression," or "controlling gene expression", refers to regulation, in whole or in part, of the expression of a nucleotide sequence, for example, regulation, in whole or in part, of the transcription of a nucleotide sequence.

The term "immunoglobulin amino acid sequence" as used herein refers to an amino acid sequence derived from a constituent amino acid sequence of an immunoglobulin. An "immunoglobulin amino acid sequence" may be, but is not limited to, an immunoglobulin (preferably an antibody) heavy or light chain and may include a variable region, a diversity region, a joining region and/or a constant region or any combination, variant or truncated form thereof. The term "immunoglobulin amino acid sequences" further includes single-chain antibodies comprised of, but not limited to, an immunoglobulin heavy chain variable region, an immunoglobulin light chain variable region and optionally a peptide linker.

The term "isolated nucleic acid" as used herein refers to a nucleic acid that has been substantially removed from other components of the cell containing the nucleic acid or from other components of chemical/synthetic reaction used to generate the nucleic acid. In specific embodiments, the nucleic acid is 50%, 60%, 70%, 80%, 90%, 95%, 99% or 100% pure. The "isolated nucleic acid" does not include nucleic acids that are members of a library, e.g. cDNA or genomic library, unless identified and separated from the other members of the library. The techniques used to isolate and characterize the nucleic acids and proteins of the present invention are well known to those of skill in the art and standard molecular biology and biochemical manuals may be consulted to select suitable protocols without undue experimentation. See, for example, Sambrook et al, 2001, Molecular Cloning: A Laboratory Manual, 3rd ed., Cold Spring Harbor Press; the content of which is herein incorporated by reference in its entirety.

As used herein, the term "locus" or "loci" refers to the site of a gene on a chromosome. Pairs of genes control hereditary traits, each in the same position on a pair of chromosomes. These gene pairs, or alleles, may both be dominant or may both be recessive in expression of that trait. In either case, the individual is said to be homozygous for the trait controlled by that gene pair. If the gene pair (alleles) consists of one dominant and one recessive trait, the individual is heterozygous for the trait controlled by the gene pair. Natural variation in genes or nucleic acid molecules caused by, for example, recombination events or resulting from mutation, gives rise to allelic variants with similar, but not identical, nucleotide sequences. Such allelic variants typically encode proteins with similar activity to that of the protein encoded by the gene to which they are compared, because natural selection typically selects against variations that alter function. Allelic variants can also comprise alterations in the untranslated regions of the gene as, for example, in the 3' or 5' untranslated regions or can involve alternate splicing of a nascent transcript, resulting in alternative exons being positioned adjacently.

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. Representative examples of the nucleic acids of the present invention include bacterial plasmid vectors including expression, cloning, cosmid and transformation vectors such as, but not limited to, plasmid vectors, animal viral vectors such as, but not limited to, modified adenovirus, influenza virus, polio virus, pox virus, retrovirus, and the like, vectors derived from bacteriophage nucleic acid, e.g., plasmids and cosmids, artificial chromosomes, such as but not limited to, Yeast Artificial Chromosomes (YACs) and Bacterial Artificial Chromosomes (BACs), and synthetic oligonucleotides like chemically synthesized DNA or RNA. The term "nucleic acid" further includes modified or derivatised nucleotides and nucleosides such as, but not limited to, halogenated nucleotides such as, but not only, 5-bromouracil, and derivatised nucleotides such as biotin-labeled nucleotides.

The term "nucleic acid vector" or "vector" as used herein refers to a natural or synthetic single or double stranded plasmid or viral nucleic acid molecule, or any other nucleic acid molecule, such as but not limited to YACs, BACs, bacteriophage-derived artificial chromosome (BBPAC), cosmid or P1 derived artificial chromosome (PAC), that can be transfected or transformed into cells and replicate independently of, or within, the host cell genome. A circular double stranded vector can be linearized by treatment with an appropriate restriction enzyme based on the nucleotide sequence of the vector. A nucleic acid can be inserted into a vector by cutting the vector with restriction enzymes and ligating the pieces together. The nucleic acid molecule can be RNA or DNA.

The terms "operably linked" or "operatively linked" refer to the configuration of the coding and control sequences so as to perform the desired function. Thus, control sequences operably linked to a coding sequence are capable of effecting the expression of the coding sequence and/or regulating in which tissues, at what developmental time points, or in response to which signals a gene is expressed. For example, a coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence. Such intervening sequences include but are not limited to enhancer sequences which are not transcribed or are not bound by polymerase.

The terms "percent sequence identity" or "percent sequence homology" or "percent sequence similarity" as used herein refer to the degree of sequence identity between two nucleic acid sequences or two amino acid sequences as determined using the algorithm of Karlin & Attschul (1990) Proc. Natl. Acad. Sci. 87: 2264-2268, modified as in Karlin & Attschul (1993) Proc. Natl. Acad. Sci. 90: 5873-5877. Such an algorithm is incorporated into the NBLAST and XBLAST programs of Attschul et al. (1990) T. Mol. Biol. Q15: 403-410. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference amino acid sequence. To obtain gapped alignments for comparison purposes, Gapped BLAST is utilized as described in Attschul et al. (1997) Nucl. Acids Res. 25: 3389-3402. When utilizing BLAST and Gapped BLAST programs, the default parameters of the respective programs (e.g. XBLAST and NBLAST) are used. Other algorithms, programs and default settings may also be suitable such as, but not only, the GCG-Sequence Analysis Package of the U.K. Human Genome Mapping Project Resource Center that includes programs for nucleotide or amino acid sequence comparisons.

A "pharmaceutical composition" is a substance that, in whole or in part, makes up a drug. "Therapeutic proteins" or "pharmaceutical proteins" include an amino acid sequence which in whole or in part makes up a drug. In one embodiment, a pharmaceutical composition includes one or more pharmaceutical proteins or therapeutic proteins.

The terms "polynucleotide" and "nucleic acid sequence" are used interchangeably herein and include, but are not limited to, coding sequences (polynucleotide(s) or nucleic acid sequence(s) which are transcribed and translated into amino acid sequence in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin is suggested by the terms described herein.

The term "probe" as used herein, when referring to a nucleic acid, refers to a nucleotide sequence that can be used to hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, biotin, and the like that are well known in the art.

The term "promoter" as used herein refers to the DNA sequence that determines the site of transcription initiation by an RNA polymerase. A "promoter-proximal element" may be a regulatory sequence within about 200 base pairs of the transcription start site. A "magnum-specific" promoter, as used herein, is a promoter that is primarily or exclusively active in the tubular gland cells of the avian magnum. Useful promoters also include exogenously inducible promoters. These are promoters that can be "turned on" in response to an exogenously supplied agent or stimulus, which is generally not an endogenous metabolite or cytokine. Examples include an antibiotic-inducible promoter, such as a tetracycline-inducible promoter, a heat-inducible promoter, a light-inducible promoter, or a laser inducible promoter. (e.g., Halloran et al. (2000) Development 127: 1953-1960; Gemer et al. (2000) Int. J. Hyperthermia 16: 171-81; Rang and Will, 2000, Nucleic Acids Res. 28: 1120-5; Hagihara et al. (1999) Cell Transplant 8: 4314; Huang et al. (1999) Mol. Med. 5: 129-37; Forster et al. (1999) Nucleic Acids Res. 27: 708-10; Liu et al. (1998) Biotechniques 24: 624-8, 630-2; the contents of which have been incorporated herein by reference in their entireties).

The term "recombinant cell" refers to a cell that has a new combination of nucleic acid segments that are not covalently linked to each other in nature in that particular configuration. A new configuration of nucleic acid segments can be introduced into an organism using a wide array of nucleic acid manipulation techniques available to those skilled in the art. A recombinant cell can be a single eukaryotic cell, such as a mammalian or avian cell (including within a transgenic mammal or avian) or a single prokaryotic cell. The recombinant cell may harbor a vector that is extragenomic. An extragenomic nucleic acid vector does not insert into the cell's genome. A recombinant cell may further harbor a vector or a portion thereof (e.g., the portion containing the regulatory sequences and the coding sequence) that is intragenomic. The term intragenomic defines a nucleic acid construct incorporated within the recombinant cell's genome.

The terms "recombinant nucleic acid" and "recombinant DNA" as used herein refer a combination of at least two nucleic acids that is not naturally found in a eukaryotic or prokaryotic cell in that particular configuration. The nucleic acids may include, but are not limited to, nucleic acid vectors, gene expression regulatory elements, origins of replication, suitable gene sequences that when expressed confer antibiotic resistance, protein-encoding sequences and the like. The term "recombinant amino acid sequence" is meant to include an amino acid sequence produced by recombinant DNA techniques such that it is distinct from a naturally occurring amino acid sequence either in its location, purity or structure. Generally, such a recombinant amino acid sequence will be present in a cell in an amount different from that normally observed in nature.

The term "sense strand" as used herein refers to a single stranded DNA molecule from a genomic DNA that may be transcribed into RNA and translated into the natural amino acid sequence product of the gene. The term "antisense strand" as used herein refers to the single strand DNA molecule of a genomic DNA that is complementary with the sense strand of the gene.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with high concentrations of salt such as, but not only, a calcium or magnesium salt, an electric field, detergent, or liposome mediated transfection, to render the host cell competent for the uptake of the nucleic acid molecules, and by such methods as sperm-mediated and restriction-mediated integration.

The term "transfecting agent" as used herein refers to a composition of matter added to the genetic material for enhancing the uptake of heterologous DNA segment(s) into a eukaryotic cell, preferably an avian cell. The enhancement is measured relative to the uptake in the absence of the transfecting agent. Examples of transfecting agents include adenovirus-transferrin-polylysine-DNA complexes. These complexes generally augment the uptake of DNA into the cell and reduce its breakdown during its passage through the cytoplasm to the nucleus of the cell. These complexes can be targeted to, e.g., the male germ cells using specific ligands that are recognized by receptors on the cell surface of the germ cell, such as the c-kit ligand or modifications thereof.

Other transfecting agents include but are not limited to lipofectin, lipfectamine, DIMRIE C, Supeffect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecytammonium bromide), DHDEAB (N,N-di-n-hexadecyl-N,N-dihydroxyethyl ammonium bromide), HDEAB (N-n-hexadecylN,N-dihydroxyethylammonium bromide), polybrene, or poly(ethylenimine) (PEI). These non-viral agents have the advantage that they can facilitate stable integration of xenogeneic DNA sequences into the vertebrate genome, without size restrictions commonly associated with virus-derived transfecting agents.

As used herein, a "transgenic animal" is any non-human animal, such as an avian species, including the chicken, in which one or more of the cells of the animal contain a heterologous nucleic acid introduced by way of human intervention, such as by transgenic techniques well known in the art. The nucleic acid is introduced into a cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animal, the transgene causes cells to express a recombinant form of the subject amino acid sequence, e.g. either agonistic or antagonistic forms, or in which the gene has been disrupted. In certain embodiments, the genome of the animal has been modified such that a heterologous gene expression element is inserted so as to be operably linked to an endogenous coding sequence. The terms "chimeric animal" or "mosaic animal" are used herein to refer to animals in which the recombinant gene is found, or in which the recombinant gene is expressed in some but not all cells of the animal. The term "tissue-specific chimeric animal" indicates that the recombinant gene is present and/or expressed in some tissues but not others.

As used herein, the term "transgene" means a nucleic acid sequence (encoding, for example, a human interferon amino acid sequence) that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location that differs from that of the natural gene or its insertion results in a knockout). A trangene also includes a regulatory sequence designed to be inserted into the genome such that it regulates the expression of an endogenous coding sequence, e.g., to increase expression and or to change the timing and or tissue specificity of expression, etc. (e.g., to effect "gene activation").

The terms "unique nucleic acid region" and "unique protein (amino acid sequence) region" as used herein refer to sequences present in a nucleic acid or protein (amino acid sequence) respectively that is not present in any other nucleic acid or protein sequence. The terms "conserved nucleic acid region" as referred to herein is a nucleotide sequence present in two or more nucleic acid sequences, to which a particular nucleic acid sequence can hybridize under low, medium or high stringency conditions. The greater the degree of conservation between the conserved regions of two or more nucleic acid sequences, the higher the hybridization stringency that will allow hybridization between the conserved region and a particular nucleic acid sequence.

This description uses gene nomenclature accepted by the Cucurbit Genetics Cooperative as it appears in the Cucurbit Genetics Cooperative Report 18:85 (1995), herein incorporated by reference in its entirety. Using this gene nomenclature, genes are symbolized by italicized Roman letters. If a mutant gene is recessive to the normal type, then the symbol and name of the mutant gene appear in italicized lower case letters.

Abbreviations

Abbreviations used in the present specification include the following: aa, amino acid(s); bp, base pair(s); cDNA, DNA complementary to RNA; ml, milliliter; min, minute(s); nt, nucleotide(s); SSC, sodium chloride-sodium citrate; ug, microgram(s); ul, microliter(s); uM, micromolar; UTR, untranslated region; DMSO, dimethyl sulfoxide.

Additional objects and aspects of the present invention will become more apparent upon review of the detailed description set forth below when taken in conjunction with the accompanying figures, which are briefly described as follows.

BRIEF DESCRIPTION OF THE FIGURES

FIG. 3 shows the PCR primers SEQ ID NOS: 1-25 used to PCR amplify and/or sequence the approximately 10 kb nucleic acid region that is 5' upstream of the chicken ovomucoid transcription start site.

FIG. 4 shows the nucleic acid sequence SEQ ID NO: 26 of the approximately 10 kb nucleic acid region that is 5' upstream of the chicken ovomucoid transcription start site.

FIG. 8A. The ovoinhibitor (OI) and adjacent ovomucoid (OM) regions are shown with transcriptional start sites indicated with bent arrows. The left and right sides of the BAC, relative to an EcoRI site found in the 3' UTR, are shown with their approximate sizes in kilobase pairs (kb). FIG. 8B. The coding region of ovomucoid is shown with exons as white boxes and introns as black boxes. C. The IRES and polynucleotide coding sequence for the light chain and heavy chain of the IgG1 inserted at the EcoRI site.

FIG. 14 shows the nucleotide sequence of the approximately 70 kb ovomucoid gene expression controlling region which is included in SEQ ID NO: 36. Also indicated in the figure is the approximately 10 kb ovomucoid gene expression controlling region which is designated Fragment A and shown in bold, the approximately 3.9 kb ovomucoid gene expression controlling region which is designated Fragment B and is shown underlined and the approximately 1.8 kb ovomucoid gene expression controlling region which is designated Fragment C and is shown in lower case.

DETAILED DESCRIPTION OF THE INVENTION

Figure 1:
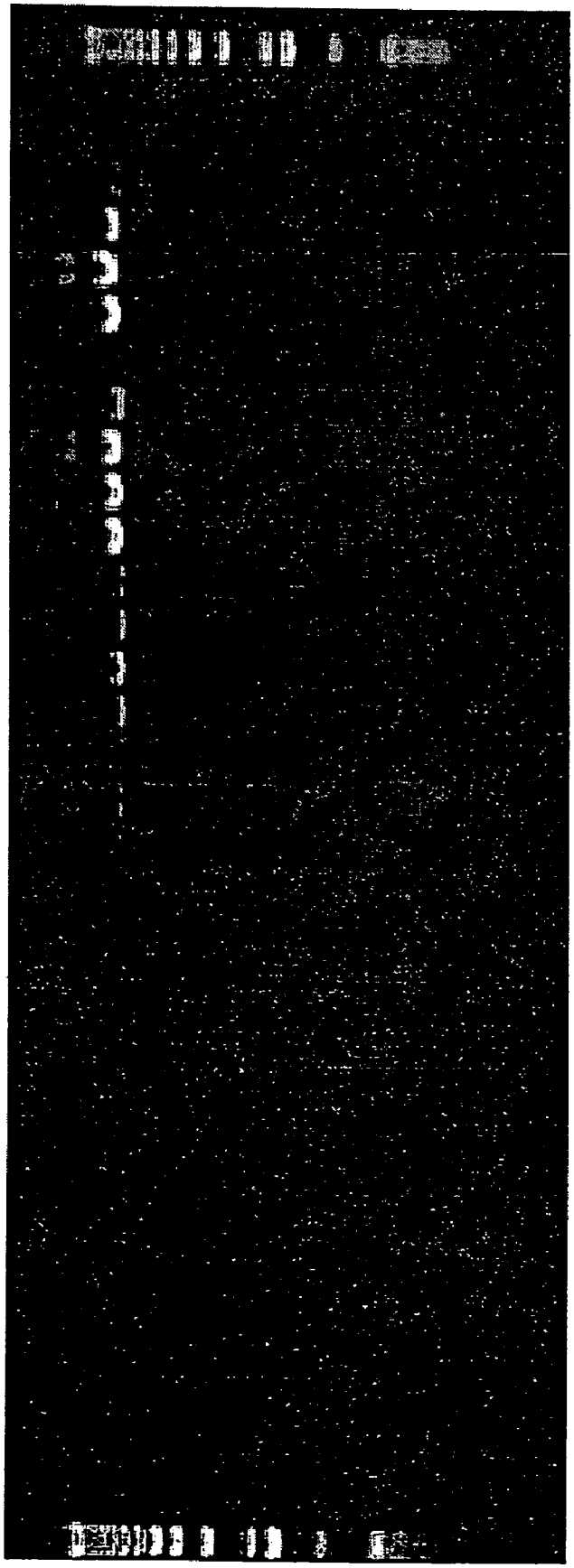
FIG. 1 illustrates an agarose gel analysis of PCR products from PCR amplification of chicken genomic DNA using the primers OVINs2 (SEQ ID NO: 1) and OVMUa2 (SEQ ID NO: 2).

The present invention relates to avian gene expression controlling regions and to methods of their use. In one embodiment, the invention relates to avian (e.g., chicken) ovomucoid promoters and to methods of using such promoters in the production of useful amino acid sequences such as peptides and proteins.

A series of PCR amplifications of template chicken genomic DNA were used to isolate the gene expression controlling region of the chicken ovomucoid locus. For example, the region of the chicken genome lying between the 3' end of the ovoinhibitor gene and the 5' transcription start site of the ovomucoid gene was PCR amplified using the primers OVINs 2, 5'-TAGGCAGAGCAATAGGACTCTCAAC-CTCGT-3' (SEQ ID NO: 1) and OVMUa2, 5'-AAGCTTCT-GCAGCACTCTGGGAGTTACTCA-3' (SEQ ID NO: 2) as described in detail in Example 1 below and FIG. 1. The approximately 10 kb fragment was blunt-ended and cleaved with the restriction endonuclease BamHI. The resulting fragments of about 4.7 kb and 5.5 kb were subcloned into the linearized plasmid vector pBluescript KS II (+/−) (Stratagene, La Jolla, Calif.). Each insert was sequenced using the primers SEQ ID NOS: 5 to 25 shown in FIGS. 2 and 3 and as described in Example 3 below. The compiled nucleic acid sequence (SEQ ID NO: 26) of the approximately 10 kb nucleic acid region that is 5' upstream of the chicken ovomucoid transcription start site is shown in FIG. 4.

SEQ ID NO: 26 includes the ovoinhibitor gene 3' untranslated region described by Scott et al. (1987) J. Biol. Chem. 262: 5899-5909, from base positions 1-255 as shown in FIG. 4. A CR1-like element (Scott et al., Biochemistry (1987) 26: 6831-6840; Genbank Accession No: M17966) is located at base positions 2761-3024 as shown in FIG. 4. The region of SEQ ID NO: 26 from base positions 9403-9920, as shown in FIG. 4, has been described in Genbank Accession No: J00897 and in Lai et al., Cell (1979) 18: 829-842 and includes a portion of the 5' untranslated region of the ovomucoid gene.

An avian ovomucoid gene region has been identified in a chicken artificial chromosome library. The library was constructed with HindIII chicken DNA inserts ligated into a BAC vector (see, Crooijmans et al. (2000) Mammalian Genome 11: 360-363, the disclosure of which is incorporated in its entirety by reference). However, the present invention contemplates the employment of any useful artificial chromosome library including, but not limited to, libraries constructed from YACs, HACs, MACs, BBPACs or PACs.

The library was screened by PCR identifying a BAC clone which included a single chicken DNA segment which extends into both the 5' untranslated region of the ovomucoid gene and the 3' ovoinhibitor gene. The nucleotide sequence of the clone, designated OMC24, is shown in SEQ ID NO: 36. The nucleotide region spanning from about nucleotide 68,296 to about nucleotide 75,815 of SEQ ID NO: 36 represents the BAC vector. The ovomucoid region spans from about nucleotide 1 to about nucleotide 68,295 of SEQ ID NO: 36 and is shown in FIG. 14.

The nucleotide sequence of the gene expression controlling region disclosed in SEQ ID NO: 26 is essentially encompassed in SEQ ID NO: 36 from about nucleotide 26,416 to about nucleotide 36,390. Nucleotide sequence alignment between SEQ ID NO: 26 and nucleotides 26,416 to 36,390 of SEQ ID NO: 36 show a 99.0% sequence homology. The chicken genomic DNAs which yielded SEQ ID NO: 26 and SEQ ID NO: 36 were isolated from different strains of white leghorn chickens (SEQ ID NO: 26—American Strain, SEQ ID NO: 36: Dutch Strain) thus showing the sequence diversity of the ovomucoid gene expression controlling region of the present invention. Other useful fragments or functional portions of SEQ ID NO: 36 can be easily obtained by standard techniques well known in the art.

Fragments or portions of certain DNA sequences which function to control gene expression can be identified by techniques that are well know to practitioners of ordinary skill in the art. For example, promoter analysis by saturation mutagenesis has been describe in Biol. Proced. Online (2001) Vol 1, No. 3, pp 64-69, the disclosure of which is incorporated by reference herein in its entirety. Also, for example, fragments or functional portions of the chicken ovomucoid gene region effective to control gene expression, for example, control transcription in a cell, can be identified by techniques disclosed in the Examples of the present specification. For example, functional fragments of SEQ ID NO: 36 can be identified by methods as disclosed in the present specification and by any useful method known in the field of molecular biology.

In one embodiment, the gene expression controlling region comprises a nucleotide or portion of a nucleotide sequence that is at least 50% homologous to the avian nucleic acid contained in SEQ ID NO: 36 or to the complement of the avian nucleic acid contained in SEQ ID NO: 36. For example, the gene expression controlling region may comprise a nucleotide sequence or portion of a nulceotide sequence that is at least 60% homologous to the avian nucleic acid contained in SEQ ID NO: 36 or its complement. In another example, the gene expression controlling region comprises a nucleotide sequence or portion of a nulceotide sequence that is at least 70% homologous to the avian nucleic acid contained in SEQ ID NO: 36 or its complement. In another example, the gene expression controlling region comprises a nucleotide sequence or portion of a nulceotide sequence that is at least 75% homologous to the avian nucleic acid contained in SEQ ID NO: 36 or its complement. In another example, the gene expression controlling region comprises a nucleotide sequence or portion of a nulceotide sequence that is at least 80% homologous to the avian nucleic acid contained in SEQ ID NO: 36 or its complement. In another example, the gene expression controlling region comprises a nucleotide sequence or portion of a nulceotide sequence that is at least 85% homologous to the avian nucleic acid contained in SEQ ID NO: 36 or its complement. In another example, the gene expression controlling region comprises a nucleotide sequence or portion of a nulceotide sequence that is at least 90% homologous to the avian nucleic acid contained in SEQ ID NO: 36 or its complement. In another example, the gene expression controlling region comprises a nucleotide sequence or portion of a nulceotide sequence that is at least 95% homologous to the avian nucleic acid contained in SEQ ID NO: 36 or its complement. In another example, the gene expression controlling region comprises a nucleotide sequence or portion of a nulceotide sequence that is at least 99% homologous to the avian nucleic acid contained in SEQ ID NO: 36 or its complement.

Nucleotide sequences encoding the heavy chain and light chain of an IgG1 monoclonal antibody were inserted into the 3' UTR of the ovomucoid transcript encoding region in two separate ovomucoid BAC clones of SEQ ID NO: 36. The heavy chain and light chain coding sequences each included a signal sequence located at their 5' ends; however, use of a signal sequence may not be required in the present invention. The resulting mRNA transcript produced by the ovomucoid gene expression controlling region for each clone contains two coding sequences; one for the ovomucoid protein and another for the antibody light chain or heavy chain downstream of the ovomucoid coding sequence. To facilitate translation of the downstream heavy chain or light chain coding sequence, an internal ribosome entry site (IRES) was inserted immediately upstream of the heavy chain or light chain coding sequence in each clone.

In another example, a CTLA4-Fc fusion coding sequence comprising a nucleotide coding sequence for the extracellular domains of the CTLA4 (cytotoxic T lymphocyte antigen 4) receptor protein linked to a nucleotide coding sequence for an immunoglobulin constant region (IgG1 Fc) was cloned into an ovomucoid BAC clone of SEQ ID NO: 36. In addition, an attB site was included in the construct. To produce this clone, the IRES-LC portion of the ovomucoid-IRES-antibody light chain clone was deleted and was replaced with an IRES-CTLA4-Fc cassette.

Figure 15:
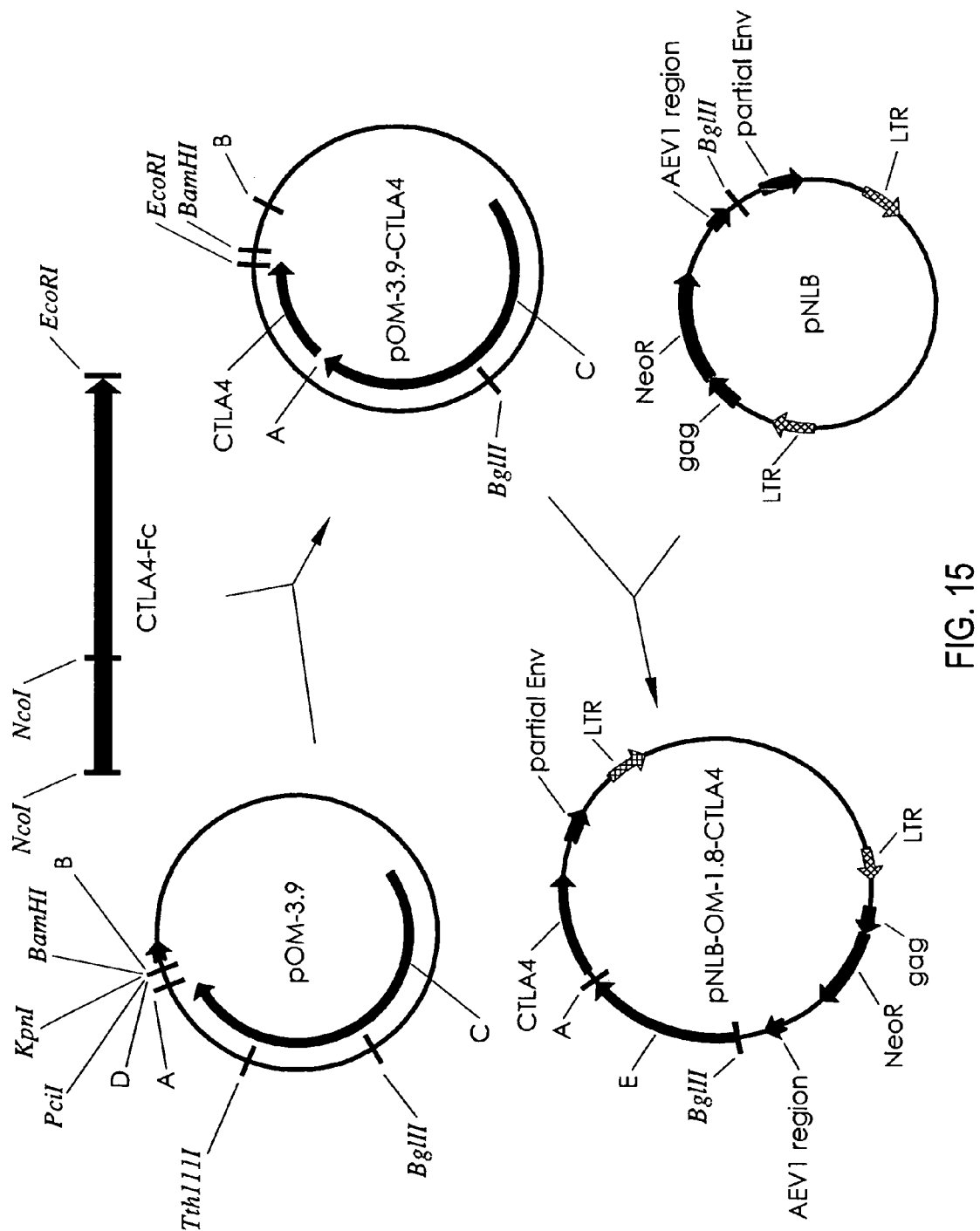
FIG. 15 shows construction of the pOM-3.9-CTLA4 expression vector which includes the approximately 3.9 kb ovomucoid gene expression controlling region (Fragment B of FIG. 14) operably linked to a CTLA4 coding sequence and the construction of pNLB-OM-1.8-CTLA4 which includes the approximately 1.8 kb ovomucoid gene expression controlling region (Fragment C of FIG. 14) operably linked to a CTLA4 coding sequence. In the figure, "A" represents the transcription start site; "B" represents the ovomucoid CDS; "C" represents the approximately 3.9 kb ovomucoid gene expression controlling region; "D" represents the translation start site; and "E" represents the approximately 1.8 kb ovomucoid gene expression controlling region. pNLB is a replication deficient avian leukosis viral vector (ALV). See, for example, U.S. Pat. No. 6,730,822, issued May 4, 2004, the disclosure of which is incorporated in its entirety herein by reference.

The present invention contemplates the introduction of an ovomucoid gene expression controlling region, for example, operably linked to a coding sequence of interest, which is present on a retrovirus vector, such as an ALV vector (e.g., replication deficient ALV vector), into an avian to produce a transgenic avian. One example of an ALV based vector contemplated for use herein is a pNLB vector described in for example, Cosset et al., 1991, J. Virology 65: 3388-3394, the disclosure of which is incorporated in its entirety herein by reference and U.S. patent application Ser. No. 10/463,980, filed Jun. 17, 2003, the disclosure of which is incorporated in its entirety herein by reference. In one example, a CTLA4-Fc fusion coding sequence was operably linked to an approximately 3.9 kb ovomucoid gene expression controlling region (Fragment B of FIG. 14). In yet another example, a CTLA4-Fc fusion coding sequence was operably linked to an approximately 1.8 kb ovomucoid gene expression controlling region (Fragment C of FIG. 14). The Promoter-coding sequence cassette was inserted into a replication deficient avian leucosis virus (ALV) based vector as shown in FIG. 15.

Disclosed above are examples of expression constructs that can be produced in accordance with the present invention. However, these are merely examples and it is contemplated that any nucleic acid sequence encoding a useful amino acid sequence can be operably linked to an avian ovomucoid gene expression controlling region of the present invention so as to be expressed in an avian cell, for example, in cells of a transgenic avian such as a chicken, turkey, duck, goose, quail, pheasant, parrot, finch, ratites including ostrich, emu or cassowary.

The present invention can be used to express, in large yields and at low cost, a wide range of desired proteins including those used as human and animal pharmaceuticals, diagnostics, and livestock feed additives. Proteins such as growth hormones, cytokines, structural proteins and enzymes, including human growth hormone, interferon, lysozyme, and β-casein, are examples of proteins that are desirably expressed in the oviduct and deposited in eggs according to the invention. Other possible proteins to be produced include, but are not limited to, albumin, α-1 antitrypsin, antithrombin III, collagen, factors VIII, IX, X (and the like), fibrinogen, hyaluronic acid, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), feed additive enzymes, somatotropin, and chymotrypsin Immunoglobulins and genetically engineered antibodies, including immunotoxins that bind to surface antigens on human tumor cells and destroy them, can also be expressed for use as pharmaceuticals or diagnostics. It is contemplated that immunoglobulin amino acid sequences expressed in avian cells following transfection by the methods of the present invention may include monomeric heavy and light chains, single-chain antibodies or multimeric immunoglobulins comprising variable heavy and light chain regions, i.e., antigen-binding domains, or intact heavy and light immunoglobulin chains.

The chicken ovomucoid gene expression controlling region of the present invention may include the nucleotide elements that are positioned 5' upstream of the transcription start site of the native chicken ovomucoid locus and which are necessary for the regulated expression of a downstream amino acid sequence-encoding nucleic acid. It is contemplated that this region may include transcription controlling regions which are regulated by certain hormones including, for example, steroid hormones and the like.

One aspect of the present invention, therefore, provides a novel isolated nucleic acid that comprises the nucleotide sequence SEQ ID NO: 26, shown in FIG. 4, (Genbank Accession No: AF 453747) and derivatives and variants thereof, that is located immediately 5' upstream of the transcription start site of the chicken ovomucoid gene locus.

In one embodiment of the present invention, the isolated nucleic acid may be isolated from an avian selected from the group consisting of a chicken, a turkey, a duck, a goose, a quail, a pheasant, a ratite, an ornamental bird or a feral bird.

In another embodiment of the present invention, the isolated nucleic acid is obtained from a chicken. In this embodiment, the isolated nucleic acid has the sequence of SEQ ID NO: 26, as shown in FIG. 4, or a variant thereof. SEQ ID NO: 26 was cloned into pBluescript KS II (+/−) vector, as described in Example 2, and named pBS-OVMUP-10. pBS-OVMUP-10 was deposited with American Type Culture Collection (ATCC), 10801 University Blvd., Manassas, Va. 20110, as ATCC No. PTA-4821 on Nov. 26, 2002 under the conditions set forth in the Budapest Treaty.

Another aspect of the invention provides nucleic acids that can hybridize under high, medium or low stringency conditions to an isolated nucleic acid comprising a chicken ovomucoid gene expression controlling region having all, a derivative of, or a portion of the nucleic acid sequence SEQ ID NO: 26 shown in FIG. 4 and direct expression of an amino acid sequence coding sequence in an avian oviduct cell. The nucleotide sequence determined from the isolation of the ovomucoid gene expression controlling region from a chicken (SEQ ID NO: 26) will allow for the generation of probes designed for use in identifying ovomucoid gene expression controlling regions, or homologs thereof in other avian species.

Fragments of a nucleic acid comprising a portion of the subject ovomucoid gene expression controlling region are also within the scope of the invention. As used herein, a fragment of the nucleic acid comprising an active portion of a ovomucoid gene expression controlling region refers to a nucleotide sequence having fewer nucleotides than the nucleotide sequence comprising the entire nucleic acid sequence of the ovomucoid gene expression controlling region.

A fragment of the ovomucoid gene expression controlling region may contain one or more of the following elements: the ovoinhibitor gene 3' untranslated region from bases positions 1-255 as shown in FIG. 4, a CR1-like element located at base positions 2761-3024 as shown in FIG. 4, the region from base positions 9403-9920, as shown in FIG. 4 which includes a portion of the 5' untranslated region of the ovomucoid gene. Alternatively, the fragment may be about 10 or about 20 or about 50 or about 75 or about 100 or about 150 or about 200 or about 250 or about 300 or about 500 or about 1000 or about 2000 or about 4000 or about 5000 or about 6000 or about 7000 or about 8000 or about 9000 or about 10,000 or about 20,000 or about 30,000 or about 40,000 or about 50,000 or about 60,000 nucleotides in length and be capable of directing expression of an operably linked heterologous gene sequence, particularly in an avian cell, for example, in an avian oviduct cell of a transgenic avian or in an avian cell in culture.

In one embodiment of the present invention, the nucleotide sequence of the isolated DNA molecule of the present invention may be used as a probe in nucleic acid hybridization assays for the detection of the ovomucoid gene expression controlling region. The nucleotide sequence of the present invention may be used in any nucleic acid hybridization assay system known in the art, including, but not limited to, Southern blots (Southern, E. M. J. Mol. Biol. 98: 508 (1975)), Northern blots (Thomas et al. (1980) Proc. Natl. Acad. Sci. 77: 5201-05), and Colony blots (Grunstein et al. (1975) Proc. Natl. Acad. Sci. 72: 3961-65), which are hereby incorporated by reference in their entireties. Alternatively, the isolated DNA molecules of the present invention can be used in a gene amplification detection procedure such as a polymerase chain reaction (Erlich et al. (1991) Science 252: 1643-51, which is hereby incorporated by reference in its entirety) or in restriction fragment length polymorphism (RFLP) diagnostic techniques, as described in Watson et al., (2d ed. 1992), Recombinant DNA, Scientific American Books, 519-522, 545-547, which is hereby incorporated by reference.

Nucleic acids constructed in accordance with the present invention can be labeled to provide a signal as a means of detection. For example, radioactive elements such as $^{32}P$, $^{3}H$, and $^{35}S$ or the like provide sufficient half-life to be useful as radioactive labels. Other materials useful for labeling synthetic nucleotides include fluorescent compounds, enzymes and chemiluminescent moieties. Methods useful in selecting appropriate labels and binding protocols for binding the labels to the synthetic nucleotides are well known to those of skill in the art. Standard immunology manuals such as *Promega: Protocol and Applications Guide,* 2nd Edition, 1991 (Promega Corp., Madison, Wis., the disclosure of which is incorporated herein in its entirety) may be consulted to select an appropriate labeling protocol without undue experimentation.

In another embodiment of the present invention, an isolated nucleic acid molecule of the present invention includes a nucleic acid that hybridizes to SEQ ID NO: 26 or the complement thereof, or the insert in pBS-OVMUP-10, under high, moderate or low stringency hybridization conditions.

In another embodiment of the present invention, an avian ovomucoid gene expression controlling region gene or nucleic acid molecule can be an allelic variant of SEQ ID NO: 26 or SEQ ID NO: 36 or a homolog from a different avian, e.g., quail, duck, etc.

The present invention also contemplates the use of anti-sense nucleic acid molecules that are designed to be complementary to a coding strand of a nucleic acid (i.e., complementary to an mRNA sequence) or, alternatively, complimentary to a 5' or 3' untranslated region of the mRNA. Another use of synthetic nucleotides is as primers (DNA or RNA) for a polymerase chain reaction (PCR), ligase chain reaction (LCR), or the like.

Synthesized oligonucleotides can be produced in variable lengths. The number of bases synthesized will depend upon a variety of factors, including the desired use for the probes or primers. Additionally, sense or anti-sense nucleic acids or oligonucleotides can be chemically synthesized using modified nucleotides to increase the biological stability of the molecule or of the binding complex formed between the anti-sense and sense nucleic acids. For example, acridine substituted nucleotides can be synthesized. Protocols for designing isolated nucleotides, nucleotide probes, and/or nucleotide primers are well-known to those of ordinary skill, and can be purchased commercially from a variety of sources (e.g., Sigma Genosys, The Woodlands, Tex. or The Great American Gene Co., Ramona, Calif.).

The nucleic acid sequence of a chicken ovomucoid gene expression controlling region nucleic acid molecule of the present invention allows one skilled in the art to, for example, (a) make copies of those nucleic acid molecules by procedures such as, but not limited to, insertion into a cell for replication by the cell, by chemical synthesis or by procedures such as PCR or LCR, (b) obtain nucleic acid molecules which include at least a portion of such nucleic acid molecules, including full-length genes, full-length coding regions, regulatory control sequences, truncated coding regions and the like, (c) obtain ovomucoid gene expression controlling region nucleic acid homologs in other avian species such as, but not limited to, turkey, duck, goose, quail, pheasant, parrot, finch, ratites including ostrich, emu and cassowary and, (d) to obtain isolated nucleic acids capable of hybridizing to an avian ovomucoid gene expression controlling region nucleic acid and be used to detect the presence of nucleic acid-related sequences by complementation between the probe and the target nucleic acid.

Such nucleic acid homologs can be obtained in a variety of ways including by screening appropriate expression libraries with antibodies of the present invention, using traditional cloning techniques to screen appropriate libraries, amplifying appropriate libraries or DNA using oligonucleotide primers of the present invention in a polymerase chain reaction or other amplification method, and screening public and/or private databases containing genetic sequences using nucleic acid molecules of the present invention to identify targets. Examples of libraries to screen, or from which to amplify nucleic acid molecules, include but are not limited to mammalian BAC libraries, genomic DNA libraries, and cDNA libraries. Similarly, sequence databases useful for screening to identify sequences in other species homologous to chicken ovomucoid gene expression controlling region include, but are not limited to, GenBank and the mammalian Gene Index database of The Institute of Genomics Research (TIGR).

Another aspect of the present invention is a recombinant DNA molecule comprising the novel isolated avian ovomucoid gene expression controlling region of the present invention operably linked to a selected amino acid sequence-encoding nucleic acid insert, and which may express the nucleic acid insert when transfected to a suitable host cell, preferably an avian cell. The nucleic acid insert may be placed in frame with a signal peptide sequence, whereby translation initiation from the transcript may start with the signal peptide and continue through the nucleic acid insert, thereby producing an expressed amino acid sequence having the desired amino acid sequence.

It is anticipated that the recombinant DNA may further comprise a polyadenylation signal sequence that will allow the transcript directed by the novel ovomucoid gene expression controlling region to proceed beyond the nucleic acid insert encoding an amino acid sequence and allow the transcript to further comprise a 3' untranslated region and a polyadenylated tail. Any functional polyadenylation signal sequence may be linked to the 3' end of the nucleic acid insert including the SV40 polyadenylation signal sequence, bovine growth hormone adenylation sequence or the like, or derivatives thereof. One embodiment of the present invention is a recombinant DNA molecule comprising the isolated avian ovomucoid gene expression controlling region of the present invention, operably linked to a nucleic acid insert encoding an amino acid sequence which may include a polyadenylation signal sequence. In certain embodiments, the recombinant DNA molecule which includes include a polyadenylation signal sequence is an artificial chromosome.

Another aspect of the present invention is to provide nucleic acid sequences of a protein optimized for expression in avian cells, and derivatives and fragments thereof. For example, it is contemplated that when the recombinant DNA is to be delivered to a recipient cell for expression therein, the sequence of the nucleic acid sequence may be modified so that the codons are optimized for the codon usage of the recipient species. When a heterologous nucleic acid is to be delivered to a recipient cell for expression therein, the sequence of the nucleic acid sequence may be modified so that the codons are optimized for the codon usage of the recipient species. For example, if the heterologous nucleic acid is transfected into a recipient chicken cell, the sequence of the expressed nucleic acid insert is optimized for chicken codon usage. This may be determined from the codon usage of at least one, and preferably more than one, protein expressed in a chicken cell. For example, the codon usage may be determined from the nucleic acid sequences encoding the proteins ovalbumin, lysozyme, ovomucin and ovotransferrin of chicken. Briefly, the DNA sequence for the target protein may be optimized using the BACKTRANSLATE® program of the Wisconsin Package, version 9.1 (Genetics Computer Group, Inc., Madison, Wis.) with a codon usage table compiled from the chicken (*Gallus gallus*) ovalbumin, lysozyme, ovomucoid, and ovotransferrin proteins. The template and primer oligonucleotides are then amplified, by any means known in the art, including but not limited to PCR with Pfu polymerase (STRATAGENE®, La Jolla Calif.).

In one exemplary embodiment of a heterologous nucleic acid for use by the methods of the present invention, a nucleic acid insert encoding the human interferon α2b amino acid sequence optimized for codon-usage by the chicken is used. Optimization of the sequence for codon usage is useful in elevating the level of translation in avian eggs.

It is contemplated to be within the scope of the present invention for any nucleic acid encoding an amino acid sequence to be optimized for expression in avian cells. It is further contemplated that the codon usage may be optimized for a particular avian species used as a source of the host cells. In one embodiment of the present invention, the heterologous amino acid sequence is encoded using the codon-usage of a chicken.

In yet another embodiment of the present invention, the recombinant DNA comprises the isolated avian ovomucoid gene expression controlling region operably linked to a nucleic acid encoding a human interferon a2b and the SV40 polyadenylation sequence.

Proteins produced in accordance with methods of the present invention may be purified by any known conventional technique. In a one embodiment, the protein is purified from chicken eggs, preferably egg whites. For example, chicken cells may be homogenized and centrifuged. The supernatant is then subjected to sequential ammonium sulfate precipitation and heat treatment. The fraction containing the protein of the present invention is subjected to gel filtration in an appropriately sized dextran or polyacrylamide column to separate the proteins. If necessary, the protein fraction may be further purified by HPLC.

In one embodiment of the present invention, the multimeric protein is an immunoglobulin, wherein the first and second heterologous amino acid sequences are an immunoglobulin heavy and light chain respectively. Illustrative examples of this and other aspects and embodiments of the present invention for the production of heterologous multimeric amino acid sequences in avian cells are fully disclosed in U.S. patent application Ser. No. 09/877,374, filed Jun. 8, 2001, published as US-2002-0108132-A1 on Aug. 8, 2002, and U.S. patent application Ser. No. 10/251,364, filed Sep. 18, 2002, now U.S. Pat. No. 7,312,374, issued Dec. 25, 2007, the disclosures of which are incorporated herein by reference in their entirety. In one embodiment of the present invention, therefore, the multimeric protein is an immunoglobulin wherein the first and second heterologous amino acid sequences are an immunoglobulin heavy and light chain respectively. Accordingly, the invention provides immunoglobulin and other multimeric proteins that have been produced by transgenic avians of the invention.

In the various embodiments of this aspect of the present invention, an immunoglobulin amino acid sequence encoded by the transcriptional unit of at least one expression vector may be an immunoglobulin heavy chain amino acid sequence comprising a variable region or a variant thereof, and may further comprise a D region, a J region, a C region, or a combination thereof. An immunoglobulin amino acid sequence encoded by the transcriptional unit of an expression vector comprising an ovomucoid gene expression controlling region may also be an immunoglobulin light chain amino acid sequence comprising a variable region or a variant thereof, and may further comprise a J region and a C region. It is also contemplated to be within the scope of the present invention for the immunoglobulin regions to be derived from the same animal species, or a mixture of species including, but not only, human, mouse, rat, rabbit and chicken. In certain embodiments, the antibodies are human or humanized.

In other embodiments of the present invention, the immunoglobulin amino acid sequence encoded by the transcriptional unit of at least one expression vector comprises an immunoglobulin heavy chain variable region, an immunoglobulin light chain variable region, and a linker peptide thereby forming a single-chain antibody capable of selectively binding an antigen.

Another aspect of the present invention provides a method for the production in an avian of a heterologous protein capable of forming an antibody suitable for selectively binding an antigen comprising the step of producing a transgenic avian incorporating at least one transgene, wherein the transgene encodes at least one heterologous amino acid sequence selected from an immunoglobulin heavy chain variable region, an immunoglobulin heavy chain comprising a variable region and a constant region, an immunoglobulin light chain variable region, an immunoglobulin light chain comprising a variable region and a constant region, and a single-chain antibody comprising two peptide-linked immunoglobulin variable regions.

In an embodiment of this method of the present invention, the isolated heterologous protein is an antibody capable of selectively binding to an antigen. In one embodiment, the antibody may be generated by combining at least one immunoglobulin heavy chain variable region and at least one immunoglobulin light chain variable region, preferably cross-linked by at least one di-sulfide bridge. The combination of the two variable regions will generate a binding site capable of binding an antigen using methods for antibody reconstitution that are well known in the art.

It is, however, contemplated to be within the scope of the present invention for immunoglobulin heavy and light chains, or variants or derivatives thereof, to be expressed in separate transgenic avians, and therefore isolated from separate media including serum or eggs, each isolate comprising a single species of immunoglobulin amino acid sequence. The method may include combining certain isolated heterologous immunoglobulin amino acid sequences, thereby producing an antibody capable of selectively binding to an antigen. In this embodiment, two individual transgenic avians may be generated wherein one transgenic produces serum or eggs having an immunoglobulin heavy chain variable region, or an amino acid sequence comprising such, expressed therein. A second transgenic avian, having a second transgene, produces serum or eggs having an immunoglobulin light chain variable region, or an amino acid sequence comprising such, expressed therein. The amino acid sequences may be isolated from their respective sera and eggs and combined in vitro to generate a binding site capable of binding an antigen.

The present invention is useful for the production of many biological products such as, pharmaceutical or therapeutic proteins. For example, the present invention can be useful for the production of biological molecules such as hormones including cytokines (i.e., secreted amino acid sequences that affect a function of cells and modulates an interaction between cells in an immune, inflammatory or hematopoietic response), antibodies and other useful pharmaceutical molecules which include amino acid sequences. Cytokines includes, but are not limited to, monokines and lymphokines. Examples of cytokines include, but are not limited to, interferon α2b, Interleukin-1 (IL-1), Interleukin-6 (IL-6), Interleukin-8 (IL-8), Tumor Necrosis Factor-α (TNF-α.) and Tumor Necrosis Factor β (TNF-β), antibodies such as polyclonal and monoclonal antibodies and fragments thereof, and immunologic binding equivalents thereof. Antibodies may include, but are not limited to polyclonal antibodies, monoclonal antibodies (MAbs), humanized or chimeric antibodies, single chain antibodies, FAb fragments, F(Ab')$_2$ fragments, fragments produced by a FAb expression library, anti-idiotypic (anti-Id) antibodies, and epitope-binding fragments thereof. Also contemplated is the production of antibody fusion proteins, for example, Fc fusion proteins in accordance with the present methods. The methods of the present invention can also be useful for producing immunoglobulin amino acid sequences which are constituent amino acid sequences of an antibody or an amino acid sequence derived therefrom. An "immunological amino acid sequence" may be, but is not limited to, an immunological heavy or light chain and may include a variable region, a diversity region, joining region and a constant region or any combination, variant or truncated form thereof. Immunological amino acid sequences also include single-chain antibodies comprised of, but not limited to, an immunoglobulin heavy chain variable region, an immunoglobulin light chain variable region and optionally a peptide linker.

Examples of certain antibodies that can be produced in methods of the invention may include but are not limited to HERCEPTIN® (Trastuzumab) (Genentech, Calif.) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/

Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-β$_2$ antibody (Cambridge Ab Tech).

Another potentially useful application of the novel isolated ovomucoid gene expression controlling region of the present invention is the possibility of increasing the amount of a heterologous protein present in a bird, (especially the chicken) by gene transfer. In most instances, a heterologous amino acid sequence-encoding nucleic acid insert transferred into the recipient animal host will be operably linked with the ovomucoid gene expression controlling region to allow the cell to initiate and continue production of the genetic product protein. A recombinant DNA molecule of the present invention can be transferred into the extra-chromosomal or genomic DNA of the host.

The recombinant ovomucoid gene expression controlling region of the present invention and amino acid sequence coding sequence, which may include an artificial chromosome and/or a polyadenylation coding sequence, may be introduced into cells by any useful method. The recombinant molecules may be inserted into a cell to which the amino acid sequence-encoding nucleic acid is heterologous (i.e. not normally present). Alternatively, as described more fully below, the recombinant DNA molecule may be introduced into cells which normally contain the amino acid sequence-encoding nucleic acid insert of the recombinant DNA molecule, for example, to correct a deficiency in the expression of an amino acid sequence, or where over-expression of the amino acid sequence is desired.

For expression in heterologous systems, the heterologous DNA molecule is inserted into the expression system or vector of the present invention in proper sense orientation and correct reading frame. The vector contains the necessary elements for the transcription and translation of the inserted protein-coding sequences, including the novel isolated ovomucoid gene expression controlling region.

U.S. Pat. No. 4,237,224 to Cohen & Boyer, which is hereby incorporated by reference in its entirety, describes the production of expression systems in the form of recombinant plasmids using restriction enzyme cleavage and ligation with DNA ligase. These recombinant plasmids are then introduced to a cell by means of transformation and replicated in cultures, including eukaryotic cells grown in tissue culture.

One aspect of the present invention, therefore, is an ovomucoid gene expression controlling region expression vector suitable for delivery to a recipient cell for replication or expression of an amino acid sequence-encoding nucleic acid of the vector therein. It is contemplated to be within the scope of the present invention for the expression vector to comprise an isolated avian ovomucoid gene expression controlling region operably linked to a nucleic acid insert encoding an amino acid sequence, and optionally a polyadenylation signal sequence. The expression vector of the present invention may further comprise a bacterial plasmid sequence, a viral nucleic acid sequence, or fragments or variants thereof that may allow for replication of the vector in a suitable host.

The recombinant nucleic acid molecules of the present invention can be delivered to cells using viruses such as vaccinia virus. Methods for making a viral recombinant vector useful for expressing a protein under the control of the ovomucoid promoter are analogous to the methods disclosed in U.S. Pat. Nos. 4,603,112; 4,769,330; 5,174,993; 5,505,941; 5,338,683; 5,494,807; 4,722,848; Paoletti, E. Proc. Natl. Acad. Sci. 93: 11349-11353 (1996); Moss Proc. Natl. Acad. Sci. 93: 11341-11348 (1996); Roizman Proc. Natl. Acad. Sci. 93: 11307-11302 (1996); Frolov et al. Proc. Natl. Acad. Sci. 93: 11371-11377 (1996); Grunhaus et al. Seminars in Virology 3: 237-252 (1993) and U.S. Pat. Nos. 5,591,639; 5,589,466; and 5,580,859 relating to DNA expression vectors, inter alia; the disclosure of each of these patents and publications is incorporated herein by reference in their entireties.

Recombinant viruses can also be generated by transfection of plasmids into cells infected with virus. Suitable vectors include, but are not limited to, viral vectors such as lambda vector system λgt11, λgt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see Studier, F. W. et. al. (1990) "Use of T7 RNA Polymerase to Direct Expression of Cloned Genes" Gene Expression Technology, vol. 185, which is hereby incorporated by reference in its entirety) and any derivatives thereof, cosmid vectors and, in certain embodiments, artificial chromosomes, such as, but not limited to, YACs, BACs, BBPACs or PACs. Such artificial chromosomes are useful in that a large nucleic acid insert can be propagated and introduced into the avian cell. Recombinant molecules can be introduced into cells via transformation, particularly transduction, conjugation, mobilization, or electroporation. The introduction of recombinant virus to embryonic cells such as blastodermal cells may be accomplished by employing replication defective or replication competent retroviral particles as disclosed in, for example, U.S. Pat. No. 6,730,822, issued May 4, 2004 and U.S. patent application Ser. No. 10/463,980, filed Jun. 17, 2003, the disclosures of which are incorporated in their entirety herein by reference. The DNA sequences are cloned into the vector using standard cloning procedures in the art, as described by Sambrook et al. Molecular Cloning: A Laboratory Manual, 3$^{rd}$ ed., Cold Spring Harbor Laboratory, Cold Springs Harbor, N.Y. (2001), which is hereby incorporated by reference in its entirety.

The vectors of the invention comprise one or more nucleotide sequences encoding a heterologous protein desired to be expressed in the transgenic avian, as well as regulatory elements such as promoters, enhancers, Matrix Attachment Regions, IRES's and other translation control elements, transcriptional termination elements, polyadenylation sequences, etc. In particular embodiments, the vector of the invention contains at least two nucleotide sequences coding for heterologous proteins, for example, but not limited to, the heavy and light chains of an immunoglobulin.

The present invention further relates to nucleic acid vectors and transgenes inserted therein, having the avian ovomucoid gene expression controlling region of the invention, that incorporate multiple amino acid sequence-encoding regions, wherein a first amino acid sequence-encoding region is operatively linked to a transcription promoter and a second amino acid sequence-encoding region is operatively linked to an IRES. For example, the vector may contain coding sequences for two different heterologous proteins (e.g., the heavy and light chains of an immunoglobulin).

Such nucleic acid constructs, when inserted into the genome of a bird and expressed therein, will generate individual amino acid sequences that may be post-translationally modified, for example, glycosylated or, in certain embodiments, form complexes, such as heterodimers with each other in the white of the avian egg. Alternatively, the expressed amino acid sequences may be isolated from an avian egg and combined in vitro, or expressed in a non-reproductive tissue such as serum. In other embodiments, for example, but not limited to, when expression of both heavy and light chains of an antibody is desired, two separate constructs, each containing a coding sequence for one of the heterologous proteins operably linked to the ovomucoid gene expression controlling region of the invention are introduced into the avian cell. Alternatively, two transgenic avians each containing one of the two heterologous proteins (e.g., one transgenic avian having a transgene encoding the light chain of an antibody and a second transgenic avian having a transgene encoding the heavy chain of the antibody) can be bred to obtain an avian containing both transgenes in its germline and expressing both transgene encoded proteins, preferably in eggs.

Once the ovomucoid gene expression controlling region of the present invention has been cloned into a vector system, it is ready to be incorporated into a host cell. Such incorporation can be carried out by the various forms of transformation noted above, depending upon the vector/host cell system. Suitable host cells include, but are not limited to, bacteria, virus, yeast, mammalian or avian cells, and the like. Alternatively, it is contemplated that the incorporation of the DNA of the present invention into a recipient cell may be by any suitable method such as, but not limited to, viral transfer, electroporation, gene gun insertion, sperm mediated transfer to an ovum, microinjection, cytoplasmic injection, pronuclear injection and the like.

Another aspect of the present invention, therefore, is a method of expressing a heterologous amino acid sequence in a eukaryotic cell by transfecting the cell with a recombinant DNA comprising an avian ovomucoid gene expression controlling region operably linked to a nucleic acid insert encoding an amino acid sequence and, optionally, a polyadenylation signal sequence, and culturing the transfected cell in a medium suitable for expression of the heterologous amino acid sequence under the control of the avian ovomucoid gene expression controlling region.

In certain embodiments, the ovomucoid gene expression controlling region directs a level of expression of the heterologous protein in avian eggs that is greater than 5 µg, 10 µg, 50 µg, 100 µg, 250 µg, 500 µg, or 750 µg, more preferably greater than 1 mg, 2 mg, 5 mg, 10 mg, 20 mg, 50 mg, 100 mg, 200 mg, 500 mg, 700 mg, 1 gram, 2 grams, 3 grams, 4 grams or 5 grams per egg. Such levels of expression can be obtained using the expression controlling regions of the invention.

In one embodiment of the method of the present invention, the recipient eukaryotic cell is derived from an avian. In one embodiment, the avian is a chicken.

Yet another aspect of the present invention is a eukaryotic cell transformed with an expression vector according to the present invention and described above. In one embodiment of the present invention, the transformed cell is a chicken oviduct cell and the nucleic acid insert comprises the chicken ovomucoid gene expression controlling region, a nucleic acid insert encoding a human interferon a2d with codons optimized for expression in an avian cell, and an SV40 polyadenylation sequence.

It is contemplated that the transfected cell according to the present invention may be transiently transfected, whereby the transfected recombinant DNA or expression vector may not be integrated into the genomic nucleic acid. It is further contemplated that the transfected recombinant DNA or expression vector may be stably integrated into the genomic DNA of the recipient cell, thereby replicating with the cell so that each daughter cell receives a copy of the transfected nucleic acid. It is still further contemplated for the scope of the present invention to include a transgenic animal (e.g., a transgenic avian) producing a heterologous protein expressed from a transfected nucleic acid according to the present invention.

One certain aspect of the present invention relates to transgenic animals including avians and methods of producing them. Transgenic animals of the present invention contain a transgene which includes an isolated ovomucoid gene expression controlling region of the present invention and which preferably, though optionally, expresses a heterologous gene in one or more cells in the animal. Transgenic avians can be produced by introduction of nucleic acid molecules disclosed herein into the cells of avians including, but not limited to chicken, turkey, duck, goose, quail, pheasants, parrots, finches, hawks, crows and ratites including ostrich, emu and cassowary. Any useful method for introducing nucleic acid into the cells of an animal may be employed in the present invention.

In one embodiment of the present invention, the transgenic animal is an avian selected from a turkey, duck, goose, quail, pheasant, ratite, an ornamental bird or a feral bird. In another embodiment, the avian is a chicken and the heterologous protein produced under the transcriptional control of the isolated avian ovomucoid gene expression controlling region according to the present invention is primarily localized to the white of an egg.

An exemplary approach for the in vivo introduction of an amino acid sequence-encoding nucleic acid operably linked to the subject novel isolated ovomucoid gene expression controlling region into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors provide efficient delivery of genes into cells, and the transferred nucleic acids are stably integrated into the chromosomal DNA of the host. Recombinant retrovirus can be constructed in the part of the retroviral coding sequence (gag, pol, env) that has been replaced by nucleic acid comprising a ovomucoid gene expression controlling region, thereby rendering the retrovirus replication defective. Protocols for producing recombinant retroviruses and for infecting cells in vitro or in vivo with such viruses may be found in Current Protocols in Molecular Biology, Ausubel et al. (1989) (eds.) Greene Publishing Associates, Sections 9.10-9.14 and other standard laboratory manuals. Examples of suitable retroviruses include pLJ, pZIP, pWE and pEM which are all well known to those skilled in the art. Examples of suitable packaging virus lines for preparing both ecotropic and amphotropic retroviral systems include psiCrip, psiCre, psi2 and psiAm.

Furthermore, it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include coupling antibodies specific for cell surface antigens to the viral env protein (Roux et al., Proc. Natl. Acad. Sci. 86: 9079-9083 (1989); Julan et al., J. Gen. Virol. 73: 3251-3255 (1992); and Goud et al., Virology 163: 251-254 (1983)) or coupling cell surface ligands to the viral env proteins (Neda et al., J. Biol. Chem. 266: 14143-14146 (1991)), all of which are incorporated herein by reference in their entireties. Coupling can be in the form of the chemical cross-linking with a protein or other moiety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector into an amphotropic vector.

Another viral gene delivery system useful in the present invention utilizes adenovirus-derived vectors. The genome of an adenovirus can be manipulated such that it encodes a gene product of interest, but is inactivated in terms of its ability to replicate in a normal lytic viral life cycle (see, for example, Berkner et al., BioTechniques 6: 616 (1988); Rosenfeld et al., Science 252: 43 1434 (1991); and Rosenfeld et al., Cell 68: 143-155 (1992)), all of which are incorporated herein by reference in their entireties. Suitable adenoviral vectors derived from the adenovirus strain Ad type 5 dl324 or other strains of adenovirus (e.g., Ad2, Ad3, Ad7 etc.) are well known to those skilled in the art. The virus particle is relatively stable and amenable to purification and concentration, and as above, can be modified so as to affect the spectrum of infectivity. Additionally, introduced adenoviral DNA (and foreign DNA contained therein) may not be integrated into the genome of a host cell but remains episomal, thereby avoiding potential problems that can occur as a result of insertional mutagenesis in situations where introduced DNA becomes integrated into the host genome (e.g., retroviral DNA). Most replication-defective adenoviral vectors currently in use and therefore favored by the present invention are deleted for all or parts of the viral E1 and E3 genes but retain as much as 80% of the adenoviral genetic material (see, e.g., Jones et al., Cell 16:683 (1979); Berkner et al., supra; and Graham et al., in Methods in Molecular Biology, E. J. Murray, (1991) Ed. (Humana, Clifton, N.J.) vol. 7. pp. 109-127), all of which are incorporated herein by reference in their entireties. Expression of an inserted gene such as, for example, encoding the human interferon $\alpha 2b$, can be under control of the exogenously added ovomucoid gene expression controlling region sequences.

Yet another viral vector system useful for delivery of, for example, the subject avian ovomucoid gene expression controlling region operably linked to a nucleic acid encoding an amino acid sequence, is the adeno-associated virus (AAV). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993)), all of which are incorporated herein by reference in their entireties.

Most non-viral methods of gene transfer rely on normal mechanisms used by eukaryotic cells for the uptake and intracellular transport of macromolecules. In one embodiment, non-viral gene delivery systems of the present invention rely on endocytic pathways for the uptake of the subject ovomucoid gene expression controlling region and operably linked amino acid sequence-encoding nucleic acid by the targeted cell. Exemplary gene delivery systems of this type include liposomal derived systems, poly-lysine conjugates, and artificial viral envelopes.

In a representative embodiment, a nucleic acid comprising the novel isolated ovomucoid gene expression controlling region of the present invention can be entrapped in liposomes bearing positive charges on their surface (e.g., lipofectins) and (optionally) which are tagged with antibodies against cell surface antigens of the target tissue (Mizuno et al., NO Shinkei Geka 20:547-551 (1992); PCT publication WO91/06309; Japanese patent application 1047381; and European patent publication EP-A-43075), all of which are incorporated herein by reference in their entireties.

In similar fashion, the gene delivery system comprises an antibody or cell surface ligand that is cross-linked with a gene binding agent such as polylysine (see, for example, PCT publications WO93/04701, WO92/22635, WO92/20316, WO92/19749, and WO92/06180), all of which are incorporated herein by reference in their entireties. It will also be appreciated that effective delivery of the subject nucleic acid constructs via receptor-mediated endocytosis can be improved using agents which enhance escape of gene from the endosomal structures. For instance, whole adenovirus or fusogenic peptides of the influenza HA gene product can be used as part of the delivery system to induce efficient disruption of DNA-containing endosomes (Mulligan et al., Science 260: 926 (1993); Wagner et al., Proc. Natl. Acad. Sci. 89:7934 (1992); and Christiano et al., Proc. Natl. Acad. Sci. 90:2122 (1993)), all of which are incorporated herein by reference in their entireties. It is further contemplated that a recombinant DNA molecule comprising the novel isolated ovomucoid gene expression controlling region of the present invention may be delivered to a recipient host cell by other non-viral methods including by gene gun, microinjection, sperm-mediated transfer as described in PCT/US02/30156, filed Sep. 23, 2002 and incorporated herein by reference in its entirety, nuclear transfer, or the like.

Suitable methods for the generation of transgenic avians having heterologous DNA incorporated therein, for example, cytoplasmic injection and pronuclear injection, are described, for example, in U.S. patent application Ser. No. 10/251,364 filed Sep. 18, 2002, now U.S. Pat. No. 7,312,374, issued Dec. 25, 2007 and U.S. patent application Ser. No. 10/679,034, filed Oct. 2, 2003, the disclosure of both of these patent applications is incorporated herein by reference in its entirety. Other methods for the introduction of nucleic acids of the present invention include those disclosed in U.S. patent application Ser. No. 10/842,606 filed May 10, 2004, the disclosure of which is incorporated herein by reference in its entirety, and other methods disclosed herein.

In various embodiments of the present invention, the expression of the transgene may be restricted to specific subsets of cells, tissues or developmental stages utilizing, for example, cis-acting sequences acting on the ovomucoid gene expression controlling region of the present invention and which control gene expression in the desired pattern. Tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

One embodiment of the present invention, therefore, is a transgenic avian having a heterologous polynucleotide sequence comprising a nucleic acid insert encoding the heterologous amino acid sequence and operably linked to the novel isolated avian ovomucoid gene expression controlling region. In an embodiment of the present invention, the transgenic avian is selected from a chicken, a turkey, a duck, a goose, a quail, a pheasant, a ratite, an ornamental bird or a feral bird. In another embodiment of the present invention, the transgenic avian is a chicken.

In still another embodiment of the transgenic avian of the present invention, the transgenic avian includes an avian ovomucoid gene expression controlling region included in SEQ ID NO: 36 or a functional portion thereof.

In yet another embodiment of the transgenic avian of the present invention, the transgenic avian further comprises a polyadenylation signal sequence.

In still yet another embodiment of the transgenic avian of the present invention, the polyadenylation signal sequence is derived from the SV40 virus.

In another embodiment of the transgenic avian of the present invention, the nucleic acid insert encoding an amino acid sequence has a codon complement optimized for protein expression in an avian.

In another embodiment of the transgenic avian of the present invention, the transgenic avian produces the heterologous amino acid sequence in the serum or an egg white. In another embodiment of the transgenic avian of the present invention, the transgenic avian produces the heterologous amino acid sequence in an egg white.

In one embodiment, certain pharmaceutical comprising agents that can modulate the regulation of the expression of an amino acid sequence-encoding nucleic acid operably linked to a ovomucoid gene expression controlling region can be administered in dosages and by techniques well known to those skilled in the medical or veterinary arts, taking into consideration such factors as the age, sex, weight, species and condition of the recipient animal, and the route of administration. Standard pharmaceutical texts, such as Remmington's Pharmaceutical Science, 17th edition, 1985 may be consulted to prepare suitable preparations, without undue experimentation. Dosages can generally range from a few hundred milligrams to a few grams.

The present invention is further illustrated by the following examples, which are provided by way of illustration and should not be construed as limiting. The contents of all references, published patents and patents cited throughout the present application are hereby incorporated by reference in their entireties.

EXAMPLE 1

PCR Amplification of Ovomucoid Promoter

Sense primer OVINs2, 5'-TAGGCAGAGCAATAG-GACTCTCAACCTCGT-3' (SEQ ID NO: 1) and the antisense primer, OVMUa2, 5'-AAGCTTCTGCAG-CACTCTGGGAGTTACTCA-3' (SEQ ID NO: 2) were designed according to the sequences of chick ovoinhibitor exon 16 (Genbank Accession No: M16141) and a fragment of the chick ovomucoid promoter region (Genbank Accession No: J00897) respectively. The template DNA for PCR amplification of the ovomucoid promoter region was prepared from white leghorn chick blood.

A series of different PCR conditions were carried out to optimize synthesis of the approximately 10.0 kb product. In these tests, the template DNA concentrations were 500 ng, 100 ng, 50 ng, or 10 ng. Two sets of primers, OVINs1 (SEQ ID NO: 3) and OVMUa1 (SEQ ID NO: 4), or OVINs2 (SEQ ID NO: 1) and OVMUa2 (SEQ ID NO: 2) shown in FIG. 3, three $Mg^{++}$ concentrations (1.0 mM, 1.5 mM and 2.0 mM) and annealing temperatures from 50° C. to 70° C. were used.

The results of the tests were as shown in FIG. 1. As shown in lanes 1 through 8, test reactions having 500 ng DNA template, the OVINs1 (SEQ ID NO: 3) and OVMUa1 (SEQ ID NO: 4) primers, 60 mM Tris-$SO_4$, pH 9.1, 18 mM $(NH_4)_2$ $SO_4$, 1.0 mM $Mg^{2+}$, and annealing temperatures between 50° C. to 58° C. gave no specific DNA product. Also, as shown in lanes 17 through 24 of FIG. 1, in test reactions having 100 ng DNA template, the OVINs1 and OVMUa1 primers, 60 mM Tris-$SO_4$, pH 9.1, 18 mM $(NH_4)_2SO_4$, 1.0 mM $Mg^{2+}$, and annealing temperatures between 50° C. to 58° C., no specific bands were seen. However, as shown in lanes 9 through 16 of FIG. 1, test reactions having 500 ng DNA template, the OVINs2 (SEQ ID NO: 1) and OVMUa2 (SEQ ID NO: 2) primers, 60 mM Tris-$SO_4$, pH 9.1, 18 mM $(NH_4)_2$ $SO_4$, 2 mM $Mg^{2+}$ and annealing temperatures between 60° C. to 68° C. have the band of the desired length of approximately 10 kb. As shown in lanes 25 through 32, reaction conditions containing 100 ng DNA template, the OVINs2 (SEQ ID NO: 1) and OVMUa2 (SEQ ID NO: 2) primers, 60 mM Tris-$SO_4$, pH 9.1, 18 mM $(NH_4)_2SO_4$, 2mM $Mg^{2+}$ and annealing temperatures between about 60° C. to about 68° C. gave an increased yield of the desired product.

An approximately 10 kb product was, therefore, detected when the following conditions were used: the optimum DNA template concentration was between about 50 ng to 500 ng; the primers were OVINs2 (SEQ ID NO: 1) and OVMUa2 (SEQ ID NO: 2); the $Mg^{2+}$ concentration was 2 mM; the annealing temperature was at or between about 60° C. to about 68° C. Each 50 µl PCR reaction consisted of 50 ng or 100 ng of template DNA, 0.1 µg each primer, 5 µl buffer B (from Elongase Enzyme Mix kit, Invitrogen Corp., Carlsbad, Calif.), 1 ml of 10 µM dNTP solution, and distilled deionized water. The PCR protocol was one cycle at 94° C. for 30 secs; thirty cycles at 94° C. for 30 secs, 60° C. for 30 secs and 68° C. for 10 mins. One cycle was performed at 68° C. for 10 mins, 35° C. for 30 mins with a final hold at 4° C. The PCR products were examined by 0.65% agarose gel analysis.

EXAMPLE 2

Cloning of PCR Products

The PCR products were purified by standard methods. Briefly, PCI (phenol:chloroform:isoamyl alcohol, 24:25:1) and chloroform extraction were performed once. The DNA was precipitated by adding 3M sodium acetate pH 5.2 to a final concentration of 0.3M together with 2.5 volumes of 100% ethanol. The DNA pellet was dried and dissolved in distilled deionized water and then sequenced on a AB13700 automatic sequencer (Applied Biosystems, Foster City, Calif.) using the primers OVINs2 (SEQ ID NO: 1) and OVMUa2 (SEQ ID NO: 2) to confirm the identity of each PCR product. After confirmation of the identities, the approximately 10 kb PCR product was treated with T4 polynucleotide kinase to add a phosphate to the 5' end. Mung bean nuclease removed any overhanging adenines from the ends of the PCR products, thereby producing a blunt end. The PCR product was purified by PCI and chloroform extraction and precipitated by standard methods. This approximately 10 kb product was then cleaved with Bam HI to give two fragments, of about 4.7 and about 5.5 kb respectively.

The vector plasmid pBluescript II KS (+/−) was cut by Bam HI and EcoRV and treated with calf intestinal alkaline phosphatase. DNA fragments to be ligated into the vector were analyzed by agarose gel electrophoresis and purified from agarose gel slices using a NucleoTrap Nucleic Acid Purification Kit (BD Biosciences Clontech, Palo Alto, Calif.). Fragments of 4.7 kb and 5.5 kb were inserted into the BamHI/EcoRV-treated pBluescript to give the constructs pBS-OVMUP4.7 and pBS-OVMUP5.5 respectively.

Positive clones were screened by XbaI/XhoI digestion. Clone pBS-OVMUP4.7, gave fragments of about 4.7 kb and 2.96 kb. Clone pBS-OVMUP5.5 gave fragments of about 5.5 kb and 2.96 kb. Apparent positive clones having the 4.7 kb insert were further confirmed by XbaI/Hind III digestion that gave three fragments of 0.5 kb, 4.2 kb and 2.9 kb. The apparent positive clones with an insert of about 5.5 kb insert were further confirmed by Xba I/Kpn I digestion that gave three fragments of 2 kb, 3.5 kb and 2.96 kb.

A construct, pBS-OVMUP-10, containing the entire approximately 10 kb PCR product cloned into the pBluescript KS II (+/−) vector was made by taking a 4.7 kb Bam HI/Xho I fragment from the pBS-OVMUP4.7 plasmid and inserting it into the Bam HI/Xba I cleaved sites of pBS-OVMUP5.5. The Xho I and Xba I cut ends were blunt-ended by treating the digested fragments with Klenow enzyme and dNTPs at 25° C. for 15 mins before the digestion with Bam HI.

EXAMPLE 3

Sequencing

Figure 2:
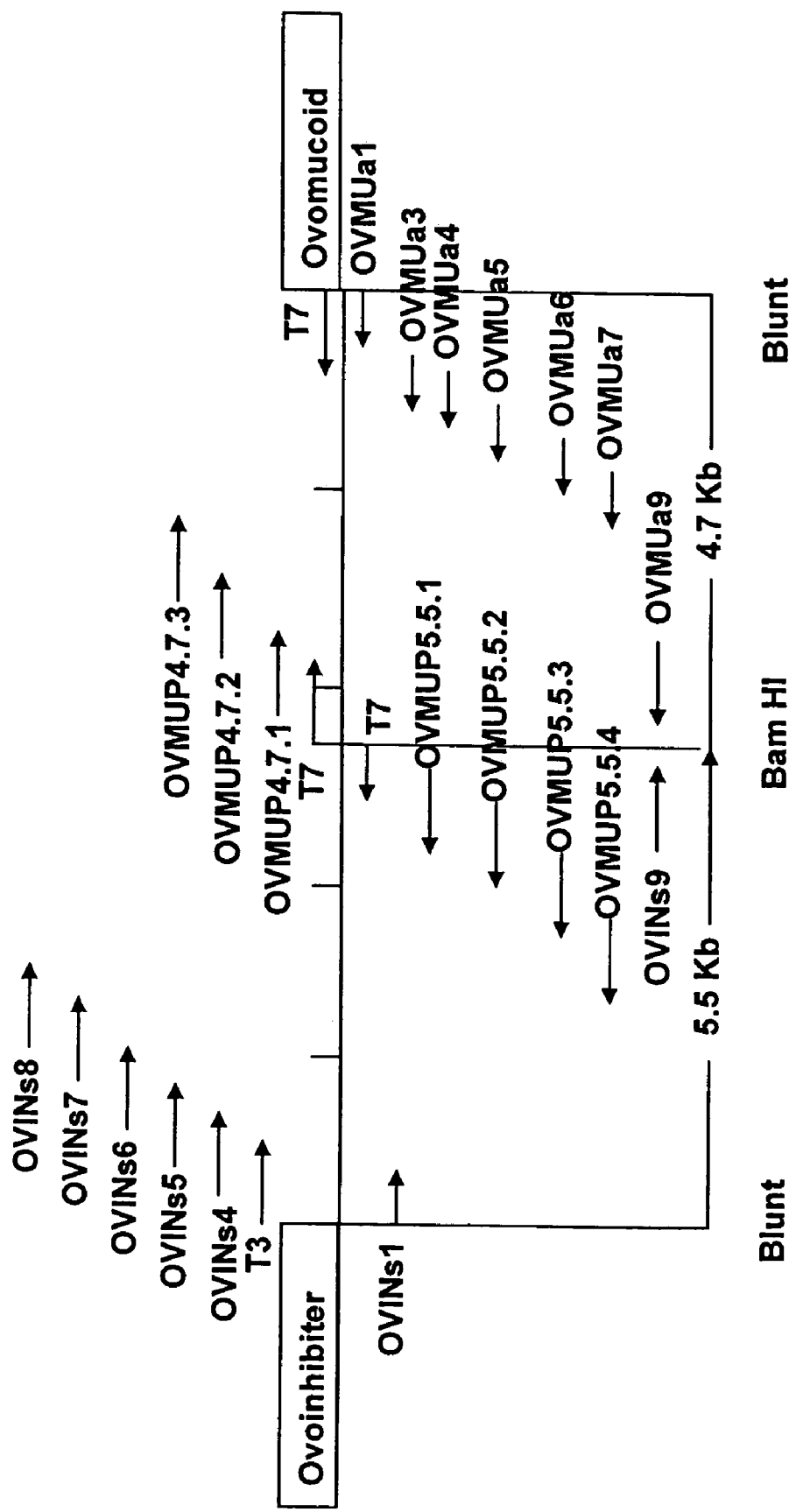
FIG. 2 illustrates the approximately 10 kb nucleic acid region that is 5' upstream of the chicken ovomucoid transcription start site, and the positions and orientations of primers used to sequence this region.

The plasmids pBS-OVMUP4.7 and pBS-OVMUP5.5 were sequenced from both ends of each insert as shown in FIG. 2. The initial primers were T7 and T3 having the nucleic acid sequences 5'-TAATACGACTCACTATAGGG-3' (SEQ ID NO: 5) and 5'-ATTAACCCTCACTAAAGGGA-3' (SEQ ID NO: 6) respectively. Subsequent primers (SEQ ID NOS: 7-25), as shown in FIG. 3, were designed according to the sequence results as they became available. The approximately 10 kb sequence was edited and assembled by the ContigExpress software of the Vector NTI Suite, version 6.0 (InforMax, Inc.). The region of the approximately 10 kb PCR product described in Example 1 above that encompassed the Bam HI junction was sequenced using the primers OVMUa9 (SEQ ID NO 27) and OVINs9 (SEQ ID NO 28) (shown in FIG. 3).

Each sequence chromatogram was visually checked for sequence accuracy and to locate base ambiguities. Regions containing ambiguous bases were re-sequenced with the same primer or, if still ambiguous, with a new primer designed to sequence the complementary strand. Sequencing of the original approximately 10 kb PCR fragment using the primers OVMUa9 (SEQ ID NO 27) and OVINs9 (SEQ ID NO 28) showed that the subcloned inserts of the plasmids pBS-OVMUP4.7 and pBS-OVMUP5.5 included all of the nucleic acid sequence of the parent fragment and no intervening BamHI—BamHI fragments were included in the final sequence SEQ ID NO: 26. The sequence (SEQ ID NO: 26) of the region lying between the 3' end of the ovoinhibitor gene and the transcription start site of the ovomucoid-encoding region is shown in FIG. 4.

EXAMPLE 4

Expression in Transfected Cultured Avian Myeloid and Oviduct Cells of Luciferase Regulated by the Approximately 10 kb Ovomucoid Promoter Construction of p10-OM-luc To facilitate insertion of coding sequences behind the ovomucoid promoter and in frame with the second ATG of the ovomucoid coding sequence, the Nco I site which overlaps the second ATG was changed to a Pci I site as depicted below. On the top is the wild type ovomucoid sequence at the start site of translation. On the bottom, the second Nco I site was changed to a Pci I site.

```
Nco I  Nco I
~~~~~~~~~~~~
MetAlaMet
CTCACCATGGCCATGGC           (SEQ ID NO:32)

GAGTGGTACCGGTACCG           (SEQ ID NO:33)

Nco I  Pci I
~~~~~~~~~~~~
MetAspMet
CTCACCATGGACATGGA           (SEQ ID NO:34)

GAGTGGTACCGGTACCG           (SEQ ID NO:35)
```

The Pci I site in the Bluescript backbone of pBS-OVMUP-10 was destroyed by cutting with Pci I, filling in the ends with Klenow polymerase and religating, creating pOM-10-alpha. The proximal promoter region was PCR amplified with primers OM-5 (SEQ ID NO.:29) and OM-6 (SEQ ID NO.:30) and template pBS-OVMUP-10. The resulting PCR product (SEQ ID NO.:31) was cut with Not I and Tth111 I and cloned into the 12059 bp Not I-Tth111 I fragment of pOM-10-alpha, thereby creating pOM-10-Pci. The 1964 Nco I-S1-treated Kpn I fragment of gwiz-luciferase (Gene Therapy Systems, Inc., San Diego, Calif.) was cloned into the 12824 Pci I-Sma I fragment of pOM-10-Pci, creating p10-OM-luc.

Primer Sequences

CGGGCAGTACCTCACCATGGACATGT (NOTE: sequence of OM5 may not be 100% complementary to the target ovomucoid sequence)

OM-5
5'-GCGCGGCCGCCCGGGACATGTCCATGGTGAGAG (SEQ ID NO:29)
TACTGCCC-3'

OM-6
5'-GGCCCGGGATTCGCTTAACTGTGACTAGG-3' (SEQ ID NO:30)

PCR product
GCGCGGCCGCCCGGGACATGTCCATGGTGAGAGTAC (SEQ ID NO:31)

TGCCCGGCTCTGCAGGCGGCTGCCGGTGCTCTGCTC

CTGAGATGGTCCCCCCGAGGCTGCCTGCAAATATAT

ACAAACGTGGCGTCCGAACTGTTGGACTGGAACACG

GAGCAGCCAGCTGAATCTGTCAGCGGCACAATGAGG

CTGGTAATATTTATTGAGGTCCTGACCTCCAGGTAA

TGGTCTGCGTCTCCCAGGCAATTGATTTTGGCTGGA

CACTTGGTTAATAGCTTGAGACAAGTGTCACATGCT

CTCAGTGGTCAAAACCAAACAAACAGACTTTTGGAC

CAAAAAAAAAAAAAACCTCTTAAGGACTCTGGTAGA

ACCCTAAATAGCACAGAATGCTGAGGGGAGTAAGGG

ACAGGTCCTTCATTCGTCTCTGCATCCACATCTCCC

AGCAGGAAGCAGCTAAGGCTCAGCACCATCGTGCCT

GCAGCTCTGCTTTCCATGCAGTTCTGCATTCTTGGA

TATTCACCTCTAGGTAAAAGCACAGGCCAGGGAGGC

TTTGTCACCAGCAGAACTGACCAACCACTGCCAGGT

GAAGCTGGCAGCACCGTATCTAACCTATGAAGTTAA

TGGTATTTAGCACTAGCTTGATAAAAGGAAGGGTTT

CTTGGCGGTTTCACTGCTTAAGTATAGAAGAGCTTG

GTAGAAGACTTGAAAGCAAGGTAAATGCTGTCAAAT

ACCACTAAAAATGTCACTTGAACCTTATCAGCAGGG

AGCACTTATTTACAGACCTAGTCACAGTTAAGCGAA

TTCCCGGGCC

The 1st and 2nd ATGs of the ovomucoid sequence are shown underlined. Note that the ovomucoid coding sequence is in reverse. The underlined, bold A is not in the wildtype sequence but was incorporated into pOM-10-Pci due to a error in the oligo OM-5.

Expression of Luciferase

For expression in avian cells of non-magnum origin, HD11 cells, a chicken myeloid cell line was used. Cells were cultured as described in Beug, H., et al. (Chicken hematopoietic cells transformed by seven strains of defective avian leukemia viruses display three distinct phenotypes of differentiation. (1979) Cell, 18: 375-90, in which these cells were referred to as HBCI cells), herein incorporated by reference in its entirety. Plasmid DNA was transfected into HD11 cells with Lipofectamine 2000 (Invitrogen Corporation, Carlsbad, Calif.) according to the manufacturer's instructions.

48 hours post-transfection, the cells were harvested and pelleted. The supernatant was removed and 20 ml of 10 mM Tris, pH 7.8, 1 mM EDTA (TE) was added. The cells were frozen at −80° C. and thawed. 5 ml of the cell suspension was mixed with 25 ml of Bright-Glo™ reagent (Bright-Glo™ Luciferase Assay System, Promega, Madison, Wis.) and relative light units per second measured on a Berthold Detection Systems (Oak Ridge, Tenn.) FB12 luminometer.

Figures 6A, 6B:
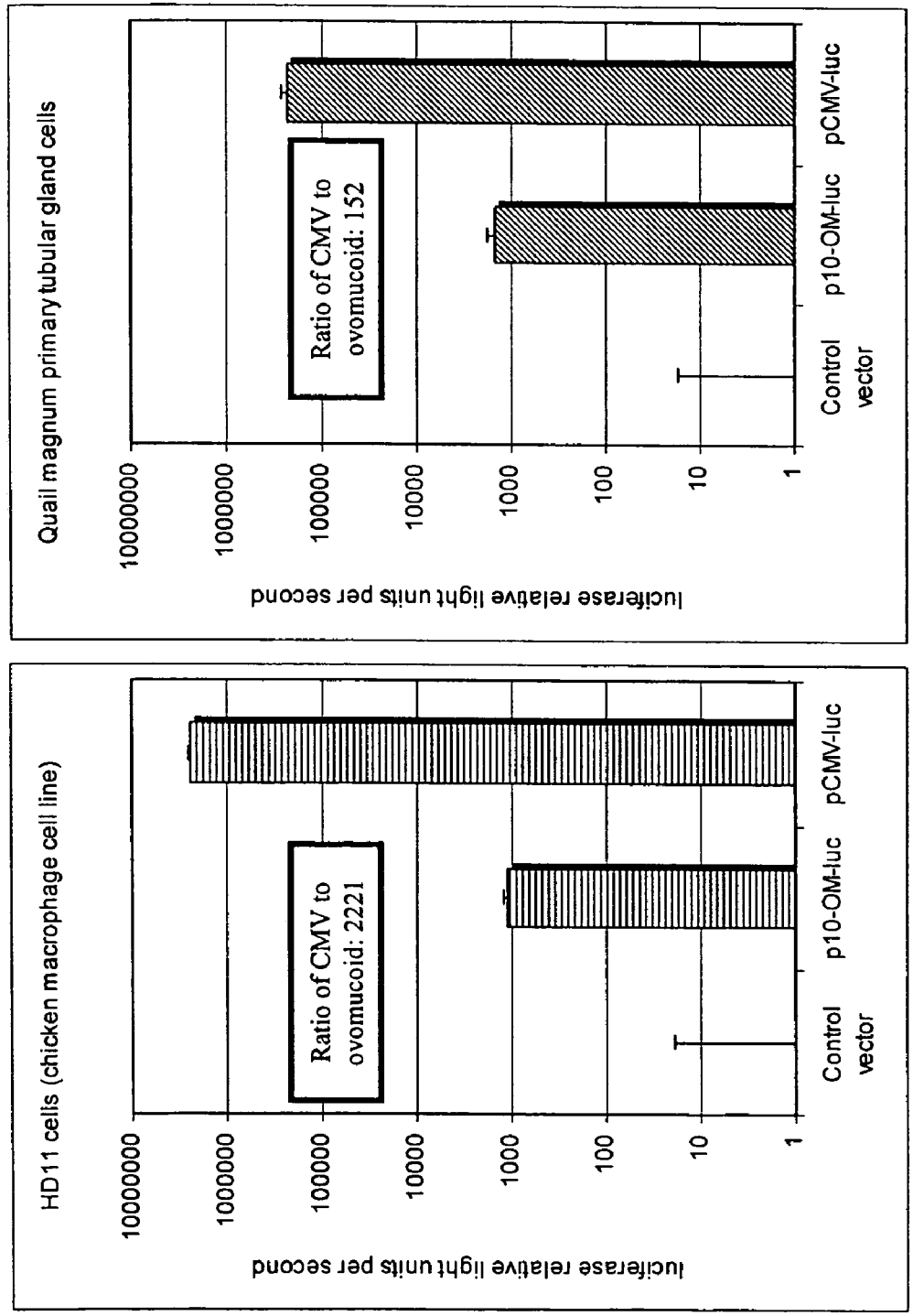
FIG. 6A shows the results of transfections of plasmids containing the ovomucoid promoter or CMV promoter linked to a luciferase gene into HD11 cells, a chicken myeloid cell line.
FIG. 6B shows the results of transfections of plasmids containing the ovomucoid promoter or CMV promoter linked to a luciferase gene into primary quail tubular gland cells isolated from the magnum portion of the oviduct of a laying quail hen.

Results are depicted in FIG. 6A. HD11 cells are permissive for the CMV promoter and is able to weakly activate the ovomucoid promoter. Some expression of the luciferase gene linked to the approximately 10 kb ovomucoid is evident.

For expression in avian oviduct cells, primary tubular gland cells were isolated as follows. The oviduct of a Japanese quail (*Coturnix coturnix japonica*) was removed and the magnum portion minced and enzymatically dissociated with 0.8 mg/ml collagenase (Sigma Chemical Co., St. Louis, Mo.) and 1.0 mg/ml dispase (Roche Molecular Biochemicals, Indianapolis, Ind.) by shaking and titurating for 30 minutes at 37° C. The cell suspension was then filtered through sterile surgical gauze, washed three times with F-12 medium (Life Technologies, Grand Island, N.Y.) by centrifugation at 200× g, and resuspended in OPTIMEM™ (Life Technologies) such that the $OD_{600}$ was approximately 2. 800 µl of the cell suspension was plated in each well of a 6-well dish. For each transfection, 4.0 µl of DMRIE-C liposomes (Life Technologies) and 2.0 µg of plasmid DNA was preincubated for 15 minutes at room temperature in 200 µl of OPTIMEM™, and then added to the oviduct cells. Cells with DNA/liposomes were incubated for about 5 hours at 37° C. in 5% $CO_2$. Next, 2.0 ml of DMEM (Life Technologies), supplemented with 15% fetal bovine serum (FBS) (Atlanta Biologicals, Atlanta, Ga.), 2× penicillin/streptomycin (Life Technologies), 50 ng/ml insulin (Sigma), $10^{-7}$ M α-estradiol (Sigma), and $10^{-6}$ M corticosterone (Sigma) were added to each well, and incubation continued for about 40 hours. Medium was then harvested and centrifuged at 110×g for 5 minutes.

For quantitation, the cells were scraped into the media with a rubber policeman. One milliliter was transferred to an eppendorf tube and the cells pelleted. The supernatant was removed and 20 ml of 10 mM Tris, ph 7.8, 1 mM EDTA (TE) was added. The cells were frozen at −80° C. and thawed. 5 ml of the cell suspension was mixed with 25 ml of Bright-Glo™ reagent (Bright-Glo™ Luciferase Assay System, Promega, Madison, Wis.) and relative light units per second measured on a Berthold Detection Systems (Oak Ridge, Tenn.) FB12 luminometer.

Figure 6C:
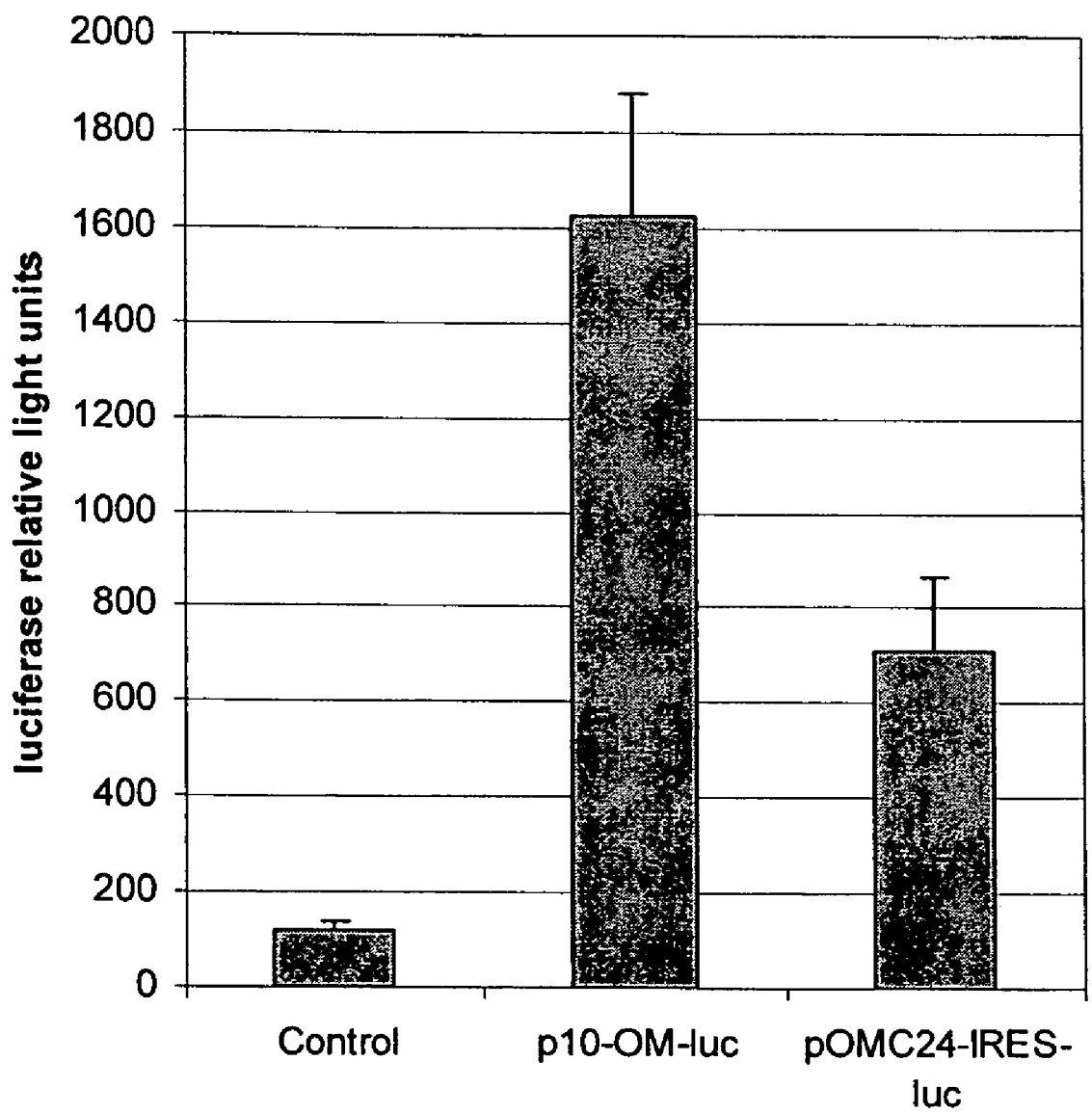
FIG. 6C shows the results of transfection into primary quail tubular gland cells isolated from the magnum of a laying quail hen for the approximately 10 kb ovomucoid promoters and the ovomucoid BAC-IRES construct each comprising an operably linked luciferase coding sequence.

The results are depicted in FIG. 6B. Expression of luciferase is evident from the CMV and approximately 10 kb ovomucoid promoters. The ovomucoid promoter has more activity relative to the CMV promoter in the tubular gland cells (ratio of CMV to ovomucoid is 152) than in the HD11 cells (ratio of CMV to ovomucoid is 2221). FIG. 6C shows the expression of luciferase from a OMC24-IRES-luc vector. This vector is the OMC24-IRES clone described in Example 6 with a luciferase coding sequence inserted 3' to the IRES.

EXAMPLE 5

Figure 5:
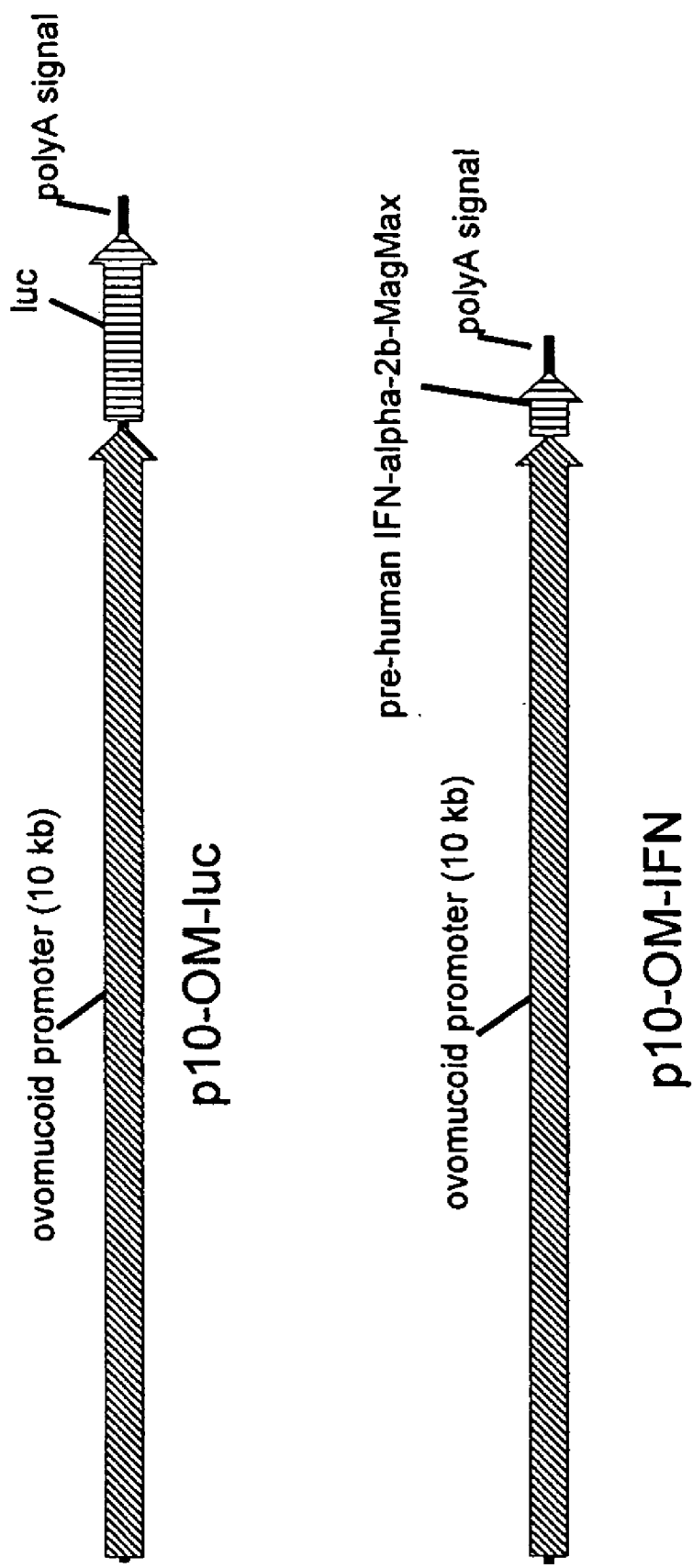
FIG. 5 illustrates the approximately 10 kb ovomucoid promoter linked to the luciferase or human IFNα-2b coding sequences.

Expression in Transfected Cultured Avian Oviduct Cells of Human Interferon α2b Regulated by the Approximately 10 kb Ovomucoid Promoter Construction of p10-OM-IFN The approximately 10 kb ovomucoid promoter fragment of Example 5 was placed in front of a MagMax IFN coding sequence creating p10-OM-IFN as seen in FIG. 5 (MagMag=codon optimized for expression in the magnum of a chicken based on the frequency of codon usage of proteins such as ovalbumin, ovomucoid, lysozyme and ovomucin).

Figure 7:
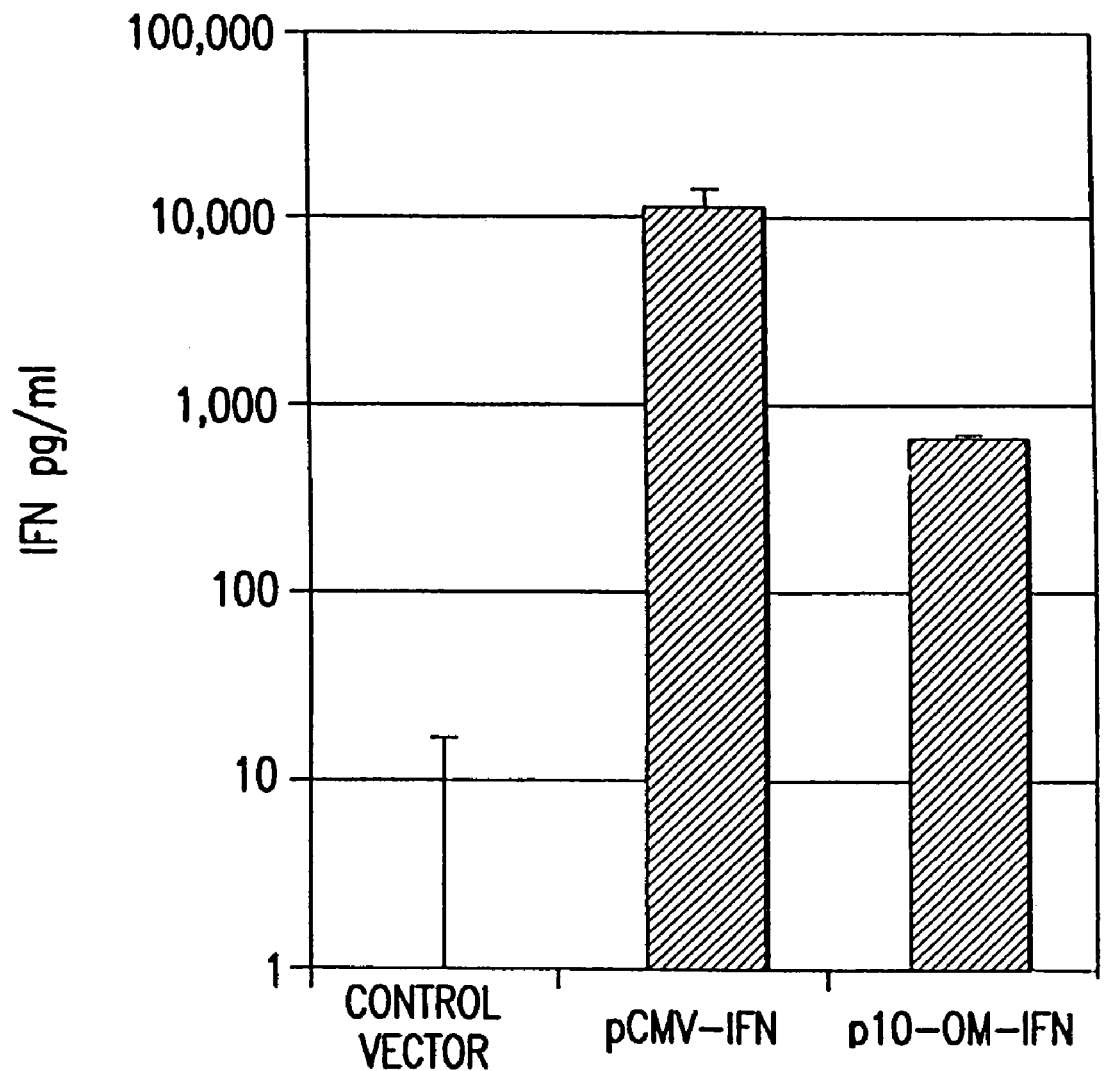
FIG. 7 shows the results of transfections of plasmids containing the ovomucoid promoter or CMV promoter linked to an interferon gene into primary quail tubular gland cells isolated from the magnum portion of the oviduct of a laying quail hen.

Quail primary tubular gland cells were isolated and treated as described in Example 4. 100 ml of supernatants were analyzed by ELISA (PBL Biomedical Laboratories, Flanders, N.J.) for human interferon α2b content. The results are depicted in FIG. 7. Expression of interferon is evident from the CMV and approximately 10 kb ovomucoid promoters.

EXAMPLE 6

Construction of an Ovomucoid Promoter-Bacterial Artificial Chromosome Expression Vector with an Antibody Heavy Chain or Antibody Light Chain Coding Sequence A chicken BAC library constructed with HindIII inserts ligated into pECBAC1 (see, Crooijmans et al., Mammalian Genome 11: 360-363, 2000, the disclosure of which is incorporated herein in its entirety by reference) was screened by PCR with two sets of primers using methods well known in the art. One primer set, OM7 and OM8, was designed to anneal in the 5' untranslated region of the ovomucoid gene. The other primer set, Ovoinhibitor 1 and Ovoinhibitor 2, was designed to anneal in exon 3 and exon 4 of the ovoinhibitor gene.

A BAC clone was identified which yielded the expected size PCR fragment for each primer set. The BAC clone which included an insert encompassing the ovoinhibitor and ovomucoid gene was sequenced by standard techniques and designated OMC24 The sequence for OMC24 is shown in SEQ ID NO: 36.

| Primer Sequences | |
|---|---|
| OM7:<br>CGGGCAGTACCTCACCATGGACATGT | (SEQ ID NO:37) |
| OM8:<br>ATTCGCTTAACTGTGACTAGG | (SEQ ID NO:38) |
| OVOINHIBITOR-1:<br>CGAGGAACTTGAAGCCTGTC | (SEQ ID NO:39) |
| OVOINHIBITOR-2:<br>GGCCTGCACTCTCCATCATA | (SEQ ID NO:40) |

Figure 8:
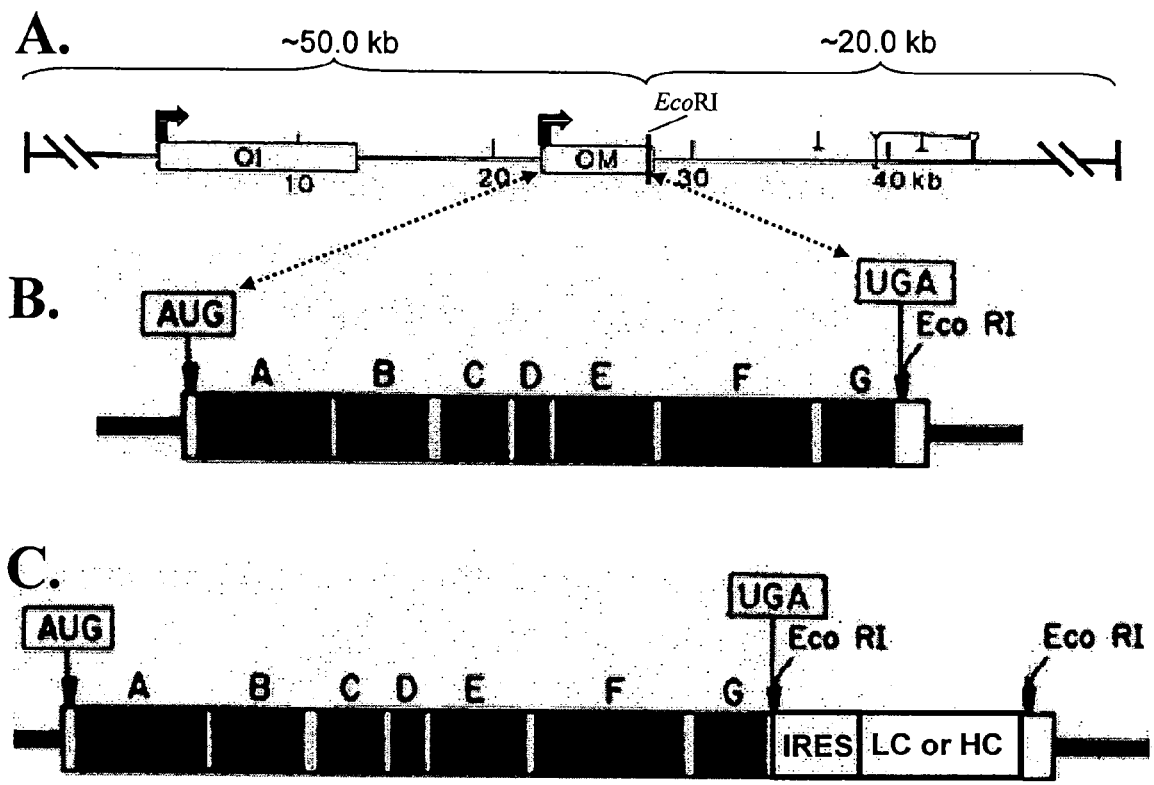
FIG. 8 shows an ovomucoid gene and bacterial artificial chromosome.

Polynucleotide sequences encoding the heavy chain and light chain of an IgG1 (IgG1K) monoclonal antibody were inserted into the 3' UTR of the ovomucoid transcript coding region in two separate OMC24 clones. The heavy chain and light chain coding sequences each included a signal sequence located at their 5' ends. For each clone, the coding sequence of each antibody chain and signal sequence was inserted into the OMC24 vector as an IRES-LC or IRES-HC cassette with the light chain and heavy chain inserts each positioned in the sense orientation SEQ ID NO: 41 shows the IRES-LC cassette inserted in the OMC24 clone. SEQ ID NO: 42 shows the IRES-HC cassette inserted in the OMC24 clone. The IRES sequence is shown in bold. The conserved regions of the IgG1 antibody light chain and heavy chain coding sequence are underlined. The nucleotides for the coding sequences of the variable regions for the IgG1 light chain and heavy chains are represented by N's. The nucleotides encoding the signal sequences in each clone are represented by italicized N's with the start codon indicated as ATG. OMC24 nucleotide sequence flanking the IRES and the antibody coding sequence is also shown for each of the two sequences. These constructs are shown in FIG. 8.

The IRES-antibody light chain and heavy chain cassettes were each inserted into an OMC24 clone at a natural EcoRI site that resides in the 3' UTR of ovomucoid at about position 41,627 of SEQ ID NO: 36. Because there are many EcoRI sites in OMC24, RecA-assisted restriction endonuclease cleavage (RARE) was used to cut only at the desired site. RecA assisted restriction endonuclease cleavage is described in Molecular Biotechnology (2001) Vol 18, pp 233 to 241, the disclosure of which is incorporated herein in its entirety by reference. A portion of the vector from which the cassettes were obtained of about 26 nucleotides in length can be seen 3' of the coding sequence of the light chain and heavy chain in SEQ ID NO: 41 and SEQ ID NO: 42.

```
OMC24-IRES-LC (SEQ ID NO:41)
gatttcactc atctcctaat aatcaggtag ctgaggagat gctgagtctg ccagttcttg ggctctgggc aggatcccat ctcctgcctt ctctaggaca gagctcagca ggcagggctc tgtggctctg tgtctaaccc acttcttcct ctcctcgctt tcagggaaag caacgggact ctcactttaa gccattttgg aaaatgctga atatcagagc tgagaaatt ccgcccctct ccctccccc cccctaacgt tactggccga agccgcttgg aataaggccg gtgtgcgttt gtctatatgt tattttccac catattgccg tcttttggca atgtgagggc ccggaaacct ggccctgtct tcttgacgag cattcctagg ggtctttccc ctctcgccaa aggaatgcaa ggtctgttga atgtcgtgaa ggaagcagtt cctctggaag cttcttgaag acaaacaacg tctgtagcga ccctttgcag gcagcggaac cccccacctg gcgacaggtg cctctgcggc caaaagccac gtgtataaga tacacctgca aaggcggcac aacccagtg ccacgttgtg
```
agttggatag ttgtggaaag agtcaaatgg ctctcctcaa gcgtattcaa caagggctg
aaggatgccc agaaggtacc ccattgtatg ggatctgatc tggggcctcg gtgcacatgc
tttacgtgtg tttagtcgag gttaaaaaac gtctaggccc cccgaaccac ggggacgtgg
ttttcctttg aaaaacacga tgataagctt gccacaacca tgnnnnnnnn nnnnnnnnnn
nnnnnnnnnn nnnnnnnnnn nnnnnnnnnn nnnnnnnnnn nnnnnnnnnn nnnnnnnnnn
nnnnnnnnnn nnnnnnnnnn nnnnnnnnnn nnnnnnnnnn nnnnnnnnnn nnnnnnnnnn
nnnnnnnnnn nnnnnnnnnn nnnnnnnnnn nnnnnnnnnn nnnnnnnnnn nnnnnnnnnn
nnnnnnnnnn nnnnnnnnnn nnnnnnnnnn nnnnnnnnnn nnnnnnnnnn nnnnnnnnnn
nnnnnnnnnn nnnnnnnnnn nnnnnnnnnn nnnnnnnnnn nnnnnnnnnn nnnnnnnnnn
nnnnnnnnnn nnnnnnnnnn nnnnnnnnnn nnnnnnnnnn nnnnnnnnnn nnnnnnnnnn
nnnacggtgg cggcgccatc tgtcttcatc ttcccgccat ctgatgagca gttgaaatct
 ggaactgcct ctgttgtgtg cctgctgaat aacttctatc ccagagaggc caaagtacag
tggaaggtgg ataacgccct ccaatcgggt aactcccagg agagtgtcac agagcaggac
agcaaggaca gcacctacag cctcagcagc accctgacgc tgagcaaagc agactacgag
aaacacaaag tctacgcctg cgaagtcacc catcagggcc tgagctcgcc cgtcacaaag
agcttcaaca ggggagagtgttagggatcc actagtccag tgtggtggaa ttcaccacag
gatccccact ggcgaatccc agcgagaggt ctcacctcgg ttcatctcgc actctgggga
gctcagctca ctcccgattt tctttctcaa taaactaaat cagcaacact cctttgtctt OMC24-IRES-HC (SEQ ID NO:42)
gatttcactc atctcctaat aatcaggtag ctgaggagat gctgagtctg ccagttcttg
ggctctgggc aggatcccat ctcctgcctt ctctaggaca gagctcagca ggcagggctc
tgtggctctg tgtctaaccc acttcttcct ctcctcgctt tcagggaaag caacgggact
ctcactttaa gccatttggg aaaatgctga atatcagagc tgagagaatt ccgcccctct
ccctccccccc ccctaacgt tactggccga agccgcttgg aataaggccg gtgtgcgttt
gtctatatgt tattttccac catattgccg tcttttggca atgtgagggc ccggaaacct
ggccctgtct tcttgacgag cattcctagg gtctttccc ctctcgccaa aggaatgcaa
ggtctgttga atgtcgtgaa ggaagcagtt cctctggaag cttcttgaag acaaacaacg
tctgtagcga ccctttgcag gcagcggaac cccccacctg cgacaggtg cctctgcggc
caaaagccac gtgtataaga tacacctgca aaggcggcac aacccagtg ccacgttgtg
agttggatag ttgtggaaag agtcaaatgg ctctcctcaa gcgtattcaa caagggctg
aaggatgccc agaaggtacc ccattgtatg ggatctgatc tggggcctcg gtgcacatgc
tttacgtgtg tttagtcgag gttaaaaaac gtctaggccc cccgaaccac ggggacgtgg
ttttcctttg aaaaacacga tgataagctt gccacaacca tgnnnnnnnn nnnnnnnnnn
nnnnnnnnnn nnnnnnnnnn nnnnnnnnnn nnnnnnnnnn nnnnnnnnnn nnnnnnnnnn
nnnnnnnnnn nnnnnnnnnn nnnnnnnnnn nnnnnnnnnn nnnnnnnnnn nnnnnnnnnn
nnnnnnnnnn nnnnnnnnnn nnnnnnnnnn nnnnnnnnnn nnnnnnnnnn nnnnnnnnnn
nnnnnnnnnn nnnnnnnnnn nnnnnnnnnn nnnnnnnnnn nnnnnnnnnn nnnnnnnnnn -continued

```
nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnntcagct agcaccaagg gcccatcggt cttccccctg gcaccctcct ccaagagcac ctctgggggc acagcggccc tgggctgcct ggtcaaggac tacttccccg aaccggtgac ggtgtcgtgg aactcaggcg ccctgaccag cggcgtgcac accttcccgg ccgtcctaca gtcctcagga ctctactccc tcagcagcgt ggtgaccgtg ccctccagca gcttgggcac ccagacctac atctgcaacg tgaatcacaa gcccagcaac accaaggtgg acaagagagt tgagcccaaa tcttgtgaca aaactcacac atgcccaccg tgcccagcac ctgaactcct gggggaccg tcagtcttcc tcttcccccc aaaacccaag gacacctca tgatctcccg gacccctgag gtcacatgcg tggtggtgga cgtgagccac gaagaccctg aggtcaagtt caactggtac gtggacggcg tggaggtgca taatgccaag acaaagccgc gggaggagca gtacaacagc acgtaccgtg tggtcagcgt cctcaccgtc ctgcaccagg actggctgaa tggcaaggag tacaagtgca aggtctccaa caaagccctc ccagccccca tcgagaaaac catctccaaa gccaaagggc agccccgaga accacaggtg tacaccctgc ccccatcccg ggatgagctg accaagaacc aggtcagcct gacctgcctg gtcaaaggct tctatcccag cgacatcgcc gtggagtggg agagcaatgg gcagccggag aacaactaca agaccacgcc tcccgtgctg gactccgacg gctccttctt cctctacagc aagctcaccg tggacaagag caggtggcag caggggaacg tcttctcatg ctccgtgatg catgaggctc tgcacaacca ctacacgcag aagagcctct ccctgtctcc gggtaaatag ggatccacta gtccagtgtg gtggaattca ccacaggatc cccactggcg aatcccagcg agaggtctca cctcggttca tctcgcactc tggggagctc agctcactcc cgattttctt
```

The resulting mRNA transcript from the ovomucoid promoter for each clone contains two coding sequences; one for the ovomucoid protein and another for the downstream light chain or heavy chain coding sequence. The internal ribosome entry site (IRES) engineered into the vectors is useful to facilitate translation of the downstream heavy chain or light chain coding sequence.

EXAMPLE 7

Production of Transgenic Hens with an Ovomucoid Promoter-Bacterial Artificial Chromosome Expression Vector Transgene 100 μg each of BAC clone OMC24-IRES-LC and OCM24-IRES-HC were linearized by enzymatic restriction digest. The digested DNA was phenol/CHCl₃ extracted, ethanol precipitated, suspended in 0.25 M KCl and diluted to a working concentration of approximately 60 μg/ml. The DNA was mixed with SV40 T antigen nuclear localization signal peptide (NLS peptide, amino acid sequence CGGPKKKRKVG (SEQ ID NO: 43) with a peptide DNA molar ratio of 100:1 (Collas and Alestrom, 1996, Mol. Reprod. Develop. 45: 431-438, the disclosure of which is incorporated by reference in its entirety). The DNA samples were allowed to associate with the SV40 T antigen NLS peptide by incubation at room temperature for 15 minutes.

Introduction of the DNA-NLS complex into an avian egg was accomplished essentially as described in U.S. patent application Ser. No. 10/251,364, filed Sep. 18, 2002, now U.S. Pat. No. 7,312,374, issued Dec. 25, 2007, the disclosure of which is incorporated in its entirety herein by reference. Briefly, the germinal disc of an avian egg was illuminated by an incident light beam and visualized by an oblique macromonitering system. A micropipette injection needle was positioned by micromanipulation such that the tip of the needle was pressed into the vitelline membrane of the avian egg to a depth of about 20 μM. The injection needle was inserted through the membrane into the germinal disc to a point where only the end of the beveled opening of the needle was visible above the membrane, while the remaining of the opening was present inside the germinal disk. The DNA-NLS was then injected into the germinal disc. Approximately 100 nanoliters of DNA were injected into a germinal disc of stage I White Leghorn embryos obtained two hours after oviposition of the previous egg.

Injected embryos were surgically transferred to recipient hens via ovum transfer according to the method of Christmann et al. (PCT Publication WO 02/20752, the disclosure of which is incorporated herein in its entirety by reference) and hard shell eggs were incubated and hatched. See, Olsen and Neher, 1948, J. Exp. Zoo. 109: 355-366, the disclosure of which is incorporated in its entirety herein by reference.

Genomic DNA samples from one-week old chicks were analyzed for the presence of OMC24-IRES-LC or HC by PCR using methods well known in the field of avian transgenics. Briefly, three hundred nanograms of genomic DNA and 1.25 units of Taq DNA polymerase (Promega) were added to a 50 μl reaction mixture of 1× Promega PCR Buffer with 1.5 mM MgCl$_2$, 200 μM of each dNTP, 5 μM primers. The reaction mixtures were heated for 4 minutes at 94° C., and then amplified for 34 cycles each consisting of: 94° C. for 1 min, 60° C. for 1 min and 72° C. for 1 min. A final cycle of 4 minutes at 72° C. was performed. PCR products were detected by visualization on a 0.8% agarose gel stained with ethidium bromide.

EXAMPLE 8

Production of Antibody by Transgenic Hens

Transgenic chicks produced as described in Example 7 were grown to maturity. Eggs were collected from the hens and egg white material was assayed for the IgG1 using sandwich ELISA.

The eggs were cracked and opened and the whole yolk portion was discarded. Both the thick and thin egg white portions were kept. 1 ml of egg white was measured and added to a plastic Stomacher 80 bag. A volume of egg white buffer (5% 1M Tris-HCl pH 9 and 2.4% NaCl) equal to two times the volume of egg white was added to the egg white. The egg white-buffer mixture was paddle homogenized in the Stomacher 80 at normal speed for one minute. The sample was allowed to stand overnight and homogenation was repeated. A 1 ml sample of the mixture was used for testing.

A Costar flat 96-well plate was coated with 100 ul of C Goat-anti-Human kappa at a concentration of 5 μg/ml in PBS. The plate was incubated at 37° C. for two hours and then washed. 200 μl of 5% PBA was added to the wells followed by an incubation at 37° C. for about 60-90 minutes followed by a wash. 100 ul of egg white samples (diluted in 1% PBA:LBP) was added to each well and the plate was incubated at 37° C. for about 60-90 min followed by a wash. 100 ul of a 1:2000 dilution of F'2 Goat anti-Human IgG Fc-AP in 1% PBA was added to the wells and the plate was incubated at 37 ° C. for 60-90 min followed by a wash.

The transgenic antibody was detected by placing 75 ul of 1 mg/ml PNPP (p-nitrophenyl phosphate) in 5× developing buffer in each well and incubating for about 10-30 mins at room temperature. The detection reaction was stopped using 75 ul of 1N NaOH. The OD405-650 nm was then determined for each sample well. Each OD405-650 nm value was compared to a standard curve to determine the amount of recombinant antibody present in each sample Approximately 0.3% of hens analyzed expressed antibody in their eggs. Two hens which expressed antibody are Hen 1251 which was found to produce an average of 19 ng of IgG per ml of egg white and Hen 4992 which was found to produce an average of 150 ng of IgG per ml of egg white.

Figure 9:
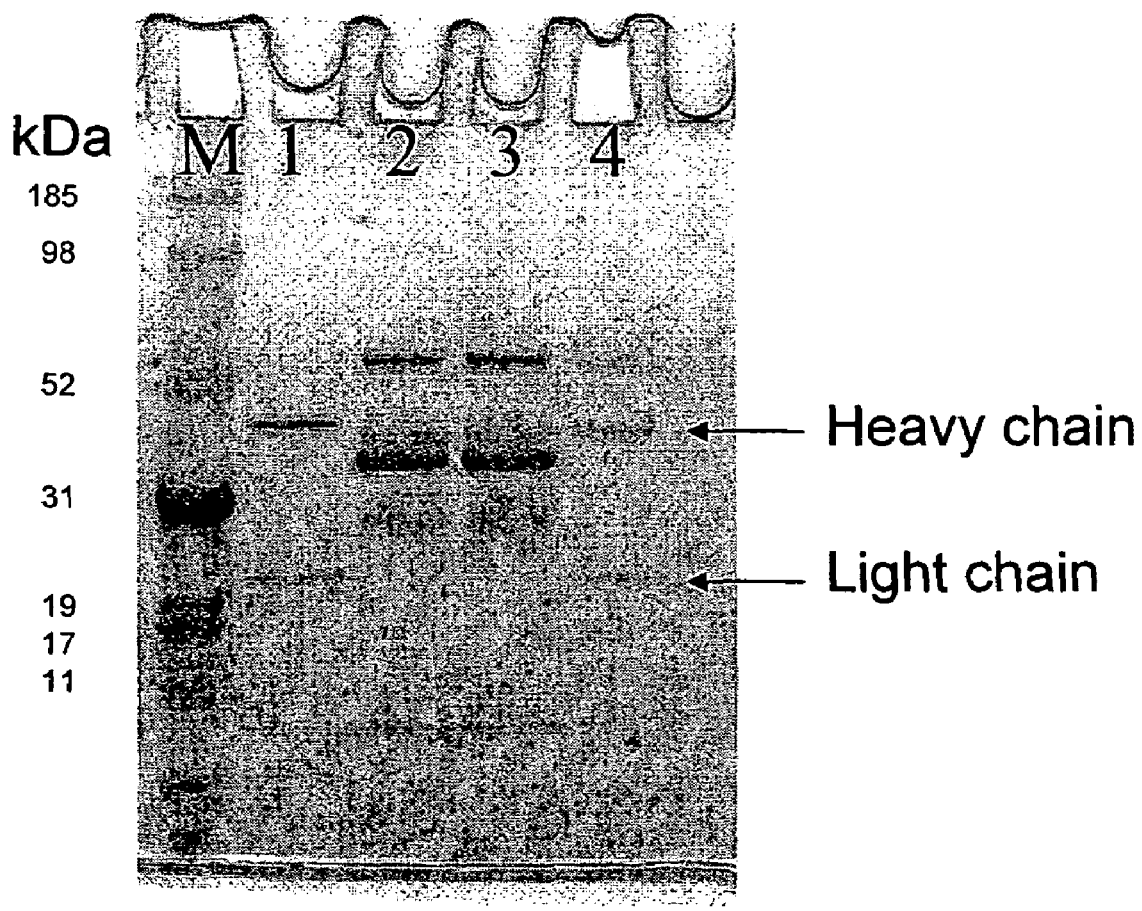
FIG. 9 shows an SDS-PAGE analysis of partially purified hMab derived from a single transgenic hen. (M) Multi-mark standard, lane 1) 1 mg purified hMab (produced by mammalian cells), lane 2) 5 mg pre-column (transgenic avian egg white), lane 3) 5 mg column flow thru from transgenic avian egg white, lane 4) partially purified hMab from transgenic avian egg white.

FIG. 9 shows the results of an SDS-PAGE analysis of the transgenic avian derived hMab compared to the same antibody produced in mammalian cells. The antibody was first purified from egg white proteins by protein A affinity chromatography. The transgenic protein (lane 4) heavy chain and light chain had virtually an identical mobility compared to heavy and light chains of the same antibody produced by standard mammalian cell culture (lane 1). Also shown are pre-chromatography transgenic egg white (lane 2) and affinity chromatography transgenic egg white flow through (lane 3).

EXAMPLE 9

Human Antibody Produced by Transgenic Hens Demonstrates Target Antigen Binding

The human monoclonal antibody produced and identified as described in Examples 7 and 8 was assayed for target antigen binding.

Antibody was captured from the egg white in microplate wells coated with the antibodies target antigen. Antigen-antibody complexes were quantitated using isotype-specific secondary antibody conjugated with alkaline phosphatase. The ability of the transgenic avian produced hMab to bind its target antigen was compared with the binding ability of the same hMab produced in mammalian cells.

Figure 10:
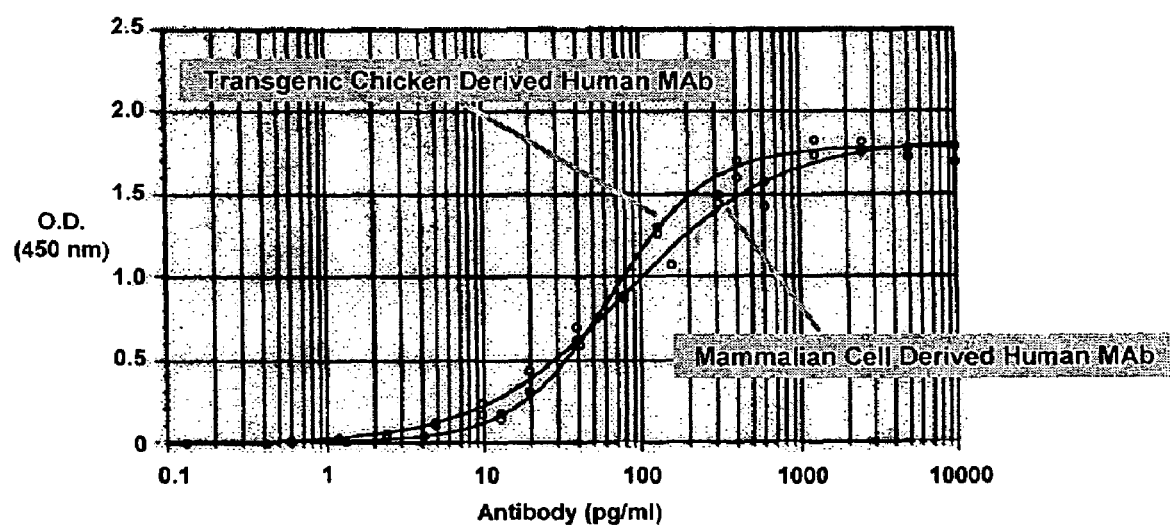
FIG. 10 shows plots of the binding ability of an IgG1 monoclonal antibody produced by a transgenic chicken and the binding ability of the same IgG1 monoclonal antibody produced by mammalian cells.

Plots showing the binding ability of each antibody are shown in FIG. 10. The plots show the level of antigen binding per picogram of antibody tested for both the antibody from transgenic chicken egg white and the antibody from a mammalian cell line. The similarity of the binding curves produced by these two antibodies indicate that the transgenic human antibody has an affinity that is substantially similar to the affinity of the antibody produced by standard methods (i.e., produced in mammalian cells).

A CHO cell line stably transfected with a plasmid that expressed the corresponding cell-surface antigen for the antibody produced by the transgenic avian was used in FACS analysis of the antibody.

Figure 11:
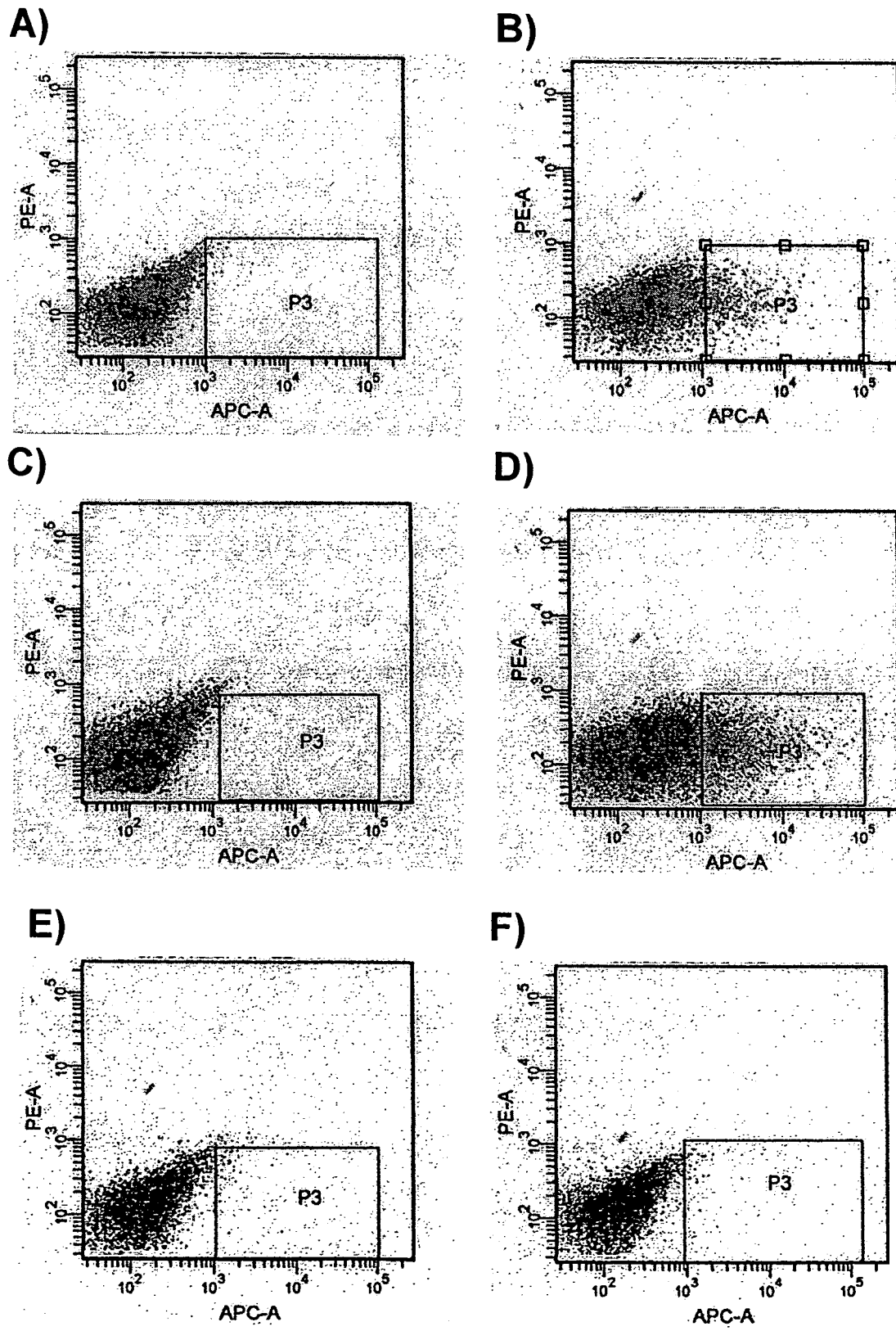
FIG. 11 shows the ability of avian derived hMab to bind target antigen expressed on a cell surface relative to the ability of the mammalian cell derived hMab.

FIG. 11 shows the ability of the transgenic avian derived hMab to bind target antigen expressed on the cell surface of CHO cells relative to the ability of the antibody produced in mammalian cells. CHO cells were transfected with either a luciferase expression plasmid (11A, 11C, and 11E) or an expression plasmid carrying cDNA of the hMab's target antigen (11B, 11D, and 11F). Cells were collected and treated with one of three primary antibodies: 1) the antigen specific hMab produced by mammalian cells (11A and 11B), the antigen specific hMab produced by a transgenic hen (11C and 11D), or 3) human antibody of the same isotype as the antibody produced by the transgenic hen but with different antigen specificity (11E and 11F). An isotype specific antibody conjugated with APC (Allophycocyanin) was used to detect primary antibodies bound to the cells. Cells were sorted by FACS, counted and signal generated by the APC of the secondary antibody was quantitated. Cells that exhibited APC-associated fluorescence are delineated with a box within each graph.

Together the ELISA and FACS data show that a human antibody molecule produced by transgenic hens can bind efficiently to its target antigen.

EXAMPLE 10

Human Antibody Produced by Transgenic Hens Demonstrates Stability

Figure 12:
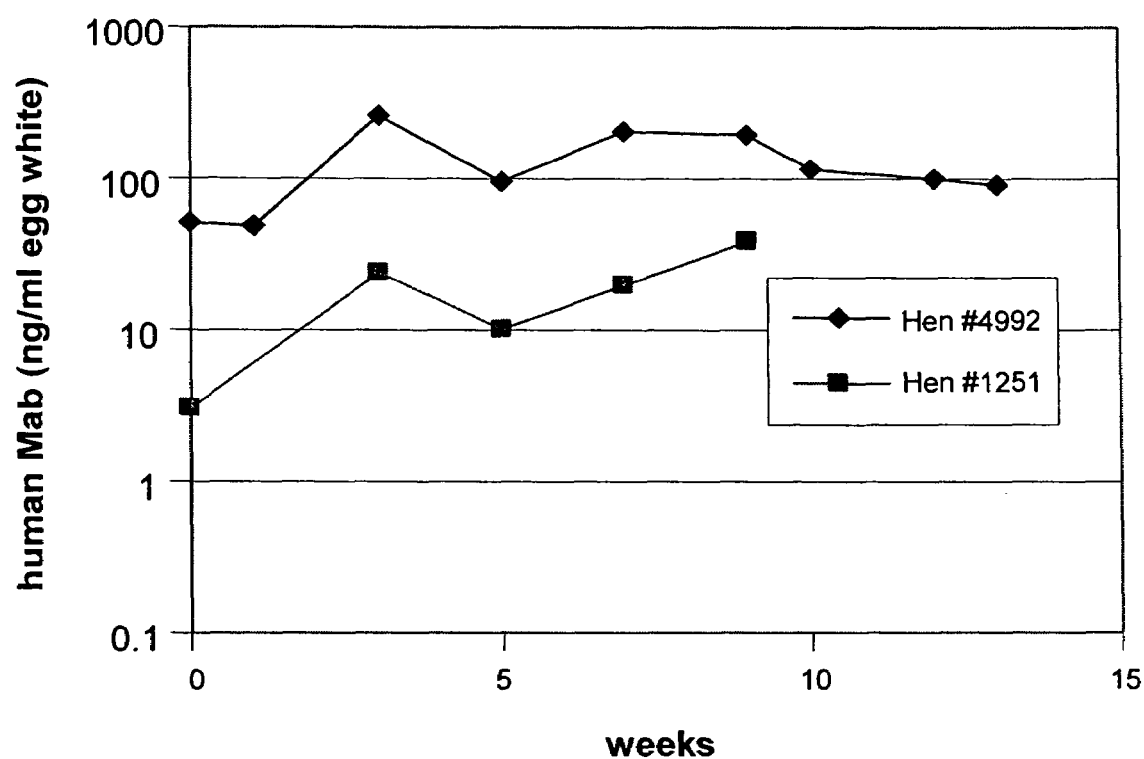
FIG. 12 shows the stability of hMab expression in transgenic hen. Eggs from transgenic hens #4992 and #1251 were collected over several weeks. The amount of hMab in egg white material was quantitated over time via sandwich ELISA for the specific human IgG1 (H+L).

FIG. 12 shows the stability of hMab expression in transgenic hen. Eggs from transgenic hens #4992 and #1251 of Example 8 were collected over several weeks. The amount of hMab in egg white material was quantitated via sandwich ELISA for the specific human IgG1. The results indicate that the antibody produced by an avian and collected in the egg white are stable over a significant period of time.

EXAMPLE 11

Human Antibody Produced by Transgenic Hens Demonstrates Target Cell Killing

The primary mechanism of action of many antibody therapeutics is the cytolysis of target antigen expressing cells via serum complement. This activity may require secondary modifications of the antibody in the form of proper glycosylation of the Fc portion of the antibody. Proper glycosylation has been shown to be essential for the antibody interaction with the C1q molecule of complement and with the Fcγ-family of receptors on effector cells.

The activity of the transgenic IgG1 antibody produced in Example 8 was assessed in antibody-dependent cellular cytotoxicity (ADCC) and complement-dependent cellular cytotoxicity (CDCC) assays using the antigen-expressing CHO cell line described in Example 9 as target cells.

ADCC assay: Surface antigen expressing CHO cells were incubated with purified transgenic MAb at 0.5 μg/ml or no MAb in serum free media. Human PBMCs (peripheral blood mononuclear cells) were added at an effector:target cell ratio of 20:1. The mixture was incubated at 37° C. for 4 hours. Cell lysis was assayed by LDH release and maximal release accomplished by addition of 1% Triton.

CDCC assay: Surface antigen expressing CHO cells were incubated overnight 37° C. with 0.5 μg/ml purified transgenic MAb or no MAb in the presence of 20% normal human serum. Plates were then washed and cell viability was assayed by LDH assay release and maximal release accomplished by addition of 1% Triton.

Activity was calculated for both the ADCC assay and the CDCC assay by methods well known in the art.

Figure 13:
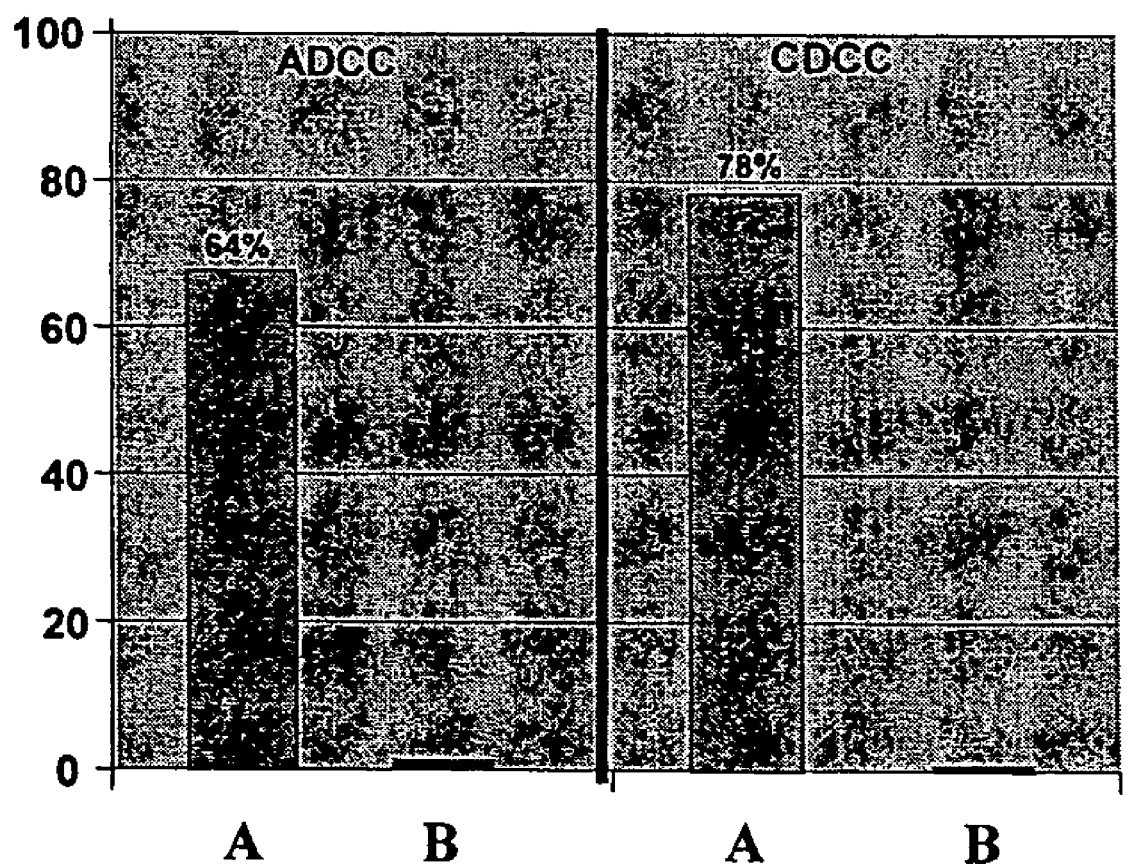
FIG. 13 shows ADCC (antibody dependent cellular cytotoxicity) and CDCC (complement-dependent cellular cytotokicity) for an IgG1 produced in transgenic avians.

FIG. 13 shows the percent cytotoxicity for incubations with the transgenic antibody (columns A) and incubations with no antibody in serum free medium (columns B). As can be seen in FIG. 13, the transgenic human antibody efficiently mediated both ADCC and CDCC activities indicating that the antibody is appropriately glycosylated during production in avians and is effective in cytolysis of target cells.

EXAMPLE 12

Construction of an Ovomucoid Promoter-Bacterial Artificial Chromosome Expression Vector with a CTLA4-Fc Fusion Coding Sequence and an attB Site An ovomucoid gene expression controlling region-bacterial artificial chromosome expression vector with a CTLA4-Fc fusion coding sequence and attB site was constructed using nucleotide coding sequences for the extracellular domains of the CTLA4 (cytotoxic T lymphocyte antigen 4) receptor protein linked to nucleotide coding sequences for an immunoglobulin constant region (IgG1 Fc). The nucleotide sequence for the vector is shown in SEQ ID NO: 44

To produce this construct, an attB fragment was inserted into an EcoRI site of the OMC24-IRES-LC clone described in Example 6. RecA-assisted restriction endonuclease cleavage (RARE) was used to cut only at the desired EcoRI site in the OMC24-IRES-LC clone. The attB fragment is shown inserted approximately at nucleotide number 26,722 to 27,029 of SEQ ID NO: 44. The attB site is shown in bold below in SEQ ID NO: 45 as it appears in the OMC24-attB-IRES-LC construct.

```
                                           SEQ ID NO:45
CCCAGAGCTG TGCAGTTGGG ATCCTAACAC CATGCAGATG

CTCCAGGACC TGCACCGAGC CCCAGCACTG GCACTCATCT

CTTCTTTCCA CCCCTCTGAG AGCAACAAGT GGCTCTGCAA

TGGCAATGTA AGTGAAACCG GGCGGGTATC TTAGAGCACC

TGGAAGCTTG CATGCCTGCA GGTCGACTCT AGAGGATCCC

CGGGTACCGA GCTCGAATTC CAGGTACCGT CGACGATGTA

GGTCACGGTC TCGAAGCCGC GGTGCGGGTG CCAGGGCGTG

CCCTTGGGCT CCCCGGGCGC GTACTCCACC TCACCCATCT

GGTCCATCAT GATGAACGGG TCGAGGTGGC GGTAGTTGAT

CCCGGCGAAC GCGCGGCGCA CCGGGAAGCC CTCGCCCTCG

AAACCGCTGG GCGCGGTGGT CACGGTGAGC ACGGGACGTG

CGACGGCGTC GGCGGGTGCG GATACGCGGG GCAGCGTCAG

CGGGTTCTCG ACGGTCACGG CGGGCATGTC GACAGCCAAG

CCGAATTCGC CCTATAGTGA GTCGTATTAC AATTCACTGG

CCGTCGTTTT ACAACGTCGT GACTGGGAAA ACCCTGGCGT

TACCCAACTT AATCGCCTTG CAGCACATCC CCCTTTCGCC
A

GCTGGCGTA ATAGCGAAGA GGCCCGCACC GATCGCCCTT

CCCAACAGTT GCGCAGCCTG AATGGCGAAT GGCGCCTGAT

GCGGTATTTT CTCCTTACGC ATCTGTGCGG TATTTCACAC

CGCATATGGT GCACTCTCAG
```

To produce the OMC24-attB-IRES-CTLA4 clone shown in SEQ ID NO: 44, the IRES-LC portion of the OMC24-attB-IRES-LC clone was deleted using RARE and was replaced with an IRES-CTLA4-Fc coding sequence (spanning approximately from nucleotides 76,124 to 77,872 of SEQ ID NO: 44). The portion of the OMC24-attB-IRES-CTLA4-Fc clone comprising the IRES and CTLA4-Fc portions is shown below in SEQ ID NO: 46. The IRES is shown in bold and the CTLA4-Fc coding region is underlined.

```
                                           SEQ ID NO:46
ATAATCAGGT AGCTGAGGAG ATGCTGAGTC TGCCAGTTCT

TGGGCTCTGG GCAGGATCCC ATCTCCTGCC TTCTCTAGGA

CAGAGCTCAG CAGGCAGGGC TCTGTGGCTC TGTGTCTAAC

CCACTTCTTC CTCTCCTCGC TTTCAGGGAA AGCAACGGGA

CTCTCACTTT AAGCCATTTT GGAAAATGCT GAATATCAGA

GCTGAGAGAA TTCCGCCCCT CTCCCTCCCC CCCCCCTAAC

GTTACTGGCC GAAGCCGCTT GGAATAAGGC CGGTGTGCGT

TTGTCTATAT GTTATTTTCC ACCATATTGC CGTCTTTTGG

CAATGTGAGG GCCCGGAAAC CTGGCCCTGT CTTCTTGACG

AGCATTCCTA GGGGTCTTTC CCCTCTCGCC AAAGGAATGC

AAGGTCTGTT GAATGTCGTG AAGGAAGCAG TTCCTCTGGA

AGCTTCTTGA AGACAAACAA CGTCTGTAGC GACCCTTTGC
```

```
-continued
AGGCAGCGGA ACCCCCCACC TGGCGACAGG TGCCTCTGCG

GCCAAAAGCC ACGTGTATAA GATACACCTG CAAAGGCGGC

ACAACCCCAG TGCCACGTTG TGAGTTGGAT AGTTGTGGAA

AGAGTCAAAT GGCTCTCCTC AAGCGTATTC AACAAGGGGC

TGAAGGATGC CCAGAAGGTA CCCCATTGTA TGGGATCTGA

TCTGGGGCCT CGGTGCACAT GCTTTACATG TGTTTAGTCG

AGGTTAAAAA AACGTCTAGG CCCCCCGAAC CACGGGGACG

TGGTTTTCCT TTGAAAAACA CGATGATAAG CTTGCCACAA

CCATGGGTGT ACTGCTCACA CAGAGGACGC TGCTCAGTCT

GGTCCTTGCA CTCCTGTTTC CAAGCATGGC GAGCATGGCA

ATGCACGTGG CCCAGCCTGC TGTGGTACTG GCCAGCAGCC

GAGGCATCGC CAGCTTTGTG TGTGAGTATG CATCTCCAGG

CAAAGCCACT GAGGTCCGGG TGACAGTGCT TCGGCAGGCT

GACAGCCAGG TGACTGAAGT CTGTGCGGCA ACCTACATGA

TGGGGAATGA GTTGACCTTC CTAGATGATT CCATCTGCAC

GGGCACCTCC AGTGGAAATC AAGTGAACCT CACTATCCAA

GGACTGAGGG CCATGGACAC GGGACTCTAC ATCTGCAAGG

TGGAGCTCAT GTACCCACCG CCATACTACC TGGGCATAGG

CAACGGAACC CAGATTTATG TAATTGATCC AGATACCGTG

CCCAGATTCT GATCAGGAGC CCAAATCTTC TGACAAAACT

CACACATCCC CACCGTCCCC AGCACCTGAA CTCCTGGGTG

GATCGTCAGT CTTCCTCTTC CCCCCAAAAC CCAAGGACAC

CCTCATGATC TCCCGGACCC CTGAGGTCAC ATGCGTGGTG

GTGGACGTGA GCCACGAAGA CCCTGAGGTC AAGTTCAACT

GGTACGTGGA CGGCGTGGAG GTGCATAATG CCAAGACAAA

GCCGCGGGAG GAGCAGTACA ACAGCACGTA CCGGGTGGTC

AGCGTCCTCA CCGTCCTGCA CCAGGACTGG CTGAATGGCA

AGGAGTACAA GTGCAAGGTC TCCAACAAAG CCCTCCCAGC

CCCCATCGAG AAAACCATCT CCAAAGCCAA AGGGCAGCCC

CGAGAACCAC AGGTGTACAC CCTGCCCCCA TCCCGGGATG

AGCTGACCAA GAACCAGGTC AGCCTGACCT GCCTGGTCAA

AGGCTTCTAT CCCAGCGACA TCGCCGTGGA GTGGGAGAGC

AATGGGCAGC CGGAGAACAA CTACAAGACC ACGCCTCCCG

TGCTGGACTC CGACGGCTCC TTCTTCCTCT ACAGCAAGCT

CACCGTGGAC AAGAGCAGGT GGCAGCAGGG GAACGTCTTC

TCATGCTCCG TGATGCATGA GGCTCTGCAC AACCACTACA

CGCAGAAGAG CCTCTCCCTG TCTCCGGGTA AATGAGGAAT

TCACCACAGG ATCCCACTG GCGAATCCCA GCGAGAGGTC

TCACCTCGGT TCATCTCGCA CTCTGGGGAG CTCAGCTCAC
```

EXAMPLE 13

Production of Transgenic Hens with an OMC24-IRES-attB-CTLA4-Fc Fusion Coding Sequence Twenty-five µg of OMC24-attB-IRES-CTLA4-Fc and 2.5 µg of SV40 integrase mRNA was placed in 200 µl of 28 mM Hepes (pH 7.4). The DNA/Hepes was mixed with an equal volume of PEI was diluted 10-fold with water and the mixture was incubated at room temperature for 15 mins. About 5 µl of the mixture was injected into chicken eggs essentially as described in Example 7.

Birds that produce egg white which includes CTLA4-Fc were identified using a procedure essentially as described in Example 8 but tailored specifically for CTLA4-Fc as is understood by a practitioner of ordinary skill in the art. Approximately 20% of the birds analyzed produced eggs positive for CTLA4-Fc.

EXAMPLE 14

Construction of an Ovomucoid Promoter-Bacterial Artificial Chromosome Expression Vector Encoding an Antibody which Binds to CD3

A single vector is constructed to include a cassette comprising an IRES attached to the coding sequence of the light chain of an IgG antibody which binds to CD3 and a cassette comprising an IRES attached to the coding sequence of the heavy chain of an IgG antibody which binds to CD3. The coding sequences for each of the antibody chains are produced by assembling synthetic oligonucleotides to form double stranded DNA segments which encode either the amino acid sequence for the antibody light chain (LC) or heavy chain (HC). Sequences for this particular antibody have been described in, for example, U.S. Pat. No. 6,706,265, the disclosure of which is incorporated in its entirety herein by reference. The IRES-LC cassette and IRES-HC cassette are each inserted into the ovomucoid UTR of a single OMC24 clone described in Example 6.

Transgenic hens which produce egg white which includes IgG antibody that binds to CD3 are produced essentially as described in Example 7.

EXAMPLE 15

Construction of an Ovomucoid Promoter-Human Artificial Chromosome Expression Vector Encoding an Antibody which Binds to CD3

A chicken HAC library constructed with genomic chicken DNA restriction digest inserts ligated into a HAC vector is screened by PCR with two sets of primers using methods well known in the art. One primer set is designed to anneal in the 5' untranslated region of the ovomucoid gene. The other primer set is designed to anneal in exon 3 and exon 4 of the ovoinhibitor gene. A single HAC-chicken DNA clone is identified that includes both the UTR and the ovoinhibitor sequences and is designated HAC-O.

Two vectors are constructed to include a cassette comprising an IRES attached to the coding sequence of either the light chain or the heavy chain of an IgG antibody which binds to CD3. The coding sequences are produced by assembling synthetic oligonucleotides to form two double stranded DNA segments which encode either the amino acid sequence of the antibody light chain (LC) or heavy chain (HC). The IRES-LC cassette and IRES-HC cassette are each inserted into the ovomucoid UTR of a HAC-O clone to produce HAC-O-IRES-LC and HAC-O-IRES-HC.

Transgenic hens which produce egg white which includes IgG antibody that binds to CD3 are produced essentially as described in Example 7.

EXAMPLE 16

Construction of an Ovomucoid Promoter P1 Derived Artificial Chromosome Expression Vector Encoding EPO A chicken PAC library constructed with chicken genomic DNA restriction digest inserts ligated into PAC vector is screened by PCR with two sets of primers using methods well known in the art. One primer set is designed to anneal in the 5' untranslated region of the ovomucoid gene. The other primer set is designed to anneal in exon 3 and exon 4 of the ovoinhibitor gene. A single PAC-chicken DNA clone is identified that includes both the UTR and the ovoinhibitor sequences and is designated PAC-O.

A vector is constructed which includes a cassette comprising an IRES attached to the coding sequence of human erythropoietin. Sequences for erythropoietin have been described in, for example, U.S. Pat. No. 4,703,008, the disclosure of which is incorporated in its entirety herein by reference. The IRES-EPO cassette is inserted into the ovomucoid UTR of the PAC-O clone.

Transgenic hens which produce egg white which includes EPO are produced essentially as described in Example 7.

EXAMPLE 17

Construction of an Ovomucoid Promoter-Bacterial Artificial Chromosome Expression Vector Encoding Human Gamma-Interferon A vector is constructed which includes a cassette coding sequence of an IRES and human gamma-interferon. Sequences for gamma-interferon have been previously described in, for example, U.S. Pat. No. 4,970,161, the disclosure of which is incorporated in its entirety herein by reference. The interferon coding sequence is inserted into the ovomucoid UTR in an OMC24 clone of Example 6.

Transgenic hens which produce egg white which includes gamma-interferon are produced essentially as described in Example 7.

EXAMPLE 18

Construction of an Ovomucoid Promoter-Yeast Artificial Chromosome Expression Vector Encoding the Fc Portion of an Antibody which Binds to CD3

A chicken YAC library constructed with restriction digest inserts ligated into YAC vector is screened by PCR with two sets of primers using methods well known in the art. One primer set is designed to anneal in the 5' untranslated region of the ovomucoid gene. The other primer set is designed to anneal in exon 3 and exon 4 of the ovoinhibitor gene. A single YAC-chicken DNA clone is identified that includes both the UTR and the ovoinhibitor sequences and is designated YAC-O.

One vector is constructed to include a cassette comprising an IRES attached to the coding sequence of the Lc portion of an IgG antibody which binds to CD3. The coding sequences are produced by assembling synthetic oligonucleotides to form two double stranded DNA segments which encode the Lc portion of an IgG antibody which binds to CD3. The IRES-Lc cassette is inserted into the ovomucoid UTR of a YAC-O clone to produce YAC-O-IRES-Lc.

Transgenic hens which produce egg white which includes the Lc portion of an IgG antibody that binds to CD3 are produced essentially as described in Example 7.

EXAMPLE 19

Construction of an Ovomucoid Promoter-Bacterial Artificial Chromosome Expression Vector Encoding a Monoclonal Antibody That Specifically Recognizes Phosphatidylinositol-3,4-Bisphosphate Two vectors are constructed to include a cassette comprising an IRES attached to the coding sequence of either the light chain or the heavy chain of a monoclonal antibody that specifically recognizes phosphatidylinositol-3,4-bisphosphate. The coding sequences are produced by assembling synthetic oligonucleotides to form two double stranded DNA segments which encode the amino acid sequence of either the antibody light chain (LC) or heavy chain (HC). Sequences for this particular antibody are disclosed in, for example, U.S. Pat. No. 6,709,833, the disclosure of which is incorporated in its entirety herein by reference. The IRES-LC cassette and IRES-HC cassette are each inserted into an OMC24 clone essentially as described in Example 6.

Transgenic hens which produce egg white that includes a monoclonal antibody that specifically recognizes phosphatidylinositol-3,4-bisphosphate are produced essentially as described in Example 7.

EXAMPLE 20

Construction of pNLB-3.9-OM-CTLA4-Fc and CTLA4 Expression Vector

The approximately 3.9 kb ovomucoid gene expression controlling region shown underlined in FIG. 14 (Fragment B) was cloned into a pBluescript vector using methodologies well know in the art to create the pOM-3.9 vector shown in FIG. 15. In order to facilitate the cloning of a coding sequence to be under the control of the approximately 3.9 kb ovomucoid gene expression controlling region, the first NcoI site that overlaps the start codon of the ovomucoid CDS (and is followed immediately by a second NcoI site) was converted into a PciI site. A NcoI 1155 bp coding sequence fragment for the extracellular domains of the CTLA4 (cytotoxic T lymphocyte antigen 4) receptor protein linked to nucleotide coding sequences for an immunoglobulin constant region (IgG1 Fc) was cloned into the PciI site of the pOM-3.9 vector to produce the pOM-3.9-CTLA4 vector as shown in FIG. 15.

EXAMPLE 21

Construction of pNLB-1.8-OM-CTLA4-Fc Expression Vector

The 2993 bp Bgl II/BamHI fragment of pOM-3.9-CTLA4 (FIG. 15) bearing a 1776 bp fragment of the ovomucoid promoter and the CTLA4-Fc coding region was inserted into the BglII site of the pNLB vector shown in FIG. 15 using standard recombinant DNA methodologies, creating pNLB-OM-1.8-CTLA4.

EXAMPLE 22

Production and Concentration of VSV-G Typed pNLB-1.8-OM-CTLA4-Fc Particles

Sentas and Isoldes are cultured in F10 (Gibco), 5% newborn calf serum (Gibco), 1% chicken serum (Gibco), 50 μg/ml phleomycin (Cayla Laboratories) and 50 μg/ml hygromycin (Sigma). Transduction particles are produced essentially as described in Cosset et al., 1991, J. Virology 65: 3388-3394, herein incorporated by reference, with the following exceptions. Two days after transfection of the retroviral vector pNLB-OM-1.8-CTLA4 (from Example 21, above) into $3\times10^5$ Sentas, virus is harvested in fresh media for 6-16 hours and filtered. All of the media is used to transduce $3\times10^6$ Isoldes in 3 100 mm plates with polybrene added to a final concentration of 4 μg/ml. The following day the media is replaced with media containing 50 μg/ml phleomycin (Cayla Laboratories), 50 μg/ml hygromycin (Gibco) and 200 μg/ml G418 (Gibco).

After 10-12 days, single $G418^R$ colonies are isolated and transferred to 24-well plates. After 7-10 days, the titer from each colony is determined by transduction of Sentas followed by G418 selection. Typically, 2 out of 60 colonies give titers at $1-3\times10^5$. Those colonies are expanded and virus concentrated to $2-7\times10^7$ as described in Allioli et al., (1994) Dev. Biol. 165:30-7, herein incorporated by reference. The virus particles are stored at −70 degrees C.

EXAMPLE 23

Direct Oviduct Transgenesis (DOT) of pNLB-1.8-OM-CTLA4-Fc Particles and Promoter Assay White Leghorn pullets which are between 10 and 20 weeks old are used in this procedure. One to ten days prior to treatment, the pullets are given daily dosages of diethylstilbestrol (DES, a potent form of estrogen) and progesterone to stimulate proliferation of magnum cells. Typically, doses for a 1 kg hen are 1 mg of DES and 0.8 mg of progesterone, injected intramuscularly in a volume of 0.1 ml of 95% ethanol or sesame oil. Testosterone may be substituted for progesterone.

Additional hormone injections may be given the day of surgery and for several days after. The day before treatment, the pullets are taken off of their diet and 1 mg of DES and 0.8 mg of progesterone per kg of pullet is injected daily for three days.

On the morning of the fourth day, the magnum of the oviduct is accessed by surgical procedures. Pullets are anesthetized with a standard dose of isoflurane. Aliquots of the concentrated pNLB-1.8-OM-CTLA4-Fc particles of Example 22 are thawed on ice. The magnum region of the oviduct is approached through a left lateral abdominal incision. Laparoscopic grasping forceps are used to secure the oviduct during the injection. Typically a volume of 0.5-0.6 ml of particles ($1-5\times10^5$ VSV-G typed particles from Example 22) is injected into three locations into the lumen of the magnum using a 1 ml syringe and 22G needle. The incision is sutured and the birds allowed to wake. The pullets are returned to their cages and given one final injection of DES and progesterone. Particle solutions remaining after injection are retitered on Isoldes and Sentas to confirm the viral titer. Six days later the same pullets are taken off their diet.

One week later the magnum is accessed through the same incision used for the injections. 0.5 ml of phosphate-buffered saline (PBS) is injected into the lumen. The lumen is gently massaged to mix the PBS with the lumen fluid. 0.1 ml PBS samples are removed from the lumen of DOT-treated hens which is assayed with a CTLA4 ELISA kit using a high sensitivity protocol reveals the presence of CTLA4 in the lumen fluid.

EXAMPLE 24

Figure 16:
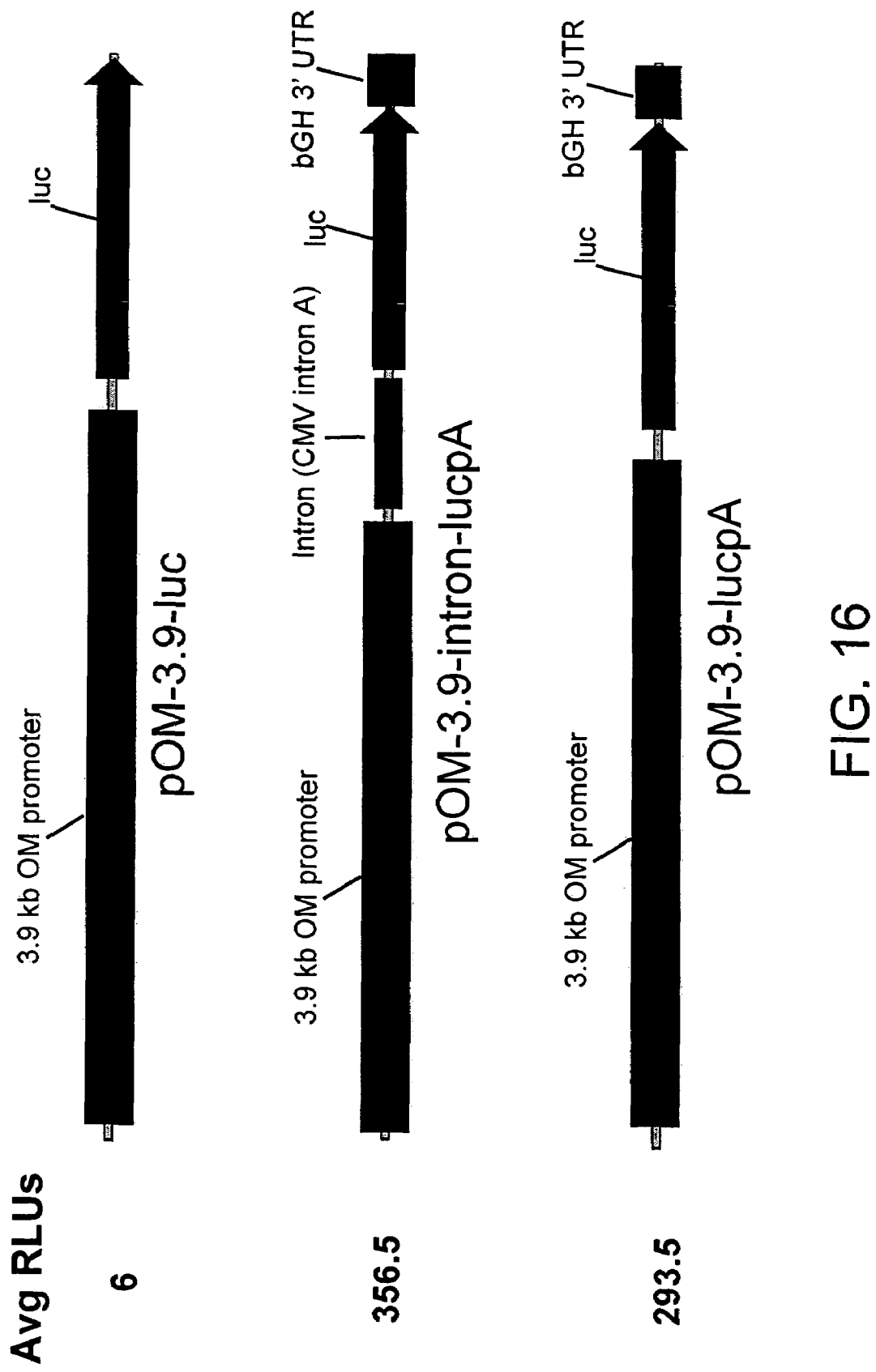
FIG. 16 shows the pOM-3.9-luc construct, the pOM-3.9-intron-lucpA construct and the pOM-3.9-lucpA construct.

Expression in Transfected Cultured Avian Myeloid and Oviduct Cells of Luciferase Regulated by the Approximetly 3.9 kb ovomucoid Promoter pOM-3.9-lucpA was constructed by cloning the 1972 bp NcoI-KpnI fragment of pCMV-luciferase (gWiz™ Expression Vector, Gene Therapy Systems, inc.) into the 7297 bp PciI-KpnI fragment of pOM-3.9. pOM-3.9-luc was constructed by cloning the 1672 bp NcoI-BamHI fragment of pCMV-luciferase (gWiZ™ Expression Vector, Gene Therapy Systems, inc.) into the 7295 bp PciI-BamHI fragment of pOM-3.9. pOM-3.9-intron-lucpA was constructed by cloning the 2899 bp SacII (mung bean nuclease treated)-KpnI fragment of pCMV-luciferase (gWiZ™ Expression Vector, Gene Therapy Systems, inc.) into the 7297 bp PciI (mung bean nuclease treated)-KpnI fragment of pOM-3.9. These constructs are shown in FIG. 16.

Primary tubular gland cells were isolated as described in Example 4. Transfection was performed for each of the six plasmids indicated in FIG. 17. 4.0 μl of DMRIE-C liposomes (Life Technologies) and 2.0 μg of DNA was preincubated for 15 minutes at room temperature each in a 200 μl aliquot of OPTIMEM™, which was then added to a well containing 800 ul of oviduct cells. Cells with DNA/liposomes were incubated for about 5 hours at 37° C. in 5% $CO_2$. 2.0 ml of DMEM (Life Technologies), supplemented with 15% fetal bovine serum (FBS) (Atlanta Biologicals, Atlanta, Ga.), 2× penicillin/streptomycin (Life Technologies), 50 ng/ml insulin (Sigma), $10^{-7}$ M α-estradiol (Sigma), and $10^{-6}$ M corticosterone (Sigma) were added to each well, and incubation continued for about 40 hours.

For each plasmid to be tested, the cells were scraped into the media with a rubber policeman. One milliliter of the resuspended cells was transferred to an eppendorf tube and the cells pelleted. The supernatant was removed and 20 ml of 10 mM Tris, ph 7.8, 1 mM EDTA (TE) was added to the cell pellet. The cells were frozen at −80° C. and thawed. 5 ml of the cell suspension was mixed with 25 ml of Bright-Glo™ reagent (Bright-Glo™ Luciferase Assay System, Promega, Madison, Wis.) and relative light units per second measured on a Berthold Detection Systems (Oak Ridge, Tenn.) FB12 luminometer.

Figure 17:
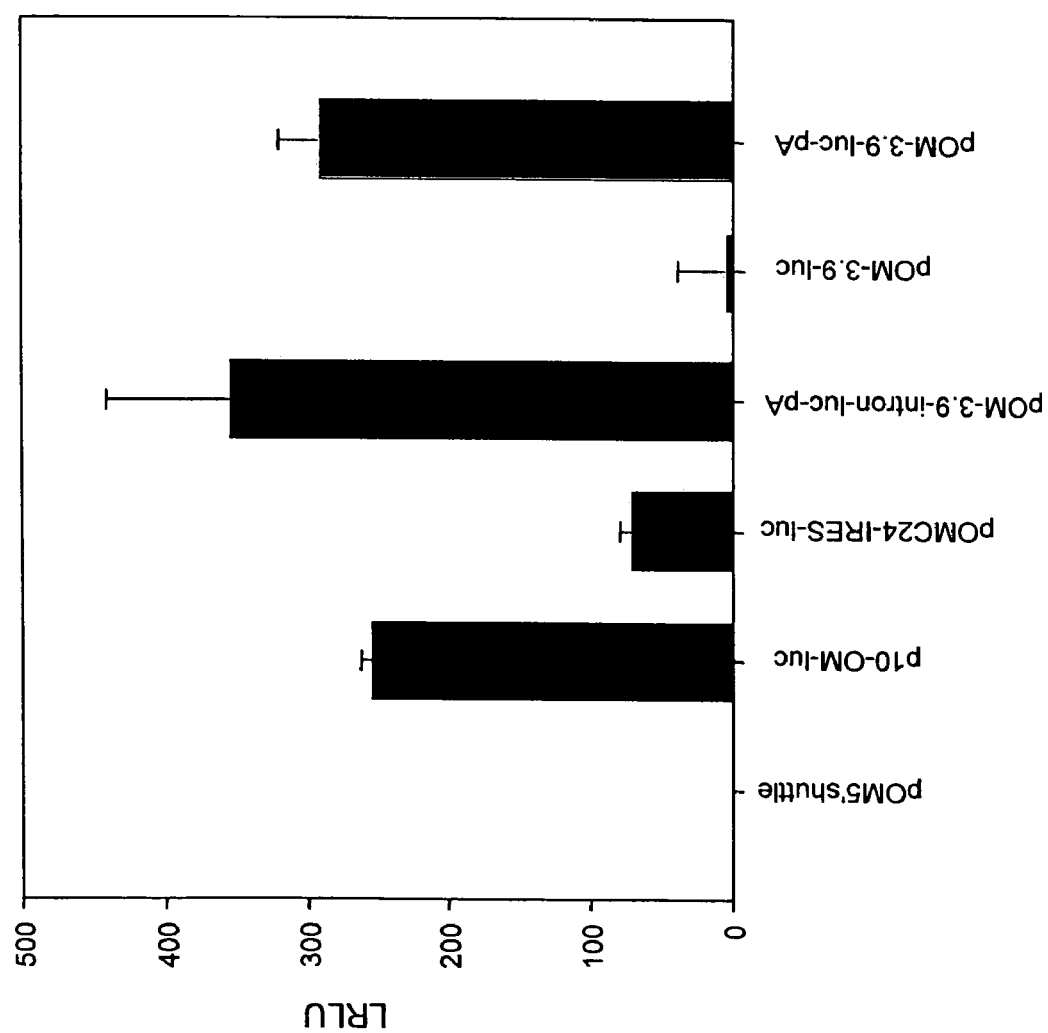
FIG. 17 shows relative measurements in a quail TGC assay for six vectors. LRLU stands for luciferase relative light units.

The results are depicted in FIG. 17. Expression of luciferase is evident from the approximately 3.9 kb OM fragment. The approximately 3.9 kb OM fragment which includes the CMV intron A appears to have more activity relative to the approximately 3.9 kb OM fragment without the CMV intron. Therefore, including an intron in an expression construct may provide for a greater level of expression by an ovomucoid gene expression controlling region, or a functional fragment, relative to the expression level provided by an identical construct without the intron.

All references cited herein are incorporated by reference herein in their entirety and for all purposes to the same extent as if each individual publication, patent or patent application is specifically and individually indicated to be incorporated by reference in its entirety for all purposes.

The citation of any publication is for its disclosure prior to the filing date and should not be construed as an admission that the present invention is not entitled to antedate such publication by virtue of prior invention.

While this invention has been described with respect to various specific examples and embodiments, it is to be understood that the invention is not limited thereto and that it can be variously practiced with the scope of the following claims.

What is claimed is:

1. A transgenic avian comprising a nucleic acid sequence encoding a heterologous protein operably linked to an ovomucoid promoter that is at least 95% identical to the nucleotide sequence of about 34,473 to about 36,248 of SEQ ID NO: 36, wherein the heterologous protein is produced in an oviduct cell of the avian.

2. The transgenic avian of claim 1, wherein the nucleic acid sequence comprises a signal sequence coding region.

3. The transgenic avian of claim 1, wherein the nucleic acid sequence comprises an IRES.

4. The transgenic avian of claim 1, wherein the nucleic acid sequence further comprises a vector.

5. The transgenic avian of claim 4, wherein the vector is selected from the group consisting of a plasmid, a viral vector, and an artificial chromosome.

6. The transgenic avian of claim 1, wherein the nucleic acid sequence further comprises a retrovirus vector.

7. The transgenic avian of claim 1, wherein the ovomucoid promoter comprises a nucleotide sequence that is at least 99% identical to the nucleotide sequence of about 34,473 to about 36,248 of SEQ ID NO: 36.

8. The transgenic avian of claim 1, wherein the ovomucoid promoter comprises the nucleotide sequence of about 34,473 to about 36,248 of SEQ ID NO: 36.

9. The transgenic avian of claim 1, wherein the transgenic avian is a chicken or a quail.

10. The transgenic avian of claim 1, wherein the transgenic avian is a chicken.

11. The transgenic avian of claim 1 wherein the oviduct cell is tubular gland cell.

12. The transgenic avian of claim 1 wherein a the nucleic acid sequence encodes at least one heterologous amino acid sequence selected from the group consisting of an immunoglobulin heavy chain variable region, an immunoglobulin heavy chain comprising a variable region and a constant region, an immunoglobulin light chain variable region, an immunoglobulin light chain comprising a variable region and a constant region, and a single-chain antibody comprising two peptide-linked immunoglobulin variable regions.

13. The transgenic avian of claim 1 wherein the heterologous protein is an antibody is selected from the group consisting of IgG, IgA, IgD, IgM and IgE.

14. The transgenic avian of claim 1 wherein the therapeutic protein is selected from the group consisting of erythropoietin (EPO), granulocyte colony-stimulating factor (G-CSF), granulocyte macrophage colony-stimulating factor (GM-CSF), CTLA4-Fc, interferon, interferon alpha, interferon beta1a, interferon beta1b, FSH and beta glucocerebrosidase.

15. The transgenic avian of claim 1 wherein the therapeutic protein is selected from the group consisting of marine MAb directed against t-lymphocyte antigen CD3, marine MAb directed against TAG-72, tumor-associated glycoprotein, FAb fragments derived from chimeric MAb directed against platelet surface receptor GPII(b)/III(a), murine MAb fragment directed against tumor-associated antigen CA 125, murine MAb fragment directed against human carcinoembryonic antigen, CEA, murine MAb fragment directed against human cardiac myosin, murine MAb fragment directed against tumor surface antigen PSMA, murine MAb fragments (EAb/FAb2 mix) directed against HMW-MAA, murine MAb fragment (FAb) directed against carcinoma-associated antigen, MAb fragments (FAb) directed against NCA 90, a surface granulocyte nonspecific cross reacting antigen, chimeric MAb directed against CD20 antigen found on surface of B lymphocytes, humanized MAb directed against the alpha chain of the IL2 receptor, chimeric MAb directed against the alpha chain of the IL2 receptor, chimeric MAb directed against TNF-alpha, humanized MAb directed against an epitope on the surface of respiratory synctial virus, humanized MAb directed against HER 2, i.e., human epidermal growth factor receptor 2, human MAb directed against cytokeratin tumor-associated antigen, anti-CTLA4, donase-alpha DNAse, TNF-alpha, IL-2-diptheria toxin fusion protein that targets cells displaying a surface IL-2 receptor, TNFR-1gG fragment fusion protein, enbrel, laronidase, teriparatide and parathyroid hormone derivatives.

16. The transgenic avian of claim 1, wherein the heterologous protein is a therapeutic protein.

17. The transgenic avian of claim 1, wherein the heterologous protein is a fusion protein.

18. The transgenic avian of claim 16, wherein the therapeutic protein is selected from the group consisting of immunoglobulins, antibodies, erythropoietin (EPO), granulocyte colony-stimulating factor (G-CSF), granulocyte macrophage colony-stimulating factor (GM-CSF), CTLA4-Fc, interferon, interferon alpha, interferon beta1a, interferon beta1b, follicle stimulating hormone (FSH) and beta glucocerebrosidase. human epidermal growth factor receptor 2 (HER 2) follicle stimulating hormone (FSH).

19. The transgenic chicken of claim 16 wherein the therapeutic protein is selected from the group consisting of murine MAb, directed against t-lymphocyte antigen CD3, murine MAb directed against TAG-72, tumor-associated glycoprotein, FAb fragments derived from chimeric MAb directed against platelet surface receptor GPII(b)/III(a), murine MAb fragment directed against tumor-associated antigen CA 125, murine MAb fragment directed against human carcinoembryonic antigen, CEA, murine MAb fragment directed against human cardiac myosin, murine MAb fragment directed against tumor surface antigen PSMA, murine MAb fragments (FAb/FAb2 mix) directed against HMW-MAA, murine MAb fragment (FAb) directed against carcinoma-associated antigen, MAb fragments (FAb) directed against NCA 90, a surface granulocyte nonspecific cross reacting antigen, humanized MAb directed against the alpha chain of the IL2 receptor, chimeric MAb directed against the alpha chain of the IL2 receptor, chimeric MAb directed against TNF-alpha, humanized MAb directed against an epitope on the surface of respiratory synctial virus, humanized MAb directed against human epidermal growth factor receptor 2 (HER 2) human MAb, directed against cytokeratin tumor-associated antigen, anti-CTLA4, chimeric MAb directed. against CD 20 surface antigen of B lymphocytes, dornase-alpha DNAse, TNF-alpha, IL-2-diptheria toxin fusion protein that targets cells displaying a surface IL-2 receptor, TNFR-1gG fragment fusion protein, enbrel, laronidase, teriparatide and parathyroid hormone derivatives.

20. The transgenic avian of claim 1 wherein the heterologous protein is selected from the group consisting of erythropoietiu (EPO), granulocyte colony-stimulating factor (G-CSF), granulocyte macrophage colony-stimulating factor (GM-CSF), CTLA4-Fc, interferon, interferon alpha, interferon beta1a, interferon beta1b, follicle stimulating hormone (FSH) and beta glucocerebrosidase.

* * * * *

```
                          SEQUENCE LISTING

<160> NUMBER OF SEQ ID NOS: 46

<210> SEQ ID NO 1
<211> LENGTH: 30
<212> TYPE: DNA
<213> ORGANISM: Artificial Sequence
<220> FEATURE:
<223> OTHER INFORMATION: Primer OVINs2

<400> SEQUENCE: 1
taggcagagc aataggactc tcaacctcgt                                    30

<210> SEQ ID NO 2
<211> LENGTH: 30
<212> TYPE: DNA
<213> ORGANISM: Artificial Sequence
<220> FEATURE:
<223> OTHER INFORMATION: Primer OVMa2

<400> SEQUENCE: 2
aagcttctgc agcactctgg gagttactca                                    30

<210> SEQ ID NO 3
<211> LENGTH: 20
<212> TYPE: DNA
<213> ORGANISM: Artificial Sequence
<220> FEATURE:
<223> OTHER INFORMATION: Primer OVINs1

<400> SEQUENCE: 3
gggaaacaat ctgccttgca                                               20

<210> SEQ ID NO 4
<211> LENGTH: 21
<212> TYPE: DNA
<213> ORGANISM: Artificial Sequence
<220> FEATURE:
<223> OTHER INFORMATION: Primer OVMUa1

<400> SEQUENCE: 4
aagccacaaa gcacgaaaga g                                             21

<210> SEQ ID NO 5
<211> LENGTH: 20
<212> TYPE: DNA
<213> ORGANISM: Artificial Sequence
<220> FEATURE:
<223> OTHER INFORMATION: Primer T3

<400> SEQUENCE: 5
taatacgact cactataggg                                               20

<210> SEQ ID NO 6
<211> LENGTH: 20
<212> TYPE: DNA
<213> ORGANISM: Artificial Sequence
<220> FEATURE:
<223> OTHER INFORMATION: Primer T7

<400> SEQUENCE: 6
``` attaccctc actaaaggga                                              20

<210> SEQ ID NO 7
<211> LENGTH: 20
<212> TYPE: DNA
<213> ORGANISM: Artificial Sequence
<220> FEATURE:
<223> OTHER INFORMATION: Primer OVINs4

<400> SEQUENCE: 7
agatgaggtg gatggtttac                                             20

<210> SEQ ID NO 8
<211> LENGTH: 20
<212> TYPE: DNA
<213> ORGANISM: Artificial Sequence
<220> FEATURE:
<223> OTHER INFORMATION: Primer OVINs5

<400> SEQUENCE: 8
cagcttctgc tagcgtaggt                                             20

<210> SEQ ID NO 9
<211> LENGTH: 20
<212> TYPE: DNA
<213> ORGANISM: Artificial Sequence
<220> FEATURE:
<223> OTHER INFORMATION: Primer OVINs6

<400> SEQUENCE: 9
acgtgaactc aaagaggcac                                             20

<210> SEQ ID NO 10
<211> LENGTH: 20
<212> TYPE: DNA
<213> ORGANISM: Artificial Sequence
<220> FEATURE:
<223> OTHER INFORMATION: Primer OVINs7

<400> SEQUENCE: 10
atctcctgag ctcggtgctt                                             20

<210> SEQ ID NO 11
<211> LENGTH: 20
<212> TYPE: DNA
<213> ORGANISM: Artificial Sequence
<220> FEATURE:
<223> OTHER INFORMATION: Primer OVINs8

<400> SEQUENCE: 11
acgaggttcc atgtctttca                                             20

<210> SEQ ID NO 12
<211> LENGTH: 31
<212> TYPE: DNA
<213> ORGANISM: Artificial Sequence
<220> FEATURE:
<223> OTHER INFORMATION: Primer OVMUa3

<400> SEQUENCE: 12
taaatagcac agaacgctga ggggagtaag g                                31

<210> SEQ ID NO 13
<211> LENGTH: 20
<212> TYPE: DNA

```
<213> ORGANISM: Artificial Sequence
<220> FEATURE:
<223> OTHER INFORMATION: Primer OVMUa4

<400> SEQUENCE: 13
gaagagcttg gtagaagact                                              20

<210> SEQ ID NO 14
<211> LENGTH: 21
<212> TYPE: DNA
<213> ORGANISM: Artificial Sequence
<220> FEATURE:
<223> OTHER INFORMATION: Primer OVMUa5

<400> SEQUENCE: 14
atggaaatat gggtttcctt c                                            21

<210> SEQ ID NO 15
<211> LENGTH: 20
<212> TYPE: DNA
<213> ORGANISM: Artificial Sequence
<220> FEATURE:
<223> OTHER INFORMATION: Primer OVMUa6

<400> SEQUENCE: 15
gcagcttatg gctaatcgct                                              20

<210> SEQ ID NO 16
<211> LENGTH: 20
<212> TYPE: DNA
<213> ORGANISM: Artificial Sequence
<220> FEATURE:
<223> OTHER INFORMATION: Primer OVMUa7

<400> SEQUENCE: 16
agtgaccact atctgacctg                                              20

<210> SEQ ID NO 17
<211> LENGTH: 20
<212> TYPE: DNA
<213> ORGANISM: Artificial Sequence
<220> FEATURE:
<223> OTHER INFORMATION: Primer OVMUa8

<400> SEQUENCE: 17
taatcaggaa ggcacacagc                                              20

<210> SEQ ID NO 18
<211> LENGTH: 20
<212> TYPE: DNA
<213> ORGANISM: Artificial Sequence
<220> FEATURE:
<223> OTHER INFORMATION: Primer OVMUP4. 7. 1

<400> SEQUENCE: 18
agatctggag cagcacttgt                                              20

<210> SEQ ID NO 19
<211> LENGTH: 20
<212> TYPE: DNA
<213> ORGANISM: Artificial Sequence
<220> FEATURE:
<223> OTHER INFORMATION: Primer OVMUP4. 7. 2

<400> SEQUENCE: 19
agcatgaagt tcctcaccca                                              20
```

<210> SEQ ID NO 20
<211> LENGTH: 20
<212> TYPE: DNA
<213> ORGANISM: Artificial Sequence
<220> FEATURE:
<223> OTHER INFORMATION: Primer OVMUP4.7.3

<400> SEQUENCE: 20
atggagagga atattccctt                                               20

<210> SEQ ID NO 21
<211> LENGTH: 18
<212> TYPE: DNA
<213> ORGANISM: Artificial Sequence
<220> FEATURE:
<223> OTHER INFORMATION: Primer OVMUP4.7.4

<400> SEQUENCE: 21
atttctccag gcgtgtgg                                                 18

<210> SEQ ID NO 22
<211> LENGTH: 18
<212> TYPE: DNA
<213> ORGANISM: Artificial Sequence
<220> FEATURE:
<223> OTHER INFORMATION: Primer OVMUP5.5.1

<400> SEQUENCE: 22
atttctccag gcgtgtgg                                                 18

<210> SEQ ID NO 23
<211> LENGTH: 20
<212> TYPE: DNA
<213> ORGANISM: Artificial Sequence
<220> FEATURE:
<223> OTHER INFORMATION: Primer VMUP5.5.2

<400> SEQUENCE: 23
atgcgagtga aggagagttc                                               20

<210> SEQ ID NO 24
<211> LENGTH: 20
<212> TYPE: DNA
<213> ORGANISM: Artificial Sequence
<220> FEATURE:
<223> OTHER INFORMATION: Primer OVMUP5.5.3

<400> SEQUENCE: 24
gcagcacgtg taagcttgta                                               20

<210> SEQ ID NO 25
<211> LENGTH: 20
<212> TYPE: DNA
<213> ORGANISM: Artificial Sequence
<220> FEATURE:
<223> OTHER INFORMATION: Primer OVMUP5.5.4

<400> SEQUENCE: 25
caaggcaaat tatcagcaga                                               20

<210> SEQ ID NO 26
<211> LENGTH: 9980
<212> TYPE: DNA
<213> ORGANISM: Gallus gallus
<220> FEATURE:

-continued

```
<221> NAME/KEY: 3'UTR
<222> LOCATION: (1)..(255)
<223> OTHER INFORMATION: 3' untranslated region of ovoinhibitor
<220> FEATURE:
<221> NAME/KEY: misc_feature
<222> LOCATION: (2761)..(3024)
<223> OTHER INFORMATION: CR1-like element
<220> FEATURE:
<221> NAME/KEY: 5'UTR
<222> LOCATION: (9403)..(9920)
<223> OTHER INFORMATION: 5' untranslated region of ovomucoid
```

<400> SEQUENCE: 26

| | | | | | |
|---|---|---|---|---|---|
| taggcagagc | aataggactc | tcaacctcgt | gagtatggca | gcatgttaac | tctgcactgg | 60 |
| agtccagcgt | gggaaacaat | ctgccttgca | catgagtctt | cgtgggccaa | tattccccaa | 120 |
| cggttttcct | tcagcttgtc | ttgtctccta | agctctcaaa | acaccttttt | ggtgaataaa | 180 |
| ctcacttggc | aacgtttatc | tgtcttacct | tagtgtcacg | tttcatccct | attccccttt | 240 |
| ctcctcctcc | gtgtggtaca | cagtggtgca | cactggttct | tctgttgatg | ttctgctctg | 300 |
| acagccaatg | tgggtaaagt | tcttcctgcc | acgtgtctgt | gttgttttca | cttcaaaaag | 360 |
| ggccctgggc | tccccttgga | gctctcaggc | atttccttaa | tcatcacagt | cacgctggca | 420 |
| ggattagtcc | ctcctaaacc | ttagaatgac | ctgaacgtgt | gctccctctt | tgtagtcagt | 480 |
| gcagggagac | gtttgcctca | agatcagggt | ccatctcacc | cacagggcca | ttcccaagat | 540 |
| gaggtggatg | gtttactctc | acaaaaagtt | ttcttatgtt | tggctagaaa | ggagaactca | 600 |
| ctgcctacct | gtgaattccc | ctagtcctgg | ttctgctgcc | actgctgcct | gtgcagcctg | 660 |
| tcccatggag | ggggcagcaa | ctgctgtcac | aaaggtgatc | ccaccctgtc | tccactgaaa | 720 |
| tgacctcagt | gccacgtgtt | gtatagggta | taaagtacgg | gagggggatg | cccggctccc | 780 |
| ttcagggttg | cagagcagaa | gtgtctgtgt | atagagtgtg | tcttaatcta | ttaatgtaac | 840 |
| agaacaactt | cagtcctagt | gttttgtggg | ctggaattgc | ccatgtggta | gggacaggcc | 900 |
| tgctaaatca | ctgcaatcgc | ctatgttctg | aaggtatttg | ggaaagaaag | ggatttgggg | 960 |
| gattgcctgt | gattggcttt | aattgaatgg | caaatcacag | gaaagcagtt | ctgctcaaca | 1020 |
| gttggttgtt | tcagccaatt | cttgcagcca | agagccgggt | gcccagcga | tataatagtt | 1080 |
| gtcacttgtg | tctgtatgga | tgacagggag | gtagggtgac | ctgaggacca | ccctccagct | 1140 |
| tctgctagcg | taggtacagt | caccacctcc | agctccacac | gagtcccatc | gtggtttacc | 1200 |
| aaagaaacac | aattatttgg | accagtttgg | aaagtcaccc | gctgaattgt | gaggctagat | 1260 |
| taatagagct | gaagagcaaa | tgttcccaac | ttgagagtac | tagttggtat | tagtatcaga | 1320 |
| ggaacagggc | catagcacct | ccatgctatt | agattccggc | tggcatgtac | ttttcaagat | 1380 |
| gatttgtaac | taacaatggc | ttattgtgct | tgtcttaagt | ctgtgtccta | atgtaaatgt | 1440 |
| tcctttggtt | tatataacct | tcttgccatt | tgctcttcag | gtgttcttgc | agaacactgg | 1500 |
| ctgctttaat | ctagtttaac | tgttgcttga | ttattcttag | ggataagatc | tgaataaact | 1560 |
| ttttgtggct | ttggcagact | ttagcttggg | cttagctccc | acattagctt | tgctgccttt | 1620 |
| ttctgtgaag | ctatcaagat | cctactcaat | gacattagct | gggtgcaggt | gtaccaaatc | 1680 |
| ctgctctgtg | gaacacattg | tctgatgata | ccgaaggcaa | acgtgaactc | aaagaggcac | 1740 |
| agagttaaga | agaagtctgt | gcaattcaga | ggaaaagcca | aagtggccat | tagacacact | 1800 |
| ttccatgcag | catttgccag | taggtttcat | ataaaactac | aaaatggaat | aaaccactac | 1860 |
| aaatgggaaa | agcctgatac | tagaatttaa | atattcaccc | aggctcaagg | ggtgtttcat | 1920 |
| ggagtaatat | cactctataa | aagtagggca | gccaattatt | cacagacaaa | gctttttttt | 1980 |

```
ttctgtgctg cagtgctgtt tttcggctga tccagggtta cttattgtgg gtctgagagc   2040
tgaatgattt ctccttgtgt catgttggtg aaggagatat ggccaggggg agatgagcat   2100
gttcaagagg aaacgttgca ttttggtggc ttgggagaaa ggtagaacga tatcaggtcc   2160
atagtgtcac taagagatct gaaggatggt tttacagaac agttgacttg gctgggtgca   2220
ggcttggctg taaatggatg gaaggatgga cagatgggtg gacagagatt tctgtgcagg   2280
agatcatctc ctgagctcgg tgcttgacag actgcagatc catcccataa ccttctccag   2340
catgagagcg cggggagctt tggtactgtt cagtctgctg cttgttgctt cctgggtgca   2400
cagtggtgat tttcttactc acacagggca aaaacctgag cagcttcaaa gtgaacaggt   2460
tgctctcata ggccattcag ttgtcaagat gaggttttg gtttcttgtt ttgtaaggtg    2520
ggaagaagca ctgaaggatc agttgcgagg gcagggggttt agcactgttc agagaagtct  2580
tattttaact cctctcatga acaaaaagag atgcaggtgc agattctggc aagcatgcag   2640
tgaaggagaa agccctgaat tctgatata tgtgcaatgt tgggcaccta acattccccg    2700
ctgaagcaca gcagctccag ctccatgcag tactcacagc tggtgcagcc ctcggctcca   2760
gggtctgagc agtgctggga ctcacgaggt tccatgtctt tcacactgat aatggtccaa   2820
tttctggaat gggtgcccat ccttggaggt ccccaaggcc aggctggctg cgtctccgag   2880
cagcccgatc tggtggtgag tagccagccc atggcaggag ttagagcctg atggtcttta   2940
aggtcccttc caacctaagc catcctacga ttctaggaat catgacttgt gagtgtgtat   3000
tgcagaggca atatttaaa gttataaatg ttttctcccc ttccttgttt gtcaaagtta    3060
tcttgatcgc cttatcaatg ctttttggagt ctccagtcat ttttcttaca mcaaaaagag  3120
gaggaagaat gaagagaatc atttaatttc ttgattgaat agtaggattc agaaagctgt   3180
acgtaatgcc gtctctttgt atcgagctgt aaggtttctc atcatttatc agcgtggtac   3240
atatcagcac ttttccatct gatgtggaaa aaaaaatcct tatcatctac agtctctgta   3300
cctaaacatc gctcagactc tttaccaaaa aagctatagg ttttaaaact acatctgctg   3360
ataatttgcc ttgttttagc tcttcttcca tatgctgcgt ttgtgagagg tgcgtggatg   3420
ggcctaaaact ctcagctgct gagcttgatg ggtgcttaag aatgaagcac tcactgctga   3480
aactgttttc atttcacagg aatgttttag tggcattgtt tttataacta catattcctc   3540
agataaatga atccagaaa taattatgca aactcactgc atccgttgca caggtcttta    3600
tctgctagca aaggaaataa tttggggatg gcaaaaacat tccttcagac atctatattt   3660
aaaggaatat aatcctggta cccacccact tcatccctca ttatgttcac actcagagat   3720
actcattctc ttgttgttat catttgatag cgttttcttt ggttctttgc cacgctctgg   3780
gctatggctg cacgctctgc actgatcagc aagtagatgc gagggaagca gcagtgagag   3840
gggctgccct cagctggcac ccagccgctc agcctaggag gggaccttgc cttttccacca  3900
gctgaggtgc agccctacaa gcttacacgt gctgcgagca ggtgagcaaa gggagtcttc   3960
atggtgtgtt tcttgctgcc cggaagcaaa actttacttt cattcattcc ccttgaagaa   4020
tgaggaatgt ttggaaacgg actgctttac gttcaatttc tctcttccct ttaaggctca   4080
gccaggggcc attgctgagg acggcatcgg ggcccctgg accaaatctg tggcacagat    4140
ggtttcactt acatcagtgg atgtgggatc tgcgcctgta atgtgtcctt ctgaaggaag   4200
gaacgtgcct tccaagtgcc agccccacag ccccagccc ctccctgtgc tgctccaatt    4260
catctcctct tcctccttct ccctttgctg tttgtgctcg ggtagaaatc atgaagattt   4320
```

```
agaagagaaa acaaaataac tggagtggaa acccaggtga tgcagttcat tcagctgtca    4380
taggtttgtc gttgctatag gtctgtatca gagatgctar caccactttg ctgtcggtgc    4440
ttaactcggg tgaactctcc ttcactcgca tcatttgcgg gccttattta catccccagc    4500
atccatcacc ctctgggaaa atgggcgcac tggatctcta atggaagact ttccctcttt    4560
cagagcctgt gggatgtgca gtgacaagaa acgtggaggg gctgagcagc agcactgccc    4620
ccagggagca ggagcggatg ccatcggtgg cagcatccca aatgatgtca gcggatgctg    4680
agcaggcagc ggacgaacgg acagaagcga tgcgtacacc ttctgttgac atggtatttg    4740
gcagcgattt aacactcgct tcctagtcct gctattctcc acaggctgca ttcaaatgaa    4800
cgaagggaag ggaggcaaaa agatgcaaaa tccgagacaa gcagcagaaa tatttcttcg    4860
ctacggaagc gtgcgcaaac aaccttctcc aacagcacca gaagagcaca gcgtaacctt    4920
tttcaagacc agaaaaggaa attcacaaag cctctgtgga taccagcgcg ttcagctctc    4980
ctgatagcag atttcttgtc aggttgcgaa tggggtatgg tgccaggagg tgcagggacc    5040
atatgatcat atacagcaca gcagtcattg tgcatgtatt aatatatatt gagtagcagt    5100
gttactttgc caaagcaata gttcagagat gagtcctgct gcatacctct atcttaaaac    5160
taacttataa atagtaaaac cttctcagtt cagccacgtg ctcctctctg tcagcaccaa    5220
tggtgcttcg cctgcaccca gctgcaagga atcagcccgt gatctcatta acactcagct    5280
ctgcaggata aattagattg ttccactctc ttttgttgtt aattacgacg gaacaattgt    5340
tcagtgctga tggtcctaat tgtcagctac agaaaacgtc tccatgcagt tccttctgcg    5400
ccagcaaact gtccaggcta tagcaccgtg atgcatgcta cctctcactc catccttctt    5460
ctctttccca ccagggagag ctgtgtgttt tcactctcag ccactctgaa caataccaaa    5520
ctgctacgca ctgcctccct cggaaagaga atccccttgt tgctttttta tttacaggat    5580
ccttcttaaa aagcagacca tcattcactg caaacccaga gcttcatgcc tctccttcca    5640
caaccgaaaa cagccggctt catttgtctt ttttaaatgc tgttttccag gtgaattttg    5700
gccagcgtgt tggctgagat ccaggagcac gtgtcagctt tctgctctca ttgctcctgt    5760
tctgcattgc ctctttctgg ggtttccaag agggggggag actttgcgcg gggatgagat    5820
aatgccccct ttcttagggt ggctgctggg cagcagagtg gctctgggtc actgtggcac    5880
caatgggagg caccagtggg ggtgtgtttt gtgcagggg gaagcattca cagaatgggg    5940
ctgatcctga agcttgcagt ccaaggcttt gtctgtgtac ccagtgaaat ccttcctctg    6000
ttacataaag cccagatagg actcagaaat gtagtcattc cagccccct cttcctcaga    6060 tctggagcag cacttgtttg cagccagtcc tccccaaaat gcacagacct cgccgagtgg    6120
agggagatgt aaacagcgaa ggttaattac ctccttgtca aaaacacttt gtggtccata    6180
gatgtttctg tcaatcttac aaaacagaac cgagaggcag cgagcactga agagcgtgtt    6240
cccatgctga gttaatgaga cttggcagct cgctgtgcag agatgatccc tgtgcttcat    6300
gggaggctgt aacctgtctc cccatcgcct tcacaccgca gtgctgtcct ggacacctca    6360
ccctccataa gctgtaggat gcagctgccc agggatcaag agacttttcc taaggctctt    6420
aggactcatc tttgccgctc agtagcgtgc agcaattact catcccaact atactgaatg    6480
ggtttctgcc agctctgctt gtttgtcaat aagcatttct tcattttgcc tctaagtttc    6540
tctcagcagc accgctctgg gtgacctgag tggccacctg gaacccgagg ggcacagcca    6600
ccacctccct gttgctgctg ctccaggac tcatgtgctg ctggatgggg ggaagcatga    6660
agttcctcac ccagacacct gggttgcaat ggctgcagcg tgctcttctt ggtatgcaga    6720
```

```
ttgtttccag ccattacttg tagaaatgtg ctgtggaagc cctttgtatc tctttctgtg   6780
gcccttcagc aaaagctgtg ggaaagctct gaggctgctt tcttgggtcg tggaggaatt   6840
gtatgttcct tctttaacaa aaattatcct taggagagag cactgtgcaa gcattgtgca   6900
cataaaacaa ttcaggttga aagggctctc tggaggtttc cagcctgact actgctcgaa   6960
gcaaggccag gttcaaagat ggctcaggat gctgtgtgcc ttcctgatta tctgtgccac   7020
caatggagga gattcacagc cactctgctt cccgtgccac tcatggagag gaatattccc   7080
ttatattcag atagaatgtt atcctttagc tcagccttcc ctataacccc atgagggagc   7140
tgcagatccc catactctcc ccttctctgg ggtgaaggcc gtgtccccca gccccccttc   7200
ccaccctgtg ccctaagcag cccgctggcc tctgctggat gtgtgcctat atgtcaatgc   7260
ctgtccttgc agtccagcct gggacattta attcatcacc agggtaatgt ggaactgtgt   7320
catcttcccc tgcagggtac aaagttctgc acggggtcct ttcggttcag gaaaaccttc   7380
actggtgcta cctgaatcaa gctctatttta ataagttcat aagcacatgg atgtgttttc   7440
ctagagatac gttttaatgg tatcagtgat ttttatttgc tttgttgctt acttcaaaca   7500
gtgcctttgg gcaggaggtg agggacgggt ctgccgttgg ctctgcagtg atttctccag   7560
gcgtgtggct caggtcagat agtggtcact ctgtggccag aagaaggaca agatggaaaa   7620
ttgcagattg agtcacgtta agcaggcatc ttggagtgat ttgaggcagt ttcatgaaag   7680
agctacgacc acttattgtt gttttcccct tttacaacag aagttttcat caaaataacg   7740
tggcaaagcc caggaatgtt tgggaaaagt gtagttaaat gttttgtaat tcatttgtcg   7800
gagtgctacc agctaagaaa aaagtcctac ctttggtatg gtagtcctgc agagaataca   7860
acatcaatat tagtttggaa aaaaacacca ccaccaccag aaactgtaat ggaaaatgta   7920
aaccaagaaa ttccttgggt aagagagaaa ggatgtcgta tactggccaa gtcctgccca   7980
gctgtcagcc tgctgaccct ctgcagttca ggaccatgaa acgtggcact gtaagacgtg   8040
tcccctgcct ttgcttgccc acagatctct gcccttgtgc tgactcctgc acacaagagc   8100
atttccctgt agccaaacag cgattagcca taagctgcac ctgactttga ggattaagag   8160
tttgcaatta agtggattgc agcaggagat cagtggcagg gttgcagatg aaatccttttt   8220 ctaggggtag ctaagggctg agcaacctgt cctacagcac aagccaaacc agccaagggt   8280
tttcctgtgc tgttcacaga ggcagggcca gctggagctg gaggaggttg tgctgggacc   8340
cttctccctg tgctgagaat ggagtgattt ctgggtgctg ttcctgtggc ttgcactgag   8400
cagctcaagg gagatcggtg ctcctcatgc agtgccaaaa ctcgtgtttg atgcagaaag   8460
atggatgtgc acctccctcc tgctaatgca gccgtgagct tatgaaggca atgagccctc   8520
agtgcagcag gagctgtagt gcactcctgt aggtgctagg gaaaatctct ggttcccagg   8580
gatgcattca taagggcaat atatcttgag gctgcgccaa atctttctga aatattcatg   8640
cgtgttccct taatttatag aaacaaacac agcagaataa ttattccaat gcctcccctc   8700
gaaggaaacc catatttcca tgtagaaatg taacctatat acacacagcc atgctgcatc   8760
cttcagaacg tgccagtgct catctcccat ggcaaaatac tacaggtatt ctcactatgt   8820
tggacctgtg aaaggaacca tggtaagaaa cttcggttaa aggtatggct gcaaaactac   8880
tcataccaaa acagcagagc tccagacctc ctcttaggaa agagccactt ggagagggat   8940
ggtgtgaagg ctggaggtga gagacagagc ctgtcccagt tttcctgtct ctattttctg   9000
aaacgtttgc aggaggaaag gacaactgta ctttcaggca tagctggtgc cctcacgtaa   9060
```

-continued

```
ataagttccc cgaacttctg tgtcatttgt tcttaagatg ctttggcaga acactttgag    9120
tcaattcgct taactgtgac taggtctgta aataagtgct ccctgctgat aaggttcaag    9180
tgacattttt agtggtattt gacagcatttt accttgcttt caagtcttct accaagctct   9240
tctatactta agcagtgaaa ccgccaagaa acccttcctt ttatcaagct agtgctaaat    9300
accattaact tcataggtta gatacggtgc tgccagcttc acctggcagt ggttggtcag    9360
ttctgctggt gacaaagcct ccctggcctg tgcttttacc tagaggtgaa tatccaagaa    9420
tgcagaactg catggaaagc agagctgcag gcacgatggt gctgagcctt agctgcttcc    9480
tgctgggaga tgtggatgca gagacgaatg aaggacctgt cccttactcc cctcagcatt    9540
ctgtgctatt tagggttcta ccagagtcct taagaggttt ttttttttt tggtccaaaa     9600 gtctgtttgt ttggttttga ccactgagag catgtgacac ttgtctcaag ctattaacca    9660
agtgtccagc caaaatcaat tgcctgggag acgcagacca ttacctggag gtcaggacct    9720
caataaatat taccagcctc attgtgccgc tgacagattc agctggctgc tccgtgttcc    9780
agtccaacag ttcggacgcc acgtttgtat atatttgcag gcagcctcgg ggggaccatc    9840
tcaggagcag agcaccggca gccgcctgca gagccgggca gtactctcac catggccatg    9900
gcaggtgtct tcgtgctgtt ctctttcgtg ctttgtggct tcctcccagg tgagtaactc    9960
ccagagtgct gcagaagctt                                                9980
```

<210> SEQ ID NO 27
<211> LENGTH: 20
<212> TYPE: DNA
<213> ORGANISM: Artificial Sequence
<220> FEATURE:
<223> OTHER INFORMATION: Primer OVMUa9

<400> SEQUENCE: 27

```
aaatgaagcc ggctgttttc                                                  20
```

<210> SEQ ID NO 28
<211> LENGTH: 20
<212> TYPE: DNA
<213> ORGANISM: Artificial Sequence
<220> FEATURE:
<223> OTHER INFORMATION: Primer OVINs9

<400> SEQUENCE: 28

```
ctctcagcca ctctgaacaa                                                  20
```

<210> SEQ ID NO 29
<211> LENGTH: 40
<212> TYPE: DNA
<213> ORGANISM: Artificial Sequence
<220> FEATURE:
<223> OTHER INFORMATION: Primer

<400> SEQUENCE: 29

```
gcgcggccgc ccgggacatg tccatggtga gagtactgcc                            40
```

<210> SEQ ID NO 30
<211> LENGTH: 29
<212> TYPE: DNA
<213> ORGANISM: Artificial Sequence
<220> FEATURE:
<223> OTHER INFORMATION: Primer

<400> SEQUENCE: 30

```
ggcccgggat tcgcttaact gtgactagg                                        29
```

<210> SEQ ID NO 31
<211> LENGTH: 802
<212> TYPE: DNA
<213> ORGANISM: Artificial Sequence
<220> FEATURE:
<223> OTHER INFORMATION: primer

<400> SEQUENCE: 31

```
gcgcggccgc ccgggacatg tccatggtga gagtactgcc cggctctgca ggcggctgcc      60
ggtgctctgc tcctgagatg gtcccccccga ggctgcctgc aaatatatac aaacgtggcg    120
tccgaactgt tggactggaa cacggagcag ccagctgaat ctgtcagcgg cacaatgagg    180
ctggtaatat ttattgaggt cctgacctcc aggtaatggt ctgcgtctcc caggcaattg    240
attttggctg acacttggt  taatagcttg agacaagtgt cacatgctct cagtggtcaa    300
aaccaaacaa acagactttt ggaccaaaaa aaaaaaaaac ctcttaagga ctctggtaga    360
accctaaata gcacagaatg ctgaggggag taagggacag gtccttcatt cgtctctgca    420
tccacatctc ccagcaggaa gcagctaagg ctcagcacca tcgtgcctgc agctctgctt    480
tccatgcagt tctgcattct tggatattca cctctaggta aaagcacagg ccagggaggc    540
tttgtcacca gcagaactga ccaaccactg ccaggtgaag ctggcagcac cgtatctaac    600
ctatgaagtt aatggtattt agcactagct tgataaaagg aagggtttct tggcggtttc    660
actgcttaag tatagaagag cttggtagaa gacttgaaag caaggtaaat gctgtcaaat    720
accactaaaa atgtcacttg aaccttatca gcagggagca cttatttaca gacctagtca    780
cagttaagcg aattcccggg cc                                             802
```

<210> SEQ ID NO 32
<211> LENGTH: 17
<212> TYPE: DNA
<213> ORGANISM: Artificial Sequence
<220> FEATURE:
<223> OTHER INFORMATION: Primer

<400> SEQUENCE: 32
ctccacatgg ccatggc                                                    17

<210> SEQ ID NO 33
<211> LENGTH: 17
<212> TYPE: DNA
<213> ORGANISM: Artificial Sequence
<220> FEATURE:
<223> OTHER INFORMATION: Primer

<400> SEQUENCE: 33
gagtggtacc ggtaccg                                                    17

<210> SEQ ID NO 34
<211> LENGTH: 17
<212> TYPE: DNA
<213> ORGANISM: Artificial Sequence
<220> FEATURE:
<223> OTHER INFORMATION: Primer

<400> SEQUENCE: 34
ctcaccatgg acatgga                                                    17

<210> SEQ ID NO 35
<211> LENGTH: 17
<212> TYPE: DNA

<213> ORGANISM: Artificial Sequence
<220> FEATURE:
<223> OTHER INFORMATION: Primer

<400> SEQUENCE: 35
gagtggtacc ggtaccg                                                    17

<210> SEQ ID NO 36
<211> LENGTH: 75815
<212> TYPE: DNA
<213> ORGANISM: chicken

<400> SEQUENCE: 36

| | | | | | |
|---|---|---|---|---|---|
| aagctttgtg | ctttctgcct | gaataaaaga | aacctgaact | ctgttcaccc | agtccctgtc | 60 |
| aggcaattac | tgacagagca | cctatggtct | gtgtttggcc | agaacatagg | ctaaggaaga | 120 |
| tacctcctgt | ttataaagca | cgcctttggc | atctggcaag | taattagtga | tggcgcatga | 180 |
| gagctctgac | tagggcaggg | tgtgggacag | gctggctcta | attgtgccct | gtttatcttg | 240 |
| ttgatgcaca | cggctggttt | ctttcaccca | cagctgtctc | tctagacaac | atacctttat | 300 |
| ggagaggaac | gtgtcttttc | caatcttggg | ttttcattca | gaattggagt | gaactggtct | 360 |
| ccatcagata | gcattggctg | cggtgattta | ttcttttaca | cttcctagtt | aagcaggata | 420 |
| actctctggc | tctgctgtgt | ctaggcaatt | taaatgattt | ataaagcata | gctgttttaa | 480 |
| ggaaatcttt | ttttaaacat | ttgacttgcc | aatgtgtggt | cctaaaggca | gaaggactgt | 540 |
| tccagagtgt | caggcagaga | cctaccctgg | atttcgttgt | tcagctaccc | attcagtgtg | 600 |
| gcttttggca | aggaattctc | tggacctgac | ttccctacct | gcagagctgg | gataagctat | 660 |
| caaaccatct | cctccacaca | ctgtgagggt | gggaaaaaaa | cccaaaccct | taaaagtgct | 720 |
| gtataaaggc | gccttaaggc | tcagtatagc | atgtgtgctg | ctgatgcccc | agacctgttt | 780 |
| gcgggtcctg | aaggtcatag | gagaactgct | cagaagagac | agaaatgctt | aagaaggttt | 840 |
| tactacaaaa | gtcttgtgat | gttaacacat | aatatcacat | tgtgcagaag | gtacaaatgc | 900 |
| cccctcctat | ccctgcacac | ctggaagctc | aaggtatgga | agggtttgtt | gtctgcagcc | 960 |
| tcttcgctgc | cctctgcttt | ttaagatcct | gggtagtgtg | ctcagtgtgt | gccctcagca | 1020 |
| gtttgggaaa | cggacatctt | catgcaaaat | taagcaagga | agtgttgctt | ttatactcag | 1080 |
| agtagaatct | aagttcttca | ggcaggctct | tgtgtgccgc | tctattaga | aataaaactc | 1140 |
| ccccggatca | gaagatgaat | gtgctcagct | aagaacacag | atttatttgc | tttacaatgc | 1200 |
| gtgctatggt | ttaagaaaaa | cacatcaggc | aaacaattta | tggtttgcca | ctgagttgtg | 1260 |
| cctgaaggaa | acacaactgt | tagagatgta | attgattggg | cggtgacgct | gtgtggattc | 1320 |
| atgggagatg | catcttggtc | agcatgtctg | tgtgaaacca | catttctggt | gctgctgcag | 1380 |
| gacgagtgcc | gggagttccg | ggatctgttc | aagaatggga | agctttcctg | cacgagggag | 1440 |
| aatgatcccg | tccgggattc | ctcggggaag | cagcacagca | ataagtgcat | catgtgtgcg | 1500 |
| gagaagttgt | gagtagagga | agccaatgtt | tgttatcgag | agtggcaatg | gggccggggt | 1560 |
| gggctcctac | agcaatgttc | tcctcacttt | ctcatcctc | tctttcagca | aaagggagaa | 1620 |
| tgagcagaag | gcgacctcaa | ccagagggaa | acaaaggtg | aggttaaagt | attgggttca | 1680 |
| tatacaagtc | tataggattc | ttacccaata | ttaccacact | tgatttcttt | gtcactctgg | 1740 |
| ggatccatgt | ggcttttcct | gcttgtatct | cgttgatgct | cttcatgcc | ctgagagaat | 1800 |
| agtttgtctg | aacgctgcag | tctatcccac | tgaccgcagt | gacatgggag | caaaccccat | 1860 |
| cgcaataaga | agctgagcag | aactgccctg | acatctggca | caagggcaag | aaggcactgc | 1920 |

```
tgctgagagc gctaatgagg ttgaaaagaa aatctgggtg agaagcttta aatgtgagct    1980
ctgagatgct caaaagttca ttatgtcgtg ggaggagagt tcagccctgt gctgtccctg    2040
gggtggctcg gtttcagctt tccctgattg gaaacctcac tctcatgatg cagctgctgt    2100
gcccttgtgc accgatactt ctctggtgag agcaattcag caaggggaag gaaaaagaag    2160
cactaagtaa atcttgccat ttctgtcttg cgaggaactg gtacggtccc cttaagcctc    2220
attcttgggg ataatcctgt ttcagtgctt ttcctaatga cagtggcaca aaaaaaatgg    2280
aagcgttaat gaaacttgct gatggcaaag ctgggaggga ggatcagcag atcactcagg    2340
actaattgga tagcactgag gcctggagta atagaaacaa gataaaatgt aataacagag    2400
agtgcaagat cacacaggca gtgattaacg agaattcctg ctcatcaatt agaaatgaca    2460
aaggataaga aagctctgca tttattagtg ggtcacggat gcggcaggcc tgagaaggag    2520
gcaaatgcac atctcagcaa ggtctgtgca gcagaggtcg ggctggcagc aaatctccag    2580
aaatactgct ttgaagagag agggtttgag agacgctgtt agggagaagc agctctgcca    2640
cagcaggtct gggggttcacc tgggggtttgg ctcattgcct ccctgtgtcc ctcctccacg    2700
ctgccagtgc tgcactggga aggtgtgggt aagaagcaat ggctaaggga tctggttata    2760
cacctcctgt atctgctatt tgggattggc tactgcaggg cctcaggtcc ctgacttaaa    2820
agtggggact tcgaagcatg tttgcattgt gctgtcgtgc cttagatgtt gctgctgggt    2880
cctcaaagtc ctgttggttg tggggtgggg gggacttctt gcttcctatg tgaagttttc    2940
tgagctgcaa cttcagcaac agctgtaaga gtgcattaag ggcagtggga gaagtgggag    3000
ggaccccatt acctcatcgg gtatcgctgg catgctttgg atagccccac gtggagcgtg    3060
acaattagag cacggcagag agctcccaac acgtgccatg caggcagagg cacccgccgc    3120
tcttctgact cactctgttt gtagccatga ggctgtgcca cgtgccctct tctctctctc    3180
acacctgggc tctcctgggg cgcgtttggg aagcctctgg aggatcggag ggatgtggca    3240
gggtgccctg actgctgctc cttccgcagg atgactgcag tgagtaccgc tcccagtttg    3300
aggctggcga acgcctgtcc tgcacgcggg agaacgaccc cgtcagggat tcctctggca    3360
agcagcacac caacaagtgc ctcatgtgtg ccgagaagct gtgagtacag ttcctggcaa    3420 cagcaaaagag ggaaacctca cattgcgaaa ctgcagcttc tgcctgtgtg gctgcgcctg    3480
ggggagtccc gagtcccagc ggccccccag gagctgctcc tgctgtaggg ctgtggctac    3540
tgcccctctt cccacctccc ccctaacccc tcagggagca gaggagaagc agggttgata    3600
gagagcagcc ctttccttgg ggcagctccc aaggaaagtt tcccacgcgt gtactttgcc    3660
ttccagatgc tctctctact cccatagagc atatgcagaa gcagccctga tatgaaagca    3720
gccacctgga gccgggatgt agcatacagt gggaatggtg aggagaaggg agaaggctta    3780
ggggtgggaa ttaggtgcag ggccaccagg gatgggagg ctggtgccta atgacatgat    3840
gctggcttgc agggcagccc caggtcctgg cagcgttcgc actgccatag tgctcctttc    3900
tttctcctct ccctttttc cagcaaaaaa gaagctcaaa gaggaggtca gtctggtgga    3960
actgcccagc gcaacaagca gtccactgca gagtgtgcaa accaggtgag actgagctca    4020
gagcctcacc aggcttggga aaaggggttg gtggatctgg ggaccccgat ggtcaagggc    4080
tgcctgtggt cctggtgttt ggggtgcagg agcctgctgg tgatggcaga gaggcaggtt    4140
gcattgcaag ccctgctagt tcatgggatg ggttttgtgta tgagcgtgca tagtgggcag    4200
ttctggactc ctctatgggg cacgcatcag agctatttct tcagaaagag ccccatggtt    4260
```

```
cctagggtcc aggggggatga gagggaagga caggagctgc tttaatctca ctgctttact    4320
gcttggttgt caaacacgat cctgccccctt ttccagaaga gctgcagtgg ctcagggtta    4380 cagcgggggtg taaatgagag acggccgttc tccacaaaca gagggtgagt acagcagcac    4440
tgggatccca gcctggcccc acaagtcctg gggtcttgac actgagaaga aacacataaa    4500
atagggcata tacaacccctt tctccttttcc aaagacattc ttgcttcccc tgcacacgaa    4560
gcactggtga ctgctacact caaaatccct ccccagcctt gccccctgaa tcctgcctcc    4620
tggcaggcac acacttgtcc tgctgcctgg tccagcgcat cctcatctgc tgacctgagg    4680
cagtgctgtg tgtgcaccat gtgctgtctg ggcactgagc gactcctctg gttttttagg    4740
gctgccaggc tctggcaggg tgcagatgct gtgttatcta agccttgagg aactctctta    4800
gtcttcctgt ttttgttggt gaggcccatt catctgcccc cagtcagcac tgccagcaga    4860
caaacagtgc acagctctcc atggcagcaa tggctgtagc atatgtaggg gccaggtttc    4920
tgggatcatc tctgtgacgg acatctcttg ctgaccgccc ataaggactc aaaagtcccg    4980
ttgcagggag tgcctccatc ccatggcaag ccaagtgccc tgttgaaaaa acaaggtgca    5040
gaataatggc aatggaccctt agtgcagttt aattccaccc tggggtgatg atgtggctga    5100
gtgggtctgc ataccccttgg ctgtgccatg agctctgtgc tttctctccc tgccagccca    5160
caaggagact tggctcagga ctgcagcccg gcacctggcc gccagggaca gagcggaggc    5220
accaacacct accagccggt atgcccagct catgtgggtc aggcacagcc tttcccagca    5280
gctgccccag tttccattgt caacctaaag cctcacaatg ggacctgtat ccttggaggg    5340
gtttaaatgg gtggtagagt ccgtaccctg atgctgtccc ctggcctcaa agaggagtga    5400
ggctgcacac gtccaaacgg gagtcactga agccagtgct gctgctggtg ttggctcact    5460
gtagaagtat gtcaggtatg agagagcatc ctccaggagg tgatggtggt gtcccttcct    5520
gcatgctgag atgttgggtt gaagactgtg gccagagcag ggtgctgggg ctgagcgggg    5580
gataaggaca aggctgataa gaggaggggga gagggagtag tgggggagga cacggtgagc    5640
aatagataac gactgtttgt ggaatcatgt gggagggaga agagggtgta tgctctctcc    5700
atctccacaa aaagaaaatt tgttattttc aaccaagcta aagcagaaat tatgaaacta    5760
ataggagaaa ataagttact ataaaaagga tgactaacct gtggatcttg ctgtcacggg    5820
gtgttgccaa gagctacagt gattaaaaaa aatgacttgc cacttatagt ccatacagca    5880
atttaggtaa catttttggaa gggataggaa atgcctttct gtggggctgg agggacctga    5940
gtgcagactg ccttaactct ctctgaagtc tctgtcactg actgcccctta gaaaaatgat    6000 attagaatag aaaaaccagg gaggcggttc aggtatggca gttttaatgc attccagagg    6060
aagcattagg cataataatg ccagtctgct tcagggctta gtggtatttc ctggtagctc    6120
cggtgaagga gtggatgctg atcagcctga ctgacgaggg gtgattcaga gagcagatct    6180
gtgtctctcc tcgctgcagg gccacccgtg ggctctgtcc cagggagatg ctgtcctgaa    6240
ggagaggtgg cagtcactgt gaggactgtg ggggactgtt ggtgtggcgg cggttgcaca    6300
cgcgtgggtc acaccgtggg cagtggtgtc tggtgtgtgg gaaggcatct ggcagggaac    6360
tgcaaaggtc agcgctgtct gtctttgtgt catcgttaat tacccaggtg agggaggaag    6420
cagcacatta atgaaattag caagtgatgt ttaaacagag ggtgttactg cagcaacctg    6480
tgccactgaa ccccctgcat tgcccagctg ggaaaccttt cttctccatg gtgctttcaa    6540
ccccatagtg ctgctgaccc cagcaaagca atgagccatt gcttagtgct gaatgggggtt    6600 ttttttctcc aagtgggaca ggaggtgaga tgtccttcct gcagctcttc tccaattgca    6660
```

```
ccatttgcag tcattgcaac attttttata ggacctggag aagggatgg gaacagagaa    6720 ttcactcctt ttgtctctgc atctttttt ttttggcctt tggtgcagag gtgggcagtg    6780
aggctgagga agagagggg ctgtaggatc tctgacctct gctgtctgaa acttgccatg    6840
attctgcagg cacctgtgcc agaatgctca tgggctgata atctaatcat gaggagtctt    6900
gttcctcctg ctccgagctc tttctagctg tgccacgtct gctttgtagg aaattcgatg    6960
cctagatgct cctgctgtta tgctggagaa taaaacgaga gggcacgctt aattagtcag    7020
agcttttcat acatgtttgc atctcttcat tccgtgggtg tcaagttgtg ctgtgtgtcg    7080
ggctgccctt gggcagctgg actcaattgt caaggttttc cctttgtttc tgccaagtgg    7140
cttgcagaag caacaggtgt gaaagctctg ataaaggaca aaggacaggt agcagaagtt    7200
tattgtattc tcgtggattt gcagggagaa gtaaaagtgc cctggactga gatgtcaggg    7260
tggatcagat gagtgtatcc atgcctggca atggggtcag ggcagctttg tccccacatc    7320
gtggctggtt ggcccaatag gaggcgttac ctctttgctg aaggtgtgat ggagctcagg    7380
gcaacgcctg gtttgtgagt gctttgagcg gtgcgcagga gggtcttgca agagaaccag    7440
caccaaatgt gatttctttc tctcttcagc tggactgtga tcgaattctg cacggggtaa    7500
agggtggaag gattttctgc agcgaatcct cacaacccgt ctgtggcact gatgggaaaa    7560
catacagaaa tgaatgtgac ttgtgttcag ctgccatgtg agtaggcgga gagatttcag    7620
taatacaggg ccatccacca ttcccgagtg tcttttgcag cacagtgttt gttttgatat    7680
accatgactc actatcaagt gtgtccttgg tgcctcgctg ttaagcaaac atagatcaaa    7740
tgtctgagat taatatgatg acagctaatt aagatacaca actttccaga gtcccttatt    7800 cccttttctgc tcaatcatag gattgtttgg ggagtaataa atgccatcaa attggaagta    7860
gcatcaaagg tttaaggagc ccacagagga ccaccgtgac gatgtcaggg agctgtggca    7920
ctggaagtga ataagcaatg tcttgttctc cctttgcagg agagcatcag tttacatcac    7980
ggtaaactac cgaggtgaat gccgaaagac tgtccctgaa atggtaagtg cctccctgct    8040
gtggcatccc atttcttgtt ctgggtgtgt gctggagacc cagcctggat cccgtatctg    8100
tggtgggatc atcagagccc tgttagcagg gtgcttgtgg ttcacatgcg taaatacact    8160
tcaggcttgg atttaaggca ttttgaggca taatctccac gttttttcca ggctgtgtgg    8220 tagggagtg acatgtctgg gaaaacatgt ggctttcctc ctgggatttt ggtgaggcca    8280
agaaaagatt gcaatcgcac aaaccataag ggcctaattt cccaaatgat atccaggcag    8340
ttggttggga aggaaatata ttccctaagt ggtatccttt tgggaaaggt cttgaatctt    8400
gtgtgattgc cttgtagtag atgagtcaaa gatttgttag tggtgctttg tcttcccgct    8460
cgtggcagct cagcggcatt cagagctttg gtttggagcc agggtgtccc agtttgtgtg    8520
tcttgagtgt atgggactga ccttagtgtt ggcatggact gttggaaagc tgagtattca    8580
tttccccagg gaaacaccga catctatccc cattccaaac ttggaatgaa tcaaaatatc    8640
aaatcagcca aatggagaag ttgtgcaagt ttttttgca atgagagaga tggcttctga    8700
atatgaattt gctgacagtt tgtaggtaaa acagtattgc ccgttgaaaa gctttagagc    8760
aaaattacca tcatagggct tttactctcc tctgcttatt gacaggatgc ccacccatcc    8820
ccacaacatt agaaatgagg catccccatt cctcttcctc tcttctgtga agtaccagag    8880
tgctctcaac gctgtttaaa gctgaagaaa aaatgcagag aaagagtttt gcttgtgatc    8940
gtgctggagg tctttgtgtc tcgccctttg gtgcgatgga gccattgctg gtttgtgtat    9000
```

```
gctgggagtg gaggcactat gcatacctgc tggtggctgt gctaatgatg ctggagacag    9060
acaaggttgg gtgtaccacg gcaactgaaa accagagagg actccctcag agttgtgcct    9120
ggctgggatt cctcaccatt ttgtgtttta ccaagacgtt ttaccagctc tccagtcttt    9180
gcagttagag gaatatgcca tacactaaaa gtcagacaat ttgtagctat tccaaggaga    9240
gctggaagca attaaaggga aagtgataag gttttcccac tggggaaaat cccccacaaa    9300
aaacacccct ccaaacaaag acttattatt tcgttcttta tgtatattgt gtcacctgaa    9360
gaatcagatt ggaaatttat ggaagcccat ttccttagca aaccccttgt gtccatcaaa    9420
gacttcccctt ttttttctca gttggaagct tatgaacaat gtactgacca gtgttatttt    9480
atgcctctga aattcatgct aacattcagc ttaatgcatc cttctgaagg cccaggcact    9540
cgctgtgtga aggagatcac agtgcctttg gcgtcagaaa tgatttcagg ctgttgcaat    9600
acgcagcacg aagatgcaaa ggcccaaaga cttgagcctt ggaaaaagat aggagattgc    9660
tgcccgaaaa tgtagtttgt ccttgagttg tgttttgaaa ttagccacgg taatgctgtg    9720
ttgcctgcca aaatgtgtgt ccaagctcag agcctgcagc cattcctgct agcaaagccc    9780
ctcctggatt tccagcagtt tgtggcagtc cttccctagc agtggctgga ttgccatcag    9840
ggagggatgg ctgtaggaag ggacaggaga aatgtggttg gagagagatc tgacattaaa    9900
gggtgcatcc ggacagcctg cactgatgtg gtggaaaacc ttcctgcaga gagagccctg    9960
gggctggctg gcagctgggc cctgctgcc tgtgtgagct ctgtgccaca accagcctcc   10020
tctgatcctt ttctgcttta ctgcagatga atgtagctga gtctagggtt tagatttcta   10080
tgtttatttt taacaaggca gctggcctct gcgtcctcca tgctgtgaca tacagctgta   10140
ttaatggtgg gtcttttccag aatgtttcac tttcaatgct gtattttttt ttattttgca   10200
gtttctcttt ttgttcagat gcttttttcac acatctccca tgtgacagat accagtctgt   10260
ccatgttagt tgacaggtca ggcaaaaaaa aaaaagggat atccagtttc tcctttttaa   10320
tctgttttct aaagaacaaa gaactcccag cttttctaatg ggcaaggcca ttttcttaca   10380
gtgctctttt tgtcatacct ttcttaagaa tgtagtagaa gggaaaagaa acaaacaaaa   10440
aacccaggac cttttccagc ttgatattgg ttttggaaag cacacagatc caggctgaaa   10500
tctgtttgtt ttctgagtct ggcagtgacc catccactgc cccatcccac ctggttcctg   10560
tggccactga gctgcccaaa ggggctgtca tgtagcccct aatgctctgc cagcgtaaca   10620
gcagtggatg tacttgtgga tccacttata ttttgctctt tctttccaga aataatggag   10680
ttcagactgc cagcaaatac cagggatcag ctgtgaccaa aggtacagtg gtgcggtgat   10740
ttgctccctc ttggacaact tgtccgcatt tcacaagggt ttgggtgtca gaccttgcct   10800
gggcaggctg ctgggtatgt ctggggcaaa gggctctgca acacacccttt ccctattgcc   10860
acagcacaag aatgaggcgt gtgtctttttg cagaagtagc aaggtgatgg aagcccctg    10920
ccaaggggc tgagcccttt ggggtgtgca aacttcatga ggacctcctc atctctcagg    10980
ggtgggcctt gcccgttcct tttccctcag atatccctgc agaggggaa ggatgctggc    11040
agagcagagt actgcagtcc ctcctcacaa ggaggtggag gtggcccaaa gcaacctggc    11100
tttgagcttt ccttgtggtt cttctgtgtc ccttgccttt tggagccata gtaataaacc    11160
cgtctgcccc ctgtttctct aggacaagta aaggaagatc tgatgtcagg caccagggaa    11220
gctgctgagt tccccagtgc tgttggatcc accttcatct ccttctgcag ccaacgggcc    11280
tgtccttgct caggtggagg gtgaagggct gtggggaccc agtggtggct tcccacgttg    11340
gccccacgca tgttgttgta gtcgctgctc ggctcgggct ctgccgcctc gctgtgtctt    11400
```

```
agcatgtttc tacaataaag ataactccac agcgtcctgt cgcttttctt cactgagcct   11460
cacgggaggg acgtgtgagt ccccgctccg gctgctcgcc acgcgtccct tgagctctaa   11520
agcaccaaac ccaagcggag atgtcagacg cagagaagaa gaacgtggtc tgggttctgt   11580
tagcagggac cagcagttgg gttctctgac tcgctgtgta gggctttggg tgtatctctt   11640
tgtctccctt cagccctttt ctcttgcctg taaaaacgga cattaaagga tgcttaccta   11700
cctcagaggg ttgtttggag attttaattg gtttacgtta gagagcccac gggtggaatt   11760
ctgttcctat gtgccaatgc tggtgtgcag gaggtttaac tgttgcagtc atggcctctt   11820
ccagccaaca cccgatgggc cgtatgtatt tcctgttctt tcgtttatgg ctgttactta   11880
aagcaaatat gttcttattt gtataaactt tattgcagga catttccaga agaccttgag   11940
tgaacgtaca gtgtttgagt ccactttagc tgtgacctga tctgcaaata cactctgctg   12000
tagataaggc tggagtaact ttcagatttt ggcagggttt cgctcaatgc caattaattt   12060
ggctccctcc acagatattg atttttttt ttcttttcaa ttaagttatc gagatctttt   12120
tttcttaatg cagctaatga aaatcgattt ttactctcat aaagtacttc cgcatgtgtc   12180
acattgatct gtctatggct tgattatcgg caggctttga catgaggtta atattttgtg   12240
tgctggtttt ttttcaccgt gtgcaaacac tgtggtttag aaatatgtta ccgctgctta   12300
tttctacgtg gaaaatccca cggcgtggtt atgcatggca gaagtcacca gtttgatcca   12360
atttagctgt ttctagggat gcaagattcc tctgcctttg agcgggtgaa tcctcgggtg   12420
ttatttatac attctgagaa ggatgaacag aagacgtaa aaacgtttgc taatgatgtc   12480
tgctggctga ttccggctaa aatcgtgtgc agggacctcg acgtgatttt tataaaggca   12540
gctcacaatt tgaggcttaa agtaagttct tgcaaatgaa aatgggcgca cttgagcgcg   12600
ctattataac ttgtagtgat ttcaagcact tagattttga aataatcgcc cataaaaacc   12660
tgcattaatt gtgctccaaa accaatgagc tgatgaggag ggtgccctgg tagcctcttt   12720
tgctggattt gagcaccttc tgaatttctc ctgccaccag cagaaattag ccacagaaat   12780
catagctgct ataagggttt attaatcaga ttacgaaact gctaagaagg cacacaacag   12840
tgacttgctg aagctgcctg tgctgctgtt agcgagcctc ccgtaggtag caatgctaac   12900
tccttccttt tagcagttta cccactgctt ccttccatca ctccttcctt ttgtagggcc   12960 tactttgca gtttgatcca gtggcttgca ggcaatatct gtccccagcg gtgctctatg   13020
cagctgacct ccaggtaggg ctccatgtga gcgatgcaat gtgttatttc catgggttc   13080 ctaagaagga ggaagcaaaa agctcaggag gtgctccaaa tatattatcc tgtcctctgt   13140
tttgctcttt gtggtgccct ttaacactgt aaagagacca taggagtcct ctatgaacct   13200
ggaaaggtac cagcactatg ggaggtcttc agtttgctgt aaattatgct ttattagagg   13260
tatttcttct gccaagaccc actgacccca tgcggctcac agtgttttct aaggctttgc   13320
aggactggtg ttacgaattg gcaccctcca ggcctctcac aaatctcctg cttctcacag   13380
cgtttcttca agttctccca agcacagctg agttttgagc tcaactgctc cctgcagggg   13440
ccttgagcct cctgcctttt tgcataaaag gtgtcaggta cttatgcaat ccttagaggc   13500
atgcaaatgc tgctctggtt atatactgag gactgttgat tctggcagaa cccttttgcag  13560 accttgtact cccttgctat ttcccaatcc ctgcagccta gcagctctgc ctaacaactg   13620
ccatagccaa cacagcagca ggctgtgcat ggtgcaaggt gatgtggaaa gggatgattg   13680
tatgaaagcg tgatgctgtg gtactgcctc tgcaggagac tcgcactatt tgtgtaagag   13740
```

```
gaccttattt gtctgctgca gagctgtttc aaggctgtcc atacacccct gtgatgctga    13800
gcccctccaa gcaatgcact gggaaaagga ggctgggggg agaccttatt gctctcctcc    13860
aatatttgaa aggtgcttac agcgagagca gggttggtct cttctcactg gtgacaggat    13920
gaggggaaat ggcctcaagt tgcaccaggg tatgtttaga ttggatatca ggaaacactt    13980
atttactaaa aggttgttaa gcactggaat cagctcccca gggaggtggt tgagtcacca    14040
tccctggatg tgtttaaaaa ctgtttggat atggtgctca gggacatgat ttagcggagg    14100
gttgttagtt agggtagtgt ggttaggttg tggttcactc gatggtcttt aaggtctttt    14160
ccaacctgag caattctatg atatggatcc ctggggcttt cagtcttatc tccctggatt    14220
atcacaggtt cagctctatg gcccatttga tttataccgg ggtctgatga acaggttttt    14280
ctcttggctc ttcagggatc ctatttagca ctttttggta cattcccctg ccctacaagt    14340
ctccctgata cacagagctc ttatccaaga cttgggacct tccctactcc agccctctgc    14400
aggaggtttc ttgctaacca gtcctccaac caggactgca gtacgacaa aagagctgga    14460
agaggtctgc aatacttccc cagcatgaag gtatgagcac tccttttgag taggttactg    14520
aaagtagtaa gatgtcaata caaccaactg caagatacaa aaccgcatga aaattcagtt    14580
tactttgatg ctgaagggct gaaaagaaat gctgtggtgt tagcacagat gcactgctgg    14640
caaagtgaaa atgagcaaag aggatgagat ggatggacag ctgatggaaa aactcttcct    14700
aattgctcca cagagcagct tgctcgcctg cagggctgca gcatggagct gcttgtgcat    14760
aatgcagaca ccccaagacc agtgctgttt gtcttagcca agacacagtt gcagctgcag    14820
caatttttc tagatgtcag ttccttccct atgttgctga caggtgtttg ctgttctgtc    14880
cctttaatct gtatcctaca gcaaacattc cttgaattta ataacttagc tggaagacaa    14940
ttgctgtgat cttgatagaa catgctgagc caatctattt taactgcaga tttagtttgc    15000
aaatactgtc tccttgccga taagattcag gtgtcatctt tgtggacatt ggcaggaatt    15060
ttcttgaccg tgacaggttt tacagagtct ggcaattaag ctgtcaagac acatttttcct   15120
ctgccaggaa gcattaattg atgatagtct tggctgcaat aggcacagag agatggatat    15180
tgtaatcaga atgaatagag gtccttgtag ttgagagcta cgttggtcca aagttttgta    15240
gtcgttgacg tttggtgata ctgagataag gaacaaggca cgagatatta gagctaaata    15300
tcaggcacag catgagaata aagacctctc tagctggaac tgttggtatc tggggagatt    15360
ttaactttct ggatgcatac tgcaaagtac taatattagt agagctactg gatgcgagag    15420
caaatagttt tccattaagt aatcccaaaa atcatgttgt tgttggtttg cttttcaagt    15480
gcgaggggtg ttggagatgt atttccctca gaaaataaac ctgatatgat tcaacctgag    15540
ctctctctgt ttaaatcaca ctgaaaatag atctgcaaat ggggattttg attaccgagt    15600
acagaatatg aaagattaaa acttgggaaa gttagggttc tgattgagaa aacttttgtt    15660
tttgtggccg acccttgcag cttacaaaaa tctgcctaaa taaggagaa aaccacattt     15720
agaacccatc caagctatgc tacttcagta ctgggcaaaa cttcaggaga cgtttgaaga    15780
aaactgaaga cgtgaagtat aaaggaatga ttgatgtgca cagtaaactt tcttggaagg    15840
taatcacgca tgggctaata tcaatcttta caaagttggc tgacttccta gataaaggaa    15900
gtacagtaga tctagtctac ccaggcagca aaaatgtttg acctgttgcc ctgtggggtg    15960
gtgtcacctg gcttgggga gggggtcag gatgaggtta caggggatgt ggaagcatac      16020
tgtggaggag caggtgggc acccacagga gttagcagtg agcagacaga aaggtggatc    16080
tgaggaccga acttcgtatt tttgttcctt gcattaatac acaaaaagca gacacacaca    16140
```

```
cagagcagat tgctgctggt ttttgttttc tttttttaaac agcagaagag caggattttt    16200
cccacagaga atggggtgac cttctaggct gtgattgcct gggctcaagc tgagatgaaa    16260
cgcagtgatg aggagcacaa aaccgtgctc tgaggttaaa taatgagggc ttcggctatc    16320
agttcagagc tcagtaaaaa ctgcagagga ggaggaagac ctaattgcat gtagccagcc    16380
acagggcaaa tgagagctgc agcgtgctgg ggcagatccg ggagcagagg ggccgtggca    16440
cgctccctgt tcactggctc ccctggagcc acacaaaagg ccccttcctg gcaattgtgc    16500
ccacatcaat cattagctag aaacccagag ctgggtaaat acgttttggc ttcccgtctt    16560
gatgacagat tgggtgttac atcacaaggt gggaccactt gatatgacaa cacgctatat    16620
attcccgctg ctacctctgc ccttcctccc ccactctgag agcaagcggg ctgtgtgtgc    16680
accgaggtgc tctgccatga ggactgccag gcagtttgta caggtggctc tggccctctg    16740
ctgctttgca ggtgagtgtt tcctgctata ccccgtaggt gactatagct agaccagaga    16800
ctaggctatc tgtgagagta tctgggtatt gtaatgtgtt agagagcctt gttccatgaa    16860
ggaatgctct ttctgacagt gtagcaaaac accagactgc aagatccagg tttcagcaaa    16920
cctcatacag acgactgttt tcgtcgtggt ttataggagc aaattgctga gggagcagtg    16980
ctagtgcagg gcaggagctt gcacgtgcaa gcactgagta taacggcaaa gcaaagctat    17040
gtgaaatggc tcctgtgtcc atgtaagcaa tacaaacact gcatcttgta tcatctataa    17100
attttctgtg ctgttcctgg cagctgaaa gtttgttgtg ggaagaacag tgctagtggt    17160
caacagccac ctgaaacgtg catgtctgag ctcctgcaag tcaaatacag agtcttgcag    17220
aagagtttaa actcagtgca ggcttgaaaa tacctacatt tcttccctgg ggcatcttag    17280
gaactggcta acacatgtgg cctcctactg aaagtgcagt gaaacttcat ttaataacct    17340
ctgattcatt ttatggacgt acatcactgg cataatgtaa aattgcattt tcctaaaccc    17400
aataagccaa tcaacaacgg tatctaaatg taactgtttc atcgaaagat ttgcatatgt    17460
catctctgca tattaataat atgtatttat tttctgtctc tacttttctt ttagatattg    17520
cctttggaat tgaggtgagt tacagatttt ttttcccatt tattcttttc tattccaggc    17580
ttctggtcaa ataagagcag tatataatta cctgatgagc aagtggatta atctaatgaa    17640
agcctggttg ctcaaataat acttgccagt gcatgattga atgatattgc caagtcacga    17700
aaaagtaaaa cacaccccgt ttatactatt ttccattcat gcaataaaat gaagaaagga    17760
agaattgtac gatcctatta tgttaacttt tggatataac tgcgttagtc caagtcaagg    17820
ggtggtagtt acctcctcga gaggaaagct gtcttaagat gataagctcc aaagcatcaa    17880
agacagtgat tctggtatct ttttctatac agtaagacac acactacagt gttcctgcct    17940
atacccatat caaagcgagg aaagcagcag ggtctgtgca gtgcatttgt ctgcaggttc    18000
ttcccacgca gttatgagat tcctgcaaat caccagagac tgcagcgtga ttggaaacga    18060
tcagattttg agttgagcgg ctgtggagca tggccaggct cccaattacc agctgccttc    18120
gttaggcgct gtctcaccca cagctctcct tcctccatgt catgcttccc ccagtcccc    18180
gcaggaaagc gtgatcagaa gaagattccc acctcctgac tgcctgagca gattccaaat    18240
gatacctcag gtgtttgtcc cggctggagc tgtgggtggc aggaggtttc atactgtct    18300
tttgttgtgg aaactgaccc cagggctgat gttgtgctgc ttccataggt taattgcagc    18360
ctgtatgcca gcggcatcgg caaggatggg acgagttggg tagcctgccc gaggaacttg    18420
aagcctgtct gtggcacaga tggctccaca tacagcaatg agtgcgggat ctgcctctac    18480
```

```
aacaggtgag cttatgtgga agcccagggg agctgcaggg caggagactc gaggtgaggg    18540
cggcagctct gtccccaaaa tatggtctgt gtggaggagt atgtgagtta gtaccaggat    18600
gctgacctcc agcctggggg tggtggctgc tctctgccat ctctgacaca gatctgcgtt    18660
cttccaggga gcacgggca aacgtggaga aggaatatga tggagagtgc aggccaaagc    18720
acgttacggt aagtccaaca gtaagatgaa gtcttgctct gttggtgccc ataaagactt    18780
atttttattt catagaatca ttgaacagct taggttggaa gggaccttaa agatcattgg    18840
gctctaaccc ccctggcctg gccgggctgc cttcaaccaa atcagtttgc ccagtcaaat    18900
gggccttggg cacctccagg gatggggcac ctgctctgct cagcctgtta cttatttact    18960 tgttttttc ccattcctgc tatccttaca gattgattgc tctccgtacc tccaagttgt    19020
aagagatggt aacaccatgg tagcctgccc aaggattctg aaaccagtct gtggctcaga    19080
tagcttcact tatgacaacg aatgtgggat ttgcgcctac aacgcgtaag tctttctgt    19140 ggagcatcct tctgggtaat tagagatggc taagtcccctt ggaaacgctt acataaaaca    19200 cttctaagc cttcttagg gtagatgttt ctgtgggact ctttgaagct ggctacttgt    19260
gattctccag ccagctgcag atttcttccc catcctctgt ctgtgctcat gaagggaatc    19320
acaaaaaaga cagaggacaa cccacagcag aggcatgaat agatcaaagt gttgctcagt    19380
gctgtgtgat atggaaatac catgcatttt ctgctcacaa gtggttgcta ccacctgtgg    19440
gctgcatcca gaccactcag cagttcctta cgtgaagggt gggaccttgc tttcttgccc    19500
cagtatctaa ggcttttcac gaggctctct aactaaaaca gctctttctt tcagagaaca    19560
tcacaccaac atttccaaac tgcacgatgg agaatgcaag ctggagatcg gctcggtaag    19620
tgtaacagaa ataaaaatcc atctcctagg gctgttaacg gagagaatcc cattgatttt    19680
cctaagaaaa tgtatgaccg ggctgatcgg gggtcccggt ccacgctctg cttcctgcct    19740
ggtgagggtg gcttctgaaa caaagcggta aaggaagagg ccccagattt tccttgcatt    19800
gtgctgtgca gattggcagg tttctctctg gaggcgacaa gcatttccac cctttgtaac    19860
aagcattcaa aattctagtg ctggtagctt ggttagatat agtgagattc ataagagcac    19920
caagcataca tatttatagg gtatagctta ttgtatattt atactggggt aagagtccag    19980
tgcctcagga agaaaagctt atatatttca gcacaaaaat tctggatgc agggagtccg    20040 ttctccaaca gacggattcc tccttatca cttcaactcc cgtgcttaac tgcagggaat    20100
ctgaattatt aagcaatcac agcactgggg aaggaaggag aaaaaccaac acaaaccaaa    20160
acaatgttaa tcagatttcc agctgttgga aaatatttcc cacttaattc aaggctgttg    20220
tgtcgatgag aagagggctg aaaaggctgt tttcagttcc tctgcctgaa ggtttcattc    20280
tctaagagag gtcccttttc ttgtctccta gagaatgagg gtagtgttct gaaagcctat    20340
ttctgataga cagtttagtt aagtgtagca gggctttgtc ctgtcacaaa aactaggaag    20400
ccgggaatac aggatgaaaa ggtgttacat tgacttctcc cgtgtagcac aggctccggg    20460
agggcttatt ctccttattt tggcaggttg actgcagtaa gtacccatcc acagtctcta    20520
aggatggcag gactttggta gcctgcccaa ggatcctgag cccggtttgc ggcaccgatg    20580
gtttcaccta tgacaacgaa tgcgggatct gcgcccacaa tgcgtaagtg ctgctcatct    20640
cccactcctc caaagtagcc agcaatgctt tgccgtgctg ggagccttcc ttctacgttg    20700
ctgcttatgc ctgttcttc aagcctctta gaaactgcat ttttttgtt gttgttctta    20760 ctgagttttc ttctgatgcc ttcttttgtga tcacagaggg aaatctgcaa gactcagaac    20820
acagctcctt ggattagtct gtgggctggg cagtgactga gcagagaaag gaatagttca    20880
```

```
gaatcttgct ttaaataaca cgagaagacg tgatgagctt gttaacgagc agagtaatgt    20940
agctatatca atacaatcgt gcagagaggc tgaagcccta ctttgttagg tacctgcttt    21000
aggctacgtc tggttcattc tgcatgcaag tgtttaaacc aagagttaaa gcatctcctt    21060
actcactttg tctccctctt tcagagagca gaggacccat gtcagcaaga agcatgatgg    21120
aaaatgcagg caggagattc ctgaagtgag tatacaacgt aaggtgtatt tctcccctttg   21180
cctctgccca ctgagctatt tgctgaggcc acgtctactc tgaaagtgag ctggcttgaa    21240
gcctggctct ctgcacgtgt cctttgggat gtgccaacgt gtatccaaca cacaaacagt    21300
gtggaagttg gcaggggga acttaggtct tttaaggatg atcactaaat gcattgccag     21360
caaagtcctt ttgtgccagt gaagtcctat tatgtttgcc ttcttttgtt tcattctata    21420
gtgcagagag aaaaggagat gatatatctt tgttggtttt tttttgttt gtttgttttg     21480
cttttctgcc atatctagca aactgtttca gtaggttgtg accccttgg atcacaagtg     21540
aagctcagtg gcatttggga ttgactgagc tgtctgccct ggtgatttgg catctcacag    21600
attacacagc gccatgtagc tcctcctggg catgagagag tttctgcaga gctgactcag    21660
gctggctttg agagaactga agtgtagcac cagcgttgtt tcagcatccc agcgtaaaag    21720
acatggattg cagcaggagg caatgctagg gtttgtcttt gagagcaagg gcttttttcag  21780
ggctgacgct cctactttt gcagattgac tgtgatcaat acccaacaag aaaaaccact     21840
ggtggcaaac tcctggtgcg ctgcccaagg attctgctcc cagtctgtgg cacagacgga    21900
tttacttatg acaacgagtg tggcatttgt gcccataatg cgtaagtact gcaaacagga    21960
cttccttttg tagcgactag ccacgttagt actgcagatg gcttcccctc caccctttcat  22020
cttcttcttt ctttctttt ttttgatagc agtatgtcta tatgtctcct gttcttcctt    22080
caacctcctg aagctctgtc gcctcggttt cctttcctga tgtgctcctc agggagctgt    22140
gggagagcca gctaacagct gagtgtccta tgagggctgt ggcatttgtg cagaggaaaa    22200
agagaatggg tctgctacaa gtagacctga gaagcctgta acttcttagg atcatgatcc    22260
ctaatggcag ccttttccctt tcagacaaca tgggactgag gttaagaaga gccacgatgg   22320
aagatgcaag gagcggagca ccccggtaag tggggatgga tgtcagatga gcgccagctc    22380
ctgtacgtgc cttgtggctg cagaggttgc taaccagggt ctgtccattc aggcagcaga    22440
gaagggaat gggccaggat ttaggtaaca aaatgtccca atactgcagg tctctggagg      22500
gaaacatcag aggcagccca gaacagcaca gcctgtttta gcacagtagg agaggaagag    22560
cagaagctgt gttagatgcc tgtgtagtca ttcagtgcta ggatttccat tgcagcagac    22620
aggttaaaaa atctctgtac cgtggtcagc caagaaaagg ctgcttgcag gaatgcacgc    22680
agaaatagct ctataaacat gcacggtaac aatatgtgct gataatatct cagcacattt    22740
attctgctta tgcagagcag ctctaaaaca ctgaaaataa ctttgtgcat ctcaagggat    22800
tgctgtatct tttctgtagt aaagacacac tgttatggtg ctgtctttgc tataatttgc    22860
tcttggactg tgtggggaaa tatgggtaat aagagctact acacaggga aggtatgcaa     22920
aacgattgtg aagtgtcaga agcttagcca gtgtagactg acttccagtg ccatcagtag    22980
atacttgctt atttatcctc aaatattgga actgttttta agtactgtga ggatttctgc    23040
agcagcagct gatgagctga tggaacagtt tcttcttgcc gttttgaaaa cgtggaaaca    23100
aaatctaagg cttagctaag tcaggcatga cctaatgtca aactggacat aacatcaaac    23160
tccttatatc aaattccttt gaataatgct tgttttgaaa cttggacata cgctgcataa    23220
```

```
ggaagatgat ctttctggtc tgctattcct ttgcgttccc tttgttagtg agcaatatca   23280
aacccaacca caattagttc atttataatg ggagactaaa ctgaaatcaa ccctgatttt   23340
tcctatggct cgaggcagtc tgtcccccag ctcccagcac ctgactcagc atccttactg   23400
ttttctcccc agcttgactg cacccaatac ctgagcaata cccaaaacgg tgaagccatt   23460
accgcctgcc ccttcatcct gcaggaggtc tgtggcactg acggcgtcac ctacagcaac   23520
gactgttctc tgtgtgccca caacatgtaa gccctgcagg tcacccactc gtgtgtcacc   23580
gcagctgctt gttgagcttt gtcaactctg ttttctctct cttccagtga attgggaacc   23640
agcgttgcca aaaagcacga tgggaggtgc agagaggagg ttcctgaggt aagcgataaa   23700
gaaaacaaga gcttgaggtg gtgcttattg cctaacaagt acaacgctgg ctggttttgg   23760
tgatgctggg tcatgccctc ctgctgccat ccttcctgca ggtaaacatc aaccctggca   23820
gcagggatgc tgtgcatttt ctgcatgtag tcagggaaag aaagagaaga ggacgggtga   23880
ggaatgagtt atgatgcagg tagcataaat gatttaaggc gttacgaaga aatctctttc   23940
ccacagcagt ctatcatacc tgccgtggga gtgtagctgt ctgttctggc aatatgggaa   24000
agggacacag agcacccgca ggtacctggt gccttctgga tacctgtgct gtgcaaaagg   24060
atgttgtgca aagatcagaa aactacctgc attttgaatg cttttaccta atgtaccaga   24120
ggattcaaac acctctctct tcctattgta aatgcgatat aatgtaatgt ataccaacaa   24180
tgaatcttgt aaaaatacca gataaactat atttggccag ctctaaacta tttacgctca   24240
ctggggaata gaaaaacaaa gccatctcat tatcttgtgt ttgaaagagt caacgtcgtg   24300
agtcagatat ttcatttcta tgcaaacaga ctatgaaatg tcattgcttt gtttcctgcg   24360
tatgctctgt gctcagacca agtcagatgc ataaatcagt gaggaagagc tcacactgga   24420
gaaactggga tagctgaaac tcaaggccag ttcttcaaat ggcataaatc attttgaact   24480
gctgttggtc cttctgtccg attgcaacac acagaaccag cccctcgcaa caaaaggcat   24540
gtcagcacat ctcctcagtt cttgtgggcc gtgacacact ccttggccac actgagcttc   24600
tcttgcagga attgcataaa tcacgccagt ttgatttgca gattatttat gagctgcgtt   24660
ttgcagcgtc ccagcaagtg gttcagcaag ctctaagggc atcgtgataa atgcagggct   24720
gaatgagtga tacgcgcctt caagctttga ttcagtcttc tccagtataa ggctgtgaca   24780
gaaaattgat agttttcaat gaagaatgag tcaatgcata accataatcc atcctgtggc   24840
agatcttgaa aggcagaggc gtaaggaagg gggttgtgtc tgagcaccct tacacagagc   24900
atttgctgcc tttgtttcct agcttgactg cagcaagtac aaaacctcca cgctgaagga   24960
tggcagacag gtggtggcct gcaccatgat ctacgatccc gtctgtgcta ccaatggtgt   25020
cacctatgcc agcgaatgca cgctgtgcgc tcacaacctg taagtactca ttcatctcca   25080
gggggaccca ccgtggctgt gactggacac atctttgagt gctgaataac atgcaagggc   25140
tctgtctaaa atctcgtgct gcatgggtcc tgtctgccta tccccgtttc cctggttgcc   25200
atggttggtg tttgagatgg gcatttagca aggcccactg ccccagtga cccagaaaaa   25260 gggttcactg cctgggaaag cattattcca aaagacacat ccctagtcct aagggcatg   25320 ttcttgctaa tgcttctcag gcaatgctta gctaatttat ctgaaattgt cctgtgtacc   25380
acatgggaac gaggttgtgc tcttgtacta cggttgtaaa tgggaagggt ttctgctaat   25440
atccatctct ccttcctcca gggagcagcg gaccaatctt ggcaagagaa agaatggaag   25500
atgtgaagag gatataacaa aggtgagtgt gaaaggatgg gcacaaagag ttacagtcgt   25560
aggggaccgt cctctgctcc acatcaaaaa ctgggggagc ggtgtgcagc cctggcgagg   25620
```

```
tcgcttggga atgtcatact ggttatagaa tagctgccat ccatcccatg ggaatggaca    25680
tggcagtgaa caggaacagt gtgaggtcac atccctcacc aggaggaact gagctgatta    25740
ctgccgtaat tttccagttt cactctttgt gctggggaa tactgtttgc tcccaggcag     25800
agactcacat cttccttgtg tgtgcaggaa cattgccgtg agttccagaa agtctctccc    25860
atctgcacca tggaatacgt accccactgt ggctctgatg gcgtaacata cagcaacaga    25920
tgtttcttct gcaacgcata tgtgtaagta taggagtgaa accccttcctg taactgctac   25980 aaacgcagag ttgattttat aaggagttct ttactaacac tttatgggtg tgtgctagac    26040
atttcggatg caccgtgacg tgcaaggagg tgctttttg cttttaaga aaaaatgcaa      26100 agcacccaca tctgcccatg tgtatgtggc ttcctgtttt atttagtttc aaagacattt    26160
tgctaatttt caccagcata gtttgtccca caagctcatc agggtatggg gaaagtactt    26220
caccaaacta cctggagcgt ttcaagtgtg tgaaacctgt catctttcct ttaattttca    26280
taatgaaagg aagtggttgg ccttctgaga ctgttcttta tcttctgcca acattatcaa    26340
catttgggct ggtaaggaga ggaacaaggc tgcagcacaa attctattgt gtttaatcct    26400
ttcttctctt ttcattaggc agagcaatag gactctcaac ctcgtgagta tggcagcgtg    26460
ttaactctgc actggagtcc atcgtgggaa acaatctgcc ttgcacatga gtcttcgtgg    26520
gccaatattc cccaacggtt ttccttcagc ttgtcttgtc tcccaagctc tcaaaacacc    26580
tttttggtga ataaactcac ttggcaacgt ttatctgtct taccttagtg tcacgtttca    26640
tccctattcc cctttctcct cctccgtgtg gtacacagtg gtgcacactg gttcttctgt    26700
tgatgttctg ctctgacagc caatgtgggt aaagttcttc ctgccatgtg tctgtgttgt    26760
tttcacttca aaaagggccc tgggctcccc ttggagctct caggcatttc cttaatcatc    26820
acagtcacgc tggcaggatt agtctctcct aaaccttaga atgacctgaa cgtgtgctcc    26880
ctctttgtag tcagtgcagg gagacgtttg cctcaagatc agggtccatc tcacccacag    26940
ggcaattccc aagatgaggt ggatggttta ctctcacaaa aagttttctt acgttttgct    27000
agaaaggaga gctcactgcc tacctgtgaa ttccccctagt cctggttctg ctgccaccgc    27060
tgcctgtgca gcctgtccca tggagggggc agcaactgct gtcacaaagg tgatcccacc    27120
ctgtctccac tgaaatgacc tcagtgccac gtgttgtata ggatataaag tacgggaggg    27180
gaatgcccgg ctcccttcag ggttgcaggg cagaagtgtc tgtgtataga gtgtgtgtct    27240
taatctatta atgcaacaga acaacttcag tcctggtgtt ttgtgggctg gaattgccca    27300
tgtggtaggg acaggcctgc taaatcactg caatcgccta tgttctgaag gtatttggga    27360
aagaaaggga tttgggggat tgcctgtgat tggctttaat tgaatggcaa atcacaggaa    27420
agcagttctg ctcaacagtt ggttgtttca gccaattctt gcagccaaag agccgggtgc    27480
ccagcgatat aatagttgtc acttgtgtct gtatggatga cagggaggta gggtgacctg    27540
aggaccaccc tccagcttct gccagcgtag gtacagtcac cacctccagc tccacacgag    27600
tcccatcgtg gttaccaaa gaaacacaat tatttggacc agtttggaaa gtcacccggt     27660
gtattgtgag gctagattaa taggctgaag gcaaatgttc ccaacttgga gatactgttg    27720
gtattgtatc agggaacagg gccatagcac ctccatgcta ttagattccg gctggcatgt    27780
acttttcaag atgatttgta actaacaatg gcttattgtg cttgtcttaa gtctgtgtcc    27840
taatgtaaat gttcctttgg tttatataac cttcttgccg tttgctcttc aggtgttctt    27900
gcagaacact ggctgcttta atctagttta actgttgctt gattattctt agggataaga    27960
```

```
tctgaataaa cttttttgtgg ctttggcaga ctttagcttg ggcttagctc ccacattagc    28020
ttttgcagcc ttttctgtga agctatcaag atcctactca gtgacattag ctgggtgcag    28080
gtgtaccaaa tcctgctctg tggaacacat tgtctgatga taccgaaggc aaacgtgaac    28140
tcaaagaggc acagagttaa gaagaagtct gtgcaattca gaggaaaagc caaagtggcc    28200
attagacaca ctttccatgc agtatttgcc agtaggtttc atataaaact acaaaatgga    28260
ataaaccact acaaatggga aaaacctgat actggaattt aaatattcac ccaggctcaa    28320
ggggtgtttc atggagtaac atcactctat aaaagtaggg cagccaatta ttcacagaca    28380
aagctttttt ttttttctgt gctgcagtgc tgttttttcgg ctgatccagg gttacttatt    28440
gtgggtctga gagctgaatg atttctcctt gtgtcatgtt ggtgaaggag atatggccag    28500
ggggagatga gcatgttcga gaggaaacgt tgcattttgg tggcttggga gaaaggtaga    28560
acgatatcag gtctacagtg tcactaaggg atctgaagga tggttttaca gaacagttga    28620
cttggctggg tgcaggcttg gctgtaaatg gatggaagga tggacagatg ggtggacaga    28680
gatttctgtg caggagatca tctcctgagc tcggtgcttg acagactgca gatccatccc    28740
ataaccttct ccagcatgag agcgcgggga gctttggtac tgttcagtct gctgcttgtt    28800
gcttcctggg tgcacagtgg tgattttctt actcacacag ggcaaaaacc tgagcagctt    28860
caaagtgaac aggttgctct cataggccat tcagttgtca agatgaggtt tttggtttct    28920
tgttttgtaa ggtgggaaga agcactgaag gatcggttgc gagggcaggg gtttagcact    28980
gttcagagaa gtcttatttt aactcctctc atgaacaaaa agagatgcag gtgcagattc    29040
tggcaaggat gcagtgaagg agaaagccct gaatttctga tatatgtgca atgttgggca    29100
cctaacattc cctgctgaag cacagcagct ccagctccat gcagtactca cagctggtgc    29160
agccctcggc tccagggtct gagcagtgct gggactcatg aggttccatg tctttcacac    29220
tgataatggt ccaatttctg gaatgggtgc ccatccttgg aggtcccaa ggccaggctg    29280 gctgcgtctc cgagcagccc gatctggtgg tgagtagcca gcccatggca ggagttagag    29340
cctgatggtc tttaaggtcc cttccaacct aagccatcct acgattctag gaatcatgac    29400
ttgtgagtgt gtattgcaga ggcaatattt taaagttata aatgttttct ccccttcctt    29460
gtttgtcaaa gttatcttga tcgccttatc aatgctttg gagtctccag tcattttct    29520 tacaacaaaa agaggaggaa gaatgaagag aatcatttaa tttcttgatt gaatagtagg    29580
attcagaaag ctgtacgtaa tgccgtctct ttgtatcgag ctgtaaggtt tctcatcatt    29640
tatcagcgtg gtacatatca gcacttttcc atctgatgtg gaaaaaaaaa tccttatcat    29700
ctacagtctc tgtacctaaa catcgctcag actctttacc aaaaaagcta taggttttaa    29760
aactacatct gctgataatt tgccttgttt tagctcttct tccatatgct gcgtttgtga    29820
gaggtgcgtg gatgggccta aactctcagt tgctgagctt gatgggtgct taagaatgaa    29880
gcactcactg ctgaaactgt tttcatttca caggaatgtt ttagtggcat tgttttata    29940 actacatatt cctcagataa atgaaatcca gaataatta tgcaaactca ctgcatccgt    30000
tgcacaggtc tttatctgct agcaaaggaa ataatttggg gatggcaaaa acattccttc    30060
agacatctat atttaaagga atataatcct ggtacccacc cacttcatcc ctcattatgt    30120
tcacactcag agatactcat tctccttgttg ttatcatttg atagcgtttt ctttggttct    30180
ttgccacgct ctgggctatg gctgcacgct ctgcactgat cagcaagtag atgcgaggga    30240
agcagcagtg agaggggctg ccctcagctg gcacccagcc gctcagccta ggaggggacc    30300
ttgcctttcc accagctgag gtgcagccct acaagcttac acgtgctgcg agcaggtgag    30360
```

```
caaagggagt cctcatggtg tgtttcttgc tgcccggaag caaaacttta ctttcattca    30420
ttccccttga agaatgagga atgtttggaa acggactgct ttacgttcaa tttctctctt    30480 cccttttaagg ctcagccagg ggccattgct gaggacggca tcggggcccc ctggaccaaa   30540
tctgtggcac agatggtttc acttacatca gtggatgtgg gatctgcgcc tgtaatgtgt   30600
ccttctgaag gaaggaacgt gccttccaag tgccagcccc acagccccca gcccctccct   30660
gtgctgctcc aattcatctc ctcttcctcc ttctccctttt gctgtttgtg ctcgggtaga   30720
aatcatgaag atttagaaga gaaaacaaaa taactggagt ggaaacccag gtgatgcagt    30780
tcattcagct gtcataggtt tgtcattgct ataggtctgt atcagagatg ctaacaccac    30840
tttgctgtcg gtgcttaact cgggtgaact ctccttcact cgcatcattt gcgggcctta    30900
tttacatccc cagcatccat caccctctgg gaaaatgggc acactggatc tctaatggaa    30960
gactttccct ctttcagagc ctgtgggatg tgcagtgaca agaaacgtgg aggggctgag    31020
cagcagcact gcccccaggg agcaggagcg gatgccatcg gtggcagcat cccaaatgat    31080
gtcagcggat gctgagcagg cagcggacga acagacagaa gcgatgcgta caccttctgt    31140
tgacatggca tttggcagcg atttaacact cgcttcctag tcctgctatt ctccacaggc    31200
tgcattcaaa tgaacgaagg gaagggaggc aaaaagatgc aaaatccgag acaagcagca    31260
gaaatatttc ttcgctacgg aagcgtgcgc aaacaacctt ctccaacagc accagaagag    31320
cacagcgtaa cctttttcaa gaccagaaaa ggaaattcac aaagcctctg tggataccag    31380
cgcgttcagc tctcctgata gcagatttct tgtcaggttg caaatggggt atggtgccag    31440
gaggtgcagg gaccatatga tcatatacag cacagcagtc attgtgcatg tattaatata    31500
tattgagtag cagtgttact ttgccaaagc aatagttcag agatgagtcc tgctgcatac    31560
ctctatctta aaactaactt ataaatagta aaaccttctc agttcagcca cgtgctcctc    31620
tctgtcagca ccaatggtgc ttcgcctgca cccagctgca aggaatcagc ccgtgatctc    31680
attaacactc agctctgcag gataaattag attgttccac tctcttttgt tgttaattac    31740 gacgaacaa ttgttcagtg ctgatggtcc taattgtcag ctacagaaaa cgtctccatg    31800
cagttccttc tgctccagca aactgtccag gctatagcac cgtgatgcat gctacctctc    31860
actccatcct tcttctcttt cccaccaggg agagctgtgt gttttcactc tcagccgctc    31920
tgaacaatac caaactgcta cgcactgcct ccctcggaaa gagaatcccc ttgttgcttt    31980
tttatttaca ggatccttct taaaaagcag accatcattc actgcaaacc cagagcttcc    32040
tgcctctcct tccacaaccg aaaacagccg gcttcatttg tcttttttaa atgctgtttt    32100
ccaggtgaat tttggccagc gtgttggctg agatccagga gcacgtgtca gctttctgct    32160
ctcattgctc ctgttctgca ttgcctcttt ctggggcttc caagagggg ggagactttg    32220 cacgggatg agataatgcc ccttttctta ggtgggctgc tgggcagcag agtggctctg    32280
ggtcactgtg gcaccaatgg gaggcaccag tgggggtgtg ttttgtgcag ggaggaagca    32340
ttcacagaat ggggctgatc ctgaagcttg cagtccaagg ctttgtctgt gtacccagtg    32400
aaatccttcc tctgttacat aaagcccaga taggactcag aaatgtagtc attccagccc    32460
ccctcttcct cagatctgga gcagcacttg tttgcagcca gtcctcccca aaatgcacag    32520
acctcgccga gtggagggag atgtaaacag cgaaggttaa ttacctcctt gtcaaaaaca    32580
ctttgtggtc catagatgtt tctgtcaatc ttacaaaaca gaaccgaggg cagcgagcac    32640
tgaaggcgtg ttcccatgct gagttaatga gacttggcag ctcgctgtgc agagatgatc    32700
```

```
cctgtgcttc atgggaggct gtaacctgtc tccccatcgc cttcacaccg cagtgctgtc   32760
ctggacacct caccctccat aagctgtagg atgcagctgc cagggatca agagactttt   32820 cctaaggctc ttaggactca tctttgccgc tcagtagcgt gcagcaatta ctcatcccaa   32880
ctatactgaa tgggtttctg ccagctctgc ttgtttgtca ataagcattt tttcattttg   32940
cctctaagtt tctctcagca gcaccgcttt gggtgacttc agtggccgcc tggaacccga   33000
ggggcacagc caccacctcc ctgttgctgc tgctccgggg actcacgtgc tgctggatgg   33060
ggggaagcat gaagttcctc acccagacac ctgggttgca atggttgcag tgtgctcttc   33120
ttggtatgca gattgtttct agccattact tgtagaaatg tgctgtggaa gcccttttgta  33180 tctctttctg tggcccttca gcaaaagctg tgggaaagct ctgaggctgc tttcttgggt   33240
cgtggaggaa ttgtatgttc cttctttaac aaaaattatc cttaggagag agcactgtgc   33300
aagcattgtg cacataaaac aattcaggtt gaaagggctc tctggaggtt ccagcctga   33360 ctactgctcg aagcaaggcc aggttcaaag atggctcagg atgctgtgtg ccttcctgat   33420
tatctgtgcc accaatggag gagattcaca gccactctgc ttcccgtgcc actcatggag   33480
aggaatattc ccttatattc agatagaatg tcatccttta gctcagcctt ccctataacc   33540
ccatgaggga gctgcagatc cccatactct cctcttctct ggggtgaagg ccgtgtcctc   33600
cagcccccct tcccaccctg tgccctgagc agcccgctgg cctctgctgg atgtgtgccc   33660
atatgtcaat gcctgtcctt gcagtccagc ctggaacatt taattcatca ccagggtaat   33720
gtggaactgt gtcatcttcc cctgcagggt acaaagttct gcacgggtc ctttcggttc    33780 aggaaaacct tcgctggtgc tacctgaatc aagctctatt taataagttc ataagcacat   33840
ggatgtgttt tcctagagat acgttttaat ggtatcagtg attttatttt gctttgttgc   33900
ttacttcaaa cagtgccttt gggcaggagg tgagggacgg gtctgccgtt ggctctgcag   33960
tgatttctcc aggcgtgtgg ctcaggtcag atagtggtca ctctgtggcc agaagaagga   34020
caaagatgga aattgcagat tgagtcatgt taagcaggca tcttggagtg atttgaggca   34080
gtttcatgaa agagctacga ccacttattg ttgttttccc cttttacaac agaagttttc   34140
atcaaaataa cgtggcaaag cccaggaatg tttgggaaaa gtgtagttaa atgttttgta   34200
attcatttgt cggagtgtta ccagctaaga aaaaagtcct acctttggta tggtagtcct   34260
gcagagaata cgacatcaat attagtttgg aaaaaaacac caccaccacc agaaactgta   34320
atggaaaatg taaaccaaga aattccttgg gtaagagaga aaggatgtcg tatactggcc   34380
aagtcctgcc cagctgtcag cctgctgacc ctctgcagct caggaccatg aaacgtggca   34440
ctgtaagacg tgtccctgcc tttgcttgct cacagatctc tgccctcgtg ctgactcctg   34500
cacacaagag catttccctg tagccaaaca gcgattagcc ataagctgca cctgactttg   34560
aggattaaga gtttgcaatt aagtggattg cagcaggaga tcagtggcag ggttgcagat   34620
gaaatccttt ctaggggtag ctaagggctg agcaacctgt cctacagcac aagccaaacc   34680
agccaagggt tttcctgtgc tgttcacaga ggcagggcca gctggagctg aggaggttg    34740 tgctgggact cttctccctg tgctgagaat ggagtgattt ctgggtgctg ttcctgtggc   34800
ttgcactgag cagctcaagg gagatcggtg ctcctcatgc agtgccaaaa ctcgtgtttg   34860
atgcagaaag atggatgtgc acctccctcc tgctaatgca gccgtgagct tatgaaggca   34920
atgagccctc agtgcagcag gagctgtagt gcactcctgt aggtgctagg gaaaatctct   34980
ggttcccagg gatgcattca taaggacaat atatcttgag gctgtgccaa atctttctga   35040
aatattcatg catgttccct taatttatag aaacaaacac agcagaataa ttattccaat   35100
```

```
gcctcccctc gaaggaaacc catatttcca tgtagaaatg taacctatat acacacagcc    35160
atgctgcatc cttcagaaca tgccagtgct catctcccat ggcaaaatac tacaggtatt    35220
ctcactatgt tggacctgtg aaaggaacca tggtaagaaa ctcaggttaa aggtatggct    35280
gcaaaactac tcataccaaa acagcagagc tccagacctc ctcttaggaa agagccactt    35340
ggagagggat ggtgtgaagg ctggaggtga gagacagagc ctgtcccagt tttcctgtct    35400
ctattttctg aaatgtctgc aggaggaaag acaactgta cttccaggca tagctggtgc    35460
cctcacgtaa ataagttccc cgaacttctg tgtcatttgt tcttaagatg ctttggcaga    35520
acactttgag tcaattcgct taactgtgac taggtctgta aataagtgct ccctgctgat    35580
aaggttcaag tgacatttttt agtggtattt gacagcattt accttgcttt caagtcttct    35640
accaagctct tctatactta agcagtgaaa ccgccaagaa acccttcctt ttatcaagct    35700
agtgctaaat accattaact tcataggtta gatacggtgc tgccagcttc acctggcagt    35760
ggttggtcag ttctgctggt gacaaagcct ccctggcctg tgcttttacc tagaggtgaa    35820
tatccaagaa tgcagaactg catggaaagc agagctgcag gcacgatggt gctgagcctt    35880
agctgcttcc tgctgggaga tgtggatgca gagacgaatg aaggacctgt cccttactcc    35940
cctcagcgtt ctgtgctatt tagggttcta ccagagtcct taagaggttt ttttttttt    36000
ttggtccaaa agtctgtttg tttggtttg accactgaga gcatgtgaca cttgtctcaa    36060
gctattaacc aagtgtccag ccaaaatcaa ttgcctggga gacgcagacc attacctgga    36120
ggtcaggacc tcaataaata ttaccagcct cattgtgccg ctgacagatt cagctggctg    36180
ctctgtgttc cagtccaaca gttcggacgc cacgtttgta tatatttgca ggcagcctcg    36240
gggggaccat ctcaggagca gagcaccggc agccgcctgc agagccgggc agtacctcac    36300
catggccatg gcaggcgtct tcgtgctgtt ctctttcgtg ctttgtggct tcctcccagg    36360
tgagtaactc ccagagtgct gcagaagctt tgtgcctgcc agtcctggct ctccttagca    36420
gaacatggtg gtgaccatca gagagagact cccctacaaa gtgcctgcaa aggctgcctc    36480
agtacatcag tattaaacgg attactgttg tgctgggtgt ctgttgggtt ctgtgctccc    36540
aacacatttc ttacgctctc agctctgtta cactgcttgc atttgctgca cagttgcata    36600
gaatggataa atgcttgaaa caaggccata acgaggtggt cagacctcca ggaactagtt    36660
agggaaatat tgtcatggcc caagcaagct ctgtgcagga acctggcagc tttcctgcaa    36720
tgcttttgct gctaatggag aaacaagaga tgcaaacaag ccaggatctg atgttctcct    36780
tctgtattta catctcatga aattacaaag tcaaagacaa gcgtggttta tttcttacac    36840
tcagcttctt taaaatgtat atccctgaca acagatgctg tgtatgtttg cttatcctgt    36900
atgtgactat ttgcatttgc atttatctct attgactcag gtttcttttc agatatgtga    36960
tagatgtttt ctagggacaa aacggatgtg tgaatagata aggaaggaaa agatattcat    37020
ttttcaatta ataaatctac ctatctctta actttttttt ttttttaaga acagagctat    37080
tcaagaactc gtttcatcag ccagcaataa gaagctaaat tatgtttatc agcattaaac    37140
aaaaatcata tatagtttgc ttagttcaag aatcgaatcg gtggaaatca ctcagtttgg    37200
ttctctgtgc tggagttttg cacacacatt tcagctagct gtggtctcac tgatcagact    37260
gcctttgttt cccattttttg tcccctttt ttccccagat gctgcctttg gggctgaggt    37320
gagtaagaga gttcttcttg tccactttc tcttttctct tttctctctc tctctttttt    37380
tccccccgtc ttaattagta tcactataat cagatcccag agtgtaaaat gttaaattat    37440
```

```
gcagttctga gctctacatc tatgctgcat gtaagtaatg tagcagtgat ataaaactgt    37500
tagatgaatt aatttctgac caactctgaa ctggtctaag ctttaagttg atcatatgtt    37560
ctactaaata atacagtggt ttgggttgga agggtccttt aagatcatct acttccaacc    37620
cctctgctat aggcagggac aactcccact agacaagatt gctcaaagct ccatccatat    37680
gatcagctgt agactgatgg ctgtagacta tagcattaaa aactacccca aagcagccta    37740
ctgaaagaag aaagtactgt gaggtgctac agcttccaaa tcccatgttg ttagacctgt    37800
tcttttgaat aaacgtgttt gtacgttgag aatgaatgag taacaatggc agaacactgg    37860
aggggccaac tctcaggctt tgcaaaatgg tgcctggggg gcatgataga tccctgctgg    37920
tttatcacat ggggagctgc atggctataa ccccattgcc cagttctctc ccactgcatg    37980
gagagaaggc tggatctggt cgctgccctg ctgaaaatgg cagatgtaac tacaaaatgt    38040
cactttgtcc tgttactgtg tgtttctttg tcaggtggac tgcagtaggt ttcccaacgc    38100
tacagacaag gaaggcaaag atgtattggt ttgcaacaag gacctccgcc ccatctgtgg    38160
taccgatgga gtcacttaca ccaacgattg cttgctgtgt gcctacagca tgtgtgtact    38220
gcagagagag ctcatactgc aagcaagcag ctgtgcttag ggctcctgac agcacccctt    38280
tccaacaaac agtgatctgt cacatgtcac ttatgtcaac tctttcaggg aaagcttgag    38340
tatcactgcg tgacactcgg ttgcctagac atcactttgg ttactgtgtc ttttttgttg    38400
atgtaattta ttcaggtttt tctcctccat ctcggggatg aggcagatga cagcccctag    38460
ggcatatttc atcccagcaa aaaaggagca aaaggatgga gaggtgctcc agtctgaatg    38520
gtccaaaaca gtcctaaaga tttcagagtc tttagatccc tgccagccac tcagtatggc    38580
actaccctct ccaatacaaa tatatatata tacaaagatg acttagccag actcagcctc    38640
attgcattag gtacatattc ccaataacga gaagctgagc ttcctaatac ctgttttccc    38700
tcttcagaga atttggaacc aatatcagca aagagcacga tggagaatgc aaggaaactg    38760
ttcctgtaag tgaaaccaag ttcatccttt gtgcagccaa aactgcttat tgacttgccc    38820
aataaataat gtaaatgctg actaagaggc catgtgagat gtcagaatct tgtattgatc    38880
atcttcaggt gaagtttcat cacaataaca caaaaaaaga ctttatttcc tgctgaggtg    38940 gcatttta gg agaccaacg cacgcgctcc gctggtctac gtggtccctg taagccctca    39000
ccagcgcttt gctgtgtgct ccttccacag atgaactgca gtagttatgc caacacgaca    39060
agcgaggacg gaaagtgat ggtcctctgc aacagggcct tcaacccgt ctgtggtact    39120 gatggagtca cctacgacaa tgagtgtctg ctgtgtgccc acaaagtgta agtaccgagc    39180
tgtgctccct tggcaggaat gggtcctgcg ctcctggcag ccactctttg agcactggga    39240
tttccaatga ggcttttct gtatggctct tggactccgt ccctcctctc cctgataacc    39300
tcatgctgtt ttcctttgtg attagaaaga gaactgtggc tttgatcttg agagagaagc    39360
agagagctgg tgggactt aagagaagca ctctgttctg tgttaactaa gttaaaaggg    39420
tctgtgtggc acacactgcc ttgcagagga cagcagtgaa cctctgctgc acctatattg    39480
taaaacaacc tagctcctag gccatgacag cctgtcacct ctcctccttt gcatcatgca    39540
atactgcaac actgtggcac atagtaccac ctcccataag gactgatatg ttgaaccagt    39600
gtgtcagaga ccagtagcat ctctgtcttc aggatcatca ggtagcattc tatatacagg    39660
gtgttgccca ggactccgag tcccatgaag tatggcaggg ttttggaac tggatgacct    39720 tcgaggtcac ttccaaccca agccattcta ttattctgtg aaagccaggg aggtgggggt    39780
gcttgcaggg ctggtatctt gagcagtgtg ggcacaaaact aggctgggca tctgcagccc    39840
```

```
atcagcactg cggggatgtg gagttcagca cagcaggatg caggcacagc tccctaacat    39900
ggattttttt cctttcagag agcagggggc cagcgttgac aagaggcatg atggtggatg    39960
taggaaggaa cttgctgctg tgagtgtgag tagcacaatg aaggagcagg ttctggtccc    40020
actgatgtca agggaaacat ggccagcatc tttagtagcc tcaggagcat cagttgtgct    40080
tcagcacaga gaagatttta ctttctacac acgtaataca cattatccac agtaatgtca    40140
ggaagggaag aggatgactg cacaggcagg gatcagtaaa agaccataag cagaaataac    40200
ccatgagggc agaactgaga ataagaactg agactagatc caggggggtca gaccaatggg    40260
ccatcaaacc catgatggtt tgatgcagag tccactcttt cagcattcat aagaattgag    40320
tagggggggag taagggtggg gtgagtacgt acggatcttc ccaaacaccc ttccaaccta    40380
cagctatgca cctcagccag gtgtgatttc tgtgtagttc acaagcctca gtggatttct    40440
ctcccatggg attctccagc ctctttctgg acctgtatac acggtagttg ggttggtttt    40500
tttttctgt ctctcttttt ttcccccccac tacaatgtcc ctcagcaaac atagtcctca    40560
tctctcaaac aaacaaatct cattctctaa gtacccagat aagagctgat ttttgcttta    40620
agcctgtggg ggagatgctg gactattata aaggtatcag tgctgcctct tctccagaca    40680
ccaatgttttt ttccatttaa tttcctgaac aggtcaggaa cacggtgcaa catgattgta    40740
agcacagcac gttcatggag cgagctgctg ctgcagctca gaaatgcagc agtcagattg    40800
tgatatgcat ctcttacaca ggaaattatg ctctattttt atattattaa atctagcata    40860
cgagaaagga catccagttt atatcagatc gtgcaaggaa gttaattatt tttagtttga    40920
tcattatcat cggcactgca gctgtagcta gggaggggtt gaagctcttc agctatcgac    40980
tccttcatat cctccacgtt acaattgtgt ttttgcaggt tgactgcagc gagtacccta    41040
agcctgactg cacggcagaa gacagacctc tctgtggctc cgacaacaaa acatatggca    41100
acaagtgcaa cttctgcaat gcagtcgtgt acgtacagcc ctgattgcat tcacgttgtc    41160
ggctgcctcc tacaggcacc agcttgcaca gttcctgctt tcgttgctga ttgctgacca    41220
ggatctgggg gcagaaaaga acaccgggca tcacgccagc cattcatttg attttttcacc    41280
agagcttgtc tggtttgtta ggatggatgt tttgaacgcc attaacctta agggaagttt    41340
tccttgctgc gaagaaaatc agatttggtg tttcattata gttttcagaa ggggttaaac    41400
gatttcactc atctcctaat aatcaggtag ctgaggagat gctgagtctg ccagttcttg    41460
ggctctgggg aggatcccat ctcctgcctt ctctaggaca gagctcagca ggcagggctc    41520
tgtggctctg tgtctaaccc acttcttcct ctcctcgctt tcagggaaag caacgggact    41580
ctcactttaa gccatttttgg aaaatgctga atatcagagc tgagaaatt caccacagga    41640
tccccactgg cgaatcccag cgagaggtct cacctcggtt catctcgcac tctggggagc    41700
tcagctcact cccgatttttc tttctcaata aactaaatca gcaacactcc tttgtcttgt    41760
ttaatgctct gcctcatgca atgttttctt ctgatttgtt ggacggtgat accagactca    41820
atatgttcca tgctcgtggc tctgggggtat aacaagaaca acatcttgct cccatccctg    41880
tcataaaagg cagaaaatta aatacagatg cataaacctc ggctgtgtga ctttgcgcat    41940
aaatgacagt cagcctccat tagtgttcag accctttttag acagctgaaa tactgctacg    42000
aactgctgat gctggctgag ctccccatgg tacgtgtggt gcactttccc tgcgcagcat    42060
tagcagtgaa agcagctcag ggtgcggtgg tggccaaacc cagggccgat cccacggcct    42120
cctgtacctg gtcataccca cgggcacagc tgctagtgag gtgcgtgctt ttcagacacg    42180
```

```
tcatataagt gtgccctgcc tacatgtctg ggtcctccaa atgacgttgc aaggtttatc   42240
tcatcttgga attgtccctt actgaccacc aagtgttttg agatgaatgc cctcctaggt   42300
ctggttctgc tcttgcctgc tggtcttttc tcatagtagt ccttgccagc ccaagtatct   42360
gagcagtgtt ttgcaatcca aggacaaagt acccctctgc ctttgagagt gtgacctctg   42420
tcattggcac attgtccgtg aaatatattt tgcttttgtc ctttgttggt gtattgaact   42480
gatgttttct tgatccacat gagagaaact ttaataaaaa ttataaaaaa taatgcctcc   42540
cttaagcatt tcttttccct gatggaatga ggccattcaa agaaggatg ctttggcggt    42600 aaaacagagg atttatgttg agatgggcag atgaatcaag cagtgatttc cagttttggat  42660 tgaacttttc tgggatccag gctgtgggcc tcatgtcatt ctgtcatcat caggctatca   42720
gtctgctgct gcaaatcctc cccacaacgc taatggcttt tagggaaaat cgcaattgtt   42780
agttctttgc taatgcccat aaaacttctt ccatcacttg tccagctcca ggactccctt   42840
cagccccagg tttccctctt gctctctctc ccagttcagt ttttctggat ttgctatgat   42900
ttgatgatgc attattgaca ggacaagggg aaatggtttc aaaccagagg agaggagatt   42960
tagactggac ataagcaaga cattttttac aatggtggtg aggcactgac agaggttgcc   43020
cagagaggtg gtggtgcccc atccatggag acagccaagg tcaggagggg ctctgagcac   43080
tgatggagct gtgggtgccc ctgttcattg caggggttg gaccagatggg ccttaaaga   43140 tcccttccaa ctcaaatgct tcaatgattc tgtgattcta ttgggttgaa gcatgccaac   43200
taagactttc cactctggaa acattcaat tcagttcaac aacatttcc agcaacagtg     43260 agaaagcact gcatataggt aagcactgat aacatgcaca tggaggaaat cctgcagcat   43320
tctctcttca ggtttgtaca gttgcccttt tgcccacagg aattttccat ggtccttcag   43380
caggcacctg tcacacactt cactggaaat aatgaagccg agggcgtact tcacatattt   43440
aaacctgcaa ttgctgttga taagaagca ttctttgtgg ctcacttgtg taagtgccat    43500
caagatttac aaccctgaca ccagagctgg aacgctggtt atttcaaagt aggggtggc    43560 taaaccaaac gtgaatgcac acagccacgc acacacagat caggtggcca tccaagggca   43620
gaagggccgc attccatgag cacgatgcac ttctgcccct tgctgctgcc caggtgagtg   43680
gctgtgctcc tgctccgtgc ttcgtcgagt gctggctgta aaaacacaac aaacatcctc   43740
agactggaaa gagctgtgtt ctacaaggac ttatttactc ctagagggat ggtgttgaaa   43800
agacttgaca tcaaagacta tcacttatgg ggtaatattt tagcaacaga actgagtggg   43860
taagaacaac tgtgggaaca gctccgcgct cggtgctagt ttatgcataa tgaaagcagt   43920
gacacgtacg tggtaccacg acatccacca ttgaacctcc gaaacgctgc agaatcacaa   43980
attcttttac tgaatggaag cgagcgtttc ccgcagtcat cctgaactga gatgcaattg   44040
gaggggctga gcggctgcag cagcgttagg ggagtttcac ctcgctgagc cctcccgtta   44100
tttcagtgct gttgtggagc tgcacgcagg agctgccgcc agtccgtgcc agctctgcgg   44160
ccctgcttcc ccggcacctt gcttatctct gagcacctgt ccttgctcat cctgtgaatc   44220
acggagaatt gctttctctt cctcccttc atttcgcgcg tccttctcca cccgggctgt    44280
aaccctcctg agaaaaaacg tagtacggaa tcgatgttgt aaacactcag cgtggcacaa   44340
cgttttgcct gaaatccctt ttgtctgaga gtcacacact gaattgcaag ttgtttattc   44400
aggacatgca ctcacggatt ttaacactaa cgaaggagat gaattgcatt tgtgtcacac   44460
ttcctattcc cttctttact ccagaccca ctgcactgaa ggtaagggac agatctttca    44520 ggttttttttt tttttttctc catcatttct ttcctcaaag cagtttccgt ataaatcatt   44580
```

```
actaatcgca ttgtgatcga gcgtttgaaa gccctgagtc atcccacagc ctgagcaata   44640
tttgctacag atattaccga gtgaaatggc cattttcatc tgatggtttc aaaaaaaaaa   44700
aaaagataat aataataata ataataataa ataaatagcg cagcattcag ttggtgtcca   44760
agttattgtc acggttactg cagcagcact gaggatgttt acatgggatt tacatcactg   44820
gaggctgaaa gggcactgca ggcgtgtacc gcgctattcg ctgccccatc cttaagctct   44880
tctttgacat ctgctgatgg tcggtgctgg gggaagcccg gggctgtggg ggtctcctgg   44940
catctgccct gctgatagct gtgctgctga gggtatttct gtgagcacaa ggctgcatcg   45000
atccacaggg cgactgcagt gcctgcgccg tacccgcaa tttctgctct cgggagcgca   45060
tcccacactg cgggtctgat ggcgtaacat atgccagcga gtgtttattc cgcaatgcat   45120
ttctgggtgt atgaaaataa atctcttcgc tcactgagtg gtgaacttca actgtcttat   45180
caacctcagg gactgcctgg agatggaagg tggttgtgtt tggcgctctc ctcttctctt   45240
gctagcaagg gcagcacttt ttttttttaaa ctgggaggat ttaccaggga ctcctttctt   45300
tcaggtaaaa agaagtcaca tttagcagag atcttcatct ccacgttggg taatttgctg   45360
aagagctcgc ttccagcaaa tacagtctat ttcctacagc ctatttgttc ttcttttaaa   45420 ttaagtctt atcgtgcctt tgaatgttag taataagagg aagtagctgg aatagctttc   45480
cgaatgttct gttttggtta agttcctctg tgatgtatcc ttaagcagag ggagggatgc   45540
acagcagaag cgcagaggtt caatctctga ggccctgagc tctttctctc cagaactcat   45600
tgagttctca ccttgctgtg ccctgcgcag cgctcacatc acagcccacc gggctccagc   45660
tcagacagga ggaccctctc tggctgtgtt ccttacaggg gatgctgccc aaagcctcgt   45720
cctgaacttt gagtgctcct gataaagcct gaagctatgc tcaataaaaa aaaaaaacct   45780
tcagcatttt ggtcttgctt tcatactacg tatcatgctg ttgttttttt tcttaagat   45840 gctgtgtgat tgcatcactg caacagtcct ggggtgtggg tcttaatggg aaaattacag   45900
ggagaaagaa cgggttgtct gatttatgaa gaaatcaacc cctccaaaag gccatgagct   45960
tctgctttct tccagatttc caaaagaaag ccactgctgg ggatgagatc cagtgcagtg   46020
ttcagggcat cctgtgcaga cattgactcc ttaggagctg aaaataaagt agtggtgggt   46080
acccgtaggt gtgggaagcc tttctgcagc cacctggtct gcctcccaaa gcagaggatg   46140
ggatgttttc ccctccgggc agcaccaaca gaggggtggc agcagggtga ggaagatgat   46200
tggcccctct gctctgctct tgtggggacc acatgcagta ttgcatccag gcctggggcc   46260
ccagcatgag aaagacgtgg aactgttgga gtgggtccat aggaggccat gaagacaatc   46320
acagggctgg agcacctctc ttatgaagaa aggctgaggg agctgggctt gttcagcatc   46380
aagaagggaa agctgagagg acacctcatt ggagtcttcc agtacttgaa gggagcttgc   46440
aagcaggaag gggaacaaac ttctacatgg tctgacagag atagaacaag ggggagtggc   46500
tttaagctaa aagagggaag atttgggtga gatgttggga agaaatactt tactcagagg   46560
ttggtgtgac actggcactg ctgcccgagc ctgtgggtgc cccatccctg tacatgagct   46620
gaaggccaga ttggatgggg ctctgtgcag cctgatctgg tggggggcag ccagcccatg   46680
gcaggggttg gggtagatgg gttgtatggc ccttttcaac ccaaaccatt caatgattct   46740
atgattctca gataagcctg cctgcccaca tctgagctca cggtgctcgc tggggtggg   46800 gtatggtaca ctaaatgatg ctcagaggac tgcacgcagg acctgccgca gacgtttatc   46860
acctcaccca ccactagct gctgcttgta gttaattacg tcagctgtca cttgtagaga   46920
```

```
atcctttgag atccttgggc ctccggaaat cttggctgat gaaaggaagg gctcagagtc    46980
atagcgttaa tttattattc attaacacca aagtgtcggc tgtacgggca gtgggctcac    47040
agtcaaatag ttaatgatct taagtgacaa tgtgtcactt tgcagacagc agagagaaca    47100
gctctcctaa gggagacagc atctttccaa ttctgcagcc attcagtgcc aagctcctct    47160
ttgggacgaa agtgaagatg aggaaggcaa tgaggatgag gaggggcctc aaggaacctg    47220
gctggcttgg agacaagtga tgatcccagc tgctctcagg gtcccagcgg tcttcaaagg    47280
gcatcttgca ggggctgtgt cctctgaaca gcaaaaccca ggtcatagag gggaaagtgt    47340
gagcagagat gggacaaatc tcccatcctg ccacggagct gcactgctaa gggggtgatg    47400
gggagcagca tgggacccca gcgttccccc catccctgca ccaggcccag ctctgcggga    47460
tggcgaggag acaaggctc tgtcacaagc atcgctggca attattattt tgttgttgct     47520
gctcaataaa atcctgacac agtacaacac aatatcctct catcattact aatctaactc    47580
tccctccagg aaatttcagg caggaaacgt tgtctgcctg ccgaggtgct ttatggcact    47640
gttctttagt ggtacctcag cacttcgtgt cattatctgg tgtcagtgaa tttaggaaat    47700
gccattcaat taccccgcaa actgattaac gcattgcgtg cagttatttt gttctgctct    47760
attttatatc agttcctctg ttttatgtat ttctctactt gttgctggcc agaacacacc    47820
tcgggccagt ctagaccttg ctgttgatgc agcttttccc cagggcttca tcagcacaaa    47880
tggtttgtca acgtggggaa aaataaaatt atgctttaaa ataaaaccac ctggagatgc    47940
tgttctgggg tctggctgtg tcacagctat tgcagcgatg gagctgaggg attgggatgt    48000
gctgggccgg atcctcagcg ctttgctata agccaaataa ttccagacac ccttcttccc    48060
tcagatatca tctgtgctta agcagcagga gatatgcagg cagcgatcag atagctgagc    48120
tgcaaggaga aatatcacaa gagcgcggct tagagcaggg gctttgctcg ctctaaattg    48180
aattcccatc tcataggag atccagtcct gcccccgtgt gcatcgctcc ggtaacagca     48240
atgtgttttg ctccatcttg cagagggtcc agaagctggg gaaaggaaat gtgtcgtgcg    48300
ttcgtccctg cagcagctcg gcccataaaa ttaatgaaaa tcttttttag gtcatggtag    48360
attacagatt tctttgagat agagaatctc aagagcagag gagaagattc tcagaaaata    48420
gcagtgatat gagatggcat aacgctgagt tggaaactgg ggaggatttc cagggttact    48480
ggaaatttac ttaagcacga gagaatgcat cgtgtgactg ccagtgcttc cccactcaca    48540
tggctataac cttcttgcat acaattacca tcttggaact tgaaatagct gaaagagttt    48600
tatttgatct tttcaatgga tcttacatct gcagaaaaaa aaaaaaaagg ctagaaataa    48660
tcctgcactc aaactcactt tactgaacca ccatcatgaa actccagcaa cacacaggga    48720
tttgggcagg cgtgttcatc ttcctcttcc catttgcaac atgtgtatgg catttcctga    48780
agctcactcc tccaaatgca ttgagacagt tgttttcat tcttcctaat gcctgcatcc      48840
acccatctgc tgatcggcaa ttatttctat cccattccct tctgtttctt attaatcaag    48900
ctctttatgc aatcccacgt aacactttgc ccagctgccc tgccctaacc actaccaatt    48960
atctcatcct gttttataga ccctgtagca agactctggc cttgctcctc ttcctctccc    49020
tgatagagct tttggtgcag ggctggctgg ctcctcaggt gttcagagga tcagaggtct    49080
cccagaagga tcttgttaat caaggacagg tgctggctat atgggaggat ggcaccgtat    49140
cctaaagctc tacaagaagg agacggagct cagcctggga ggacagagag aagcagcagc    49200
acaggtttca ggatccaggg atggcagacc tgggtgtggg ctcataggat tgaagaaggg    49260
ataggctgtg ctcctgtagc ctcactgcag aagcagcact gctatctccc cagcgaagct    49320
```

```
gtgtgtgccc catccctgga ggtgctcagg accaggtggg atggggccct gggcagtctg    49380
agccggaggg agcagccggc ccacagcagg ggttggaatg gggtgggttt taagttcccc    49440
tccaaccaaa gccatttctt gatctctgtt ggtggctggt gcaagttctg aggaaacctc    49500
attttcagct caggcgttct tgtccctggg gaaaaatcaa tattaatgct tcagtgatta    49560
ctgctcgcct tccaaatgtg cttctgatca gttcaagaaa tctgacagtc acgtcgctca    49620
ggatgctaag aatacaacag aaacagcttt gaaaggaacc cttcaactct tgatatttgt    49680
gaatgagctc caaagaacat tactcattta tttttcagga aaatgatttc attgacatga    49740
acaggccaaa gcctacaagc tctgttttgt gactgcagct ccttacactt tcagctgcat    49800
tttcatgatt tatgtgccca tgatgagact tgaacacctc ccaggataat gggaaaagca    49860
gttctgattt cccatttaaa acgtaggctg cctttaagcc atgtgtgtgg ctcaggctcc    49920
ttctgaagca caaggtgttt ccacccctcg ctccttttc attacaactt tcaatcaaaa    49980
atgtgtttta tgagatattt gttttgccat gtatctgtga cggagttgaa cccccttagtg    50040 aaacctctgt tcttcactta gctgagaggt atttcttagg gaatgtgatg ccctaaattt    50100
attgtggtgt aatagaaggg gggatgtgtg gactcacctt ctgtttgttg tggctgcagt    50160
ggttttatgc actacctgag tattaagcaa gcccttttca tctgcacgga acacctcctg    50220
cttgccagtg ggatgaaaca acaacaacaa agatttaagg tttgctattc tcaatgtttc    50280
ttaatcgggt tcacattgat tgccaacaga tgaataattc ctccttctcc atggatgtac    50340
ctcttaaact tgtgaagtct taggtaacgc ttttctgctg tgatgactgt ttcagtcccc    50400
tcagtgagaa atcaggcgca ccagtaagac acaaaggaga ccgtggagat gttcattgtg    50460
ccctcagcat ctccaaaagg cactgctgcc tgccgagccc cagacttcgc tcctgtaaaa    50520
gcaaagcatg tccaattctg ctgtgccata agagtcctgt ggagcccaga cacggcgtag    50580
cgtgtgtaac atagcgtgca cgagctcaaa cgctttcaac aaatcagctt ttttgctttg    50640
ccaacttcca tatgtaattt cacaacatct agtattgaga cagtgctgtt gtttgggcag    50700
cataaatcac tcattgtaca gcagggcgcc tctcttaaca agttgggtgt agttcatgtt    50760
tttgtctaat tcctctgcgc atctctctaa caaacaacta ttctttaggg ctcgactcaa    50820
taatcaatac atttttttca gtttacagag caaataatta cttgacctga tgacttcaca    50880
aggttaggga gatgggtgta taaagtctgc agtgtgaagg cagagcaaca tctctgcaga    50940
ccttgagagc aacaggtctg caagtaacag gctgcacagc cacctctgcc atggaggcaa    51000
tgagagctgc tgcccctcctt ggattggtgc ttctcagctc cttcctggt aagttgtttt    51060 tgttacattc tctgcttata tctctactcc tactgaacta atgtggttc aggatgcctt    51120 tagaatccta aaagagagct cagcctgccg gagaagtgat ggtttggtaa acatgagct    51180 ctcttctaat gatctttatc cttgtgcaaa tatttacgta actctagcag gatgcctctg    51240
tctgacataa actcattatc ctcagtaagt ctcatagcac tcgagagaga aaatgtatac    51300
cctatttctt ccttagtgag tcaaagttta tattttcacc caaaatggct attttttta    51360 atcataggat atagcttgct tataggaact ggataaaata tttaggaaac aagtaattct    51420
cagtgataaa aaagaagtat gtgatgactc tgtagggaaa ttgataattc cagaggaatt    51480
gtaaccaagg acgccgtaac attctgtatt ttataacctc tgttttttcc agatattgtt    51540
tctggtcatc aacgggtgag tagcagatct gcatcattta gttgtggttt ctatgaatag    51600
atgaataatt catactcaca ccatatccta cgggagccta gagggagaaa aaaaaaaaag    51660
```

-continued

```
aaaagaaaat aacaagggaa ggagaaaaag ggcccccagg aattatgtga cattttcccc    51720
ccagcaaata agaaaacatc tttgtcagag aaagataacg taccacgttg gtgataagag    51780
ttggcaatta ataatgcaga gtgggagccg gcgtggcaca gcgtgccagc agaaaatctg    51840
cacagctttt ccctaactgc ctccatatct cccctgcctg attccctgag gacccatcag    51900
tcagtcgtgt gtctgccatg ccaaaagcct cagtagtgac actgtgctca ggcatactgt    51960
aaggaacgct gtaatttgct cccacttctt caccgtggag gagtgacaga gaataaaatg    52020
accgcctgca gcacggctat gcgtggaaaa cacaagcaga cccttccgtg ccctgcagag    52080
ctgtcccact tgtgctcttc ccaggcctcc tgcggtgagt accggctgtt aggcagcagg    52140
aacctcgcct gttccaggat cttccagccc gtctgtggca ccataacat cacctacccc    52200
aatgagtgct cgctctgcag agaaatcctg tgagtagcga tcgcccgatt acccatcgtg    52260
atggctcagg tggcagacag aagccttttg aattgtgact aatcacgggt ggattcgatt    52320
ttttttcccc ctgtttctgt cttcccagag tgcaggctgt gtttcttcct tgtcaaaact    52380
cctgagtcta attaattagt ggggctgggc gtggagaggc ttgatgagtg aggtgactgc    52440
atggcaccac caggttaacc cttccccctcc ttctctccta gccggagtgg gacggttgac    52500
aagaagcacg atgggaggtg tgtgaaggta tggttccagc tcagccactg tgtggagcga    52560
tggcagaatc ccttcccagc actgattgta catttagaat ggacagctcc aaacccattg    52620
gaaatgtaac agaaaggaag aatttcaggt ctttatata tatatatata tatatatata    52680
tgtatgtatt aatttcattt tgaacagtgc aaatctgttt caacggtgag ttttgagatg    52740
ttatcttgtg tagcacagct gacttaaaaa cagaatcctc tcatttcaat aatcctttgg    52800
tgttgttgaa atagttccct ttagacttag acagaagtct gttgaaatta agaagttccc    52860
caaggaagtc tggattttga ctaaatcata attttgtaac agggaaaaag aaaaaaaaaa    52920
aggattccat cagaacatct accctgaggt ttgtttatca atacacgag ctgccacgaa    52980
gtggagaagt gtctctattt ttagattaga gagataatgt aaagaaacac tccggctgtg    53040
caattgaaca taatgctaca attttcactt cagtacactc agagtaatgg caggaacacc    53100
gaggtgagca tcagctccat tttcaagtgg agcagacatt tcacagcagc agttgctgcc    53160
atgtagggca tgttaggcac agatcctatg tggtggcatt tggggtggaa agccctaaga    53220
tgacaccaac aaaacccatt ctgtgaaccc atttcctcca ggattctgct gggctcatgt    53280
cctcaaaggc aggacttcac ctgcctgtgc tcccttgccc gcactgtgct gggttggaag    53340
ctcacatctc catacagccc cactcaccgt gagtctgggg gtgggagaca cctctcacac    53400
catgcaccat tacacagggc tgacggaagt gttgttctgt ggctgtttca ggttgattgc    53460
actggctaca tgagaacaac tgatgggctt ggaacagcct gcatccagca gtacagcccg    53520
ctctatgcca ccaacgggct cgtctacagc aacaagtgca ccttctgctc ggcagtggcg    53580
tgagtggtgg gtcacaccct gggtgctggg gtctgggtgg tggtgtttgc agcatattga    53640
ggcttctgga gtggctgtgc tgtgctcatt cattctcaac ttgctttctt ccccaaggaa    53700
tggagaggac atagatctgc tcgctgttgg aaaagagccc gaggtaaagc tcgaaagtct    53760
gcgctatgaa ctgttgttat aatatattat acagcacaaa ttcagtgagt cagaactacg    53820
caatagcaat gtcttcactg tgctggtgta tttgtcctgg aaaagggtt tgaggaaaat    53880
gactcaagta tgccagggtc agaggacgat gaacaaaact cctggctcct gtgtcagtat    53940
cacctgcaca gccctgaca gggttgatg ctcagagcat tgttcagatg gtggctgtgc    54000
cagaggtgct caccgctcct ggtgagcgtg gggctcatgc agcaccagct gtcattactt    54060
```

```
gggtgggtgg acttcatagt gtgctgttgg agacacactg cttcctggca gcccctctct    54120
gctggctgct gaaccagagc agagcaggta gcggccgcc agccggggag cactgctttg     54180
gctgtgtcgc tgcttctgag ggtatttagt agattttttcc ctctgacttc tccttttgtg  54240
ctctgctggg caagagcatt agaatttgca gagttgctag aacaacagga gcctgcatct   54300
gaaaaaatgt ttttttttgct ttgccatgac ataaatgtaa agcgcccatg taggaaaata  54360
caccaaacaa aggcttctca atacgttctt gctccattac ctacagattg actgcagtga   54420
attcaagagc actgatgcct actgcactga agagtacatg cccctttgcg gctctgacgg   54480
cgtaacgtat gggaacaaat gccacttctg cattgcagtt ttgtaagtac agtgctcccc   54540
atgcagccat gaaccactg ctgtgccgga gtatgaaggc agaagctgcc aggaagcctt    54600
tgtgctcccg ttatcccctt ggtaaatccg tccccatccc caacctgatc ccagctctac   54660
ctctgctgtg ccttccccaa gcactgcaga tcttgaacac aggtgagtct tctcctccc    54720
tcaccattaa attcagattc tcatttgcgg gctcatagcg ctcctgatcc atccctgcga   54780
gagtaatttg agtggtaact gtagaaggag tatccaaaat tacagggttt gtcccagatc   54840
tctctaacat gacaaaacgt gtaacctggg gaatcaggag acgggtgaag gtgcaactgg   54900
gacagcatgg agcattggct tgcccatgca aagtcagcag tggcaccatc agggctataa   54960
aaccaccttc catgtcagtg attttggcct cctcctttct ctgcaggaag agtcatggat   55020
ctctgtctct gcagcaccgt ggagaatgct gaatgctgga tcgtaaccct taccctcatc   55080
catctttcac ttccaaagcc tgcaattcca acacgctctt ccccgctccc tgctgtacat   55140
tgctttctgc cttgacccgc cagtaaatca cagacagcaa ctctcttcgc catgggctgg   55200
tgtgttattt atttatttat ttatttattg ttgttattat ttttccagg gcagaggtaa    55260
aagtcttcag gctttcaggc acttatctgt caggcaggag aagttttgaa ataaaccaca   55320
ataaaggcca aagtgcaaca cccatcacac aaaagccata agccctcacg aaagtgcgtc   55380
accccattcc aaaccatcag aagaggaaat gttgctataa aacacatgct gctctcccca   55440
gttctgtgtc ttacagcaca taaatggatt tgctttaaga gtcaggatgt ggctttgtag   55500
aagcacggag ccctggagga agcagtcctt ttgggagcct tggtatggag gaaagatggc   55560
tttgatacac ctgagcaagg ggcaagtctg gcggcacgtt acaaggaggc ttatggcaaa   55620
gggaggagac tatctcacag ggaagaaaat taggaactgt tgcttccttg aagggtgtgt   55680
cccttgagag tgtggtgatc agcagaaaat tgcagccagc tgggcaaggc tgtaatgagc   55740
ctaatgagga ccagaggaga aaccagattg gctcaggct tcttggaaaa gagatctgaa    55800
aagctgcact gggagcgttt gaggcagagg aaagagaaag gactcttcag gaaaaggttt   55860
gggagtcttc atgcctagaa aagaaaggac agaaggagtg cttggtagct ccaaggtcgt   55920
ttctgtctgc agtgaaaggt gatgtgtgga tgatgcgtgt gagcgttcac agtgatgtgc   55980
catctctttg ggcgagtcaa ggaatgagta tgcaaacaac aggtgaaaag tcccaagtgc   56040
ctccactcat gccaccttcc ccttcctttc tccacctccc atcctctcat tacgtaggaa   56100
gacattcagc tgttcaggct gatattgagg acaaaatctg tgacttccaa gcttttctct   56160
ggctttatttt cctgaaatag gctgtatctt gacctagaaa tcttatgggt gcttcctgcc  56220
agaagatggg aagctgtcct ttaatagcgt gtcagggcag tgctccgtcc taggaagaca   56280
gatggaactt tgaaatgttt attctattag cacaggcagt ataaagcaca gtgtgcctct   56340
gtgcctgctg gtgagaaaag gcaagctgca gagccgtgag ggtgctccct gctaatctgc   56400
```

```
ctagaaggga aaagagtaga caagaaatag catatgctac tactgaatgt gagcagaaga    56460
cctttagtga aggacacagc tcagctgtaa tgtcctgttg gccaggaggt ttgttgagtt    56520
atcgcagagc ggtagagttc tggtcagagc aggaaggtgc cttcaacagc aagatcccat    56580
ggtaggcctc ttctgcagtg tgctggcaca agcctggtac ctgctcagga gcaaaaaaag    56640
gctttggaaa agctcaaaga agggctgatg tcttacaggg aaaggagggg caaaaggcaa    56700
gtgcagagca tatggctgta cagacaaaaa cccttcagaa aatggaaaag gtttttatca    56760
agtaagccca gaagttggcc cagtgcaggt aaacacttgg ctaggtaaca gtgaggctct    56820
gcccagccat acccattcct ctgtaaggca aatcccaggt gcctttgtct tgtctggtcc    56880
tgttctgttc ctattttttct gagaaatcag acagaacttc cccacctaca gcatcaagca    56940
gctactttat aggtgaagaa gtgcaaagag aagcaataag gataatcacc acttggctaa    57000
tttagtctct tcctctcagc ccacaaagga ctggtccctg tggtacattt tctaaggctt    57060
ttcccagtca gctgtgctgt agcaaatgaa atgtttggct agataaagag ctgaggtatt    57120
agtgctgggg cggcgagcag tgtctggagc aagaaaaggc aaacgaggga ttctgcgagt    57180
ggcagaacta agcctgattt tgaatggcgt tgtggctggc ggacttgtaa attatatgag    57240
aggctgtgct gtgagctcac cctaatagac atctgagaac tcacctgtca atcgcggttc    57300
ctctgctgtg tgggttttat ggtgtctagt gagctgcaag ctctaatgct ttcccaggtg    57360
cagggcagtt gtggcattgc tctcctacag aaactctcac ttgctggctg aggatgttta    57420
ggaagtcctt ggttgctaga aaaaatatat tgaagtgctt ttttttgtttg tttgtttttcc    57480
attcttgtgt gaaattttgt tggaatcaca gaatcataga ggttgaaaga gaaactctgg    57540
aaattatcaa gttcaacccc ttgctaaagc aggcttcata cagtaggttg cagttacaac    57600
atttgctggg gaaatgaata tgaagatctg tctataaaga gtgttcccat agcacttgtt    57660
tctttaggaa agcatgctga aattctaaag gctgtgccta tctgaagaga tactttgcaa    57720
gtggtgcaac taaatgctgc tcttggtgga gagatggctg gagatggatc gatggttggg    57780
tgatcttcgt ggtctttttcc aactttaatg attctatgat tctatactct ttacacagaa    57840
tcagctggga atagagtgag agtctcctga ttccccacca aattcctttg attgatgctt    57900
ggtgtggaag cagagctctg ggacacgttg gtgagtgtga aaactggaaa acattgacag    57960
ctatagttta aatagttcag ggaggagagg cagccatcct atgtgggact ctgcacacgg    58020
ctatgagagc atcagtgcgc ttctccaccc caacccaaca aatttagagc catcctccaa    58080
aatagccagg gaacaacgca taattggttt cacagacaac acattctcat gctgtgattt    58140
atttcgtaat gtctggtgag tgtcatcacg ccgtgctcaa agcctggagc tggcattcag    58200
cgaggaccca gagaatgaaa attaccagct tccccgatga atcaccactt tgaaaattca    58260
cccttgtgag aatcctgtga ctattcagaa aaaaaaaaa aaaagaagaa gaagaagaag    58320
aagatattac aggcccaagt ctatcagtca tgtaattagc ccttttctagg tttgatgtgg    58380
acagggcggc attcctaaag caccataaac acggccggga ccaataatgg ctctagaatc    58440
gaagcggaga agttctcaca attaaggtga ggaatgaggc cagcagcgga taggtacata    58500
aatacacgga ggcagggccg tgagcacgct gtgggcttgt ggctgagaca acacctccca    58560
aaccggtcgc ttgccgggga ctaaagagc agcatgaagg caacaggcac ctcggtgctc    58620
ctcagcctgc tgctgctgct gtcgttcttc tcgggtaagt tatatttctg tagcctagaa    58680
agaaacttta tgacgagagc aacttcgagag agccttgatc aacggatgac aggcttgaag    58740
agaaagctga gcaagtagaa aatatctgcg ggactcgctt gcttgtgtca catctttcca    58800
```

```
ttcctcgtgt gcctccgcag tgaataacac tgtggaggtg tcactgggag acagaatgag    58860
caaattgtaa gcagctcgtt cagcagaggc accaaagcag agcgtaatta tgagttttgg    58920
tggaaatgtt tgctggagag ctttgctgaa ccagttagaa aagaaactca tacctcaggg    58980
tcatcagctc ctgttctgat gctaagcact tgggggttgg tgttctcctc agagatgtgg    59040
cagcgtaatt agatgaaagt ttcagcttcc aaatacgttg cagaggaggg ctcgaaaatt    59100
aaattcagat gtcctcgagg aacccgaaca aagagggcaa attgaaaggg tccagcgttt    59160
atttatcttg aggtttacac gtctctctgt tggtctgggg aggctggctg atggtttggg    59220
ggtgtgtagg gcacaccggg gtgctcaaat gctcgcgtgc ggccgatgcg aatgtggaag    59280
cgttgcggtg gccattactg aagactgcag accaaggatt atttatactt gtttttctgt    59340
gaataatttg aataaagaat tcgcttgaga aaatcgcagg ctgtgcatgg agagaagagg    59400
tgaattactt tgtacacatc attaattatg aaatattcat ctgtctttaa ttgagtctta    59460
attggggctg ggttccgtca gagtgctaaa gcttctttcc aaggccaggc agaatagcag    59520
caaactctgt gatctcaaat aagataaaca gatgccaaga gacgttctca caaagtcttg    59580
tgtagctgca tgtaatattt ataaaaatta tctaatgagc tgttttgtaa ataatatgca    59640
gatagcccta acggcggctt ccctgtccag cctagctgag gatgtgacag atacagcagt    59700
ggcaaggatc aaacactgaa aggcatcgca gcaggcagaa gctgggtggg gtgatggatg    59760
gtcccgctga gcgtgatgct gcaatgctcc cagcctgcac cctaaccaaa gggatgcccc    59820
attgcaatgc gccccagccc ctgcagcgct gtgtgcagcc cactccctgt ccccgacacc    59880
acaggatcca tcccgtggct gtgacctggc cccatgcaaa gtttgcaggc aggaaatagc    59940
aaagaggatg gactgattgt ctccaggccc agagcctgtg cctgcagcag gtattttgc     60000
tctgctgctg tctggcactg cctgttctgc cccagatcac gccaggctat ccctttgtat    60060
ctcatccgga tgaggctgtt ctgggagcct cggctgtgct gtactgcaga cggctctgat    60120
gctgactgcg gggtctcctc catctcccct gtgtgctttt gttaccgtac tggccagttt    60180
tgtaattcag aggtgcaaga gcctaaaagc cataagactc aatgaagctt taaaatctct    60240
gctgagagag gctcagctct tacatagctc cccgcttccc cggcggtggc tgcctgccag    60300
ggagatgggt ttatgtgtct gtggtgcagt tagcagctga atgactgatt acatggtatt    60360
ttagtaacat ttttcaaata gcaaaatact gaaaagcaat tccgataatg tatttcctac    60420
ccctcctcca ccacacagaa cggcagagga gggaaaacct ggtgtgtgct gtgctgcagt    60480
ttgcaagggg atttgtgact tcggttcagt cctctcagaa aataatgcta atgtggataa    60540
aatctttttt tttgttgcaa ttctaggtgt agcagctcaa gacattgaag aggttagtgc    60600
agctctttct gctttctgaa tctgcatttt ctcctggctc tggaagaatg cttttctaac    60660
agatcttggt gcattggtgc atgctgaact gctttgggtt ttgctgggat caggtgggtc    60720
ctgccaaggt gccccaatgc ttcggagtgc tcacacagta caggggtgtt agctatggcc    60780
acagtagcaa acaagttggg gatgatttag ctggtttagc acatgctccc catggtctga    60840
tccagcacag ggctgtctgc agtatcgctt ctgtctgctt tgctcctcca cgaaacaaat    60900
gtgatatcag gagtgatata ctcctttaaa ccatatccat aactgggggct tgtccaaaag    60960
cctgttcact tcatagaatc attaaggttg gaaagaccac tatggtcatc gagtgcaacc    61020
actccatgcc cagatccctg tgtatggcag ccccaggcca cgtggtggtg tgagctgcat    61080
ggtaccgggc actgatatgg ggctgcatca gtgctgatgc tctcctgttg aacccactca    61140
```

```
tgttcttgga acaccagagc tgctccctgg tggtgacagc ttccctcctc tgccacaggg   61200
cagaaattcc cccatttcag ccagttctga caggcctttg tttttcaagt aagcaggccg   61260
tgcctcgttg ctgcttttgg cctctgggtg ggaagaagat cacattagag atcttctttc   61320
ctgtttggaa agcgaaaccc gacggtttat tgctgttatt attttttgatt tcttttgcag   61380 atctgcaaag agttcttaaa caggagcgtg ttctgcacca gggagtccaa ccctcactgc   61440
ggcacggatg gcgtgacgta cggcaacaag tgtgccttct gcaaggccgt gctgtaagtg   61500
ggggcggtgg gatacggacc cacacaggga tggtccactt ccaacccgc gctgctgctc    61560 ccctcacaca gagcaatccc tggccataga atcatagaac tagagaatgg ttaaggttgg   61620
aaaagaccaa taagtgcatc tagttcaaat ggcagctcct caccgccacg cttgggaata   61680
tttcagctta atgttgattc atttctaggc ttagtgtgat gctcatagcc gtacagagat   61740
ggcacagagc ctgggaggcc attgtacctg cctgtacctt ctgcgtgggc taaattgatg   61800
cacattttcc tctgtgtgcc acaggctgaa gctctccctg tccacacctc tggatgctga   61860
agtgtgtgga ggaacgcagg cttatgcatg ccaaattatt agaggaaagt catagactcg   61920
tagaatcata gattcgtttg agtcgaatgg gacctttgaa ggtcatctgg tccagcatcc   61980
ctgcaacgag cagggaaagt gctgaaatga aagtctgaat ggacttagtg gaaaagtaca   62040
caaaatctca gaggaagggc tgcagtttct cctctcctgt ctcctctaaa ggagctgtaa   62100
taggagccaa cacctctgga ctgaaggcct gcaaaaattg atttatcctt atcaatcctg   62160
cactctggag gctgccttat cctaaggaaa attagagaag agggaaagat ggcttgatgc   62220
tccctgtgag gcaccagagt gaggcaaatg atcgtgctcg gagggacaag ctccctgtcc   62280
cagccgctgt gtctgtgctg gatgccatac actgctttgt ttccataccg ctccttttac   62340
aggaggagtg gagggaagat acgattgaag cacatgggga agtgctgagc ctgagcacca   62400
agcactgatc ttcgtcggtc acaggtgcag gagcctgggc acggcagcag ctgtcctcat   62460
ctctgccata tctgctcaat aaagtaaagc tcagcacacc tccttgactg gattccttt    62520 tccataacac ccggataagc cttccatgca gccgtgctag cagctaaaat gtttgccgca   62580
ctgtgctgtt acatcttaga atcacagaat caggcaccat gctgcctgag caggagcaat   62640
gattcccaca gctcttccat gccatgccat gccatgccat gccatgccat gccatgccat   62700
gccatgccat gccatgccat gccatgccat gccatgccat cccatcccat cccatcccat   62760
cccatcccac tgacaaatgg acacatggcc acccagcttg actgtcccat gggtgggtga   62820
cagcatgcaa cgttgcctct cagcagcctc cccatatgtg tccctctcgc tgaggtgtga   62880
gcatgaaggt ggcagagagc tatgagtggt gtggctgtgg atgcctcatc tgcttgggaa   62940
gccagaagca aacaggctga ggctgaggag tgttgctgca tgtaagcctg caccgggaag   63000
gtggcagggg aagctggctt taggcagaaa cacaaaggct ttgctttcct tgtgtgtcct   63060
aagagaggac tttgcctcaa agactgtcaa ctcgccagca tcaggttgca gttgcacaca   63120
aacttgattt ctttctttag ttttcacact gctgctctct ctctccttga tgctggctgg   63180
aaaatccttc tttgcgccag cgagggaaaa taaagcctat agtctctccc cattcgctgt   63240
acaaaatata cacagggaaa tgcttgtggc atccctcgt taaaacgttg gcagcacatc    63300
aatgggactc tactcactta atgttgaaca cttaagtttc aaagggagct ttagattta    63360 tcgtgaggtc agccaactca ttttgcaaac acctctatgc tgagcatctc agctcctgga   63420 tggtgttttgg acagagctga gtgtttgcct gtggtgccac gctgcaggct ttgaagtgaa   63480
ttgggacatt atattttgta gccaaggaga gttgcagttt gctttgttcc aattcagatg   63540
```

```
tttctttagt aaacacaaca gctagacctc cagaacatgg ataagcttga ggggaggaaa   63600
aagcacctcc tgcacgagga cagctgatca caaaggaccc cagtgggcag tgggagaacc   63660
ttcatcatcc tctctaccgc ctggatcagg atgagccctg catacccttt ccaactggag   63720
ttaccctgtg agccaacttg tggctctgga gtagtgctgt atctcaatac agtttctcag   63780
atgggaagag gcatttcaat gagagggggg atatgggaca tttctatgcc tgagatggct   63840
ctcggagact ccaaaagcct cacggcgtat ccccatgcct aatccttttt aatctggagg   63900
ctgaaataac aaggacagat cacaagagaa cagaagcggc gagacttctc tgctttataa   63960
tcagcctgca ttttgctctt tcagtgcaaa cagcaaatag aaccgcctct gtaccctcc    64020 agacccaacc accatcccca gcaacactgt ggcaggctgg agaagggtgg ctctgcccct   64080
ccttgcctca actggttgtg tcagcacgac cataaccaga gctctccttg ccccagctg    64140 ggcttatcca tgtaaacctc tcagtgcccc aggagctggc tggtggtcct gtccatttca   64200
ctttcctcca gcaggtgttc cctttaacaa gcatccaagt gcctggagca ggagcaggca   64260
ctgcagaaga tgagctcagg caaggacatg gcatgtgggg atccatgctg ttgtgcaatg   64320
cagatgacgt tagatacgtg caaagcagat ctcagcaatc acccaacgac tcataactgc   64380
aatcatggaa cgcaattgca tctggaagta aaaagcaca gtgataccag gaagctcttg    64440
ttaatggcac agccattttg gagcaatttg cccaggtggg gagagccctc acagcgcctt   64500
cagtcacagg gagtggtgtg agtgccccca tggctgctcc cagccccag ccctgggtga    64560 tgggggtcac ttggctgtaa ccctctgaac acagggacag tgacagagcc ctctggcctg   64620
gctgagctct tggctacgtc cagctgcagt cctgggcaca tactgaacca gaaagcaagc   64680
attcagctgg tattttttcct ttaatttcct tcctccacat tttaagttgt gggattttt   64740 tttttttttt ttgacagctt tgagagatga gtgagtcacg aagcactcga gatctctatt   64800
agataacaga gcatctctgc agctcttcct ggggagggga ttccttggac caagggccaa   64860
ggctgggtga gaattgtccc agcatcacag tggctgctcc atcacctgac acagcccctc   64920
tgcagtgaaa caaggaagc attacatctt tgcacggctg ctttcactga acaaaagcg    64980 ctgcttcaca gctgagcacc atgatgaagg ggaaggagca tctccatgat gaaggggaag   65040
gagcatctcc acatctccat cacgagctct gctctgctgg tgatgcggct gacaccatgg   65100
tgtgccctga ctcctggccc atttaactgc tgtgcaccag tgcctcctcc ccagcatagc   65160
cctgtgtccc tgccacaact cattgcaatc ctttgtccta cttcttccct tgacattcac   65220
agctcttgat aaggcttttt gagccactcc tggctgatgt gggctggtgg ttcctgctgc   65280
agggttccca ccacccagct gggcagcatt cggttgttgt tccagttccc aggggattgg   65340
gacagattgg aagggtcttt gggactgtgg aagagtatct cctgaagtca gggcagactg   65400
ctcagcgctt tgtcccatcc agacttgaaa acatccaagg gtggagaaca cacagactcc   65460
ctgggctgcc agtcccagag tttgactgtc atcacgttga agacttttg ccttgtctcc    65520 atttgcaacc tctttccttt cagctgcccc atctctcagc catgcaccac tggggagccc   65580
agctctgtct ggtcaggaac agagcccttta cagagccaca gcatcctcct gaagtgtcca   65640
tctcaccact cagcctcagc aagtgctcca gccctcaact cccatttcc attatctttc    65700 tatcactgga tatgggaggg aaggcagagc tgtggggcca agagaaacga ttgctcagga   65760
ggcagttggg agaactttat tgcaaagcac tgaagagata taaagtgaca tttgcaggaa   65820
aaagtagaag ggtatctgtg tgtgttggtt cctttaagga ttagagagca gctgagcttt   65880
```

```
gggatgagag ggctcccaga tgctgtgaat cagctaacag atccctccac cccgtcattg   65940
gtggtgaagt taaatagggg cccaggggaa acatcagggt tgttttttctt tttacggact   66000
ccagagcaag gagaaggtga gggggttgtg ctttggaatg ggagtgaaag agtttgttgg   66060
tgttttcctc tccccagaat aagtagtgtg gtgtaggagc gtctcatagg agtagctgcg   66120
ttaattgtgg ctggtgttag catcctataa tgttgctcca gaaatgctgg agcaggctta   66180
taatgatgtg tatgtattac cataatacat gaagggagaa tggggggggg ggggtagat   66240
ttaagatgta tgcccttaga aaggcgggtg tcacttaaag aagtacttgc tttatagctc   66300
cagtgataga attcattgag atactctgaa cctatgggc atgaagtgac cagatcttca   66360
gtttggtcag ctctgggggt ttctgggggg agcggggata gagcctcaat ccaggtctga   66420
aagacaaggc tgagatgtgc tgggcctggg gtgctgccct gagcaacgtg gggctggccc   66480
tagagagcag cattagtgcc tgcagcaggg ctggcccttg tgcccagtgt gtggggtaag   66540
gtggggaacg taggtgctgc ataatgtggt gcttctgatc taaaactgct ctgttaattg   66600
ggagtgacca gagatggccc tatggctttc ttcccaaaga gctctgtgtc cttctctgca   66660
gggtaatctg tgataaaaac atcgcctatg ctctgccctg cagatgcagg ggttttttgtc   66720
atcctccttc tcgagacata ctctaatcct tacgcaagca gggagctcca agcttttggt   66780
gataacctct caaggaggag ctggaagggc agctctgccg agcagtgact gcgctgcacg   66840
gggcgcatcc tgcaggaggc ggtggtgtaa gcgggactcc gctcgttccc ggctatgggg   66900
ctccccctgc tgaccgccgg gcggtggcca ggagacctcg gggccgctgc tgcccctcgg   66960
tggtgctttt cgggacagct ttcaggatgg ggcagcccag ctgctctcgc ggggaattaa   67020
gcggctcggt gcagggcggc acggcgctga gctgccccag caaagcgccg ctcgtcccgc   67080
ggcaccttcg gtagatgctc tctgcttggc agctccttgg tcgttctctt ggccggtggc   67140
caccccagca tcgctcgggg ctcggtgcca tcccccccag ggcctgcgga ggtgccggtg   67200
cccgtcccgg gggtggcgga cgggcggtgc agtaccgatg ctgggcgctg ggtgctgccg   67260
cagaccgagc ggcgctgcgc ggctccgggg cgctcctgga gtgcgagctg agcaacctgg   67320
tagaaaaata agtgttgtcc cgtgataaac gtcatcgtgc tgagctctca gactctgcca   67380
gaggcctgaa tgaagctgcg tcaggggaga atcaggttgg ggctaaggaa aggtcctgcc   67440
ccagagggcg gtgggtatag aagggtgcc cagggcagtg ggtgcagtgc tgggctccca   67500
gagctggagg agcgtctgga cagtgctcag gtttggatgt tgggtggttt tctgaaggga   67560
cggattctgg gctcgtttat cctgagggtc ccttccaact tgggttgttc tattcaatga   67620
atattgttta tgttcattct attctatgat cttgttcagg ctctcactgc tgcctccaag   67680
ggttcagctc ccccagagct ggcagggctt cagccacttg cttacagtgc tcatttcatg   67740
cctggcccat ggcttctgcc tgagccttgt gggagatcag ctgctgccag aaacccagcc   67800
ctcagcactc cacttgccca gcttgctgcc ttagtagtct aacttggcag tggtctgaca   67860
tgacttgagg ttgttttttta tttccaaggt gccactgact tttttccttc catagtttct   67920
ggaagcattt ccttcctact tgactgagtc gtgctctgtg gatctgtaat tatccacctt   67980
ggctatgtgt cctttacggg attttatatg ttaacctccc aagatcattt tgctgctctc   68040
atcttagtgc ctgctgtgag ctccaccagc accacactgg atgagctgca ggctgaggcc   68100
gggcacctct cctgactctg ctcttctctg accccagagc tgtgcagttg ggatcctaac   68160
accatgcaga tgctccagga cctgcaccga gccccagcac tggcactcat ctcttctttc   68220
caccccctctg agagcaacaa gtggctctgc aatggcaatg taagtgaaac cgggcgggta   68280
```

```
tcttagagca cctggaagct tgcatgcctg caggtcgact ctagaggatc cccgggtacc   68340
gagctcgaat tcgccctata gtgagtcgta ttacaattca ctggccgtcg ttttacaacg   68400
tcgtgactgg gaaaaccctg gcgttaccca acttaatcgc cttgcagcac atcccccttt   68460
cgccagctgg cgtaatagcg aagaggcccg caccgatcgc ccttcccaac agttgcgcag   68520
cctgaatggc gaatgcgcc  tgatgcggta ttttctcctt acgcatctgt gcggtatttc   68580
acaccgcata tggtgcactc tcagtacaat ctgctctgat gccgcatagt taagccagcc   68640
ccgacacccg ccaacacccg ctgacgcgaa cccttgcgg  ccgcatcgaa tataacttcg   68700
tataatgtat gctatacgaa gttattagcg atgagctcgg acttccattg ttcattccac   68760
ggacaaaaac agagaaagga acgacagag  gccaaaaagc tcgctttcag cacctgtcgt   68820
ttcctttctt ttcagagggt attttaaata aaacattaa  gttatgacga agaagaacgg   68880
aaacgcctta aaccggaaaa ttttcataaa tagcgaaaac ccgcgaggtc gccgccccgt   68940
aacctgtcgg atcaccggaa aggacccgta aagtgataat gattatcatc tacatatcac   69000
aacgtgcgtg gaggccatca aaccacgtca aataatcaat tatgacgcag gtatcgtatt   69060
aattgatctg catcaactta acgtaaaaac aacttcagac aatacaaatc agcgacactg   69120
aatacggggc aacctcatgt ccgagctcgc gagctcgtcg acagcgacac acttgcatcg   69180
gatgcagccc ggttaacgtg ccggcacggc ctgggtaacc aggtattttg tccacataac   69240
cgtgcgcaaa atgttgtgga taagcaggac acagcagcaa tccacagcag gcatacaacc   69300
gcacaccgag gttactccgt tctacaggtt acgacgacat gtcaatactt gcccttgaca   69360
ggcattgatg gaatcgtagt ctcacgctga tagtctgatc gacaatacaa gtgggaccgt   69420
ggtcccagac cgataatcag accgacaaca cgagtgggat cgtggtccca gactaataat   69480
cagaccgacg atacgagtgg gaccgtggtc ccagactaat aatcagaccg acgatacgag   69540
tgggaccgtg gttccagact aataatcaga ccgacgatac gagtgggacc gtggtcccag   69600
actaataatc agaccgacga tacgagtggg accatggtcc cagactaata atcagaccga   69660
cgatacgagt gggaccgtgg tcccagtctg attatcagac cgacgatacg agtgggaccg   69720
tggtcccaga ctaataatca gaccgacgat acgagtggga ccgtggtccc agactaataa   69780
tcagaccgac gatacgagtg gaccgtggt  cccagtctga ttatcagacc gacgatacaa   69840
gtggaacagt gggcccagag agaatattca ggccagttat gctttctggc ctgtaacaaa   69900
ggacattaag taaagacaga taaacgtaga ctaaaacgtg gtcgcatcag ggtgctggct   69960
tttcaagttc cttaagaatg gcctcaattt tctctataca ctcagttgga acacgagacc   70020
tgtccaggtt aagcaccatt ttatcgccct tatacaatac tgtcgctcca ggagcaaact   70080
gatgtcgtga gcttaaacta gttcttgatg cagatgacgt tttaagcaca gaagttaaaa   70140
gagtgataac ttcttcagct tcaaatatca ccccagcttt tttctgctca tgaaggttag   70200
atgcctgctg cttaagtaat tcctctttat ctgtaaaggc ttttgaagt  gcatcacctg   70260 accgggcaga tagttcaccg gggtgagaaa aaagagcaac aactgattta ggcaatttgg   70320
cggtgttgat acagcgggta ataatcttac gtgaaatatt ttccgcatca gccagcgcag   70380
aaatatttcc agcaaattca ttctgcaatc ggcttgcata acgctgacca cgttcataag   70440
cacttgttgg gcgataatcg ttacccaatc tggataatgc agccatctgc tcatcatcca   70500
gctcgccaac cagaacacga taatcacttt cggtaagtgc agcagcttta cgacggcgac   70560
tcccatcggc aatttctatg acaccagata ctcttcgacc gaacgccggt gtctgttgac   70620
```

```
cagtcagtag aaaagaaggg atgagatcat ccagtgcgtc ctcagtaagc agctcctggt   70680
cacgttcatt acctgaccat acccgagagg tcttctcaac actatcaccc cggagcactt   70740
caagagtaaa cttcacatcc cgaccacata caggcaaagt aatggcatta ccgcgagcca   70800
ttactcctac gcgcgcaatt aacgaatcca ccatcggggc agctggtgtc gataacgaag   70860
tatcttcaac cggttgagta ttgagcgtat gttttggaat aacaggcgca cgcttcatta   70920
tctaatctcc cagcgtggtt taatcagacg atcgaaaatt tcattgcaga caggttccca   70980
aatagaaaga gcatttctcc aggcaccagt tgaagagcgt tgatcaatgg cctgttcaaa   71040
aacagttctc atccggatct gacctttacc aacttcatcc gtttcacgta caacattttt   71100
tagaaccatg cttccccagg catcccgaat ttgctcctcc atccacgggg actgagagcc   71160
attactattg ctgtatttgg taagcaaaat acgtacatca ggctcgaacc ctttaagatc   71220
aacgttcttg agcagatcac gaagcatatc gaaaaactgc agtgcggagg tgtagtcaaa   71280
caactcagca ggcgtgggaa caatcagcac atcagcagca catacgacat taatcgtgcc   71340
gatacccagg ttaggcgcgc tgtcaataac tatgacatca tagtcatgag caacagtttc   71400
aatggccagt cggagcatca ggtgtggatc ggtgggcagt ttaccttcat caaatttgcc   71460
cattaactca gtttcaatac ggtgcagagc cagacaggaa ggaataatgt caagccccgg   71520
ccagcaagtg ggctttattg cataagtgac atcgtccttt tccccaagat agaaaggcag   71580
gagagtgtct tctgcatgaa tatgaagatc tggtacccat ccgtgataca ttgaggctgt   71640 tccctgggg tcgttacctt ccacgagcaa aacacgtagc cccttcagag ccagatcctg   71700
agcaagatga acagaaactg aggttttgta aacgccacct ttatgggcag caaccccgat   71760
caccggtgga aatacgtctt cagcacgtcg caatcgcgta ccaaacacat cacgcatatg   71820
attaatttgt tcaattgtat aaccaacacg ttgctcaacc cgtcctcgaa tttccatatc   71880
cgggtgcggt agtcgccctg ctttctcggc atctctgata gcctgagaag aaaccccaac   71940
taaatccgct gcttcaccta ttctccagcg ccgggttatt ttcctcgctt ccgggctgtc   72000
atcattaaac tgtgcaatgg cgatagcctt cgtcatttca tgaccagcgt ttatgcactg   72060
gttaagtgtt tccatgagtt tcattctgaa catcctttaa tcattgcttt gcgtttttt   72120 attaaatctt gcaatttact gcaaagcaac aacaaaatcg caaagtcatc aaaaaaccgc   72180
aaagttgttt aaaataagag caacactaca aaggagata agaagagcac atacctcagt   72240
cacttattat cactagcgct cgccgcagcc gtgtaaccga gcatagcgag cgaactggcg   72300
aggaagcaaa gaagaactgt tctgtcagat agctcttacg ctcagcgcaa gaagaaatat   72360
ccaccgtggg aaaaactcca ggtagaggta cacacgcgga tagccaattc agagtaataa   72420
actgtgataa tcaaccctca tcaatgatga cgaactaacc cccgatatca ggtcacatga   72480
cgaagggaaa gagaaggaaa tcaactgtga caaactgccc tcaaatttgg cttccttaaa   72540
aattacagtt caaaaagtat gagaaaatcc atgcaggctg aaggaaacag caaaactgtg   72600
acaaattacc ctcagtaggt cagaacaaat gtgacgaacc accctcaaat ctgtgacaga   72660
taaccctcag actatcctgt cgtcatgaa gtgatatcgc ggaaggaaaa tacgatatga   72720
gtcgtctggc ggcctttctt tttctcaatg tatgagaggc gcattggagt tctgctgttg   72780
atctcattaa cacagacctg caggaagcgg cggcggaagt caggcatacg ctggtaactt   72840
tgaggcagct ggtaacgctc tatgatccag tcgattttca gagagacgat gcctgagcca   72900
tccggcttac gatactgaca cagggattcg tataaacgca tggcatacgg attggtgatt   72960
tcttttgttt cactaagccg aaactgcgta aaccggttct gtaacccgat aaagaaggga   73020
```

```
atgagatatg ggttgatatg tacactgtaa agccctctgg atggactgtg cgcacgtttg   73080
ataaaccaag gaaaagattc atagccttt  tcatcgccgg catcctcttc agggcgataa   73140
aaaaccactt ccttccccgc gaaactcttc aatgcctgcc gtatatcctt actggcttcc   73200
gcagaggtca atccgaatat ttcagcatat ttagcaacat ggatctcgca gataccgtca   73260
tgttcctgta gggtgccatc agattttctg atctggtcaa cgaacagata cagcatacgt   73320
ttttgatccc gggagagact atatgccgcc tcagtgaggt cgtttgactg gacgattcgc   73380
gggctatttt tacgtttctt gtgattgata accgctgttt ccgccatgac agatccatgt   73440
gaagtgtgac aagtttttag attgtcacac taaataaaaa agagtcaata agcagggata   73500
actttgtgaa aaaacagctt cttctgaggg caatttgtca cagggttaag ggcaatttgt   73560
cacagacagg actgtcattt gagggtgatt tgtcacactg aaagggcaat ttgtcacaac   73620
accttctcta gaaccagcat ggataaaggc ctacaaggcg ctctaaaaaa gaagatctaa   73680
aaactataaa aaaaataatt ataaaaatat ccccgtggat aagtggataa ccccaaggga   73740
agttttttca ggcatcgtgt gtaagcagaa tatataagtg ctgttccctg gtgcttcctc   73800
gctcactcga gggcttcgcc ctgtcgctcg actgcggcga gcactactgg ctgtaaaagg   73860
acagaccaca tcatggttct gtgttcatta ggttgttctg tccattgctg acataatccg   73920
ctccacttca acgtaacacc gcacgaagat ttctattgtt cctgaaggca tattcaaatc   73980
gttttcgtta ccgcttgcag gcatcatgac agaacactac ttcctataaa cgctacacag   74040
gctcctgaga ttaataatgc ggatctctac gataatggga gattttcccg actgtttcgt   74100
tcgcttctca gtggataaca gccagcttct ctgtttaaca gacaaaaaca gcatatccac   74160
tcagttccac atttccatat aaaggccaag gcatttattc tcaggataat tgtttcagca   74220
tcgcaaccgc atcagactcc ggcatcgcaa actgcacccg gtgccgggca gccacatcca   74280
gcgcaaaaac cttcgtgtag acttccgttg aactgatgga cttatgtccc atcaggcttt   74340
gcagaacttt cagcggtata ccggcataca gcatgtgcat cgcataggaa tggcggaacg   74400
tatgtggtgt gaccggaaca gagaacgtca caccgtcagc agcagcggcg gcaaccgcct   74460
ccccaatcca ggtcctgacc gttctgtccg tcacttccca gatccgcgct ttctctgtcc   74520
ttcctgtgcg acgttacgc  cgctccatga gcttatcgcg aataaatacc tgtgacggaa   74580
gatcacttcg cagaataaat aaatcctggt gtccctgttg ataccgggaa gccctgggcc   74640
aacttttggc gaaaatgaga cgttgatcgg cacgtaagag gttccaactt tcaccataat   74700
gaaataagat cactaccggg cgtatttttt gagttatcga gattttcagg agctaaggaa   74760
gctaaaatgg agaaaaaaat cactggatat accaccgttg atatatccca atggcatcgt   74820
aaagaacatt ttgaggcatt tcagtcagtt gctcaatgta cctataacca gaccgttcag   74880
ctggatatta cggccttttt aaagaccgta agaaaaata  agcacaagtt ttatccggcc   74940
tttattcaca ttcttgcccg cctgatgaat gctcatccgg aatttacatc tggaattacg   75000
tatggcaatg aaagacggtg agctggtgat atgggatagt gttcacccct gttacaccgt   75060
tttccatgag caaactgaaa cgttttcatc gctctggagt gaataccacg acgatttccg   75120
gcagtttcta cacatatatt cgcaagatgt ggcgtgttac ggtgaaaacc tggcctattt   75180
ccctaaaggg tttattgaga atatgttttt cgtctcagcc aatccctggg tgagtttcac   75240
cagttttgat ttaaacgtgg ccaatatgga caacttcttc gcccccgttt tcaccatggg   75300
caaatattat acgcaaggcg acaaggtgct gatgccgctg gcgattcagg ttcatcatgc   75360
```

```
cgtttgtgat ggcttccatg tcggcagaat gcttaatgaa ttacaacagt actgcgatga      75420
gtggcagggc ggggcgtaat ttttttaagg cagttattgg tgcccttaaa cgcctggttg      75480
ctacgcctga ataagtgata ataagcggat gaatggcaga aattcgatga taagctgtca      75540
aacatgagaa ttggtcgacg gcccgggcgg ccgcaagggg ttcgcgttgg ccgattcatt      75600
aatgcagctg gcacgacagg tttcccgact ggaaagcggg cagtgagcgc aacgcaatta      75660
atgtgagtta gctcactcat taggcacccc aggctttaca ctttatgctt ccggctcgta      75720
tgttgtgtgg aattgtgagc ggataacaat ttcacacagg aaacagctat gaccatgatt      75780
acgccaagct atttaggtga cactatagaa tactc                                 75815

<210> SEQ ID NO 37
<211> LENGTH: 26
<212> TYPE: DNA
<213> ORGANISM: chicken

<400> SEQUENCE: 37
cgggcagtac ctcaccatgg acatgt                                               26

<210> SEQ ID NO 38
<211> LENGTH: 21
<212> TYPE: DNA
<213> ORGANISM: chicken

<400> SEQUENCE: 38
attcgcttaa ctgtgactag g                                                    21

<210> SEQ ID NO 39
<211> LENGTH: 20
<212> TYPE: DNA
<213> ORGANISM: chicken

<400> SEQUENCE: 39
cgaggaactt gaagcctgtc                                                      20

<210> SEQ ID NO 40
<211> LENGTH: 20
<212> TYPE: DNA
<213> ORGANISM: chicken

<400> SEQUENCE: 40
ggcctgcact ctccatcata                                                      20

<210> SEQ ID NO 41
<211> LENGTH: 1680
<212> TYPE: DNA
<213> ORGANISM: chicken
<220> FEATURE:
<221> NAME/KEY: misc_feature
<222> LOCATION: (823)..(1203)
<223> OTHER INFORMATION: n is a, c, g, or t

<400> SEQUENCE: 41
gatttcactc atctcctaat aatcaggtag ctgaggagat gctgagtctg ccagttcttg         60
ggctctgggc aggatcccat ctcctgcctt tctaggaca gagctcagca ggcagggctc        120
tgtggctctg tgtctaaccc acttcttcct ctcctcgctt tcagggaaag caacgggact       180
ctcactttaa gccatttggg aaaatgctga atatcagagc tgagagaatt ccgcccctct       240
ccctcccccc ccctaacgt tactggccga agccgcttgg aataaggccg gtgtgcgttt        300
gtctatatgt tattttccac catattgccg tcttttggca atgtgagggc ccggaaacct       360
```

```
ggccctgtct tcttgacgag cattcctagg ggtctttccc ctctcgccaa aggaatgcaa    420
ggtctgttga atgtcgtgaa ggaagcagtt cctctggaag cttcttgaag acaaacaacg    480
tctgtagcga cccttttgcag gcagcggaac cccccacctg gcgacaggtg cctctgcggc   540
caaaagccac gtgtataaga tacacctgca aggcggcac  aaccccagtg ccacgttgtg    600
agttggatag ttgtgaaaag agtcaaatgg ctctcctcaa gcgtattcaa caaggggctg    660
aaggatgccc agaaggtacc ccattgtatg ggatctgatc tggggcctcg gtgcacatgc    720
tttacgtgtg tttagtcgag gttaaaaaac gtctaggccc cccgaaccac ggggacgtgg    780
ttttcctttg aaaaacacga tgataagctt gccacaacca tgnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnnnn   1200
nnnacggtgg cggcgccatc tgtcttcatc ttcccgccat ctgatgagca gttgaaatct    1260
ggaactgcct ctgttgtgtg cctgctgaat aacttctatc ccagagaggc caaagtacag    1320
tggaaggtgg ataacgccct ccaatcgggt aactcccagg agagtgtcac agagcaggac    1380
agcaaggaca gcacctacag cctcagcagc accctgacgc tgagcaaagc agactacgag    1440
aaacacaaag tctacgcctg cgaagtcacc catcagggcc tgagctcgcc cgtcacaaag    1500
agcttcaaca ggggagagtg ttagggatcc actagtccag tgtggtggaa ttcaccacag    1560
gatccccact ggcgaatccc agcgagaggt ctcacctcgg ttcatctcgc actctgggga   1620
gctcagctca ctcccgattt tctttctcaa taaactaaat cagcaacact cctttgtctt   1680
```

<210> SEQ ID NO 42
<211> LENGTH: 2340
<212> TYPE: DNA
<213> ORGANISM: chicken
<220> FEATURE:
<221> NAME/KEY: misc_feature
<222> LOCATION: (823)..(1224)
<223> OTHER INFORMATION: n is a, c, g, or t

<400> SEQUENCE: 42

```
gatttcactc atctcctaat aatcaggtag ctgaggagat gctgagtctg ccagttcttg     60
ggctctgggc aggatcccat ctcctgcctt ctctaggaca gagctcagca ggcagggctc    120
tgtggctctg tgtctaaccc acttcttcct ctcctcgctt tcagggaaag caacgggact    180
ctcactttaa gccattttgg aaaatgctga atatcagagc tgagagaatt ccgcccctct    240 ccctccccccc ccctaacgt tactggccga agccgcttgg aataaggccg gtgtgcgttt    300
gtctatatgt tattttccac catattgccg tcttttggca atgtgagggc ccggaaacct    360
ggccctgtct tcttgacgag cattcctagg ggtctttccc ctctcgccaa aggaatgcaa    420
ggtctgttga atgtcgtgaa ggaagcagtt cctctggaag cttcttgaag acaaacaacg    480
tctgtagcga cccttttgcag gcagcggaac cccccacctg gcgacaggtg cctctgcggc   540
caaaagccac gtgtataaga tacacctgca aggcggcac aaccccagtg ccacgttgtg     600
agttggatag ttgtgaaaag agtcaaatgg ctctcctcaa gcgtattcaa caaggggctg    660
```

```
aaggatgccc agaaggtacc ccattgtatg ggatctgatc tggggcctcg gtgcacatgc    720
tttacgtgtg tttagtcgag gttaaaaaac gtctaggccc cccgaaccac ggggacgtgg    780
ttttcctttg aaaaacacga tgataagctt gccacaacca tgnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnntcagct agcaccaagg gcccatcggt cttccccctg   1260
gcaccctcct ccaagagcac ctctgggggc acagcggccc tgggctgcct ggtcaaggac   1320
tacttccccg aaccggtgac ggtgtcgtgg aactcaggcg ccctgaccag cggcgtgcac   1380
accttcccgg ccgtcctaca gtcctcagga ctctactccc tcagcagcgt ggtgaccgtg   1440
ccctccagca gcttgggcac ccagacctac atctgcaacg tgaatcacaa gcccagcaac   1500
accaaggtgg acaagagagt tgagcccaaa tcttgtgaca aaactcacac atgcccaccg   1560
tgcccagcac ctgaactcct ggggggaccg tcagtcttcc tcttcccccc aaaacccaag   1620
gacaccctca tgatctcccg gacccctgag gtcacatgcg tggtggtgga cgtgagccac   1680
gaagaccctg aggtcaagtt caactggtac gtggacggcg tggaggtgca taatgccaag   1740
acaaagccgc gggaggagca gtacaacagc acgtaccgtg tggtcagcgt cctcaccgtc   1800
ctgcaccagg actggctgaa tggcaaggag tacaagtgca aggtctccaa caaagccctc   1860
ccagccccca tcgagaaaac catctccaaa gccaagggc agccccgaga ccacaggtg   1920 tacaccctgc ccccatcccg ggatgagctg accaagaacc aggtcagcct gacctgcctg   1980
gtcaaaggct tctatcccag cgacatcgcc gtggagtggg agagcaatgg gcagccggag   2040
aacaactaca agaccacgcc tcccgtgctg gactccgacg gctccttctt cctctacagc   2100
aagctcaccg tggacaagag caggtggcag caggggaacg tcttctcatg ctccgtgatg   2160
catgaggctc tgcacaacca ctacacgcag aagagcctct ccctgtctcc gggtaaatag   2220
ggatccacta gtccagtgtg gtggaattca ccacaggatc cccactggcg aatcccagcg   2280
agaggtctca cctcggttca tctcgcactc tggggagctc agctcactcc cgattttctt   2340

<210> SEQ ID NO 43
<211> LENGTH: 11
<212> TYPE: PRT
<213> ORGANISM: SV40

<400> SEQUENCE: 43

Cys Gly Gly Pro Lys Lys Lys Arg Lys Val Gly
1               5                   10

<210> SEQ ID NO 44
<211> LENGTH: 77872
<212> TYPE: DNA
<213> ORGANISM: chicken

<400> SEQUENCE: 44
attcaccaca ggatccccac tggcgaatcc cagcgagagg tctcacctcg gttcatctcg     60
cactctgggg agctcagctc actcccgatt ttctttctca ataaactaaa tcagcaacac    120
```

```
tcctttgtct tgtttaatgc tctgcctcat gcaatgtttt cttctgattt gttggacggt    180
gataccagac tcaatatgtt ccatgctcgt ggctctgggg tataacaaga acaacatctt    240
gctcccatcc ctgtcataaa aggcagaaaa ttaaatacag atgcataaac ctcggctgtg    300
tgactttgcg cataaatgac agtcagcctc cattagtgtt cagacccttt tagacagctg    360
aaatactgct acgaactgct gatgctggct gagctcccca tggtacgtgt ggtgcacttt    420
ccctgcgcag cattagcagt gaaagcagct cagggtgcgg tggtggccaa acccagggcc    480
gatcccacgg cctcctgtac ctggtcatac ccacgggcac agctgctagt gaggtgcgtg    540
cttttcagac acgtcatata agtgtgccct gcctacatgt ctgggtcctc caaatgacgt    600
tgcaaggttt atctcatctt ggaattgtcc cttactgacc accaagtgtt ttgagatgaa    660
tgccctccta ggtctggttc tgctcttgcc tgctggtctt ttctcatagt agtccttgcc    720
agcccaagta tctgagcagt gttttgcaat ccaaggacaa agtacccctc tgcctttgag    780
agtgtgacct ctgtcattgg cacattgtcc gtgaaatata ttttgctttt gtcctttgtt    840
ggtgtattga actgatgttt tcttgatcca catgagagaa actttaataa aaattataaa    900
aaataatgcc tcccttaagc atttcttttc cctgatggaa tgaggccatt caaaagaagg    960
atgctttggc ggtaaaacag aggatttatg ttgagatggg cagatgaatc aagcagtgat   1020
ttccagtttg gattgaactt ttctgggatc caggctgtgg gcctcatgtc attctgtcat   1080
catcaggcta tcagtctgct gctgcaaatc ctccccacaa cgctaatggc ttttagggaa   1140
aatcgcaatt gttagttctt tgctaatgcc cataaaactt cttccatcac ttgtccagct   1200
ccaggactcc cttcagcccc aggtttccct cttgctctct ctcccagttc agttttttctg   1260 gatttgctat gatttgatga tgcattattg acaggacaag gggaaatggt tcaaaccag    1320 aggagaggag atttagactg gacataagca agacattttt tacaatggtg gtgaggcact   1380
gacagaggtt gcccagagag gtggtggtgc cccatccatg gagacagcca aggtcaggag   1440
gggctctgag cactgatgga gctgtgggtg cccctgttca ttgcaggggg ttggaccaga   1500
tggcctttaa agatcccttc caactcaaat gcttcaatga ttctgtgatt ctattgggtt   1560
gaagcatgcc aactaagact ttccactctg gaaaacattc aattcagttc aacaacattt   1620
tccagcaaca gtgagaaagc actgcatata ggtaagcact gataacatgc acatggagga   1680
aatcctgcag cattctctct tcaggtttgt acagttgccc ttttgcccac aggaattttc   1740
catggtcctt cagcaggcac ctgtcacaca cttcactgga aataatgaag ccgagggcgt   1800
acttcacata tttaaacctg caattgctgt tgataaagaa gcattcttttg tggctcactt   1860 gtgtaagtgc catcaagatt tacaaccctg acaccagagc tggaacgctg gttatttcaa   1920
agtagggggt ggctaaacca aacgtgaatg cacacagcca cgcacacaca gatcaggtgg   1980
ccatccaagg gcagaagggc cgcattccat gagcacgatg cacttctgcc ctttgctgct   2040
gcccaggtga gtggctgtgc tcctgctccg tgcttcgtcg agtgctggct gtaaaaacac   2100
aacaaacatc ctcagactgg aaagagctgt gttctacaag gacttattta ctcctagagg   2160
gatggtgttg aaaagacttg acatcaaaga ctatcactta ggggtaata ttttagcaac    2220 agaactgagt gggtaagaac aactgtggga acagctccgc gctcggtgct agtttatgca   2280
taatgaaagc agtgacacgt acgtggtacc acgacatcca ccattgaacc tccgaaacgc   2340
tgcagaatca caaattcttt tactgaatgg aagcgagcgt ttcccgcagt catcctgaac   2400
tgagatgcaa ttggaggggc tgagcggctg cagcagcgtt aggggagttt cacctcgctg   2460
agccctcccg ttatttcagt gctgttgtgg agctgcacgc aggagctgcc gccagtccgt   2520
```

```
gccagctctg cggccctgct tccccggcac cttgcttatc tctgagcacc tgtccttgct    2580
catcctgtga atcacggaga attgcttttct cttcctccct ttcatttcgc gcgtccttct    2640
ccacccgggc tgtaaccctc ctgagaaaaa acgtagtacg gaatcgatgt tgtaaacact    2700
cagcgtggca caacgttttg cctgaaatcc cttttgtctg agagtcacac actgaattgc    2760
aagttgttta ttcaggacat gcactcacgg attttaacac taacgaagga gatgaattgc    2820
atttgtgtca cacttcctat tcccttcttt actccagacc ccactgcact gaaggtaagg    2880
gacagatctt tcaggttttt ttttttttt ctccatcatt tctttcctca aagcagtttc    2940
cgtataaatc attactaatc gcattgtgat cgagcgtttg aaagccctga gtcatcccac    3000
agcctgagca atatttgcta cagatattac cgagtgaaat ggccattttc atctgatggt    3060
ttcaaaaaaa aaaaaagat aataataata ataataataa taaataaata gcgcagcatt      3120
cagttggtgt ccaagttatt gtcacggtta ctgcagcagc actgaggatg tttacatggg    3180
atttacatca ctggaggctg aaagggcact gcaggcgtgt accgcgctat tcgctgcccc    3240
atccttaagc tcttctttga catctgctga tggtcggtgc tgggggaagc ccggggctgt    3300
gggggtctcc tggcatctgc cctgctgata gctgtgctgc tgagggtatt tctgtgagca    3360
caaggctgca tcgatccaca gggcgactgc agtgcctgcg ccgtaccccg caatttctgc    3420
tctcgggagc gcatcccaca ctgcgggtct gatggcgtaa catatgccag cgagtgttta    3480
ttccgcaatg catttctggg tgtatgaaaa taaatctctt cgctcactga gtggtgaact    3540
tcaactgtct tatcaacctc agggactgcc tggagatgga aggtggttgt gtttggcgct    3600
ctcctcttct cttgctagca agggcagcac ttttttttt aaactgggag gatttaccag    3660
ggactccttt ctttcaggta aaagaagtc acatttagca gagatcttca tctccacgtt    3720
gggtaatttg ctgaagagct cgcttccagc aaatacagtc tatttcctac agcctatttg    3780
ttcttctttt aaattaagtc tttatcgtgc ctttgaatgt tagtaataag aggaagtagc    3840
tggaatagct ttccgaatgt tctgttttgg ttaagttcct ctgtgatgta tccttaagca    3900
gagggaggga tgcacagcag aagcgcagag gttcaatctc tgaggccctg agctctttct    3960
ctccagaact cattgagttc tcaccttgct gtgccctgcg cagcgctcac atcacagccc    4020
accgggctcc agctcagaca ggaggaccct ctctggctgt gttccttaca ggggatgctg    4080
cccaaagcct cgtcctgaac tttgagtgct cctgataaag cctgaagcta tgctcaataa    4140
aaaaaaaaaa ccttcagcat tttggtcttg ctttcatact acgtatcatg ctgttgtttt    4200
tttttcttaa gatgctgtgt gattgcatca ctgcaacagt cctgggtgt gggtcttaat     4260 gggaaaatta cagggagaaa gaacgggttg tctgatttat gaagaaatca acccctccaa    4320
aaggccatga gcttctgctt tcttccagat ttccaaaaga aagccactgc tggggatgag    4380
atccagtgca gtgttcaggg catcctgtgc agacattgac tccttaggag ctgaaaataa    4440
agtagtggtg ggtacccgta ggtgtgggaa gcctttctgc agccacctgg tctgcctccc    4500
aaagcagagg atgggatgtt ttcccctccg ggcagcacca acagagggt ggcagcaggg     4560 tgaggaagat gattggcccc tctgctctgc tcttgtgggg accacatgca gtattgcatc    4620
caggcctggg gccccagcat gagaaagacg tggaactgtt ggagtgggtc cataggaggc    4680
catgaagaca atcacagggc tggagcacct ctcttatgaa gaaggctga gggagctggg     4740 cttgttcagc atcaagaagg gaaagctgag aggacacctc attggagtct tccagtactt    4800
gaagggagct tgcaagcagg aaggggaaca aacttctaca tggtctgaca gagatagaac    4860
```

-continued

```
aaggggagt ggctttaagc taaaagaggg aagatttggg tgagatgttg ggaagaaata    4920
ctttactcag aggttggtgt gacactggca ctgctgccca gagctgtggg tgccccatcc    4980
ctgtacatga gctgaaggcc agattggatg gggctctgtg cagcctgatc tggtgggggg    5040
cagccagccc atggcagggg ttggggtaga tgggttgtat ggccttttc aacccaaacc    5100 attcaatgat tctatgattc tcagataagc ctgcctgccc acatctgagc tcacggtgct    5160 cgctggggt ggggtatggt acactaaatg atgctcagag gactgcacgc aggacctgcc    5220
gcagacgttt atcacctcac ccaccactta gctgctgctt gtagttaatt acgtcagctg    5280
tcacttgtag agaatccttt gagatccttg gcctccgga aatcttggct gatgaaagga    5340
agggctcaga gtcatagcgt taatttatta ttcattaaca ccaaagtgtc ggctgtacgg    5400
gcagtgggct cacagtcaaa tagttaatga tcttaagtga caatgtgtca ctttgcagac    5460
agcagagaga acagctctcc taagggagac agcatctttc caattctgca gccattcagt    5520
gccaagctcc tctttgggac gaaagtgaag atgaggaagg caatgaggat gaggaggggc    5580
ctcaaggaac ctggctggct tggagacaag tgatgatccc agctgctctc agggtcccag    5640
cggtcttcaa agggcatctt gcaggggctg tgtcctctga acagcaaaac ccaggtcata    5700
gaggggaaag tgtgagcaga gatgggacaa atctcccatc ctgccacgga gctgcactgc    5760 taaggggtg atggggagca gcatgggacc ccagcgttcc ccccatccct gcaccaggcc    5820
cagctctgcg ggatggcgag gaggacaagg ctctgtcaca agcatcgctg gcaattatta    5880
ttttgttgtt gctgctcaat aaaatcctga cacagtacaa cacaatatcc tctcatcatt    5940
actaatctaa ctctccctcc aggaaatttc aggcaggaaa cgttgtctgc ctgccgaggt    6000
gctttatggc actgttcttt agtggtacct cagcacttcg tgtcattatc tggtgtcagt    6060
gaatttagga aatgccattc aattaccccg caaactgatt aacgcattgc gtgcagttat    6120
tttgttctgc tctattttat atcagttcct ctgttttatg tatttctcta cttgttgctg    6180
gccagaacac acctcgggcc agtctagacc ttgctgttga tgcagctttt ccccagggct    6240
tcatcagcac aaatggtttg tcaacgtggg gaaaaataaa attatgcttt aaaataaaac    6300
cacctggaga tgctgttctg gggtctggct gtgtcacagc tattgcagcg atggagctga    6360
gggattggga tgtgctgggc cggatcctca gcgctttgct ataagccaaa taattccaga    6420 caccettctt ccctcagata tcatctgtgc ttaagcagca ggagatatgc aggcagcgat    6480
cagatagctg agctgcaagg agaaatatca caagagcgcg gcttagagca ggggctttgc    6540
tcgctctaaa ttgaattccc atcctcatag gagatccagt cctgccccg tgtgcatcgc    6600 tccggtaaca gcaatgtgtt ttgctccatc ttgcagaggg tccagaagct ggggaaagga    6660
aatgtgtcgt gcgttcgtcc ctgcagcagc tcggcccata aaattaatga aaatcttttt    6720
taggtcatgg tagattacag atttctttga gatagagaat ctcaagagca gaggagaaga    6780
ttctcagaaa atagcagtga tatgagatgg cataacgctg agttggaaac tggggaggat    6840
ttccagggtt actggaaatt tacttaagca cgagagaatg catcgtgtga ctgccagtgc    6900
ttccccactc acatggctat aaccttcttg catacaatta ccatcttgga acttgaaata    6960
gctgaaagag tttatttga tcttttcaat ggatcttaca tctgcagaaa aaaaaaaaa    7020 aggctagaaa taatcctgca ctcaaactca ctttactgaa ccaccatcat gaaactccag    7080
caacacacag ggatttgggc aggcgtgttc atcttcctct tcccatttgc aacatgtgta    7140
tggcatttcc tgaagctcac tcctccaaat gcattgagac agttgttttt cattcttcct    7200
aatgcctgca tccacccatc tgctgatcgg caattatttc tatcccattc ccttctgttt    7260
```

```
cttattaatc aagctctttta tgcaatccca cgtaacactt tgcccagctg ccctgcccta    7320
accactacca attatctcat cctgttttat agaccctgta gcaagactct ggccttgctc    7380
ctcttcctct ccctgataga gcttttggtg cagggctggc tggctcctca ggtgttcaga    7440
ggatcagagg tctcccagaa ggatcttgtt aatcaaggac aggtgctggc tatatgggag    7500
gatggcaccg tatcctaaag ctctacaaga aggagacgga gctcagcctg gaggacaga     7560 gagaagcagc agcacaggtt tcaggatcca gggatggcag acctgggtgt gggctcatag    7620
gattgaagaa gggataggct gtgctcctgt agcctcactg cagaagcagc actgctatct    7680
ccccagcgaa gctgtgtgtg ccccatccct ggaggtgctc aggaccaggt gggatggggc    7740
cctgggcagt ctgagccgga gggagcagcc ggcccacagc aggggttgga atggggtggg    7800
ttttaagttc ccctccaacc aaagccattt cttgatctct gttggtggct ggtgcaagtt    7860
ctgaggaaac ctcatttca gctcaggcgt tcttgtccct ggggaaaaat caatattaat     7920
gcttcagtga ttactgctcg ccttccaaat gtgcttctga tcagttcaag aaatctgaca    7980
gtcacgtcgc tcaggatgct aagaatacaa cagaaacagc tttgaaagga acccttcaac    8040
tcttgatatt tgtgaatgag ctccaaagaa cattactcat ttattttca ggaaaatgat     8100 ttcattgaca tgaacaggcc aaagcctaca agctctgttt tgtgactgca gctccttaca    8160
ctttcagctg cattttcatg atttatgtgc ccatgatgag acttgaacac ctcccaggat    8220
aatgggaaaa gcagttctga tttcccattt aaaacgtagg ctgcctttaa gccatgtgtg    8280
tggctcaggc tccttctgaa gcacaaaggt gttccacccc tcgctccttt ttcattacaa    8340
ctttcaatca aaaatgtgtt ttatgagata tttgttttgc catgtatctg tgacggagtt    8400
gaacccctta gtgaaacctc tgttcttcac ttagctgaga ggtatttctt agggaatgtg    8460
atgccctaaa tttattgtgg tgtaatagaa ggggggatgt gtggactcac cttctgtttg    8520
ttgtggctgc agtggtttta tgcactacct gagtattaag caagcccttt tcatctgcac    8580
ggaacacctc ctgcttgcca gtgggatgaa acaacaacaa caaagattta aggtttgcta    8640
ttctcaatgt ttcttaatcg ggttcacatt gattgccaac agatgaataa ttcctccttc    8700
tccatggatg tacctcttaa acttgtgaag tcttaggtaa cgcttttctg ctgtgatgac    8760
tgtttcagtc ccctcagtga gaaatcaggc gcaccagtaa gacacaaagg agaccgtgga    8820
gatgttcatt gtgccctcag catctccaaa aggcactgct gcctgccgag ccccagactt    8880
cgctcctgta aaagcaaagc atgtccaatt ctgctgtgcc ataagagtcc tgtggagccc    8940
agacacggcg tagcgtgtgt aacatagcgt gcacgagctc aaacgctttc aacaaatcag    9000
cttttttgct ttgccaactt ccatatgtaa tttcacaaca tctagtattg agacagtgct    9060
gttgtttggg cagcataaat cactcattgt acagcagggc gcctctctta caagttggg     9120 tgtagttcat gttttttgtct aattcctctg cgcatctctc taacaaacaa ctattcttta   9180
gggctcgact caataatcaa tacatttttt tcagtttaca gagcaaataa ttacttgacc    9240
tgatgacttc acaaggttag gggagatgggt gtataaagtc tgcagtgtga aggcagagca    9300
acatctctgc agaccttgag agcaacaggt ctgcaagtaa caggctgcac agccacctct    9360
gccatggagg caatgagagc tgctgccctc cttggattgg tgcttctcag ctcctttcct    9420
ggtaagttgt ttttgttaca ttctctgctt atatctctac tcctactgaa ctaaatgtgg    9480
ttcaggatgc ctttagaatc ctaaaagaga gctcagcctg ccggagaagt gatggtttgg    9540
taaaacatga gctctcttct aatgatcttt atccttgtgc aaatatttac gtaactctag    9600
```

```
caggatgcct ctgtctgaca taaactcatt atcctcagta agtctcatag cactcgagag    9660
agaaaatgta taccctattt cttccttagt gagtcaaagt ttatattttc acccaaaatg    9720
gctatttttt ttaatcatag gatatagctt gcttatagga actggataaa atatttagga    9780
aacaagtaat tctcagtgat aaaaaagaag tatgtgatga ctctgtaggg aaattgataa    9840
ttccagagga attgtaacca aggacgccgt aacattctgt attttataac ctctgttttt    9900
tccagatatt gtttctggtc atcaacgggt gagtagcaga tctgcatcat ttagttgtgg    9960
tttctatgaa tagatgaata attcatactc acaccatatc ctacgggagc ctagagggag   10020
aaaaaaaaaa aagaaaagaa aataacaagg gaaggagaaa aagggccccc aggaattatg   10080
tgacattttt cccccagcaa ataagaaaac atctttgtca gagaaagata acgtaccacg   10140
ttggtgataa gagttggcaa ttaataatgc agagtgggga ccggcgtggc acagcgtgcc   10200
agcagaaaat ctgcacagct tttccctaac tgcctccata tctcccctgc ctgattccct   10260
gaggacccat cagtcagtcg tgtgtctgcc atgccaaaag cctcagtagt gacactgtgc   10320
tcaggcatac tgtaaggaac gctgtaattt gctcccactt cttcaccgtg gaggagtgac   10380
agagaataaa atgaccgcct gcagcacggc tatgcgtgga aaacacaagc agacccttcc   10440
gtgccctgca gagctgtccc acttgtgctc ttcccaggcc tcctgcggtg agtaccggct   10500
gttaggcagc aggaacctcg cctgttccag gatcttccag cccgtctgtg gcaccaataa   10560
catcacctac cccaatgagt gctcgctctg cagagaaatc ctgtgagtag cgatcgcccg   10620
attacccatc gtgatggctc aggtggcaga cagaagcctt ttgaattgtg actaatcacg   10680
ggtggattcg attttttttc cccctgtttc tgtcttccca gagtgcaggc tgtgtttctt   10740
ccttgtcaaa actcctgagt ctaattaatt agtggggctg ggcgtggaga ggcttgatga   10800
gtgaggtgac tgcatggcac caccaggtta acccttcccc tccttctctc ctagccggag   10860
tgggacggtt gacaagaagc acgatgggag gtgtgtgaag gtatggttcc agctcagcca   10920
ctgtgtggag cgatggcaga atcccttccc agcactgatt gtacatttag aatggacagc   10980
tccaaaccca ttggaaatgt aacagaaagg aagaatttca ggtcttttat atatatatat   11040
atatatatat atatgtatgt attaatttca ttttgaacag tgcaaatctg tttcaacggt   11100
gagttttgag atgttatctt gtgtagcaca gctgacttaa aaacagaatc ctctcatttc   11160
aataatcctt tggtgttgtt gaaatagttc cctttagact tagacagaag tctgttgaaa   11220
ttaagaagtt ccccaaggaa gtctggattt tgactaaatc ataatttgt aacagggaaa    11280
aagaaaaaaa aaaaggattc catcagaaca tctaccctga ggtttgttta tcaatacacg   11340
gagctgccac gaagtggaga agtgtctcta tttttagatt agagagataa tgtaaagaaa   11400
cactccggct gtgcaattga acataatgct acaattttca cttcagtaca ctcagagtaa   11460
tggcaggaac accgaggtga gcatcagctc cattttcaag tggagcagac atttcacagc   11520
agcagttgct gccatgtagg gcatgttagg cacagatcct atgtggtggc atttggggtg   11580
gaaagcccta agatgacacc aacaaaaccc attctgtgaa cccatttcct ccaggattct   11640
gctgggctca tgtcctcaaa ggcaggactt cacctgcctg tgctcccttg cccgcactgt   11700
gctgggttgg aagctcacat ctccatacag ccccactcac cgtgagtctg ggggtgggag   11760
acacctctca caccatgcac cattacacag ggctgacgaa agtgttgttc tgtggctgtt   11820
tcaggttgat tgcactggct acatgagaac aactgatggg cttggaacag cctgcatcca   11880
gcagtacagc ccgctctatg ccaccaacgg gctcgtctac agcaacaagt gcaccttctg   11940
ctcggcagtg gcgtgagtgg tgggtcacac cctgggtgct ggggtctggg tggtggtgtt   12000
```

```
tgcagcatat tgaggcttct ggagtggctg tgctgtgctc attcattctc aacttgcttt   12060
cttccccaag gaatggagag gacatagatc tgctcgctgt tggaaaagag cccgaggtaa   12120
agctcgaaag tctgcgctat gaactgttgt tataatatat tatacagcac aaattcagtg   12180
agtcagaact acgcaatagc aatgtcttca ctgtgctggt gtatttgtcc tggaaaaagg   12240
gtttgaggaa aatgactcaa gtatgccagg gtcagaggac gatgaacaaa actcctggct   12300
cctgtgtcag tatcacctgc acagccctg  acaggggttg atgctcagag cattgttcag   12360
atggtggctg tgccagaggt gctcaccgct cctggtgagc gtggggctca tgcagcacca   12420
gctgtcatta cttgggtggg tggacttcat agtgtgctgt tggagacaca ctgcttcctg   12480
gcagcccctc tctgctggct gctgaaccag agcagagcag gtagcgggcc gccagccggg   12540
gagcactgct ttggctgtgt cgctgcttct gagggtattt agtagatttt tccctctgac   12600
ttctcctttt gtgctctgct gggcaagagc attagaattt gcagagttgc tagaacaaca   12660
ggagcctgca tctgaaaaaa tgttttttt  gctttgccat gacataaatg taaagcgccc   12720
atgtaggaaa atacaccaaa caaaggcttc tcaatacgtt cttgctccat tacctacaga   12780
ttgactgcag tgaattcaag agcactgatg cctactgcac tgaagagtac atgccccttt   12840
gcggctctga cggcgtaacg tatgggaaca aatgccactt ctgcattgca gttttgtaag   12900
tacagtgctc cccatgcagc catgaaacca ctgctgtgcc ggagtatgaa ggcagaagct   12960
gccaggaagc ctttgtgctc ccgttatccc cttggtaaat ccgtccccat ccccaacctg   13020
atcccagctc tacctctgct gtgccttccc caagcactgc agatcttgaa cacaggtgag   13080
tcttctccct ccctcaccat taaattcaga ttctcatttg cgggctcata gcgctcctga   13140
tccatccctg cgagagtaat ttgagtggta actgtagaag gagtatccaa aattacaggg   13200
tttgtcccag atctctctaa catgacaaaa cgtgtaacct ggggaatcag gagacgggtg   13260
aaggtgcaac tgggacagca tggagcattg gcttgcccat gcaaagtcag cagtggcacc   13320
atcagggcta taaaaccacc ttccatgtca gtgattttgg cctcctcctt tctctgcagg   13380
aagagtcatg gatctctgtc tctgcagcac cgtggagaat gctgaatgct ggatcgtaac   13440
ctttaccctc atccatcttt cacttccaaa gcctgcaatt ccaacacgct cttccccgct   13500
ccctgctgta cattgctttc tgccttgacc cgccagtaaa tcacagacag caactctctt   13560
cgccatgggc tggtgtgtta tttatttatt tatttattta ttgttgttat tattttttcc   13620
agggcagagg taaagtcttc aggctttca  ggcacttatc tgtcaggcag agaagttt    13680 gaaataaacc acaataaagg ccaaagtgca acacccatca cacaaaagcc ataagccctc   13740
acgaaagtgc gtcacccccat tccaaaccat cagaagagga aatgttgcta taaaacacat  13800
gctgctctcc ccagttctgt gtcttacagc acataaatgg atttgcttta agagtcagga   13860
tgtggctttg tagaagcacg gagccctgga ggaagcagtc cttttgggag ccttggtatg   13920
gaggaaagat ggctttgata cacctgagca aggggcaagt ctggcggcac gttacaagga   13980
ggcttatggc aaagggagga gactatctca caggaagaa  aattaggaac tgttgcttcc   14040
ttgaagggtg tgtcccttga gagtgtggtg atcagcagaa aattgcagcc agctgggcaa   14100
ggctgtaatg agcctaatga ggaccagagg agaaaccaga ttgggctcag gcttcttgga   14160
aaagagatct gaaaagctgc actgggagcg tttgaggcag aggaaagaga aaggactctt   14220
caggaaaagg tttgggagtc ttcatgccta gaaaagaaag gacagaagga gtgcttggta   14280
gctccaaggt cgtttctgtc tgcagtgaaa ggtgatgtgt ggatgatgcg tgtgagcgtt   14340
```

```
cacagtgatg tgccatctct ttgggcgagt caaggaatga gtatgcaaac aacaggtgaa    14400
aagtcccaag tgcctccact catgccacct tccccttcct ttctccacct cccatcctct    14460
cattacgtag gaagacattc agctgttcag gctgatattg aggacaaaat ctgtgacttc    14520
caagcttttc tctggcttta tttcctgaaa taggctgtat cttgacctag aaatcttatg    14580
ggtgcttcct gccagaagat gggaagctgt cctttaatag cgtgtcaggg cagtgctccg    14640
tcctaggaag acagatggaa cttgaaatg tttattctat tagcacaggc agtataaagc    14700
acagtgtgcc tctgtgcctg ctggtgagaa aaggcaagct gcagagccgt gagggtgctc    14760
cctgctaatc tgcctagaag ggaaaagagt agacaagaaa tagcatatgc tactactgaa    14820
tgtgagcaga agacctttag tgaaggacac agctcagctg taatgtcctg ttggccagga    14880
ggtttgttga gttatcgcag agcggtagag ttctggtcag agcaggaagg tgccttcaac    14940
agcaagatcc catggtaggc ctcttctgca gtgtgctggc acaagcctgg tacctgctca    15000
ggagcaaaaa aaggctttgg aaaagctcaa agaagggctg atgtcttaca gggaaaggga    15060
gggcaaaagg caagtgcaga gcatatggct gtacagacaa aaaccttca gaaaatggaa    15120 aaggttttta tcaagtaagc ccagaagttg gcccagtgca ggtaaacact tggctaggta    15180
acagtgaggc tctgcccagc catacccatt cctctgtaag gcaaatccca ggtgccttg    15240 tcttgtctgg tcctgttctg ttcctatttt tctgagaaat cagacagaac ttccccacct    15300
acagcatcaa gcagctactt tataggtgaa gaagtgcaaa gagaagcaat aaggataatc    15360
accacttggc taatttagtc tcttcctctc agcccacaaa ggactggtcc ctgtggtaca    15420
ttttctaagg cttttcccag tcagctgtgc tgtagcaaat gaaatgtttg gctagataaa    15480
gagctgaggt attagtgctg gggcggcgag cagtgtctgg agcaagaaaa ggcaaacgag    15540
ggattctgcg agtggcagaa ctaagcctga ttttgaatgg cgttgtggct ggcggacttg    15600
taaattatat gagaggctgt gctgtgagct caccctaata gacatctgag aactcacctg    15660
tcaatcgcgg ttcctctgct gtgtgggttt tatggtgtct agtgagctgc aagctctaat    15720
gctttcccag gtgcagggca gttgtggcat tgctctccta cagaaactct cacttgctgg    15780
ctgaggatgt ttaggaagtc cttggttgct agaaaaaata tattgaagtg ctttttttgt    15840
ttgtttgttt tccattcttg tgtgaaattt tgttggaatc acagaatcat agaggttgaa    15900
agagaaactc tggaaattat caagttcaac cccttgctaa agcaggcttc atacagtagg    15960
ttgcagttac aacatttgct ggggaaatga atatgaagat ctgtctataa agagtgttcc    16020
catagcactt gtttctttag gaaagcatgc tgaaattcta aaggctgtgc ctatctgaag    16080
agatactttg caagtggtgc aactaaatgc tgctcttggt ggagagatgg ctggagatgg    16140
atcgatggtt gggtgatctt cgtggtcttt tccaacttta atgattctat gattctatac    16200
tctttacaca gaatcagctg gaatagagt gagagtctcc tgattcccca ccaaattcct    16260
ttgattgatg cttggtgtgg aagcagagct ctggacacg ttggtgagtg tgaaaactgg    16320
aaaacattga cagctatagt ttaaatagtt cagggaggag aggcagccat cctatgtggg    16380
actctgcaca cggctatgag agcatcagtg cgcttctcca ccccaaccca acaaatttag    16440
agccatcctc caaaatagcc agggaacaac gcataattgg tttcacagac aacacattct    16500
catgctgtga tttatttcgt aatgtctggt gagtgtcatc acgccgtgct caaagcctgg    16560
agctggcatt cagcgaggac ccagagaatg aaaattacca gcttcccga tgaatcacca    16620 ctttgaaaat tcacccttgt gagaatcctg tgactattca gaaaaaaaaa aaaaaagaa    16680 gaagaagaag aagaagatat tacaggccca agtctatcag tcatgtaatt agcccttct    16740
```

```
aggtttgatg tggacagggc ggcattccta aagcaccata aacacggccg ggaccaataa    16800
tggctctaga atcgaagcgg agaagttctc acaattaagg tgaggaatga ggccagcagc    16860
ggataggtac ataaatacac ggaggcaggg ccgtgagcac gctgtgggct tgtggctgag    16920
acaacacctc ccaaaccggt cgcttgccgg ggactaaaag agcagcatga aggcaacagg    16980
cacctcggtg ctcctcagcc tgctgctgct gctgtcgttc ttctcgggta agttatattt    17040
ctgtagccta gaaagaaact ttatgacgag agcaacttca gagagccttg atcaacggat    17100
gacaggcttg aagagaaagc tgagcaagta gaaaatatct gcgggactcg cttgcttgtg    17160
tcacatcttt ccattcctcg tgtgcctccg cagtgaataa cactgtggag gtgtcactgg    17220
gagacagaat gagcaaattg taagcagctc gttcagcaga ggcaccaaag cagagcgtaa    17280
ttatgagttt tggtggaaat gtttgctgga gagctttgct gaaccagtta gagaagaaac    17340
tcatacctca gggtcatcag ctcctgttct gatgctaagc acttgggggt tggtgttctc    17400
ctcagagatg tggcagcgta attagatgaa agtttcagct tccaaatacg ttgcagagga    17460
gggctcgaaa attaaattca gatgtcctcg aggaacccga acaaagaggg caaattgaaa    17520
gggtccagcg tttatttatc ttgaggttta cacgtctctc tgttggtctg gggaggctgg    17580
ctgatggttt gggggtgtgt agggcacacc ggggtgctca aatgctcgcg tgcggccgat    17640
gcgaatgtgg aagcgttgcg gtggccatta ctgaagactg cagaccaagg attatttata    17700 cttgttttttc tgtgaataat ttgaataaag aattcgcttg agaaaatcgc aggctgtgca    17760
tggagagaag aggtgaatta cttttgtacac atcattaatt atgaaatatt catctgtctt    17820
taattgagtc ttaattgggg ctgggttccg tcagagtgct aaagcttctt tccaaggcca    17880
ggcagaatag cagcaaactc tgtgatctca aataagataa acagatgcca agagacgttc    17940
tcacaaagtc ttgtgtagct gcatgtaata tttataaaaa ttatctaatg agctgttttg    18000
taaataatat gcagatagcc ctaacggcgg cttccctgtc cagcctagct gaggatgtga    18060
cagatacagc agtggcaagg atcaaacact gaaaggcatc gcagcaggca gaagctgggt    18120
ggggtgatgg atggtcccgc tgagcgtgat gctgcaatgc tcccagcctg caccctaacc    18180
aaagggatgc cccattgcaa tgcgccccag cccctgcagc gctgtgtgca gcccactccc    18240
tgtccccgac accacaggat ccatcccgtg gctgtgacct ggccccatgc aaagtttgca    18300
ggcaggaaat agcaaagagg atggactgat tgtctccagg cccagagcct gtgcctgcag    18360
caggtatttt tgctctgctg ctgtctggca ctgcctgttc tgcccagat cacgccaggc    18420 tatccctttg tatctcatcc ggatgaggct gttctgggag cctcggctgt gctgtactgc    18480
agacggctct gatgctgact gcggggtctc ctccatctcc cctgtgtgct tttgttaccg    18540
tactggccag ttttgtaatt cagaggtgca agagcctaaa agccataaga ctcaatgaag    18600
ctttaaaatc tctgctgaga gaggctcagc tcttacatag ctccccgctt ccccggcggt    18660
ggctgcctgc cagggagatg ggtttatgtg tctgtggtgc agttagcagc tgaatgactg    18720
attacatggt attttagtaa cattttcaa atagcaaaat actgaaaagc aattccgata    18780
atgtatttcc taccctcct ccaccacaca gaacggcaga ggagggaaaa cctggtgtgt    18840
gctgtgctgc agtttgcaaa gggatttgtg acttcggttc agtcctctca gaaaataatg    18900
ctaatgtgga taaaatcttt ttttttgttg caattctagg tgtagcagct caagacattg    18960
aagaggttag tgcagctctt tctgctttct gaatctgcat tttctcctgg ctctggaaga    19020
atgcttttct aacagatctt ggtgcattgg tgcatgctga actgctttgg gttttgctgg    19080
```

```
gatcaggtgg gtcctgccaa ggtgcccaa tgcttcggag tgctcacaca gtacaggggt    19140
gttagctatg gccacagtag caaacaagtt ggggatgatt tagctggttt agcacatgct    19200
ccccatggtc tgatccagca cagggctgtc tgcagtatcg cttctgtctg ctttgctcct    19260
ccacgaaaca aatgtgatat caggagtgat atactccttt aaaccatatc cataactggg    19320
gcttgtccaa aagcctgttc acttcataga atcattaagg ttggaaagac cactatggtc    19380
atcgagtgca accactccat gcccagatcc ctgtgtatgg cagccccagg ccacgtggtg    19440
gtgtgagctg catggtaccg ggcactgata tggggctgca tcagtgctga tgctctcctg    19500
ttgaacccac tcatgttctt ggaacaccag agctgctccc tggtggtgac agcttccctc    19560
ctctgccaca gggcagaaat tcccccattt cagccagttc tgacaggcct tgttttttca    19620
agtaagcagg ccgtgcctcg ttgctgcttt tggcctctgg gtgggaagaa gatcacatta    19680
gagatcttct ttcctgtttg gaaagcgaaa cccgacggtt tattgctgtt attattttg     19740
atttcttttg cagatctgca aagagttctt aaacaggagc gtgttctgca ccagggagtc    19800
caaccctcac tgcggcacgg atggcgtgac gtacggcaac aagtgtgcct tctgcaaggc    19860
cgtgctgtaa gtgggggcgg tgggatacgg acccacacag ggatggtcca cttccaaccc    19920
cgcgctgctg ctcccctcac acagagcaat ccctggccat agaatcatag aactagagaa    19980
tggttaaggt tggaaaagac caataagtgc atctagttca aatggcagct cctcaccgcc    20040
acgcttggga atatttcagc ttaatgttga ttcatttcta ggcttagtgt gatgctcata    20100
gccgtacaga gatggcacag agcctgggag gccattgtac ctgcctgtac cttctgcgtg    20160
ggctaaattg atgcacattt tcctctgtgt gccacaggct gaagctctcc ctgtccacac    20220
ctctggatgc tgaagtgtgt ggaggaacgc aggcttatgc atgccaaatt attagaggaa    20280
agtcatagac tcgtagaatc atagattcgt ttgagtcgaa tgggacccttt gaaggtcatc    20340
tggtccagca tccctgcaac gagcaggaa agtgctgaaa tgaaagtctg aatggactta     20400
gtggaaaagt acacaaaatc tcagaggaag ggctgcagtt tctcctctcc tgtctcctct    20460
aaaggagctg taataggagc caacacctct ggactgaagg cctgcaaaaa ttgatttatc    20520
cttatcaatc ctgcactctg gaggctgcct tatcctaagg gaaattagag aagagggaaa    20580
gatggcttga tgctccctgt gaggcaccag agtgaggcaa atgatcgtgc tcggagggac    20640
aagctccctg tcccagccgc tgtgtctgtg ctggatgcca tacactgctt tgtttccata    20700
ccgctccttt tacaggagga gtggagggaa gatacgattg aagcacatgg ggaagtgctg    20760
agcctgagca ccaagcactg atcttcgtcg gtcacaggtg caggagcctg ggcacggcag    20820
cagctgtcct catctctgcc atatctgctc aataaagtaa agctcagcac acctccttga    20880
ctggattcct ttttccataa cacccggata agccttccat gcagccgtgc tagcagctaa    20940
aatgtttgcc gcactgtgct gttacatctt agaatcacag aatcaggcac catgctgcct    21000
gagcaggagc aatgattccc acagctcttc catgccatgc catgccatgc catgccatgc    21060
catgccatgc catgccatgc catgccatgc catgccatgc catgccatgc catcccatcc    21120
catcccatcc catcccatcc cactgacaaa tggacacatg gccacccagc ttgactgtcc    21180
catgggtggg tgacagcatg caacgttgcc tctcagcagc ctccccatat gtgtccctct    21240
cgctgaggtg tgagcatgaa ggtggcagag agctatgagt ggtgtggctg tggatgcctc    21300
atctgcttgg gaagccagaa gcaaacaggc tgaggctgag gagtgttgct gcatgtaagc    21360
ctgcaccggg aaggtggcag gggaagctgg ctttaggcag aaaacacaaag gctttgcttt    21420
ccttgtgtgt cctaagagag gactttgcct caaagactgt caactcgcca gcatcaggtt    21480
```

```
gcagttgcac acaaacttga tttctttctt tagttttcac actgctgctc tctctctcct   21540
tgatgctggc tggaaaatcc ttctttgcgc cagcgaggga aaataaagcc tatagtctct   21600
ccccattcgc tgtacaaaat atacacaggg aaatgcttgt ggcatcccct cgttaaaacg   21660
ttggcagcac atcaatggga ctctactcac ttaatgttga acacttaagt ttcaaaggga   21720
gctttagatt ttatcgtgag gtcagccaac tcattttgca aacacctcta tgctgagcat   21780
ctcagctcct ggatggtgtt tggacagagc tgagtgtttg cctgtggtgc cacgctgcag   21840
gctttgaagt gaattgggac attatatttt gtagccaagg agagttgcag tttgctttgt   21900
tccaattcag atgtttcttt agtaaacaca acagctagac ctccagaaca tggataagct   21960
tgaggggagg aaaaagcacc tcctgcacga ggacagctga tcacaaagga ccccagtggg   22020
cagtgggaga accttcatca tcctctctac cgcctggatc aggatgagcc ctgcataccc   22080
tttccaactg gagttaccct gtgagccaac ttgtggctct ggagtagtgc tgtatctcaa   22140
tacagttcct cagatgggaa gaggcatttc aatgagaggg gggatatggg acatttctat   22200
gcctgagatg gctctcggag actccaaaag cctcacggcg tatccccatg cctaatcctt   22260
tttaatctgg aggctgaaat aacaaggaca gatcacaaga gaacagaagc ggcgagactt   22320
ctctgcttta taatcagcct gcatttgct ctttcagtgc aaacagcaaa tagaaccgcc   22380
tctgtacccc tccagaccca accaccatcc ccagcaacac tgtggcaggc tggagaaggg   22440
tggctctgcc cctccttgcc tcaactggtt gtgtcagcac gaccataacc agagctctcc   22500
ttggccccag ctgggcttat ccatgtaaac ctctcagtgc cccaggagct ggctggtggt   22560
cctgtccatt tcactttcct ccagcaggtg ttcccttaa caagcatcca agtgcctgga   22620
gcaggagcag gcactgcaga agatgagctc aggcaaggac atggcatgtg gggatccatg   22680
ctgttgtgca atgcagatga cgttagatac gtgcaaagca gatctcagca atcacccaac   22740
gactcataac tgcaatcatg gaacgcaatt gcatctggaa gtataaaagc acagtgatac   22800
caggaagctc ttgttaatgg cacagccatt ttggagcaat ttgcccaggt ggggagagcc   22860
ctcacagcgc cttcagtcac agggagtggt gtgagtgccc ccatggctgc tcccagcccc   22920
cagccctggg tgatgggggt cacttggctg taaccctctg aacacaggga cagtgagaca   22980
gccctctggc ctggctgagc tcttggctac gtccagctgc agtcctgggc acatactgaa   23040
ccagaaagca agcattcagc tggtattttt cctttaattt ccttcctcca cattttaagt   23100
tgtgggattt tttttttttt ttttgacag ctttgagaga tgagtgagtc acgaagcact   23160
cgagatctct attagataac agagcatctc tgcagctctt cctggggagg gagttccttg   23220
gaccaagggc caaggctggg tgagaattgt cccagcatca cagtggctgc tccatcacct   23280
gacacagccc ctctgcagtg aaacaaggga agcattacat ctttgcacgg ctgctttcac   23340
tgaacaaaaa gcgctgcttc acagctgagc accatgatga aggggaagga gcatctccat   23400
gatgaagggg aaggagcatc tccacatctc catcacgagc tctgctctgc tggtgatgcg   23460
gctgacacca tggtgtgccc tgactcctgg cccatttaac tgctgtgcac cagtgcctcc   23520
tccccagcat agccctgtgt ccctgccaca actcattgca atcctttgtc ctacttcttc   23580
ccttgacatt cacagctctt gataaggctt tttgagccac tcctggctga tgtgggctgg   23640
tggttcctgc tgcagggttc ccaccaccca gctgggcagc attcggttgt tgttccagtt   23700
cccagggggat tgggacagat tggaagggtc tttgggactg tggaagagta tctcctgaag   23760
tcagggcaga ctgctcagcg ctttgtccca tccagacttg aaaacatcca agggtggaga   23820
```

```
acacacagac tccctgggct gccagtccca gagtttgact gtcatcacgt tgaagacttt    23880
ttgccttgtc tccatttgca acctctttcc tttcagctgc cccatctctc agccatgcac    23940
cactggggag cccagctctg tctggtcagg aacagagccc ttacagagcc acagcatcct    24000
cctgaagtgt ccatctcacc actcagcctc agcaagtgct ccagccctca actcccattt    24060
tccattatct ttctatcact ggatatggga gggaaggcag agctgtgggg ccaagagaaa    24120
cgattgctca ggaggcagtt gggagaactt tattgcaaag cactgaagag atataaagtg    24180
acatttgcag gaaaaagtag aagggtatct gtgtgtgttg gttcctttaa ggattagaga    24240
gcagctgagc tttgggatga gagggctccc agatgctgtg aatcagctaa cagatccctc    24300
caccccgtca ttggtggtga agttaaatag gggcccaggg gaaacatcag ggttgttttt    24360
cttttacgg actccagagc aaggagaagg tgaggggggtt gtgctttgga atgggagtga    24420
aagagtttgt tggtgttttc ctctccccag aataagtagt gtggtgtagg agcgtctcat    24480
aggagtagct gcgttaattg tggctggtgt tagcatccta taatgttgct ccagaaatgc    24540
tggagcaggc ttataatgat gtgtatgtat taccataata catgaaggga gaatgggggg    24600
ggggggggta gatttaagat gtatgcccct agaaaggcgg gtgtcactta agaagtact    24660
tgctttatag ctccagtgat agaattcatt gagatactct gaacctatgg ggcatgaagt    24720
gaccagatct tcagtttggt cagctctggg ggtttctggg gggagcgggg atagagcctc    24780
aatccaggtc tgaaagacaa ggctgagatg tgctgggcct ggggtgctgc cctgagcaac    24840
gtggggctgg ccctagagag cagcattagt gcctgcagca gggctggccc ttgtgcccag    24900
tgtgtggggt aaggtgggga acgtaggtgc tgcataatgt ggtgcttctg atctaaaact    24960
gctctgttaa ttgggagtga ccagagatgg ccctatggct ttcttcccaa agagctctgt    25020
gtccttctct gcagggtaat ctgtgataaa acatcgcct atgctctgcc ctgcagatgc    25080
agggtttttt gtcatcctcc ttctcgagac atactctaat ccttacgcaa gcagggagct    25140
ccaagctttt ggtgataacc tctcaaggag gagctggaag ggcagctctg ccgagcagtg    25200
actgcgctgc acggggcgca tcctgcagga ggcggtggtg taagcgggac tccgctcgtt    25260
cccggctatg gggctccccc tgctgaccgc cgggcggtgg ccaggagacc tcggggccgc    25320
tgctgcccct cggtggtgct tttcgggaca gctttcagga tggggcagcc cagctgctct    25380
cgcggggaat taagcggctc ggtgcagggc ggcacggcgc tgagctgccc cagcaaagcg    25440
ccgctcgtcc cgcggcacct tcggtagatg ctctctgctt ggcagctcct tggtcgttct    25500
cttggccggt ggccacccca gcatcgctcg gggctcggtg ccatccccc cagggcctgc    25560
ggaggtgccg gtgcccgtcc cggggtggc ggacgggcgg tgcagtaccg atgctgggcg    25620
ctgggtgctg ccgcagaccg agcggcgctg cgcggctccg gggcgctcct ggagtgcgag    25680
ctgagcaacc tggtagaaaa ataagtgttg tcccgtgata aacgtcatcg tgctgagctc    25740
tcagactctg ccagaggcct gaatgaagct gcgtcagggg agaatcaggt tggggctaag    25800
gaaaggtcct gccccagagg gcggtgggta tagaaggggt gcccagggca gtgggtgcag    25860
tgctgggctc ccagagctgg aggagcgtct ggacagtgct caggtttgga tgttgggtgg    25920
ttttctgaag ggacggattc tgggctcgtt tatcctgagg gtcccttcca acttgggttg    25980
ttctattcaa tgaatattgt ttatgttcat tctattctat gatcttgttc aggctctcac    26040
tgctgcctcc aagggttcag ctcccccaga gctggcaggg cttcagccac ttgcttacag    26100
tgctcatttc atgcctggcc catggcttct gcctgagcct tgtgggagat cagctgctgc    26160
cagaaaccca gccctcagca ctccacttgc ccagcttgct gccttagtag tctaacttgg    26220
```

```
cagtggtctg acatgacttg aggttgtttt ttatttccaa ggtgccactg acttttttcc    26280
ttccatagtt tctggaagca tttccttcct acttgactga gtcgtgctct gtggatctgt    26340
aattatccac cttggctatg tgtcctttac gggattttat atgttaacct cccaagatca    26400
ttttgctgct ctcatcttag tggctgctgt gagctccacc agcaccacac tggatgagct    26460
gcaggctgag gccgggcacc tctcctgact ctgctcttct ctgacccag agctgtgcag     26520 ttgggatcct aacaccatgc agatgctcca ggacctgcac cgagcccag cactggcact     26580 catctcttct ttccacccct ctgagagcaa caagtggctc tgcaatggca atgtaagtga    26640
aaccgggcgg gtatcttaga gcacctggaa gcttgcatgc ctgcaggtcg actctagagg    26700
atccccgggt accgagctcg aattccaggt accgtcgacg atgtaggtca cggtctcgaa    26760
gccgcggtgc gggtgccagg gcgtgccctt gggctccccg ggcgcgtact ccacctcacc    26820
catctggtcc atcatgatga acgggtcgag gtggcggtag ttgatcccgg cgaacgcgcg    26880
gcgcaccggg aagccctcgc cctcgaaacc gctgggcgcg gtggtcacgg tgagcacggg    26940
acgtgcgacg gcgtcggcgg gtgcggatac gcggggcagc gtcagcgggt tctcgacggt    27000
cacggcgggc atgtcgacag ccaagccgaa ttcgccctat agtgagtcgt attacaattc    27060
actggccgtc gttttacaac gtcgtgactg ggaaaaccct ggcgttaccc aacttaatcg    27120
ccttgcagca catccccctt tcgccagctg gcgtaatagc gaagaggccc gcaccgatcg    27180
cccttcccaa cagttgcgca gcctgaatgg cgaatggcgc ctgatgcggt attttctcct    27240
tacgcatctg tgcggtattt cacaccgcat atggtgcact ctcagtacaa tctgctctga    27300
tgccgcatag ttaagccagc cccgacaccc gccaacaccc gctgacgcga accccttgcg    27360
gccgcatcga atataacttc gtataatgta tgctatacga agttattagc gatgagctcg    27420
gacttccatt gttcattcca cggacaaaaa cagagaaagg aaacgacaga ggccaaaaag    27480
ctcgctttca gcacctgtcg tttcctttct tttcagaggg tatttaaat aaaaacatta     27540 agttatgacg aagaagaacg gaaacgcctt aaaccggaaa attttcataa atagcgaaaa    27600
cccgcgaggt cgccgccccg taacctgtcg gatcaccgga aaggacccgt aaagtgataa    27660
tgattatcat ctacatatca caacgtgcgt ggaggccatc aaaccacgtc aaataatcaa    27720
ttatgacgca ggtatcgtat taattgatct gcatcaactt aacgtaaaaa caacttcaga    27780
caatacaaat cagcgacact gaatacgggg caacctcatg tccgagctcg cgagctcgtc    27840
gacagcgaca cacttgcatc ggatgcagcc cggttaacgt gccggcacgg cctgggtaac    27900
caggtatttt gtccacataa ccgtgcgcaa aatgttgtgg ataagcagga cacagcagca    27960
atccacagca ggcatacaac cgcacaccga ggttactccg ttctacaggt tacgacgaca    28020
tgtcaatact tgcccttgac aggcattgat ggaatcgtag tctcacgctg atagtctgat    28080
cgacaataca agtgggaccg tggtcccaga ccgataatca gaccgacaac acgagtggga    28140
tcgtggtccc agactaataa tcagaccgac gatacgagtg ggaccgtggt cccagactaa    28200
taatcagacc gacgatacga gtgggaccgt ggttccagac taataatcag accgacgata    28260
cgagtgggac cgtggtccca gactaataat cagaccgacg atacgagtgg gaccatggtc    28320
ccagactaat aatcagaccg acgatacgag tgggaccgtg gtcccagtct gattatcaga    28380
ccgacgatac gagtgggacc gtggtcccag actaataatc agaccgacga tacgagtggg    28440
accgtggtcc cagactaata atcagaccga cgatacgagt gggaccgtgg tcccagtctg    28500
attatcagac cgacgataca gtggaacag tgggcccaga gagaatattc aggccagtta     28560
```

```
tgctttctgg cctgtaacaa aggacattaa gtaaagacag ataaacgtag actaaaacgt   28620
ggtcgcatca gggtgctggc ttttcaagtt ccttaagaat ggcctcaatt ttctctatac   28680
actcagttgg aacacgagac ctgtccaggt taagcaccat tttatcgccc ttatacaata   28740
ctgtcgctcc aggagcaaac tgatgtcgtg agcttaaact agttcttgat gcagatgacg   28800
ttttaagcac agaagttaaa agagtgataa cttcttcagc ttcaaatatc accccagctt   28860
ttttctgctc atgaaggtta gatgcctgct gcttaagtaa ttcctctttta tctgtaaagg   28920 ctttttgaag tgcatcacct gaccgggcag atagttcacc ggggtgagaa aaaagagcaa   28980
caactgattt aggcaatttg gcggtgttga tacagcgggt aataatctta cgtgaaatat   29040
tttccgcatc agccagcgca gaaatatttc agcaaattc attctgcaat cggcttgcat   29100
aacgctgacc acgttcataa gcacttgttg ggcgataatc gttacccaat ctggataatg   29160
cagccatctg ctcatcatcc agctcgccaa ccagaacacg ataatcactt cggtaagtg   29220 cagcagcttt acgacggcga ctcccatcgg caatttctat acaccagat actcttcgac   29280 cgaacgccgg tgtctgttga ccagtcagta gaaagaagg gatgagatca tccagtgcgt   29340
cctcagtaag cagctcctgg tcacgttcat tacctgacca tacccgagag gtcttctcaa   29400
cactatcacc ccggagcact tcaagagtaa acttcacatc ccgaccacat acaggcaaag   29460
taatggcatt accgcgagcc attactccta cgcgcgcaat taacgaatcc accatcgggg   29520
cagctggtgt cgataacgaa gtatcttcaa ccggttgagt attgagcgta tgttttggaa   29580
taacaggcgc acgcttcatt atctaatctc ccagcgtggt ttaatcagac gatcgaaaat   29640
ttcattgcag acaggttccc aaatagaaag agcatttctc caggcaccag ttgaagagcg   29700
ttgatcaatg gcctgttcaa aaacagttct catccggatc tgacctttac caacttcatc   29760
cgtttcacgt acaacatttt ttagaaccat gcttccccag gcatcccgaa tttgctcctc   29820
catccacggg gactgagagc cattactatt gctgtatttg gtaagcaaaa tacgtacatc   29880
aggctcgaac cctttaagat caacgttctt gagcagatca cgaagcatat cgaaaaactg   29940
cagtgcggag gtgtagtcaa acaactcagc aggcgtggga acaatcagca catcagcagc   30000
acatacgaca ttaatcgtgc cgatacccag gttaggcgcg ctgtcaataa ctatgacatc   30060
atagtcatga gcaacagttt caatggccag tcggagcatc aggtgtggat cggtgggcag   30120
tttaccttca tcaaatttgc ccattaactc agtttcaata cggtgcagag ccagacagga   30180
aggaataatg tcaagccccg gccagcaagt gggctttatt gcataagtga catcgtcctt   30240
ttccccaaga tagaaaggca ggagagtgtc ttctgcatga atatgaagat ctggtaccca   30300
tccgtgatac attgaggctg ttccctgggg gtcgttacct tccacgagca aaacacgtag   30360 cccctttcaga gccagatcct gagcaagatg aacagaaact gaggttttgt aaacgccacc   30420
tttatgggca gcaaccccga tcaccggtgg aaatacgtct tcagcacgtc gcaatcgcgt   30480
accaaacaca tcacgcatat gattaatttg ttcaattgta taaccaacac gttgctcaac   30540
ccgtcctcga atttccatat ccgggtgcgg tagtcgccct gctttctcgg catctctgat   30600
agcctgagaa gaaaccccaa ctaaatccgc tgcttcacct attctccagc gccgggttat   30660
tttcctcgct tccgggctgt catcattaaa ctgtgcaatg gcgatagcct tcgtcatttc   30720
atgaccagcg tttatgcact ggttaagtgt tccatgagtt tcattctga acatccttta   30780 atcattgctt tgcgtttttt tattaaatct tgcaatttac tgcaaagcaa caacaaaatc   30840
gcaaagtcat caaaaaaccg caaagttgtt taaaataaga gcaacactac aaaaggagat   30900
aagaagagca catacctcag tcacttatta tcactagcgc tcgccgcagc cgtgtaaccg   30960
```

```
agcatagcga gcgaactggc gaggaagcaa agaagaactg ttctgtcaga tagctcttac   31020
gctcagcgca agaagaaata tccaccgtgg gaaaaactcc aggtagaggt acacacgcgg   31080
atagccaatt cagagtaata aactgtgata atcaaccctc atcaatgatg acgaactaac   31140
ccccgatatc aggtcacatg acgaagggaa agagaaggaa atcaactgtg acaaactgcc   31200
ctcaaatttg gcttccttaa aaattacagt tcaaaaagta tgagaaaatc catgcaggct   31260
gaaggaaaca gcaaaactgt gacaaattac cctcagtagg tcagaacaaa tgtgacgaac   31320
caccctcaaa tctgtgacag ataaccctca gactatcctg tcgtcatgga agtgatatcg   31380
cggaaggaaa atacgatatg agtcgtctgg cggcctttct ttttctcaat gtatgagagg   31440
cgcattggag ttctgctgtt gatctcatta acacagacct gcaggaagcg gcggcggaag   31500
tcaggcatac gctggtaact ttgaggcagc tggtaacgct ctatgatcca gtcgattttc   31560
agagagacga tgcctgagcc atccggctta cgatactgac acagggattc gtataaacgc   31620
atggcatacg gattggtgat ttcttttgtt tcactaagcc gaaactgcgt aaaccggttc   31680
tgtaacccga taaagaaggg aatgagatat gggttgatat gtacactgta aagccctctg   31740
gatggactgt gcgcacgttt gataaaccaa ggaaaagatt catagccttt ttcatcgccg   31800
gcatcctctt cagggcgata aaaaaccact tccttccccg cgaaactctt caatgcctgc   31860
cgtatatcct tactggcttc cgcagaggtc aatccgaata tttcagcata tttagcaaca   31920
tggatctcgc agataccgtc atgttcctgt agggtgccat cagatttctt gatctggtca   31980
acgaacagat acagcatacg ttttgatcc cgggagagac tatatgccgc ctcagtgagg   32040
tcgtttgact ggacgattcg cgggctattt ttacgtttct tgtgattgat aaccgctgtt   32100
tccgccatga cagatccatg tgaagtgtga caagttttta gattgtcaca ctaaataaaa   32160
aagagtcaat aagcagggat aactttgtga aaaaacagct tcttctgagg gcaatttgtc   32220
acagggttaa gggcaatttg tcacagacag gactgtcatt tgagggtgat ttgtcacact   32280
gaaagggcaa tttgtcacaa caccttctct agaaccagca tggataaagg cctacaaggc   32340
gctctaaaaa agaagatcta aaaactataa aaaaaataat tataaaaata tccccgtgga   32400
taagtggata accccaaggg aagttttttc aggcatcgtg tgtaagcaga atatataagt   32460
gctgttccct ggtgcttcct cgctcactcg agggcttcgc cctgtcgctc gactgcggcg   32520
agcactactg gctgtaaaag gacagaccac atcatggttc tgtgttcatt aggttgttct   32580
gtccattgct gacataatcc gctccacttc aacgtaacac cgcacgaaga tttctattgt   32640
tcctgaaggc atattcaaat cgttttcgtt accgcttgca ggcatcatga cagaacacta   32700
cttcctataa acgctacaca ggctcctgag attaataatg cggatctcta cgataatggg   32760
agattttccc gactgtttcg ttcgcttctc agtggataac agccagcttc tctgtttaac   32820
agacaaaaac agcatatcca ctcagttcca catttccata taaaggccaa ggcatttatt   32880
ctcaggataa ttgtttcagc atcgcaaccg catcagactc cggcatcgca aactgcaccc   32940
ggtgccgggc agccacatcc agcgcaaaaa ccttcgtgta gacttccgtt gaactgatgg   33000
acttatgtcc catcaggctt tgcagaactt tcagcggtat accggcatac agcatgtgca   33060
tcgcatagga atggcggaac gtatgtggtg tgaccggaac agagaacgtc acaccgtcag   33120
cagcagcggc ggcaaccgcc tccccaatcc aggtcctgac cgttctgtcc gtcacttccc   33180
agatccgcgc tttctctgtc cttcctgtgc gacggttacg ccgctccatg agcttatcgc   33240
gaataaatac ctgtgacgga agatcacttc gcagaataaa taaatcctgg tgtccctgtt   33300
```

```
gataccggga agccctgggc caacttttgg cgaaaatgag acgttgatcg gcacgtaaga   33360
ggttccaact ttcaccataa tgaaataaga tcactaccgg gcgtattttt tgagttatcg   33420
agattttcag gagctaagga agctaaaatg gagaaaaaaa tcactggata taccaccgtt   33480
gatatatccc aatggcatcg taaagaacat tttgaggcat tcagtcagt tgctcaatgt    33540 acctataacc agaccgttca gctggatatt acggcctttt taaagaccgt aaagaaaaat   33600
aagcacaagt tttatccggc ctttattcac attcttgccc gcctgatgaa tgctcatccg   33660
gaatttacat ctggaattac gtatggcaat gaaagacggt gagctggtga tatgggatag   33720
tgttcaccct tgttacaccg ttttccatga gcaaactgaa acgttttcat cgctctggag   33780
tgaataccac gacgatttcc ggcagtttct acacatatat tcgcaagatg tggcgtgtta   33840
cggtgaaaac ctggcctatt tccctaaagg gtttattgag aatatgtttt tcgtctcagc   33900
caatccctgg gtgagtttca ccagttttga tttaaacgtg gccaatatgg acaacttctt   33960
cgcccccgtt ttcaccatgg gcaaatatta tacgcaaggc gacaaggtgc tgatgccgct   34020
ggcgattcag gttcatcatg ccgtttgtga tggcttccat gtcggcagaa tgcttaatga   34080
attacaacag tactgcgatg agtggcaggg cggggcgtaa ttttttttaag gcagttattg   34140 gtgcccttaa acgcctggtt gctacgcctg aataagtgat aataagcgga tgaatggcag   34200
aaattcgatg ataagctgtc aaacatgaga attggtcgac ggcccgggcg gccgcaaggg   34260
gttcgcgttg gccgattcat taatgcagct ggcacgacag gtttcccgac tggaaagcgg   34320
gcagtgagcg caacgcaatt aatgtgagtt agctcactca ttaggcaccc caggctttac   34380
actttatgct tccggctcgt atgttgtgtg gaattgtgag cggataacaa tttcacacag   34440
gaaacagcta tgaccatgat tacgccaagc tatttaggtg acactataga atactcaagc   34500
tttgtgcttt ctgcctgaat aaaagaaacc tgaactctgt tcacccagtc cctgtcaggc   34560
aattactgac agagcaccta tggtctgtgt ttggccagaa cataggctaa ggaagatacc   34620
tcctgtttat aaagcacgcc tttggcatct ggcaagtaat tagtgatggc gcatgagagc   34680
tctgactagg gcagggtgtg ggacaggctg gctctaattg tgccctgttt atcttgttga   34740
tgcacacggc tggtttcttt cacccacagc tgtctctcta gacaacatac ctttatggag   34800
aggaacgtgt cttttccaat cttgggtttt cattcagaat tggagtgaac tggtctccat   34860
cagatagcat tggctgcggt gatttattct tttacacttc ctagttaagc aggataactc   34920
tctggctctg ctgtgtctag gcaatttaaa tgatttataa agcatagctg ttttaaggaa   34980
atcttttttt aaacatttga cttgccaatg tgtggtccta aaggcagaag gactgttcca   35040
gagtgtcagg cagagaccta ccctggattt cgttgttcag ctacccattc agtgtggctt   35100
ttggcaagga attctctgga cctgacttcc ctacctgcag agctgggata agctatcaaa   35160
ccatctcctc cacacactgt gagggtggga aaaaaccca aaccttaaa agtgctgtat    35220 aaaggcgcct taaggctcag tatagcatgt gtgctgctga tgcccagac ctgtttgcgg    35280 gtcctgaagg tcataggaga actgctcaga agagacagaa atgcttaaga aggttttact   35340
acaaaagtct tgtgatgtta acacataata tcacattgtg cagaaggtac aaatgccccc   35400
tcctatccct gcacacctgg aagctcaagg tatggaaggg tttgttgtct gcagcctctt   35460
cgctgccctc tgcttttta gatcctgggt agtgtgctca gtgtgtgccc tcagcagttt    35520
gggaaacgga catcttcatg caaaattaag caaggaagtg ttgcttttat actcagagta   35580
gaatctaagt tcttcaggca ggctcttgtg tgccgcctct attagaaata aaactccccc   35640
ggatcagaag atgaatgtgc tcagctaaga acacagattt atttgcttta caatgcgtgc   35700
```

```
tatggtttaa gaaaaacaca tcaggcaaac aatttatggt ttgccactga gttgtgcctg    35760
aaggaaacac aactgttaga gatgtaattg attgggcggt gacgctgtgt ggattcatgg    35820
gagatgcatc ttggtcagca tgtctgtgtg aaaccacatt tctggtgctg ctgcaggacg    35880
agtgccggga gttccgggat ctgttcaaga atgggaagct ttcctgcacg agggagaatg    35940
atcccgtccg ggattcctcg gggaagcagc acagcaataa gtgcatcatg tgtgcggaga    36000
agttgtgagt agaggaagcc aatgtttgtt atcgagagtg gcaatggggc cggggtgggc    36060
tcctacagca atgttctcct cactttctca tccttctctt tcagcaaaag ggagaatgag    36120
cagaaggcga cctcaaccag agggaaacaa aaggtgaggt taaagtattg ggttcatata    36180
caagtctata ggattcttac ccaatattac cacacttgat ttctttgtca ctctggggat    36240
ccatgtggct tttcctgctt gtatctcgtt gatgctcttt catgccctga gagaatagtt    36300
tgtctgaacg ctgcagtcta tcccactgac cgcagtgaca tgggagcaaa ccccatcgca    36360
ataagaagct gagcagaact gccctgacat ctggcacaag ggcaagaagg cactgctgct    36420
gagagcgcta atgaggttga aaagaaaatc tgggtgagaa gctttaaatg tgagctctga    36480
gatgctcaaa agttcattat gtcgtgggag gagagttcag ccctgtgctg tccctgggt     36540 ggctcggttt cagctttccc tgattggaaa cctcactctc atgatcagc tgctgtgccc     36600 ttgtgcaccg atacttctct ggtgagagca attcagcaag gggaaggaaa aagaagcact    36660
aagtaaatct tgccatttct gtcttgcgag gaactggtac ggtccccttta agcctcattc    36720 ttggggataa tcctgtttca gtgcttttcc taatgacagt ggcacaaaaa aaatggaagc    36780
gttaatgaaa cttgctgatg gcaaagctgg gagggaggat cagcagatca ctcaggacta    36840
attggatagc actgaggcct ggagtaatag aaacaagata aaatgtaata acagagagtg    36900
caagatcaca caggcagtga ttaacgagaa ttcctgctca tcaattagaa atgacaaagg    36960
ataagaaagc tctgcattta ttagtgggtc acggatgcgg caggcctgag aaggaggcaa    37020
atgcacatct cagcaaggtc tgtgcagcag aggtcgggct ggcagcaaat tccagaaat    37080 actgctttga agagagaggg tttgagagac gctgttaggg agaagcagct ctgccacagc    37140
aggtctgggg ttcacctggg gtttggctca ttgcctccct gtgtccctcc tccacgctgc    37200
cagtgctgca ctgggaaggt gtgggtaaga agcaatggct aagggatctg gttatacacc    37260
tcctgtatct gctatttggg attggctact gcagggcctc aggtccctga cttaaaagtg    37320
gggacttcga agcatgtttg cattgtgctg tcgtgcctta gatgttgctg ctgggtcctc    37380
aaagtcctgt tggttgtggg gtgggggga cttcttgctt cctatgtgaa gtttctgag    37440 ctgcaacttc agcaacagct gtaagagtgc attaagggca gtgggagaag tgggagggac    37500
cccattacct catcgggtat cgctggcatg ctttggatag ccccacgtgg agcgtgacaa    37560
ttagagcacg gcagagagct cccaacacgt gccatgcagg cagaggcacc cgccgctctt    37620
ctgactcact ctgtttgtag ccatgaggct gtgccacgtg ccctcttctc tctctcacac    37680
ctgggctctc ctggggcgcg tttgggaagc ctctggagga tcggagggat gtggcagggt    37740
gccctgactg ctgctccttc cgcaggatga ctgcagtgag taccgctccc agtttgaggc    37800
tggcggacgc ctgtcctgca cgcgggagaa cgacccccgtc agggattcct ctggcaagca    37860
gcacaccaac aagtgcctca tgtgtgccga gaagctgtga gtacagttcc tggcaacagc    37920
aaagagggaa acctcacatt gcgaaactgc agcttctgcc tgtgtggctg cgcctggggg    37980
agtcccgagt cccagcggcc ccccaggagc tgctcctgct gtagggctgt ggctactgcc    38040
```

```
cctcttccca cctccccct aaccctcag ggagcagagg agaagcaggg ttgatagaga    38100
gcagccctt ccttggggca gctcccaagg aaagtttccc acgcgtgtac tttgccttcc    38160
agatgctctc tctactccca tagagcatat gcagaagcag ccctgatatg aaagcagcca    38220
cctggagccg ggatgtagca tacagtggga atggtgagga gaagggagaa ggcttagggg    38280
tgggaattag gtgcagggcc accagggatg gggaggctgg tgcctaatga catgatgctg    38340
gcttgcaggg cagccccagg tcctggcagc gttcgcactg ccatagtgct cctttctttc    38400
tcctctccct tttttccagc aaaaagaag ctcaaagagg aggtcagtct ggtggaactg    38460
cccagcgcaa caagcagtcc actgcagagt gtgcaaacca ggtgagactg agctcagagc    38520
ctcaccaggc ttgggaaaag gggttggtgg atctggggac cccgatggtc aagggctgcc    38580
tgtggtcctg gtgtttgggg tgcaggagcc tgctggtgat ggcagagagg caggttgcat    38640
tgcaagccct gctagttcat gggatgggtt tgtgtatgag cgtgcatagt gggcagttct    38700
ggactcctct atggggcacg catcagagct atttcttcag aaagagcccc atggttccta    38760
gggtccaggg ggatgagagg gaaggacagg agctgcttta atctcactgc tttactgctt    38820
ggttgtcaaa cacgatcctg cccctttcc agaagagctg cagtggctca gggttacagc    38880
ggggtgtaaa tgagagacgg ccgttctcca caaacagagg gtgagtacag cagcactggg    38940
atcccagcct ggccccacaa gtcctggggt cttgacactg agaagaaaca cataaaatag    39000
ggcatataca acccttctc cttttccaaag acattcttgc ttccctgca cacgaagcac    39060
tggtgactgc tacactcaaa atccctcccc agccttgccc cctgaatcct gcctcctggc    39120
aggcacacac ttgtcctgct gcctggtcca gcgcatcctc atctgctgac ctgaggcagt    39180
gctgtgtgtg caccatgtgc tgtctgggca ctgagcgact cctctgggtt tttagggctg    39240
ccaggctctg gcagggtgca gatgctgtgt tatctaagcc ttgaggaact ctcttagtct    39300
tcctgttttt gttggtgagg cccattcatc tgccccagt cagcactgcc agcagacaaa    39360
cagtgcacag ctctccatgg cagcaatggc tgtagcatat gtaggggcca ggtttctggg    39420
atcatctctg tgacggacat ctcttgctga ccgcccataa ggactcaaaa gtcccgttgc    39480
agggagtgcc tccatcccat ggcaagccaa gtgccctgtt gaaaaaacaa ggtgcagaat    39540
aatggcaatg gaccttagtg cagtttaatt ccaccctggg gtgatgatgt ggctgagtgg    39600
gtctgcatac ccttggctgt gccatgagct ctgtgctttc tctccctgcc agcccacaag    39660
gagacttggc tcaggactgc agcccggcac ctggccgcca gggacagagc ggaggcacca    39720
acacctacca gccggtatgc ccagctcatg tgggtcaggc acagcctttc ccagcagctg    39780
ccccagtttc cattgtcaac ctaaagcctc acaatgggac ctgtatcctt ggagggttt    39840
aaatgggtgg tagagtccgt accctgatgc tgtcccctgg cctcaaagag gagtgaggct    39900
gcacacgtcc aaacgggagt cactgaagcc agtgctgctg ctggtgttgg ctcactgtag    39960
aagtatgtca ggtatgagag agcatcctcc aggaggtgat ggtggtgtcc cttcctgcat    40020
gctgagatgt tgggttgaag actgtggcca gagcagggtg ctgggctga gcggggata    40080
aggacaaggc tgataagagg aggggagagg gagtagtggg ggaggacacg gtgagcaata    40140
gataacgact gtttgtggaa tcatgtggga gggagaagag ggtgtatgct ctctccatct    40200
ccacaaaaag aaaatttgtt attttcaacc aagctaaagc agaaattatg aaactaatag    40260
gagaaaataa gttactataa aaaggatgac taacctgtgg atcttgctgt cacggggtgt    40320
tgccaagagc tacagtgatt aaaaaaaatg acttgccact tatagtccat acagcaattt    40380
aggtaacatt ttggaaggga taggaaatgc ctttctgtgg ggctggaggg acctgagtgc    40440
```

```
agactgcctt aactctctct gaagtctctg tcactgactg cccttagaaa aatgatatta   40500
gaatagaaaa accagggagg cggttcaggt atggcagttt taatgcattc cagaggaagc   40560
attaggcata ataatgccag tctgcttcag ggcttagtgg tatttcctgg tagctccggt   40620
gaaggagtgg atgctgatca gcctgactga cgaggggtga ttcagagagc agatctgtgt   40680
ctctcctcgc tgcagggcca cccgtgggct ctgtcccagg gagatgctgt cctgaaggag   40740
aggtggcagt cactgtgagg actgtggggg actgttggtg tggcggcggt tgcacacgcg   40800
tgggtcacac cgtgggcagt ggtgtctggt gtgtgggaag gcatctggca gggaactgca   40860
aaggtcagcg ctgtctgtct ttgtgtcatc gttaattacc caggtgaggg aggaagcagc   40920
acattaatga aattagcaag tgatgtttaa acagagggtg ttactgcagc aacctgtgcc   40980
actgaaccccc ctgcattgcc cagctgggaa acctttcttc tccatggtgc tttcaacccc   41040
atagtgctgc tgaccccagc aaagcaatga gccattgctt agtgctgaat gggggttttt   41100
ttctccaagt gggacaggag gtgagatgtc cttcctgcag ctcttctcca attgcaccat   41160
ttgcagtcat tgcaacattt tttataggac ctggagaagg ggatgggaac agagaattca   41220
ctccttttgt ctctgcatct tttttttttt ggcctttggt gcagaggtgg gcagtgaggc   41280
tgaggaagag agggggctgt aggatctctg acctctgctg tctgaaactt gccatgattc   41340
tgcaggcacc tgtgccagaa tgctcatggg ctgataatct aatcatgagg agtcttgttc   41400
ctcctgctcc gagctctttc tagctgtgcc acgtctgctt tgtaggaaat tcgatgccta   41460
gatgctcctg ctgttatgct ggagaataaa acgagagggc acgcttaatt agtcagagct   41520
tttcatacat gtttgcatct cttcattccg tgggtgtcaa gttgtgctgt gtgtcgggct   41580
gcccttgggc agctggactc aattgtcaag gttttccctt tgtttctgcc aagtggcttg   41640
cagaagcaac aggtgtgaaa gctctgataa aggacaaagg acaggtagca gaagtttatt   41700
gtattctcgt ggatttgcag ggagaagtaa aagtgccctg gactgagatg tcagggtgga   41760
tcagatgagt gtatccatgc ctggcaatgg ggtcagggca gctttgtccc cacatcgtgg   41820
ctggttggcc caataggagg cgttacctct ttgctgaagg tgtgatggag ctcagggcaa   41880
cgcctggttt gtgagtgctt tgagcggtgc gcaggagggt cttgcaagag aaccagcacc   41940
aaatgtgatt tctttctctc ttcagctgga ctgtgatcga attctgcacg gggtaaaggg   42000
tggaaggatt ttctgcagcg aatcctcaca acccgtctgt ggcactgatg ggaaaacata   42060
cagaaatgaa tgtgacttgt gttcagctgc catgtgagta ggcggagaga tttcagtaat   42120
acagggccat ccaccattcc cgagtgtctt ttgcagcaca gtgtttgttt tgatatacca   42180
tgactcacta tcaagtgtgt ccttggtgcc tcgctgttaa gcaaacatag atcaaatgtc   42240
tgagattaat atgatgacag ctaattaaga tacacaactt tccagagtcc cttattccct   42300
ttctgctcaa tcataggatt gttttgggag taataaatgc catcaaattg gaagtagcat   42360
caaaggttta aggagcccac agaggaccac cgtgacgatg tcagggagct gtggcactgg   42420
aagtgaataa gcaatgtctt gttctcccct tgcaggagag catcagttta catcacggta   42480
aactaccgag gtgaatgccg aaagactgtc cctgaaatgg taagtgcctc cctgctgtgg   42540
catcccattt cttgttctgg gtgtgtgctg gagacccagc ctggatcccg tatctgtggt   42600
gggatcatca gagccctgtt agcagggtgc ttgtggttca catgcgtaaa tacacttcag   42660
gcttggattt aaggcatttt gaggcataat ctccacgttt tttccaggct gtgtggtagg   42720
ggagtgacat gtctgggaaa acatgtggct ttcctcctgg gattttggtg aggccaagaa   42780
```

```
aagattgcaa tcgcacaaac cataagggcc taatttccca aatgatatcc aggcagttgg   42840
ttgggaagga aatatattcc ctaagtggta tccttttggg aaaggtcttg aatcttgtgt   42900
gattgccttg tagtagatga gtcaaagatt tgttagtggt gctttgtctt cccgctcgtg   42960
gcagctcagc ggcattcaga gctttggttt ggagccaggg tgtcccagtt tgtgtgtctt   43020
gagtgtatgg gactgacctt agtgttggca tggactgttg gaaagctgag tattcatttc   43080
cccagggaaa caccgacatc tatccccatt ccaaacttgg aatgaatcaa aatatcaaat   43140
cagccaaatg gagaagttgt gcaagttttt tttgcaatga gagagatggc ttctgaatat   43200
gaatttgctg acagtttgta ggtaaaacag tattgcccgt tgaaaagctt tagagcaaaa   43260
ttaccatcat agggctttta ctctcctctg cttattgaca ggatgcccac ccatccccac   43320
aacattagaa atgaggcatc cccattcctc ttcctctctt ctgtgaagta ccagagtgct   43380
ctcaacgctg tttaaagctg aagaaaaaat gcagagaaag agttttgctt gtgatcgtgc   43440
tggaggtctt tgtgtctcgc cctttggtgc gatggagcca ttgctggttt gtgtatgctg   43500
ggagtggagg cactatgcat acctgctggt ggctgtgcta atgatgctgg agacagacaa   43560
ggttgggtgt accacggcaa ctgaaaacca gagaggactc cctcagagtt gtgcctggct   43620
gggattcctc accattttgt gttttaccaa gacgttttac cagctctcca gtctttgcag   43680
ttagaggaat atgccataca ctaaaagtca gacaatttgt agctattcca aggagagctg   43740
gaagcaatta aagggaaagt gataaggttt tccactggg gaaaatcccc cacaaaaaac   43800
acccctccaa acaaagactt attatttcgt tctttatgta tattgtgtca cctgaagaat   43860
cagattggaa atttatggaa gcccatttcc ttagcaaacc ccttgtgtcc atcaaagact   43920 tcccttttt ttctcagttg gaagcttatg aacaatgtac tgaccagtgt tattttatgc   43980
ctctgaaatt catgctaaca ttcagcttaa tgcatccttc tgaaggccca ggcactcgct   44040
gtgtgaagga gatcacagtg cctttggcgt cagaaatgat ttcaggctgt tgcaatacgc   44100
agcacgaaga tgcaaaggcc caaagacttg agccttggaa aaagatagga gattgctgcc   44160
cgaaaatgta gtttgtcctt gagttgtgtt ttgaaattag ccacggtaat gctgtgttgc   44220
ctgccaaaat gtgtgtccaa gctcagagcc tgcagccatt cctgctagca aagcccctcc   44280
tggatttcca gcagtttgtg gcagtccttc cctagcagtg gctggattgc catcagggag   44340
ggatggctgt aggaagggac aggagaaatg tggttggaga gagatctgac attaaagggt   44400
gcatccggac agcctgcact gatgtggtgg aaaaccttcc tgcagagaga gccctggggc   44460
tggctggcag ctgggcccct gctgcctgtg tgagctctgt gccacaacca gcctcctctg   44520
atcctgttct gctttactgc agatgaatgt agctgagtct agggtttaga tttctatgtt   44580 tattttaac aaggcagctg gcctctgcgt cctccatgct gtgacataca gctgtattaa   44640
tggtgggtct ttccagaatg tttcactttc aatgctgtat ttttttttat tttgcagttt   44700 ctcttttgt tcagatgctt tttcacacat ctcccatgtg acagatacca gtctgtccat   44760
gttagttgac aggtcaggca aaaaaaaaa agggatatcc agtttctcct ttttaatctg   44820
ttttctaaag aacaaagaac tcccagcttt ctaatgggca aggccatttt cttacagtgc   44880 tcttttgtc atacctttct taagaatgta gtagaaggga aagaaacaa acaaaaaacc   44940 caggaccttt tccagcttga tattggtttt ggaaagcaca cagatccagg ctgaaatctg   45000
tttgttttct gagtctggca gtgacccatc cactgcccca tcccacctgg ttcctgtggc   45060
cactgagctg cccaaagggg ctgtcatgta gcccctaatg ctctgccagc gtaacagcag   45120
tggatgtact tgtggatcca cttatatttt gctctttctt tccagaaata atggagttca   45180
```

```
gactgccagc aaataccagg gatcagctgt gaccaaaggt acagtggtgc ggtgatttgc   45240
tccctcttgg acaacttgtc cgcatttcac aagggtttgg gtgtcagacc ttgcctgggc   45300
aggctgctgg gtatgtctgg ggcaaagggc tctgcaacac acccttccct attgccacag   45360
cacaagaatg aggcgtgtgt cttttgcaga agtagcaagg tgatgggaag cccctgccaa   45420
gggggctgag ccctttgggg tgtgcaaact tcatgaggac ctcctcatct ctcaggggtg   45480
ggccttgccc gttccttttc cctcagatat ccctgcagag ggggaaggat gctggcagag   45540
cagagtactg cagtcccccc tcacaaggag gtggaggtgg cccaaagcaa cctggctttg   45600
agctttcctt gtggttcttc tgtgtccctt gccttttgga gccatagtaa taaacccgtc   45660
tgccccctgt ttctctagga caagtaaagg aagatctgat gtcaggcacc agggaagctg   45720
ctgagttccc cagtgctgtt ggatccacct tcatctcctt ctgcagccaa cgggcctgtc   45780
cttgctcagg tggagggtga agggctgtgg ggacccagtg gtggcttccc acgttggccc   45840
cacgcatgtt gttgtagtcg ctgctcggct cgggctctgc cgcctcgctg tgtcttagca   45900
tgtttctaca ataaagataa ctccacagcg tcctgtcgct tttcttcact gagcctcacg   45960
ggagggacgt gtgagtcccc gctccggctg ctcgccacgc gtcccttgag ctctaaagca   46020
ccaaacccaa gcggagatgt cagacgcaga aagaagaac gtggtctggg ttctgttagc   46080
agggaccagc agttgggttc tctgactcgc tgtgtagggc tttgggtgta tctctttgtc   46140
tcccttcagc cctttctctc tgcctgtaaa aacggacatt aaaggatgct tacctacctc   46200
agagggttgt ttggagattt taattggttt acgttagaga gcccacgggt ggaattctgt   46260
tcctatgtgc caatgctggt gtgcaggagg tttaactgtt gcagtcatgg cctcttccag   46320
ccaacacccg atgggccgta tgtatttcct gttctttcgt ttatggctgt tacttaaagc   46380
aaatatgttc ttatttgtat aaactttatt gcaggacatt tccagaagac cttgagtgaa   46440
cgtacagtgt ttgagtccac tttagctgtg acctgatctg caaatacact ctgctgtaga   46500
taaggctgga gtaactttca gattttggca gggtttcgct caatgccaat taatttggct   46560
ccctccacag atattgattt ttttttttct tttcaattaa gttatcgaga tctttttttc   46620
ttaatgcagc taatgaaaat cgattttac tctcataaag tacttccgca tgtgtcacat   46680
tgatctgtct atggcttgat tatcggcagg ctttgacatg aggttaatat tttgtgtgct   46740 ggttttttttt caccgtgtgc aaacactgtg gtttagaaat atgttaccgc tgcttatttc   46800
tacgtggaaa atcccacggc gtggttatgc atggcagaag tcaccagttt gatccaattt   46860
agctgtttct agggatgcaa gattcctctg cctttgagcg ggtgaatcct cgggtgttat   46920
ttatacattc tgagaaggat gaacagaaga cggtaaaaac gtttgctaat gatgtctgct   46980
ggctgattcc ggctaaaatc gtgtgcaggg acctcgacgt gattttata aaggcagctc   47040 acaatttgag gcttaaagta agttcttgca aatgaaaatg ggcgcacttg agcgcgctat   47100
tataacttgt agtgatttca agcacttaga ttttgaaata atcgcccata aaaacctgca   47160
ttaattgtgc tccaaaacca atgagctgat gaggagggtg ccctggtagc ctcttttgct   47220
ggatttgagc accttctgaa tttctcctgc caccagcaga aattagccac agaaatcata   47280
gctgctataa gggtttatta atcagattac gaaactgcta agaaggcaca caacagtgac   47340
ttgctgaagc tgcctgtgct gctgttagcg agcctcccgt aggtagcaat gctaactcct   47400
tccttttagc agtttaccca ctgcttcctt ccatcactcc ttccttttgt agggcctact   47460
tttgcagttt gatccagtgg cttgcaggca atatctgtcc ccagcggtgc tctatgcagc   47520
```

```
tgacctccag gtagggctcc atgtgagcga tgcaatgtgt tatttccatg gggttcctaa    47580
gaaggaggaa gcaaaaagct caggaggtgc tccaaatata ttatcctgtc ctctgttttg    47640
ctctttgtgg tgcccttta acactgtaaag agaccatagg agtcctctat gaacctggaa    47700
aggtaccagc actatgggag gtcttcagtt tgctgtaaat tatgctttat tagaggtatt    47760
tcttctgcca agaccactg acccatgcg gctcacagtg ttttctaagg ctttgcagga      47820
ctggtgttac gaattggcac cctccaggcc tctcacaaat ctcctgcttc tcacagcgtt    47880
tcttcaagtt ctcccaagca cagctgagtt ttgagctcaa ctgctccctg caggggcctt    47940
gagcctcctg cctttttgca taaaaggtgt caggtactta tgcaatcctt agaggcatgc    48000
aaatgctgct ctggttatat actgaggact gttgattctg gcagaaccct ttgcagacct    48060
tgtactccct tgctatttcc caatccctgc agcctagcag ctctgcctaa caactgccat    48120
agccaacaca gcagcaggct gtgcatggtg caaggtgatg tggaaaggga tgattgtatg    48180
aaagcgtgat gctgtggtac tgcctctgca ggagactcgc actatttgtg taagaggacc    48240
ttatttgtct gctgcagagc tgtttcaagg ctgtccatac accctgtga tgctgagccc      48300 ctccaagcaa tgcactggga aaggaggct gggggagac cttattgctc tcctccaata       48360
tttgaaaggt gcttacagcg agagcagggt tggtctcttc tcactggtga caggatgagg    48420
ggaaatggcc tcaagttgca ccagggtatg tttagattgg atatcaggaa acacttattt    48480
actaaaaggt tgttaagcac tggaatcagc tccccaggga ggtggttgag tcaccatccc    48540
tggatgtgtt taaaaactgt ttggatatgg tgctcaggga catgatttag cggagggttg    48600
ttagttaggg tagtgtggtt aggttgtggt tcactcgatg gtctttaagg tcttttccaa    48660
cctgagcaat tctatgatat ggatccctgg ggctttcagt cttatctccc tggattatca    48720
caggttcagc tctatggccc atttgattta taccggggtc tgatgaacag gttttctct     48780 tggctcttca gggatcctat ttagcacttt ttggtacatt cccctgccct acaagtctcc    48840
ctgatacaca gagctcttat ccaagacttg ggaccttccc tactccagcc ctctgcagga    48900
ggtttcttgc taaccagtcc tccaaccagg actgcagtac acgacaaaga gctggaagag    48960
gtctgcaata cttccccagc atgaaggtat gagcactcct tttgagtagg ttactgaaag    49020
tagtaagatg tcaatacaac caactgcaag atacaaaacc gcatgaaaat tcagtttact    49080
ttgatgctga agggctgaaa agaaatgctg tggtgttagc acagatgcac tgctggcaaa    49140
gtgaaaatga gcaaagagga tgagatggat ggacagctga tggaaaaact cttcctaatt    49200
gctccacaga gcagcttgct cgcctgcagg gctgcagcat ggagctgctt gtgcataatg    49260
cagacacccc aagaccagtg ctgtttgtct tagccaagac acagttgcag ctgcagcaat    49320
tttttctaga tgtcagttcc ttccctatgt tgctgacagg tgtttgctgt tctgtccctt    49380
taatctgtat cctacagcaa acattccttg aatttaataa cttagctgga agacaattgc    49440
tgtgatcttg atagaacatg ctgagccaat ctatttaac tgcagattta gtttgcaaat      49500
actgtctcct tgccgataag attcaggtgt catctttgtg gacattggca ggaattttct    49560
tgaccgtgac aggttttaca gagtctggca attaagctgt caagacacat tttcctctgc    49620
caggaagcat taattgatga tagtcttggc tgcaataggc acagagagat ggatattgta    49680
atcagaatga atagaggtcc ttgtagttga gagctacgtt ggtccaaagt tttgtagtcg    49740
ttgacgtttg gtgatactga gataaggaac aaggcacgag atattagagc taaatatcag    49800
gcacagcatg agaataaaga cctctctagc tggaactgtt ggtatctggg gagattttaa    49860
ctttctggat gcatactgca aagtactaat attagtagag ctactggatg cgagagcaaa    49920
```

```
tagtttttcca ttaagtaatc ccaaaaatca tgttgttgtt ggtttgcttt tcaagtgcga    49980
ggggtgttgg agatgtattt ccctcagaaa ataaacctga tatgattcaa cctgagctct    50040
ctctgtttaa atcacactga aaatagatct gcaaatgggg attttgatta ccgagtacag    50100
aatatgaaag attaaaactt gggaaagtta gggttctgat tgagaaaact tttgttttg    50160 tggccgaccc ttgcagctta caaaaatctg cctaaataaa ggagaaaacc acatttagaa    50220
cccatccaag ctatgctact tcagtactgg gcaaaacttc aggagacgtt tgaagaaaac    50280
tgaagacgtg aagtataaag gaatgattga tgtgcacagt aaactttctt ggaaggtaat    50340
cacgcatggg ctaatatcaa tctttacaaa gttggctgac ttcctagata aggaagtac    50400 agtagatcta gtctacccag gcagcaaaaa tgtttgacct gttgccctgt ggggtggtgt    50460
cacctgggct tggggagggg ggtcaggatg aggttacagg ggatgtggaa gcatactgtg    50520
gaggagcagg tggggcaccc acaggagtta gcagtgagca gacagaaagg tggatctgag    50580
gaccgaactt cgtattttg ttccttgcat taatacacaa aaagcagaca cacacacaga    50640
gcagattgct gctggttttt gttttctttt ttaaacagca gaagagcagg atttttccca    50700
cagagaatgg ggtgaccttc taggctgtga ttgcctgggc tcaagctgag atgaaacgca    50760
gtgatgagga gcacaaaacc gtgctctgag gttaaataat gagggcttcg gctatcagtt    50820
cagagctcag taaaaactgc agaggaggag gaagacctaa ttgcatgtag ccagccacag    50880
ggcaaatgag agctgcagcg tgctggggca gatccgggag cagaggggcc gtggcacgct    50940
ccctgttcac tggctcccct ggagccacac aaaaggcccc ttcctggcaa ttgtgcccac    51000
atcaatcatt agctagaaac ccagagctgg gtaaatacgt tttggcttcc cgtcttgatg    51060
acagattggg tgttacatca caaggtggga ccacttgata tgacaacacg ctatatattc    51120
ccgctgctac ctctgccctt cctcccccac tctgagagca agcgggctgt gtgtgcaccg    51180
aggtgctctg ccatgaggac tgccaggcag tttgtacagg tggctctggc cctctgctgc    51240
tttgcaggtg agtgtttcct gctataccc gtaggtgact atagctagac cagagactag    51300
gctatctgtg agagtatctg ggtattgtaa tgtgttagag agccttgttc catgaaggaa    51360
tgctctttct gacagtgtag caaaacacca gactgcaaga tccaggtttc agcaaacctc    51420
atacagacga ctgttttcgt cgtggtttat aggagcaaat tgctgaggga gcagtgctag    51480
tgcagggcag gagcttgcac gtgcaagcac tgagtataac ggcaaagcaa agctatgtga    51540
aatggctcct gtgtccatgt aagcaataca aacactgcat cttgtatcat ctataaattt    51600
tctgtgctgt tcctggcagc tgagaagttt gttgtgggaa gaacagtgct agtggtcaac    51660
agccacctga aacgtgcatg tctgagctcc tgcaagtcaa atacagagtc ttgcagaaga    51720
gtttaaactc agtgcaggct tgaaaatacc tacatttctt ccctggggca tcttaggaac    51780
tggctaacac atgtggcctc ctactgaaag tgcagtgaaa cttcatttaa taacctctga    51840
ttcattttat ggacgtacat cactggcata atgtaaaatt gcattttcct aaacccaata    51900
agccaatcaa caacggtatc taaatgtaac tgtttcatcg aaagatttgc atatgtcatc    51960
tctgcatatt aataatatgt atttattttc tgtctctact tttcttttag atattgcctt    52020
tggaattgag gtgagttaca gattttttt cccatttatt cttttctatt ccaggcttct    52080
ggtcaaataa gagcagtata taattacctg atgagcaagt ggattaatct aatgaaagcc    52140
tggttgctca ataatacttt gccagtgcat gattgaatga tattgccaag tcacgaaaaa    52200
gtaaaacaca ccccgtttat actattttcc attcatgcaa taaaatgaag aaaggaagaa    52260
```

```
ttgtacgatc ctattatgtt aacttttgga tataactgcg ttagtccaag tcaaggggtg    52320
gtagttacct cctcgagagg aaagctgtct taagatgata agctccaaag catcaaagac    52380
agtgattctg gtatctttt ctatacagta agacacacac tacagtgttc ctgcctatac    52440
ccatatcaaa gcgaggaaag cagcagggtc tgtgcagtgc atttgtctgc aggttcttcc    52500
cacgcagtta tgagattcct gcaaatcacc agagactgca gcgtgattgg aaacgatcag    52560
attttgagtt gagcggctgt ggagcatggc caggctccca attaccagct gccttcgtta    52620
ggcgctgtct cacccacagc tctccttcct ccatgtcatg cttcccccag tcccccgcag    52680
gaaagcgtga tcagaagaag attcccacct cctgactgcc tgagcagatt ccaaatgata    52740
cctcaggtgt ttgtcccggc tggagctgtg ggtggcagga ggtttccata ctgtcttttg    52800
ttgtggaaac tgaccccagg gctgatgttg tgctgcttcc ataggttaat tgcagcctgt    52860
atgccagcgg catcggcaag gatgggacga gttgggtagc ctgcccgagg aacttgaagc    52920
ctgtctgtgg cacagatggc tccacataca gcaatgagtg cgggatctgc ctctacaaca    52980
ggtgagctta tgtggaagcc caggggagct gcagggcagg agactcgagg tgagggcggc    53040
agctctgtcc ccaaaatatg gtctgtgtgg aggagtatgt gagttagtac caggatgctg    53100
acctccagcc tggggtggt ggctgctctc tgccatctct gacacagatc tgcgttcttc    53160
cagggagcac ggggcaaacg tggagaagga atatgatgga gagtgcaggc caaagcacgt    53220
tacggtaagt ccaacagtaa gatgaagtct tgctctgttg gtgcccataa agacttattt    53280
ttatttcata gaatcattga acagcttagg ttggaaggga ccttaaagat cattgggctc    53340
taacccccct ggcctggccg ggctgccttc aaccaaatca gtttgcccag tcaaatgggc    53400
cttgggcacc tccagggatg gggcacctgc tctgctcagc ctgttactta tttacttgtt    53460
tttttcccat tcctgctatc cttacagatt gattgctctc cgtacctcca agttgtaaga    53520
gatggtaaca ccatggtagc ctgcccaagg attctgaaac cagtctgtgg ctcagatagc    53580
ttcacttatg acaacgaatg tgggatttgc gcctacaacg cgtaagtctt ttctgtggag    53640
catccttctg ggtaattaga gatggctaag tcccttggaa acgcttacat aaaacacttt    53700
ctaagccttt cttagggtag atgtttctgt gggactcttt gaagctggct acttgtgatt    53760
ctccagccag ctgcagattt cttccccatc ctctgtctgt gctcatgaag ggaatcacaa    53820
aaaagacaga ggacaaccca cagcagaggc atgaatagat caaagtgttg ctcagtgctg    53880
tgtgatatgg aaataccatg cattttctgc tcacaagtgg ttgctaccac ctgtgggctg    53940
catccagacc actcagcagt tccttacgtg aagggtggga ccttgctttc ttgccccagt    54000
atctaaggct tttcacgagg ctctctaact aaaacagctc tttctttcag agaacatcac    54060
accaacattt ccaaactgca cgatggagaa tgcaagctgg agatcggctc ggtaagtgta    54120
acagaaataa aaatccatct cctagggctg ttaacggaga gaatcccatt gattttccta    54180
agaaaatgta tgaccgggct gatcgggggt cccggtccac gctctgcttc ctgcctggtg    54240
agggtggctt ctgaaacaaa gcggtaaagg aagaggcccc agattttcct tgcattgtgc    54300
tgtgcagatt ggcaggtttc tctctggagg cgacaagcat ttccacccct tgtaacaagc    54360
attcaaaatt ctagtgctgg tagcttggtt agatatagtg agattcataa gagcaccaag    54420
catacatatt tatagggtat agcttattgt atatttatac tggggtaaga gtccagtgcc    54480
tcaggaagaa aagcttatat atttcagcac aaaaattctg ggatgcaggg agtccgttct    54540
ccaacagacg gattcctcct ttatcacttc aactcccgtg cttaactgca gggaatctga    54600
attattaagc aatcacagca ctggggaagg aaggagaaaa accaacacaa accaaaacaa    54660
```

```
tgttaatcag atttccagct gttggaaaat atttcccact taattcaagg ctgttgtgtc    54720
gatgagaaga gggctgaaaa ggctgttttc agttcctctg cctgaaggtt tcattctcta    54780
agagaggtcc cttttcttgt ctcctagaga atgagggtag tgttctgaaa gcctatttct    54840
gatagacagt ttagttaagt gtagcagggc tttgtcctgt cacaaaaact aggaagccgg    54900
gaatacagga tgaaaaggtg ttacattgac ttctcccgtg tagcacaggc tccgggaggg    54960
cttattctcc ttattttggc aggttgactg cagtaagtac ccatccacag tctctaagga    55020
tggcaggact ttggtagcct gcccaaggat cctgagcccg gtttgcggca ccgatggttt    55080
cacctatgac aacgaatgcg ggatctgcgc ccacaatgcg taagtgctgc tcatctccca    55140
ctcctccaaa gtagccagca atgctttgcc gtgctgggag ccttccttct acgttgctgc    55200
ttatgcctgt ttcttcaagc ctcttagaaa ctgcattttt tttgttgttg ttcttactga    55260
gttttcttct gatgccttct ttgtgatcac gaggggaaat ctgcaagact cagaacacag    55320
ctccttggat tagtctgtgg gctgggcagt gactgagcag agaaaggaat agttcagaat    55380
cttgctttaa ataacacgag aagacgtgat gagcttgtta acgagcagag taatgtagct    55440
atatcaatac aatcgtgcag agaggctgaa gccctacttt gttaggtacc tgctttaggc    55500
tacgtctggt tcattctgca tgcaagtgtt taaaccaaga gttaaagcat ctccttactc    55560
actttgtctc cctctttcag agagcagagg acccatgtca gcaagaagca tgatggaaaa    55620
tgcaggcagg agattcctga agtgagtata caacgtaagg tgtatttctc cccttgcctc    55680
tgcccactga gctatttgct gaggccacgt ctactctgaa agtgagctgg cttgaagcct    55740
ggctctctgc acgtgtcctt tgggatgtgc caacgtgtat ccaacacaca aacagtgtgg    55800
aagttgggca gggggaactt aggtctttta aggatgatca ctaaatgcat tgccagcaaa    55860
gtccttttgt gccagtgaag tcctattatg tttgccttct tttgtttcat tctatagtgc    55920
agagagaaaa ggagatgata tatctttgtt ggttttttttt ttgtttgttt gttttgcttt    55980
tctgccatat ctagcaaact gtttcagtag gttgtgaccc cttt ggatca caagtgaagc    56040 tcagtggcat ttgggattga ctgagctgtc tgccctggtg atttggcatc tcacagatta    56100
cacagcgcca tgtagctcct cctgggcatg agagagtttc tgcagagctg actcaggctg    56160
gctttgagag aactgaagtg tagcaccagc gttgtttcag catcccagcg taaaagacat    56220
ggattgcagc aggaggcaat gctagggttt gtctttgaga gcaagggctt tttcagggct    56280
gacgctccta cttttt gcag attgactgtg atcaataccc aacaagaaaa accactggtg    56340
gcaaactcct ggtgcgctgc ccaaggattc tgctcccagt ctgtggcaca gacggattta    56400
cttatgacaa cgagtgtggc atttgtgccc ataatgcgta agtactgcaa acaggacttc    56460
cttttgtagc gactagccac gttagtactg cagatggctt cccctccacc cttcatcttc    56520 ttctttctttt ctttttttttt gatagcagta tgtctatatg tctcctgttc ttccttcaac    56580
ctcctgaagc tctgtcgcct cggtttcctt tcctgatgtg ctcctcaggg agctgtggga    56640
gagccagcta acagctgagt gtcctatgag ggctgtggca tttgtgcaga ggaaaaagag    56700
aatgggtctg ctacaagtag acctgagaag cctgtaactt cttaggatca tgatccctaa    56760
tggcagcctt tccctttcag acaacatggg actgaggtta agaagagcca cgatggaaga    56820
tgcaaggagc ggagcacccc ggtaagtggg gatggatgtc agatgagcgc cagctcctgt    56880
acgtgccttg tggctgcaga ggttgctaac cagggtctgt ccattcaggc agcagagaag    56940
gggaatgggc caggatttag gtaacaaaat gtcccaatac tgcaggtctc tggagggaaa    57000
```

```
catcagaggc agcccagaac agcacagcct gttttagcac agtaggagag gaagagcaga  57060
agctgtgtta gatgcctgtg tagtcattca gtgctaggat ttccattgca gcagacaggt  57120
taaaaaatct ctgtaccgtg gtcagccaag aaaaggctgc ttgcaggaat gcacgcagaa  57180
atagctctat aaacatgcac ggtaacaata tgtgctgata atatctcagc acatttattc  57240
tgcttatgca gagcagctct aaaacactga aataaccttt gtgcatctca agggattgct  57300
gtatcttttc tgtagtaaag acacactgtt atggtgctgt ctttgctata atttgctctt  57360
ggactgtgtg gggaaatatg ggtaataaga gctactacac aggggaaggt atgcaaaacg  57420
attgtgaagt gtcagaagct tagccagtgt agactgactt ccagtgccat cagtagatac  57480
ttgcttattt atcctcaaat attggaactg ttttttaagta ctgtgaggat ttctgcagca  57540
gcagctgatg agctgatgga acagtttctt cttgccgttt tgaaaacgtg gaaacaaaat  57600
ctaaggctta gctaagtcag gcatgaccta atgtcaaact ggacataaca tcaaactcct  57660
tatatcaaat tcctttgaat aatgcttgtt ttgaaacttg gacatacgct gcataaggaa  57720
gatgatcttt ctggtctgct attcctttgc gttccctttg ttagtgagca atatcaaacc  57780
caaccacaat tagttcattt ataatgggag actaaactga aatcaaccct gattttcct  57840
atggctcgag gcagtctgtc ccccagctcc cagcacctga ctcagcatcc ttactgtttt  57900
ctccccagct tgactgcacc caatacctga gcaataccca aaacggtgaa gccattaccg  57960
cctgccctt catcctgcag gaggtctgtg gcactgacgg cgtcacctac agcaacgact  58020
gttctctgtg tgcccacaac atgtaagccc tgcaggtcac ccactcgtgt gtcaccgcag  58080
ctgcttgttg agctttgtca actctgtttt ctctctcttc cagtgaattg ggaaccagcg  58140
ttgccaaaaa gcacgatggg aggtgcagag aggaggttcc tgaggtaagc gataaagaaa  58200
acaagagctt gaggtggtgc ttattgccta acaagtacaa cgctggctgg ttttggtgat  58260
gctgggtcat gccctcctgc tgccatcctt cctgcaggta acatcaaacc ctggcagcag  58320
ggatgctgtg cattttctgc atgtagtcag ggaaagaaag agaagaggac gggtgaggaa  58380
tgagttatga tgcaggtagc ataaatgatt taaggcgtta cgaagaaatc tctttcccac  58440
agcagtctat catacctgcc gtgggagtgt agctgtctgt tctggcaata tgggaaaggg  58500
acacagagca cccgcaggta cctggtgcct tctggatacc tgtgctgtgc aaaaggatgt  58560
tgtgcaaaga tcagaaaact acctgcattt tgaatgcttt tacctaatgt accagaggat  58620
tcaaacacct ctctcttcct attgtaaatg cgatataatg taatgtatac caacaatgaa  58680
tcttgtaaaa ataccagata aactatattt ggccagctct aaactattta cgctcactgg  58740
ggaatagaaa aacaaagcca tctcattatc ttgtgtttga aagagtcaac gtcgtgagtc  58800
agatatttca tttctatgca aacagactat gaaatgtcat tgctttgttt cctgcgtatg  58860
ctctgtgctc agaccaagtc agatgcataa atcagtgagg aagagctcac actggagaaa  58920
ctgggatagc tgaaactcaa ggccagttct tcaaatggca taaatcattt tgaactgctg  58980
ttggtccttc tgtccgattg caacacacag aaccagcccc tcgcaacaaa aggcatgtca  59040
gcacatctcc tcagttcttg tgggccgtga cacactcctt ggccacactg agcttctctt  59100
gcaggaattg cataaatcac gccagtttga tttgcagatt atttatgagc tgcgttttgc  59160
agcgtcccag caagtggttc agcaagctct aagggcatcg tgataaatgc agggctgaat  59220
gagtgatacg cgccttcaag ctttgattca gtcttctcca gtataaggct gtgacagaaa  59280
attgatagtt tcaatgaag aatgagtcaa tgcataacca taatccatcc tgtggcagat  59340
cttgaaaggc agaggcgtaa ggaaggggt tgtgtctgag cacccttaca cagagcattt  59400
```

```
gctgcctttg tttcctagct tgactgcagc aagtacaaaa cctccacgct gaaggatggc    59460
agacaggtgg tggcctgcac catgatctac gatcccgtct gtgctaccaa tggtgtcacc    59520
tatgccagcg aatgcacgct gtgcgctcac aacctgtaag tactcattca tctccagggg    59580
gacccaccgt ggctgtgact ggacacatct ttgagtgctg aataacatgc aagggctctg    59640
tctaaaatct cgtgctgcat gggtcctgtc tgcctatccc cgtttccctg gttgccatgg    59700
ttggtgtttg agatgggcat ttagcaaggc ccactgcccc cagtgaccca gaaaaagggt    59760
tcactgcctg ggaaagcatt attccaaaag acacatccct agtccttaag ggcatgttct    59820
tgctaatgct tctcaggcaa tgcttagcta atttatctga aattgtcctg tgtaccacat    59880
gggaacgagg ttgtgctctt gtactacggt tgtaaatggg aagggtttct gctaatatcc    59940
atctctcctt cctccaggga gcagcggacc aatcttggca agagaaagaa tggaagatgt    60000
gaagaggata taacaaaggt gagtgtgaaa ggatgggcac aaagagttac agtcgtaggg    60060
gaccgtcctc tgctccacat caaaaactgg gggagcggtg tgcagccctg gcgaggtcgc    60120
ttgggaatgt catactggtt atagaatagc tgccatccat cccatgggaa tggacatggc    60180
agtgaacagg aacagtgtga ggtcacatcc ctcaccagga ggaactgagc tgattactgc    60240
cgtaattttc cagtttcact cttttgtgctg ggggaatact gtttgctccc aggcagagac    60300
tcacatcttc cttgtgtgtg caggaacatt gccgtgagtt ccagaaagtc tctcccatct    60360
gcaccatgga atacgtaccc cactgtggct ctgatggcgt aacatacagc aacagatgtt    60420
tcttctgcaa cgcatatgtg taagtatagg agtgaaaccc ttcctgtaac tgctacaaac    60480
gcagagttga ttttataagg agttctttac taacactttta tgggtgtgtg ctagacattt    60540
cggatgcacc gtgacgtgca aggaggtgct ttttgctttt ttaagaaaaa atgcaaagca    60600
cccacatctg cccatgtgta tgtggcttcc tgttttattt agtttcaaag acattttgct    60660
aattttcacc agcatagttt gtcccacaag ctcatcaggg tatggggaaa gtacttcacc    60720
aaactacctg gagcgtttca agtgtgtgaa acctgtcatc tttcctttaa ttttcataat    60780
gaaaggaagt ggttggcctt ctgagactgt tctttatctt ctgccaacat tatcaacatt    60840
tgggctggta aggagaggaa caaggctgca gcacaaattc tattgtgttt aatcctttct    60900
tctcttttca ttaggcagag caataggact ctcaacctcg tgagtatggc agcgtgttaa    60960
ctctgcactg gagtccatcg tgggaaacaa tctgccttgc acatgagtct tcgtgggcca    61020
atattcccca acggttttcc ttcagcttgt cttgtctccc aagctctcaa aacacctttt    61080
tggtgaataa actcacttgg caacgtttat ctgtcttacc ttagtgtcac gtttcatccc    61140
tattcccctt tctcctcctc cgtgtggtac acagtggtgc acactggttc ttctgttgat    61200
gttctgctct gacagccaat gtgggtaaag ttcttcctgc catgtgtctg tgttgttttc    61260
acttcaaaaa gggccctggg ctcccctttgg agctctcagg catttcctta atcatcacag    61320
tcacgctggc aggattagtc tctcctaaac cttagaatga cctgaacgtg tgctccctct    61380
ttgtagtcag tgcagggaga cgtttgcctc aagatcaggg tccatctcac ccacagggca    61440
attcccaaga tgaggtggat ggtttactct cacaaaaagt tttcttacgt tttgctagaa    61500
aggagagctc actgcctacc tgtgaattcc cctagtcctg gttctgctgc caccgctgcc    61560
tgtgcagcct gtcccatgga gggggcagca actgctgtca caaaggtgat cccaccctgt    61620
ctccactgaa atgaccctcag tgccacgtgt tgtataggat ataaagtacg ggaggggaat    61680
gcccggctcc cttcagggtt gcagggcaga agtgtctgtg tatagagtgt gtgtcttaat    61740
```

```
ctattaatgc aacagaacaa cttcagtcct ggtgttttgt gggctggaat tgcccatgtg   61800
gtagggacag gcctgctaaa tcactgcaat cgcctatgtt ctgaaggtat ttgggaaaga   61860
aagggatttg ggggattgcc tgtgattggc tttaattgaa tggcaaatca caggaaagca   61920
gttctgctca acagttggtt gtttcagcca attcttgcag ccaaagagcc gggtgcccag   61980
cgatataata gttgtcactt gtgtctgtat ggatgacagg gaggtagggt gacctgagga   62040
ccaccctcca gcttctgcca gcgtaggtac agtcaccacc tccagctcca cacgagtccc   62100
atcgtggttt accaaagaaa cacaattatt tggaccagtt tggaaagtca cccggtgtat   62160
tgtgaggcta gattaatagg ctgaaggcaa atgttcccaa cttggagata ctgttggtat   62220
tgtatcaggg aacagggcca tagcacctcc atgctattag attccggctg gcatgtactt   62280
ttcaagatga tttgtaacta acaatggctt attgtgcttg tcttaagtct gtgtcctaat   62340
gtaaatgttc ctttggttta tataaccttc ttgccgtttg ctcttcaggt gttcttgcag   62400
aacactggct gctttaatct agtttaactg ttgcttgatt attcttaggg ataagatctg   62460
aataaacttt ttgtggcttt ggcagacttt agcttgggct tagctcccac attagctttt   62520
gcagcctttt ctgtgaagct atcaagatcc tactcagtga cattagctgg gtgcaggtgt   62580
accaaatcct gctctgtgga acacattgtc tgatgatacc gaaggcaaac gtgaactcaa   62640
agaggcacag agttaagaag aagtctgtgc aattcagagg aaaagccaaa gtggccatta   62700
gacacacttt ccatgcagta tttgccagta ggtttcatat aaaactacaa aatggaataa   62760
accactacaa atgggaaaaa cctgatactg gaatttaaat attcacccag gctcaagggg   62820
tgtttcatgg agtaacatca ctctataaaa gtagggcagc caattattca cagacaaagc   62880
tttttttttt ttctgtgctg cagtgctgtt tttcggctga tccagggtta cttattgtgg   62940
gtctgagagc tgaatgattt ctccttgtgt catgttggtg aaggagatat ggccagggg   63000
agatgagcat gttcgagagg aaacgttgca ttttggtggc ttgggagaaa ggtagaacga   63060
tatcaggtct acagtgtcac taagggatct gaaggatggt tttacagaac agttgacttg   63120
gctgggtgca ggcttggctg taaatggatg gaaggatgga cagatgggtg gacagagatt   63180
tctgtgcagg agatcatctc ctgagctcgg tgcttgacag actgcagatc catcccataa   63240
ccttctccag catgagagcg cggggagctt tggtactgtt cagtctgctg cttgttgctt   63300
cctgggtgca cagtggtgat tttcttactc acacagggca aaaacctgag cagcttcaaa   63360
gtgaacaggt tgctctcata ggccattcag ttgtcaagat gaggttttg gtttcttgtt   63420
ttgtaaggtg ggaagaagca ctgaaggatc ggttgcgagg gcaggggttt agcactgttc   63480
agagaagtct tattttaact cctctcatga acaaaaagag atgcaggtgc agattctggc   63540
aaggatgcag tgaaggagaa agccctgaat ttctgatata tgtgcaatgt tgggcaccta   63600
acattccctg ctgaagcaca gcagctccag ctccatgcag tactcacagc tggtgcagcc   63660
ctcggctcca gggtctgagc agtgctggga ctcatgaggt tccatgtctt tcacactgat   63720
aatggtccaa tttctggaat gggtgcccat ccttggaggt ccccaaggcc aggctggctg   63780
cgtctccgag cagcccgatc tggtggtgag tagccagccc atggcaggag ttagagcctg   63840
atggtctta aggtcccttc caacctaagc catcctacga ttctaggaat catgacttgt   63900
gagtgtgtat tgcagaggca atatttaaa gttataaatg ttttctcccc ttccttgttt   63960
gtcaaagtta tcttgatcgc cttatcaatg cttttggagt ctccagtcat ttttcttaca   64020
acaaaaagag gaggaagaat gaagagaatc atttaatttc ttgattgaat agtaggattc   64080
agaaagctgt acgtaatgcc gtctctttgt atcgagctgt aaggtttctc atcatttatc   64140
```

```
agcgtggtac atatcagcac tttccatct gatgtggaaa aaaaaatcct tatcatctac    64200
agtctctgta cctaaacatc gctcagactc tttaccaaaa aagctatagg ttttaaaact    64260
acatctgctg ataatttgcc ttgttttagc tcttcttcca tatgctgcgt tgtgagagg    64320
tgcgtggatg ggcctaaact ctcagttgct gagcttgatg ggtgcttaag aatgaagcac    64380
tcactgctga aactgttttc atttcacagg aatgttttag tggcattgtt tttataacta    64440
catattcctc agataaatga aatccagaaa taattatgca aactcactgc atccgttgca    64500
caggtcttta tctgctagca aaggaaataa tttggggatg gcaaaaacat tccttcagac    64560
atctatattt aaaggaatat aatcctggta cccacccact tcatccctca ttatgttcac    64620
actcagagat actcattctc ttgttgttat catttgatag cgttttcttt ggttctttgc    64680
cacgctctgg gctatggctg cacgctctgc actgatcagc aagtagatgc gagggaagca    64740
gcagtgagag gggctgccct cagctggcac ccagccgctc agcctaggag gggaccttgc    64800
cttccacca gctgaggtgc agccctacaa gcttacacgt gctgcgagca ggtgagcaaa    64860
gggagtcctc atggtgtgtt tcttgctgcc cggaagcaaa actttacttt cattcattcc    64920
ccttgaagaa tgaggaatgt ttggaaacgg actgctttac gttcaatttc tctcttccct    64980
ttaaggctca gccaggggcc attgctgagg acggcatcgg ggcccctgg accaaatctg    65040
tggcacagat ggtttcactt acatcagtgg atgtgggatc tgcgcctgta atgtgtcctt    65100
ctgaaggaag gaacgtgcct tccaagtgcc agccccacag ccccagccc ctccctgtgc    65160
tgctccaatt catctcctct tcctccttct ccctttgctg tttgtgctcg ggtagaaatc    65220
atgaagattt agaagagaaa acaaaataac tggagtggaa acccaggtga tgcagttcat    65280
tcagctgtca taggtttgtc attgctatag gtctgtatca gagatgctaa caccactttg    65340
ctgtcggtgc ttaactcggg tgaactctcc ttcactcgca tcatttgcgg gccttattta    65400
catccccagc atccatcacc ctctgggaaa atgggcacac tggatctcta atggaagact    65460
ttccctcttt cagagcctgt gggatgtgca gtgacaagaa acgtggaggg gctgagcagc    65520
agcactgccc ccaggagca ggagcggatg ccatcggtgg cagcatccca aatgatgtca    65580
gcggatgctg agcaggcagc ggacgaacag acagaagcga tgcgtacacc ttctgttgac    65640
atggcatttg gcagcgattt aacactcgct tcctagtcct gctattctcc acaggctgca    65700
ttcaaatgaa cgaagggaag ggaggcaaaa agatgcaaaa tccgagacaa gcagcagaaa    65760
tatttcttcg ctacggaagc gtgcgcaaac aaccttctcc aacagcacca gaagagcaca    65820
gcgtaacctt tttcaagacc agaaaaggaa attcacaaag cctctgtgga taccagcgcg    65880
ttcagctctc ctgatagcag atttcttgtc aggttgcaaa tggggtatgg tgccaggagg    65940
tgcagggacc atatgatcat atacagcaca gcagtcattg tgcatgtatt aatatatatt    66000
gagtagcagt gttactttgc caaagcaata gttcagagat gagtcctgct gcatacctct    66060
atcttaaaac taacttataa atagtaaaac cttctcagtt cagccacgtg ctcctctctg    66120
tcagcaccaa tggtgcttcg cctgcaccca gctgcaagga atcagcccgt gatctcatta    66180
acactcagct ctgcaggata aattagattg ttccactctc ttttgttgtt aattacgacg    66240
gaacaattgt tcagtgctga tggtcctaat tgtcagctac agaaaacgtc tccatgcagt    66300
tccttctgct ccagcaaact gtccaggcta tagcaccgtg atgcatgcta cctctcactc    66360
catccttctt ctctttccca ccaggggagag ctgtgtgttt tcactctcag ccgctctgaa    66420
caataccaaa ctgctacgca ctgcctccct cggaaagaga atcccttgt tgcttttta     66480
```

```
tttacaggat ccttcttaaa aagcagacca tcattcactg caaacccaga gcttcctgcc   66540
tctccttcca caaccgaaaa cagccggctt catttgtctt ttttaaatgc tgttttccag   66600
gtgaattttg gccagcgtgt tggctgagat ccaggagcac gtgtcagctt tctgctctca   66660
ttgctcctgt tctgcattgc ctctttctgg ggcttccaag agggggggag actttgcacg   66720
gggatgagat aatgcccctt ttcttagggt ggctgctggg cagcagagtg gctctgggtc   66780
actgtggcac caatgggagg caccagtggg ggtgtgtttt gtgcagggag gaagcattca   66840
cagaatgggg ctgatcctga agcttgcagt ccaaggcttt gtctgtgtac ccagtgaaat   66900
ccttcctctg ttacataaag cccagatagg actcagaaat gtagtcattc cagccccct   66960 cttcctcaga tctggagcag cacttgtttg cagccagtcc tccccaaaat gcacagacct   67020
cgccgagtgg agggagatgt aaacagcgaa ggttaattac ctccttgtca aaaacacttt   67080
gtggtccata gatgtttctg tcaatcttac aaaacagaac cgagggcagc gagcactgaa   67140
ggcgtgttcc catgctgagt taatgagact tggcagctcg ctgtgcagag atgatccctg   67200
tgcttcatgg gaggctgtaa cctgtctccc catcgccttc acaccgcagt gctgtcctgg   67260
acacctcacc ctccataagc tgtaggatgc agctgcccag ggatcaagag acttttccta   67320
aggctcttag gactcatctt tgccgctcag tagcgtgcag caattactca tcccaactat   67380
actgaatggg tttctgccag ctctgcttgt ttgtcaataa gcattttttc attttgcctc   67440
taagtttctc tcagcagcac cgctttgggt gacttcagtg gccgcctgga acccgagggg   67500
cacagccacc acctccctgt tgctgctgct ccggggactc acgtgctgct ggatgggggg   67560
aagcatgaag ttcctcaccc agacacctgg gttgcaatgg ttgcagtgtg ctcttcttgg   67620
tatgcagatt gtttctagcc attacttgta gaaatgtgct gtggaagccc tttgtatctc   67680
tttctgtggc ccttcagcaa aagctgtggg aaagctctga ggctgctttc ttgggtcgtg   67740
gaggaattgt atgttccttc tttaacaaaa attatcctta ggagagagca ctgtgcaagc   67800
attgtgcaca taaaacaatt caggttgaaa gggctctctg gaggtttcca gcctgactac   67860
tgctcgaagc aaggccaggt tcaaagatgg ctcaggatgc tgtgtgcctt cctgattatc   67920
tgtgccacca atggaggaga ttcacagcca ctctgcttcc cgtgccactc atggagagga   67980
atattccctt atattcagat agaatgtcat cctttagctc agccttccct ataaccccat   68040
gagggagctg cagatcccca tactctcctc ttctctgggg tgaaggccgt gtcctccagc   68100 ccccttccc accctgtgcc ctgagcagcc cgctggcctc tgctggatgt gtgcccatat   68160
gtcaatgcct gtccttgcag tccagcctgg aacatttaat tcatcaccag ggtaatgtgg   68220
aactgtgtca tcttcccctg cagggtacaa agttctgcac ggggtccttt cggttcagga   68280
aaaccttcgc tggtgctacc tgaatcaagc tctatttaat aagttcataa gcacatggat   68340
gtgttttcct agagatacgt tttaatggta tcagtgattt ttatttgctt tgttgcttac   68400
ttcaaacagt gcctttgggc aggaggtgag ggacgggtct gccgttggct ctgcagtgat   68460
ttctccaggc gtgtggctca ggtcagatag tggtcactct gtggccagaa aaggacaaa   68520 gatggaaatt gcagattgag tcatgttaag caggcatctt ggagtgattt gaggcagttt   68580
catgaaagag ctacgaccac ttattgttgt tttcccctttt tacaacagaa gttttcatca   68640
aaataacgtg gcaaagccca ggaatgtttg ggaaaagtgt agttaaatgt tttgtaattc   68700
atttgtcgga gtgttaccag ctaagaaaaa agtcctacct ttggtatggt agtcctgcag   68760
agaatacgac atcaatatta gtttggaaaa aaacaccacc accaccagaa actgtaatgg   68820
aaaatgtaaa ccaagaaatt ccttgggtaa gagagaaagg atgtcgtata ctggccaagt   68880
```

```
cctgcccagc tgtcagcctg ctgaccctct gcagctcagg accatgaaac gtggcactgt   68940
aagacgtgtc cctgcctttg cttgctcaca gatctctgcc ctcgtgctga ctcctgcaca   69000
caagagcatt tccctgtagc caaacagcga ttagccataa gctgcacctg actttgagga   69060
ttaagagttt gcaattaagt ggattgcagc aggagatcag tggcagggtt gcagatgaaa   69120
tcctttctag gggtagctaa gggctgagca acctgtccta cagcacaagc caaaccagcc   69180
aagggttttc ctgtgctgtt cacagaggca gggccagctg gagctggagg aggttgtgct   69240
gggactcttc tccctgtgct gagaatggag tgatttctgg gtgctgttcc tgtggcttgc   69300
actgagcagc tcaagggaga tcggtgctcc tcatgcagtg ccaaaactcg tgtttgatgc   69360
agaaagatgg atgtgcacct ccctcctgct aatgcagccg tgagcttatg aaggcaatga   69420
gccctcagtg cagcaggagc tgtagtgcac tcctgtaggt gctagggaaa atctctggtt   69480
cccagggatg cattcataag gacaatatat cttgaggctg tgccaaatct ttctgaaata   69540
ttcatgcatg ttcccttaat ttatagaaac aaacacagca gaataattat tccaatgcct   69600
cccctcgaag gaaacccata tttccatgta gaaatgtaac ctatatacac acagccatgc   69660
tgcatccttc agaacatgcc agtgctcatc tcccatggca aaatactaca ggtattctca   69720
ctatgttgga cctgtgaaag gaaccatggt aagaaactca ggttaaaggt atggctgcaa   69780
aactactcat accaaaacag cagagctcca gacctcctct taggaaagag ccacttggag   69840
agggatggtg tgaaggctgg aggtgagaga cagagcctgt cccagttttc ctgtctctat   69900
tttctgaaat gtctgcagga ggaaaggaca actgtacttt caggcatagc tggtgccctc   69960
acgtaaataa gttccccgaa cttctgtgtc atttgttctt aagatgcttt ggcagaacac   70020
tttgagtcaa ttcgcttaac tgtgactagg tctgtaaata agtgctccct gctgataagg   70080
ttcaagtgac attttagtg gtatttgaca gcatttacct tgctttcaag tcttctacca   70140
agctcttcta tacttaagca gtgaaaccgc caagaaaccc ttccttttat caagctagtg   70200
ctaaatacca ttaacttcat aggttagata cggtgctgcc agcttcacct ggcagtggtt   70260
ggtcagttct gctggtgaca aagcctcct ggcctgtgct tttacctaga ggtgaatatc   70320
caagaatgca gaactgcatg gaaagcagag ctgcaggcac gatggtgctg agccttagct   70380
gcttcctgct gggagatgtg gatgcagaga cgaatgaagg acctgtccct tactcccctc   70440
agcgttctgt gctatttagg gttctaccag agtccttaag aggttttttt ttttttttgg   70500
tccaaaagtc tgtttgtttg gttttgacca ctgagagcat gtgacacttg tctcaagcta   70560
ttaaccaagt gtccagccaa aatcaattgc ctgggagacg cagaccatta cctggaggtc   70620
aggacctcaa taaatattac cagcctcatt gtgccgctga cagattcagc tggctgctct   70680
gtgttccagt ccaacagttc ggacgccacg tttgtatata tttgcaggca gcctcggggg   70740
gaccatctca ggagcagagc accggcagcc gcctgcagag ccgggcagta cctcaccatg   70800
gccatggcag gcgtcttcgt gctgttctct ttcgtgcttt gtggcttcct cccaggtgag   70860
taactcccag agtgctgcag aagctttgtg cctgccagtc ctggctctcc ttagcagaac   70920
atggtggtga ccatcagaga gagactcccc tacaaagtgc ctgcaaaggc tgcctcagta   70980
catcagtatt aaacggatta ctgttgtgct gggtgtctgt tgggtctgt gctcccaaca   71040
catttcttac gctctcagct ctgttacact gcttgcattt gctgcacagt tgcatagaat   71100
ggataaatgc ttgaaacaag gccataacga ggtggtcaga cctccaggaa ctagttaggg   71160
aaatattgtc atggcccaag caagctctgt gcaggaacct ggcagctttc ctgcaatgct   71220
```

```
tttgctgcta atggagaaac aagagatgca aacaagccag gatctgatgt tctccttctg    71280
tatttacatc tcatgaaatt acaaagtcaa agacaagcgt ggtttatttc ttacactcag    71340
cttctttaaa atgtatatcc ctgacaacag atgctgtgta tgtttgctta tcctgtatgt    71400
gactatttgc atttgcattt atctctattg actcaggttt cttttcagat atgtgataga    71460
tgttttctag ggacaaaacg gatgtgtgaa tagataagga aggaaaagat attcatttt     71520 caattaataa atctacctat ctcttaactt tttttttttt ttaagaacag agctattcaa    71580
gaactcgttt catcagccag caataagaag ctaaattatg tttatcagca ttaaacaaaa    71640
atcatatata gtttgcttag ttcaagaatc gaatcggtgg aaatcactca gtttggttct    71700
ctgtgctgga gttttgcaca cacatttcag ctagctgtgg tctcactgat cagactgcct    71760
ttgtttccca ttttttgtccc cttttttttcc ccagatgctg cctttggggc tgaggtgagt    71820
aagagagttc ttcttgtcca cttttctctt ttctcttttc tctctctctc tttttttccc    71880
cccgtcttaa ttagtatcac tataatcaga tcccagagtg taaaatgtta aattatgcag    71940
ttctgagctc tacatctatg ctgcatgtaa gtaatgtagc agtgatataa aactgttaga    72000
tgaattaatt tctgaccaac tctgaactgg tctaagcttt aagttgatca tatgttctac    72060
taaataatac agtggtttgg gttggaaggg tcctttaaga tcatctactt ccaaccccctc   72120 tgctataggc agggacaact cccactagac aagattgctc aaagctccat ccatatgatc    72180
agctgtagac tgatggctgt agactatagc attaaaaact accccaaagc agcctactga    72240
aagaagaaag tactgtgagg tgctacagct tccaaatccc atgttgttag acctgttctt    72300
ttgaataaac gtgtttgtac gttgagaatg aatgagtaac aatggcagaa cactggaggg    72360
gccaactctc aggcttttgca aaatggtgcc tgggggcat gatagatccc tgctggttta    72420
tcacatgggg agctgcatgg ctataacccc attgcccagt tctctcccac tgcatggaga    72480
gaaggctgga tctggtcgct gccctgctga aaatggcaga tgtaactaca aaatgtcact    72540
ttgtcctgtt actgtgtgtt tctttgtcag gtggactgca gtaggtttcc caacgctaca    72600
gacaaggaag gcaaagatgt attggttttgc aacaaggacc tccgcccccat ctgtggtacc    72660 gatggagtca cttacaccaa cgattgcttg ctgtgtgcct acagcatgtg tgtactgcag    72720
agagagctca tactgcaagc aagcagctgt gcttagggct cctgacagca cccctttcca    72780
acaaacagtg atctgtcaca tgtcacttat gtcaactctt tcagggaaag cttgagtatc    72840
actgcgtgac actcggttgc ctagacatca ctttggttac tgtgtctttt ttgttgatgt    72900 aattattca ggtttttctc ctccatctcg gggatgaggc agatgacagc ccctagggca    72960
tatttcatcc cagcaaaaaa ggagcaaaag gatggagagg tgctccagtc tgaatggtcc    73020
aaaacagtcc taaagatttc agagtctttta gatccctgcc agccactcag tatggcacta    73080
ccctctccaa tacaaatata tatatataca aagatgactt agccagactc agcctcattg    73140
cattaggtac atattcccaa taacgagaag ctgagcttcc taatacctgt tttccctctt    73200
cagagaattt ggaaccaata tcagcaaaga gcacgatgga gaatgcaagg aaactgttcc    73260
tgtaagtgaa accaagttca tcctttgtgc agccaaaact gcttattgac ttgcccaata    73320
aataatgtaa atgctgacta agaggccatg tgagatgtca gaatcttgta ttgatcatct    73380
tcaggtgaag tttcatcaca ataacacaaa aaaagacttt atttcctgct gaggtggcat    73440
tttaggagac ccaacgcacg cgctccgctg gtctacgtgg tccctgtaag ccctcaccag    73500
cgctttgctg tgtgctccctt ccacagatga actgcagtag ttatgccaac acgacaagcg    73560
aggacggaaa agtgatggtc ctctgcaaca gggccttcaa ccccgtctgt ggtactgatg    73620
```

```
gagtcaccta cgacaatgag tgtctgctgt gtgcccacaa agtgtaagta ccgagctgtg   73680
ctcccttggc aggaatgggt cctgcgctcc tggcagccac tctttgagca ctgggatttc   73740
caatgaggct ttttctgtat ggctcttgga ctccgtccct cctctccctg ataacctcat   73800
gctgttttcc tttgtgatta gaaagagaac tgtggctttg atcttgagag agaagcagag   73860
agctgggtgg ggacttaaga gaagcactct gttctgtgtt aactaagtta aaagggtctg   73920
tgtggcacac actgccttgc agaggacagc agtgaacctc tgctgcacct atattgtaaa   73980
acaacctagc tcctaggcca tgacagcctg tcacctctcc tcctttgcat catgcaatac   74040
tgcaacactg tggcacatag taccacctcc cataaggact gatatgttga accagtgtgt   74100
cagagaccag tagcatctct gtcttcagga tcatcaggta gcattctata tacagggtgt   74160
tgcccaggac tccgagtccc atgaagtatg gcaggggttt tggaactgga tgaccttcga   74220
ggtcacttcc aacccaagcc attctattat tctgtgaaag ccaggaggt ggggtgctt    74280 gcagggctgg tatcttgagc agtgtgggca caaactaggc tgggcatctg cagcccatca   74340
gcactgcggg gatgtggagt tcagcacagc aggatgcagg cacagctccc taacatggat   74400
ttttttcctt tcagagagca gggggccagc gttgacaaga ggcatgatgg tggatgtagg   74460
aaggaacttg ctgctgtgag tgtgagtagc acaatgaagg agcaggttct ggtcccactg   74520
atgtcaaggg aaacatggcc agcatcttta gtagcctcag gagcatcagt tgtgcttcag   74580
cacagagaag attttacttt ctacacacgt aatacacatt atccacagta atgtcaggaa   74640
gggaagagga tgactgcaca ggcagggatc agtaaaagac cataagcaga aataacccat   74700
gagggcagaa ctgagaataa gaactgagac tagatccagg gggtcagacc aatgggccat   74760
caaacccatg atggtttgat gcagagtcca ctctttcagc attcataaga attgagtagg   74820
ggggagtaag ggtggggtga gtacgtacgg atcttcccaa acacccttcc aacctacagc   74880
tatgcacctc agccaggtgt gatttctgtg tagttcacaa gcctcagtgg atttctctcc   74940
catgggattc tccagcctct ttctggacct gtatacacgg tagttgggtt ggttttttt    75000 ttctgtctct cttttttcc cccactaca atgtccctca gcaaacatag tcctcatctc    75060
tcaaacaaac aaatctcatt ctctaagtac ccagataaga gctgattttt gctttaagcc   75120
tgtgggggag atgctggact attataaagg tatcagtgct gcctcttctc cagacaccaa   75180
tgttttttcc atttaatttc ctgaacaggt caggaacacg gtgcaacatg attgtaagca   75240
cagcacgttc atggagcgag ctgctgctgc agctcagaaa tgcagcagtc agattgtgat   75300
atgcatctct tacacaggaa attatgctct attttatat tattaaatct agcatacgag    75360
aaaggacatc cagtttatat cagatcgtgc aaggaagtta attatttta gtttgatcat    75420 tatcatcggc actgcagctg tagctaggga ggggttgaag ctcttcagct atcgactcct   75480
tcatatcctc cacgttacaa ttgtgttttt gcaggttgac tgcagcgagt accctaagcc   75540
tgactgcacg gcagaagaca gacctctctg tggctccgac aacaaaacat atggcaacaa   75600
gtgcaacttc tgcaatgcag tcgtgtacgt acagccctga ttgcattcac gttgtcggct   75660
gcctcctaca ggcaccagct tgcacagttc ctgctttcgt tgctgattgc tgaccaggat   75720 ctggggcag aaaagaacac cgggcatcac gccagccatt catttgattt ttcaccagag    75780
cttgtctggt ttgttaggat ggatgttttg aacgccatta accttaaggg aagttttcct   75840
tgctgcgaag aaaatcagat ttggtgtttc attatagttt tcagaagggg ttaaacgatt   75900
tcactcatct cctaataatc aggtagctga ggagatgctg agtctgccag ttcttgggct   75960
```

-continued

```
ctgggcagga tcccatctcc tgccttctct aggacagagc tcagcaggca gggctctgtg   76020
gctctgtgtc taacccactt cttcctctcc tcgctttcag ggaaagcaac gggactctca   76080
ctttaagcca ttttggaaaa tgctgaatat cagagctgag agaattccgc ccctctccct   76140
cccccccccc taacgttact ggccgaagcc gcttggaata aggccggtgt gcgtttgtct   76200
atatgttatt ttccaccata ttgccgtctt ttggcaatgt gagggcccgg aaacctggcc   76260
ctgtcttctt gacgagcatt cctagggggtc tttcccctct cgccaaagga atgcaaggtc   76320
tgttgaatgt cgtgaaggaa gcagttcctc tggaagcttc ttgaagacaa caacgtctg    76380
tagcgaccct ttgcaggcag cggaaccccc cacctggcga caggtgcctc tgcggccaaa   76440
agccacgtgt ataagataca cctgcaaagg cggcacaacc ccagtgccac gttgtgagtt   76500
ggatagttgt ggaaagagtc aaatggctct cctcaagcgt attcaacaag gggctgaagg   76560
atgcccagaa ggtaccccat tgtatgggat ctgatctggg gcctcggtgc acatgcttta   76620
catgtgttta gtcgaggtta aaaaaacgtc taggcccccc gaaccacggg gacgtggttt   76680
tcctttgaaa aacacgatga taagcttgcc acaaccatgg gtgtactgct cacacagagg   76740
acgctgctca gtcggtcct tgcactcctg tttccaagca tggcgagcat ggcaatgcac    76800
gtggcccagc ctgctgtggt actggccagc agccgaggca tcgccagctt tgtgtgtgag   76860
tatgcatctc caggcaaagc cactgaggtc cgggtgacag tgcttcggca ggctgacagc   76920
caggtgactg aagtctgtgc ggcaacctac atgatgggga atgagttgac cttcctagat   76980
gattccatct gcacgggcac ctccagtgga aatcaagtga acctcactat ccaaggactg   77040
agggccatgg acacgggact ctacatctgc aaggtggagc tcatgtaccc accgccatac   77100
tacctgggca taggcaacgg aacccagatt tatgtaattg atccagatac cgtgcccaga   77160
ttctgatcag gagcccaaat cttctgacaa aactcacaca tccccaccgt ccccagcacc   77220
tgaactcctg ggtggatcgt cagtcttcct cttccccccca aaacccaagg acaccctcat   77280
gatctcccgg acccctgagg tcacatgcgt ggtggtggac gtgagccacg aagaccctga   77340
ggtcaagttc aactggtacg tggacggcgt ggaggtgcat aatgccaaga caaagccgcg   77400
ggaggagcag tacaacagca cgtaccgggt ggtcagcgtc ctcaccgtcc tgcaccagga   77460
ctggctgaat ggcaaggagt acaagtgcaa ggtctccaac aaagccctcc cagcccccat   77520
cgagaaaacc atctccaaag ccaaagggca gccccgagaa ccacaggtgt acaccctgcc   77580
cccatcccgg gatgagctga ccaagaacca ggtcagcctg acctgcctgg tcaaaggctt   77640
ctatcccagc gacatcgccg tggagtggga gagcaatggg cagccggaga caactacaa    77700
gaccacgcct cccgtgctgg actccgacgg ctccttcttc ctctacagca agctcaccgt   77760
ggacaagagc aggtggcagc aggggaacgt cttctcatgc tccgtgatgc atgaggctct   77820
gcacaaccac tacacgcaga agagcctctc cctgtctccg ggtaaatgag ga           77872
```

<210> SEQ ID NO 45
<211> LENGTH: 780
<212> TYPE: DNA
<213> ORGANISM: SV40

<400> SEQUENCE: 45

```
cccagagctg tgcagttggg atcctaacac catgcagatg ctccaggacc tgcaccgagc    60
cccagcactg gcactcatct cttctttcca cccctctgag agcaacaagt ggctctgcaa   120
tggcaatgta agtgaaaccg gcgggtatc ttagagcacc tggaagcttg catgcctgca   180
ggtcgactct agaggatccc cgggtaccga gctcgaattc caggtaccgt cgacgatgta   240
```

```
ggtcacggtc tcgaagccgc ggtgcgggtg ccagggcgtg cccttgggct ccccgggcgc      300
gtactccacc tcacccatct ggtccatcat gatgaacggg tcgaggtggc ggtagttgat      360
cccggcgaac gcgcggcgca ccgggaagcc ctcgccctcg aaaccgctgg gcgcggtggt      420
cacggtgagc acgggacgtg cgacggcgtc ggcgggtgcg gatacgcggg gcagcgtcag      480
cgggttctcg acggtcacgg cgggcatgtc gacagccaag ccgaattcgc cctatagtga      540
gtcgtattac aattcactgg ccgtcgtttt acaacgtcgt gactgggaaa accctggcgt      600
tacccaactt aatcgccttg cagcacatcc cctttcgcc agctggcgta atagcgaaga      660
ggcccgcacc gatcgccctt cccaacagtt gcgcagcctg aatggcgaat ggcgcctgat      720
gcggtatttt ctccttacgc atctgtgcgg tatttcacac cgcatatggt gcactctcag      780
```

<210> SEQ ID NO 46
<211> LENGTH: 1957
<212> TYPE: DNA
<213> ORGANISM: human

<400> SEQUENCE: 46

```
ataatcaggt agctgaggag atgctgagtc tgccagttct tgggctctgg gcaggatccc       60
atctcctgcc ttctctagga cagagctcag caggcagggc tctgtggctc tgtgtctaac      120
ccacttcttc ctctcctcgc tttcagggaa agcaacggga ctctcacttt aagccatttt      180
ggaaaatgct gaatatcaga gctgagagaa ttccgcccct ctccctcccc cccccctaac      240
gttactggcc gaagccgctt ggaataaggc cggtgtgcgt ttgtctatat gttattttcc      300
accatattgc cgtctttttgg caatgtgagg gcccggaaac ctggccctgt cttcttgacg      360
agcattccta ggggtctttc ccctctcgcc aaaggaatgc aaggtctgtt gaatgtcgtg      420
aaggaagcag ttcctctgga agcttcttga agacaaacaa cgtctgtagc gaccctttgc      480
aggcagcgga accccccacc tggcgacagg tgcctctgcg gccaaaagcc acgtgtataa      540
gatacacctg caaaggcggc acaaccccag tgccacgttg tgagttggat agttgtggaa      600
agagtcaaat ggctctcctc aagcgtattc aacaaggggc tgaaggatgc ccagaagta       660 cccccattgta tgggatctga tctggggcct cggtgcacat gctttacatg tgtttagtcg      720
aggttaaaaa aacgtctagg cccccgaac acgggggacg tggttttcct ttgaaaaaca       780
cgatgataag cttgccacaa ccatgggtgt actgctcaca cagaggacgc tgctcagtct      840
ggtccttgca ctcctgtttc caagcatggc gagcatggca atgcacgtgg cccagcctgc      900
tgtggtactg gccagcagcc gaggcatcgc cagctttgtg tgtgagtatg catctccagg      960
caaagccact gaggtccggg tgacagtgct tcggcaggct gacagccagg tgactgaagt     1020
ctgtgcggca acctacatga tggggaatga gttgaccttc ctagatgatt ccatctgcac     1080 gggcaccctcc agtggaaatc aagtgaacct cactatccaa ggactgaggg ccatggacac     1140
gggactctac atctgcaagg tggagctcat gtacccaccg ccatactacc tgggcatagg     1200
caacggaacc cagatttatg taattgatcc agatcccgtg cccagattct gatcaggagc     1260
ccaaatcttc tgacaaaact cacacatccc caccgtcccc agcacctgaa ctcctggtgg     1320
gatcgtcagt cttcctcttc cccccaaaac caaggacac cctcatgatc tcccggaccc      1380
ctgaggtcac atgcgtggtg gtggacgtga gccacgaaga ccctgaggtc aagttcaact     1440
ggtacgtgga cggcgtggag gtgcataatg ccaagacaaa gccgcgggag gagcagtaca     1500
acagcacgta ccgggtggtc agcgtcctca ccgtcctgca ccaggactgg ctgaatggca     1560
```

-continued

```
aggagtacaa gtgcaaggtc tccaacaaag ccctcccagc ccccatcgag aaaaccatct   1620
ccaaagccaa agggcagccc cgagaaccac aggtgtacac cctgccccca tcccgggatg   1680
agctgaccaa gaaccaggtc agcctgacct gcctggtcaa aggcttctat cccagcgaca   1740
tcgccgtgga gtgggagagc aatgggcagc cggagaacaa ctacaagacc acgcctcccg   1800
tgctggactc cgacggctcc ttcttcctct acagcaagct caccgtggac aagagcaggt   1860
ggcagcaggg gaacgtcttc tcatgctccg tgatgcatga ggctctgcac aaccactaca   1920
cgcagaagag cctctccctg tctccgggta aatgagg                            1957
```